United States Patent
Clader et al.

(10) Patent No.: US 7,348,328 B2
(45) Date of Patent: Mar. 25, 2008

(54) MCH ANTAGONISTS FOR THE TREATMENT OF OBESITY

(75) Inventors: John W. Clader, Cranford, NJ (US); Anandan Palani, Bridgewater, NJ (US); Ruo Xu, Watchung, NJ (US); Mark D. McBriar, Stewartsville, NJ (US); Jing Su, Scotch Plains, NJ (US); Haiqun Tang, Belle Mead, NJ (US)

(73) Assignee: Schering Corporation, Kenilworth, NJ (US)

( * ) Notice: Subject to any disclaimer, the term of this patent is extended or adjusted under 35 U.S.C. 154(b) by 573 days.

(21) Appl. No.: 10/308,782

(22) Filed: Dec. 3, 2002

(65) Prior Publication Data

US 2004/0122017 A1 Jun. 24, 2004

Related U.S. Application Data

(60) Provisional application No. 60/399,853, filed on Jul. 31, 2002, provisional application No. 60/337,262, filed on Dec. 4, 2001.

(51) Int. Cl.
 *A61K 31/497* (2006.01)
 *C07D 237/02* (2006.01)
 *C07D 265/30* (2006.01)
(52) U.S. Cl. .................... 514/252.12; 544/63; 544/224
(58) Field of Classification Search ........... 514/252.12; 544/63, 224, 400; 548/579, 336.1; 546/230
See application file for complete search history.

(56) References Cited

U.S. PATENT DOCUMENTS 5,908,830 A 6/1999 Smith et al.

FOREIGN PATENT DOCUMENTS

| EP | 0507291 A1 | 10/1992 |
| EP | 0955293 A1 | 11/1999 |
| WO | WO99/64394 | 12/1999 |
| WO | WO01/85714 A1 | 11/2001 |

OTHER PUBLICATIONS

P. Grammaticakis: "Contribution à l'étude spectrale de quelques derives de l'isocyanate de phyényle. I. Absorption dans l'ultra-violet moyen des derives phénylcarbamyleés de quelques amines, hydroxylamines, phénylhydrazines, cétimines et oximes" *Bull. Chim. Soc. Fr.* Paragraph C, 667 (1947).
Shimada, et al., "Mice lacking melanin-concentrating hormone are hypophagic and lean" *Nature* 396:670-674(1998).
Borowsky, et al., "Antidepressant, anxiolytic and anorectic effects of a melanin-concentrating hormone-1 receptor antagonist" *Nature Medicine* 8:825-830(2002).
PCT International Search Report dated Mar. 10, 2003 for corresponding PCT Application No. PCT/US02/38408.

*Primary Examiner*—James O. Wilson
*Assistant Examiner*—Ebenezer Sackey
(74) *Attorney, Agent, or Firm*—William Y. Lee; Palaiyur S. Kalyanaraman

(57) ABSTRACT

The present invention discloses compounds which, are novel antagonists for melanin-concentrating hormone (MCH), as well as methods for preparing such compounds. In another embodiment, the invention discloses pharmaceutical compositions comprising such MCH antagonists as well as methods of using them to treat obesity, metabolic disorders, eating disorders such as hyperphagia, and diabetes.

10 Claims, No Drawings

MCH ANTAGONISTS FOR THE TREATMENT OF OBESITY

CROSS REFERENCE TO RELATED APPLICATIONS

This application claims the benefit of U.S. Provisional Applications 60/337,262 filed on Dec. 4, 2001 and 60/399,853 filed on Jul. 31, 2002.

FIELD OF THE INVENTION

This invention relates to antagonists for melanin-concentrating hormone (MCH) and their use in the treatment of metabolic and eating disorders, novel compounds having MCH receptor modulatory activity, pharmaceutical compositions containing one or more such modulators, methods of preparing such modulators and methods of using such modulators to treat obesity, diabetes and related disorders.

BACKGROUND OF THE INVENTION

MCH, a cyclic peptide, was first identified over a decade ago in teleost fish where it appears to regulate color change. More recently, MCH has been the subject of investigation for its possible role as a regulator of eating behavior in mammals. As reported by Shimada et al., Nature, Vol. 396 (Dec. 17, 1998), pp. 670-673, MCH-deficient mice have reduced body weight and leanness due to hypophagia (reduced feeding). In view of their findings, it was suggested that antagonists of MCH may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist. Further, MCH receptor antagonists may also be useful in the treatment of depression and/or anxiety. Borowksy et al., Nature Medicine, 8, pp. 825-830 (Aug. 1, 2002).

SUMMARY OF THE INVENTION

In one embodiment, this invention provides novel compounds having MCH antagonist activity. These compounds are represented by structural formula I:

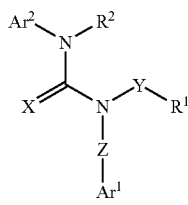

formula I or a pharmaceutically acceptable salt or solvate of said compound, isomer or racemic mixture wherein $Ar^1$ is aryl, heteroaryl, $(R^7)_p$-Substituted aryl or $(R^7)_p$-substituted heteroaryl, wherein p is a number from 1 to 3 and when p is more than 1, each $R^7$ can be the same or different and is independently selected from the group consisting of alkyl, cycloalkyl, halo, —CN, alkoxy, —$CF_3$, —$OCF_3$, —C(O)N($R^8$)$_2$, —N($R^9$)$_2$, ($C_1$-$C_6$)alkylene-N($R^9$)$_2$—S-alkyl, —S(O)-alkyl, —S($O_2$)-alkyl, —S($O_2$)N($R^8$)$_2$, —N($R^8$)C(O)$R^5$, ($C_1$-$C_6$)N($R^8$)C(O)$R^5$, $NO_2$, —C(O)alkyl, C($O_2$)$R^8$, C($R^8$)$_2$O$R^8$, C=NO$R^8$ and a cyclic moiety selected from the group consisting of

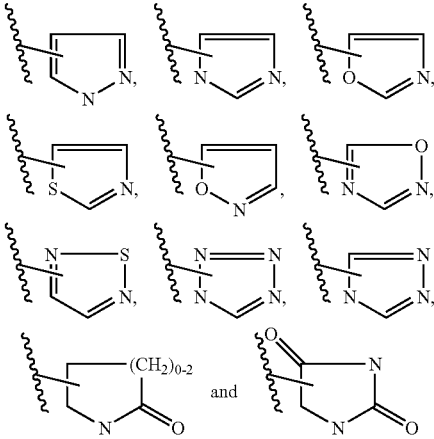

wherein said cyclic moiety, together with $Ar^1$, can optionally form a fused aromatic moiety such as indole, indolone, benzimidazole, benzoxazole, benzothiazole, benzisoxazole, or benztriazole; and further wherein if two $R^7$ groups are adjacent, said adjacent $R^7$ moieties can optionally be joined together to form a methylenedioxy or ethylenedioxy moiety, $Ar^2$ is aryl, heteroaryl, $(R^7)_p$-substituted aryl or $(R^7)_p$-substituted heteroaryl, wherein p is a number from 1 to 3 and when p is more than 1, each $R^7$ can be the same or different and is independently selected from the group consisting of alkyl, cycloalkyl, halo, —CN, alkoxy, —$CF_3$, —$OCF_3$, —C(O)N($R^8$)$_2$, —N($R^9$)$_2$, ($C_1$-$C_6$)alkylene-N($R^9$)$_2$—S-alkyl, —S(O)-alkyl, —S($O_2$)-alkyl, —S($O_2$)N($R^8$)$_2$, —N($R^8$)C(O)$R^5$, ($C_1$-$C_6$)N($R^8$)C(O)$R^5$, $NO_2$, —C(O)alkyl, C($O_2$)$R^8$, C($R^8$)$_2$O$R^8$, C=NO$R^8$ and a cyclic moiety selected from the group consisting of

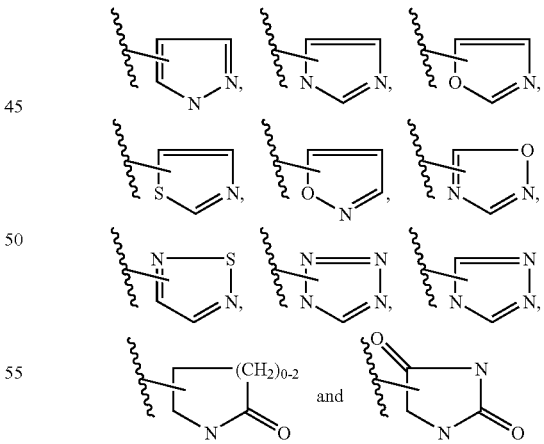

wherein said cyclic moiety, together with $Ar^1$, can optionally form a fused aromatic moiety such as indole, indolone, benzimidazole, benzoxazole, benzothiazole, benzisoxazole, or benztriazole; and further wherein if two $R^7$ groups are adjacent, said adjacent $R^7$ moieties can optionally be joined together to form a methylenedioxy or ethylenedioxy moiety;

X is O, S or N—(CN);

Y is a single bond or alkylene group;

Z is a $C_4$-$C_8$ cycloalkylene or $C_4$-$C_8$ heterocycloalkylene wherein each of said $C_4$-$C_8$ cycloalkylene or $C_4$-$C_8$ heterocycloalkylene group optionally containing one or two double bonds inside the cyclic ring and optionally substituted with 1 to 4 $R^6$ groups on the ring wherein each $R^6$ is independently selected from the group consisting of alkyl, cycloalkyl, —OH, —N($R^9$)$_2$, —$NR^9$COalkyl, alkoxy and —OC(O)-alkyl, with the proviso that when $R^6$ is —OH or —N($R^9$)$_2$, $R^6$ is not attached to a carbon adjacent to a nitrogen and when two $R^6$ groups are —OH, neither $R^6$ is on the same carbon on Z and further that two $R^6$ groups can be optionally joined together so that Z and said two $R^6$ groups together form a bicycloalkylene or bicycloheteroalkylene group containing from 5 to 12 atoms;

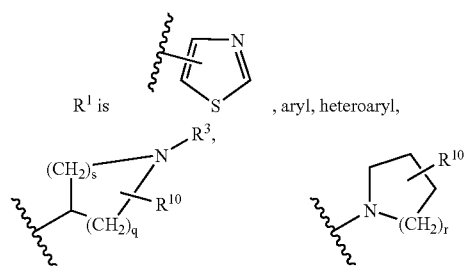

$R^1$ is , aryl, heteroaryl, where s and q independently number 0 to 6, the sum of s and q is 2 to 6 and r numbers 0 to 3;

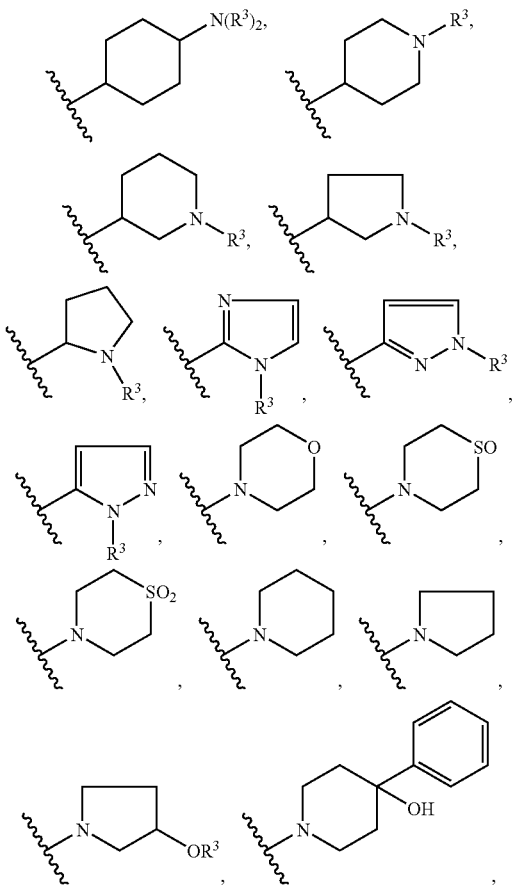

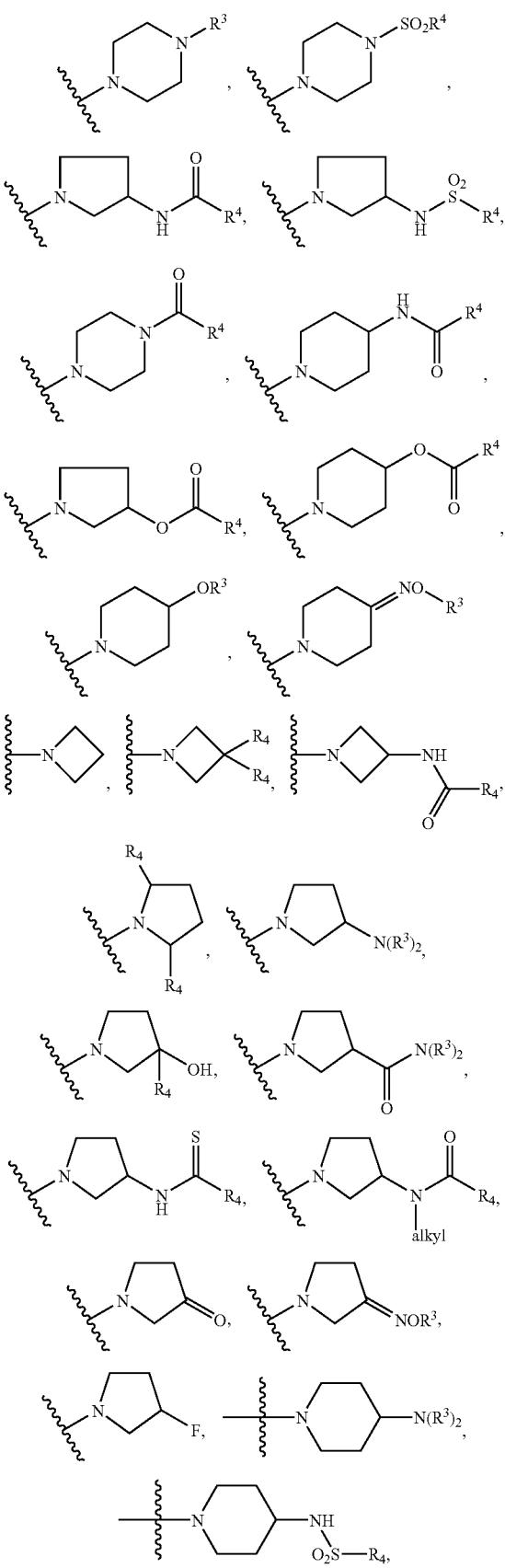

-continued

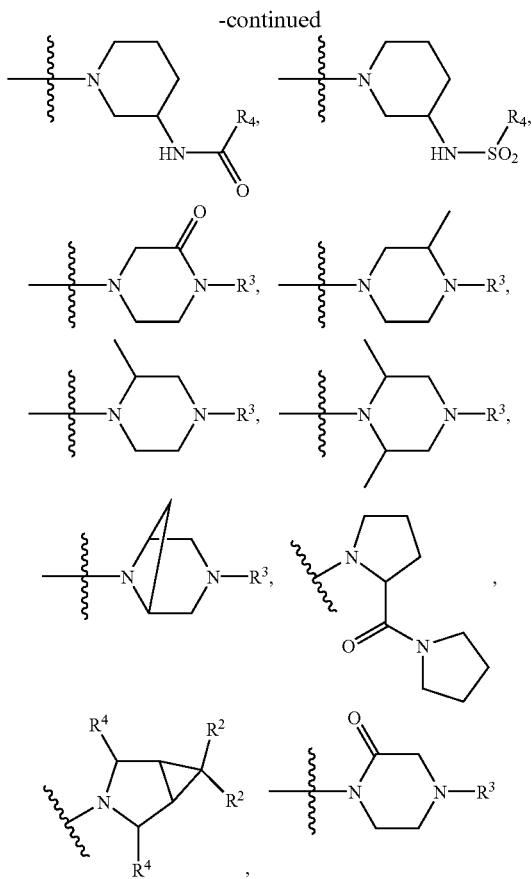

or R$^1$ is
—N(R$^3$)$_2$, —N(H)C(O)alkyleneN(R$^3$)$_2$, —C(O)N(H)alkyleneN(R$^3$)$_2$, —C(O)N(alkyl)alkyleneN(R$^3$)$_2$, -alkyleneC(H)(OH)alkyleneN(R$^3$)$_2$, —N(alkyl)alkyleneN(R$^3$)$_2$, —N(H)alkyleneC(O)R$^5$, —N(alkyl)alkyleneN(alkyl)S(O$_2$)R$^5$ or —N(alkyl)alkyleneC(O)N(R$^3$)$_2$;

R$^2$ is hydrogen or alkyl;

each R$^3$ is independently hydrogen, alkyl, cycloalkyl, cycloalkylalkyl, alkoxyalkylene-, aryl, aralkyl, heteroaryl, heterocyclyl, heteroaralkyl, —S(O$_2$)alkyl, —S(O$_2$)aryl, —S(O$_2$)N(H)alkyl, —S(O$_2$)N(alkyl)$_2$, —S(O$_2$)alkyl, —S(O$_2$)heterocycloalkyl, —C(O)alkyl, —C(O)aryl, —C(O)heteroaryl, —C(O)heterocycloalkyl, —C(O)N(H)alkyl, —C(O)N(alkyl)$_2$, —C(O)N(H)aryl, —C(O)Oalkyl, —C(O)Oaryl or alkylene-C(O)Oalkyl, wherein each of said alkyl, alkylene, alkoxy, aralkyl, aryl, heteroaryl, heteroaralkyl or cycloalkyl group can independently be nonsubstituted, halosubstituted or hydroxysubstituted;

R$^4$ is R$^3$, alkoxy or —N(R$^3$)$_2$, with the proviso that when R$^4$ is attached to a sulfur atom then R$^4$ is not hydrogen;

R$^5$ is hydrogen, —N(R$^3$)$_2$, alkyl, cycloalkyl, cycloalkylalkyl, aryl, aralkyl, heteroaralkyl, alkoxy or alkoxyalkylene-, wherein each of said alkyl, alkylene, alkoxy, aralkyl, aryl, heteroaralkyl or cycloalkyl group can independently be nonsubstituted, halosubstituted or hydroxysubstituted;

R$^8$ is hydrogen, alkyl or cycloalkyl;

R$^9$ is hydrogen, —C(O)alkyl or —S(O$_2$)alkyl.

R$^{10}$ is R$^5$ or halogen;

with the following provisos:

that each R$^3$ of —N(R$^3$)$_2$ can be same or different and is independently selected;

that each R$^8$ and R$^9$ of —C(O)N(R$^8$)$_2$, —N(R$^9$)$_2$ and —S(O$_2$)N(R$^8$)$_2$ can be the same or different and is independently selected; and that in the above chemical formulas, each R$^3$ and R$^4$ can be the same or different and is independently selected.

This invention is also directed to pharmaceutical compositions for the treatment of metabolic disorders such as obesity, and eating disorders such as hyperphagia. In one aspect, this invention is also directed to pharmaceutical compositions for the treatment of obesity which comprise an obesity treating amount of a compound of formula I, or a pharmaceutically acceptable salt or solvate of said compound and a pharmaceutically acceptable carrier.

DETAILED DESCRIPTION

The present invention relates to compounds that are represented by structural formula I, or a pharmaceutically acceptable salt or solvate, wherein the various moieties are as described above.

The compounds of formula I can be administered as racemic mixtures or enantiomerically pure compounds.

A preferred group of compounds are compounds of formula I wherein

Ar$^1$ is aryl, heteroaryl, (R$^7$)$_p$-substituted aryl or (R$^7$)$_p$-substituted heteroaryl, wherein p is a number from 1 to 3 and when p is more than 1, each R$^7$ can be the same or different and is independently selected from the group consisting of alkyl, cycloalkyl, halo, —CN, alkoxy, —CF$_3$, —OCF$_3$, —C(O)N(R$^8$)$_2$, —N(R$^9$)$_2$, (C$_1$-C$_6$)alkylene-N(R$^9$)$_2$—S-alkyl, —S(O)-alkyl, —S(O$_2$)-alkyl, —S(O$_2$)N(R$^8$)$_2$, —N(R$^8$)C(O)R$^5$, (C$_1$-C$_6$)N(R$^8$)C(O)R$^5$, NO$_2$, —C(O)alkyl, C(O$_2$)R$^8$, C(R$^8$)$_2$OR$^8$, C=NOR$^8$ and a cyclic moiety selected from the group consisting of

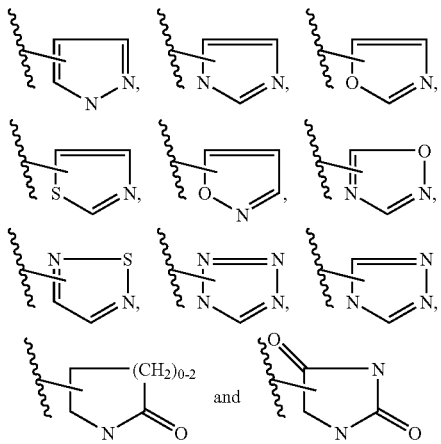

wherein said cyclic moiety, together with Ar$^1$, can optionally form a fused aromatic moiety such as indole, indolone, benzimidazole, benzoxazole, benzothiazole, benzisoxazole, or benztriazole; and further wherein if two R$^7$ groups are adjacent, said adjacent R$^7$ moieties can optionally be joined together to form a methylenedioxy or ethylenedioxy moiety, Ar$^2$ is aryl, heteroaryl, (R$^7$)$_p$-substituted aryl or (R$^7$)$_p$-substituted heteroaryl, wherein p is a number from 1 to 3 and when p is more than 1, each R$^7$ can be the same or different and is independently selected from the group consisting of alkyl, cycloalkyl, halo, —CN, alkoxy, —CF$_3$, —OCF$_3$, —C(O)N(R$^8$)$_2$, —N(R$^9$)$_2$, (C$_1$-C$_6$)alkylene-N(R$^9$)$_2$—S- alkyl, —S(O)-alkyl, —S(O$_2$)-alkyl, —S(O$_2$)N(R$^8$)$_2$, —N(R$^8$)C(O)R$^5$, (C$_1$-C$_6$)N(R$^8$)C(O)R$^5$, NO$_2$, —C(O)alkyl, C(O$_2$)R$^8$, C(R$^8$)$_2$OR$^8$, C=NOR$^8$ and a cyclic moiety selected from the group consisting of

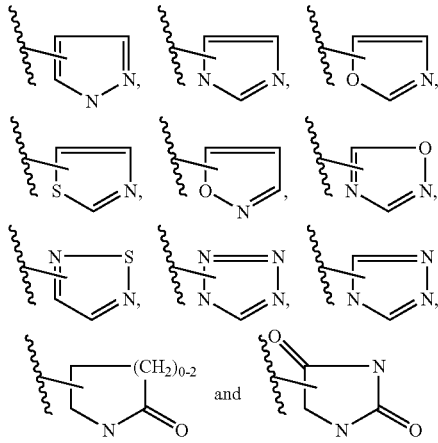

wherein said cyclic moiety, together with Ar$^1$, can optionally form a fused aromatic moiety such as indole, indolone, benzimidazole, benzoxazole, benzothiazole, benzisoxazole, or benztriazole; and further wherein if two R$^7$ groups are adjacent, said adjacent R$^7$ moieties can optionally be joined together to form a methylenedioxy or ethylenedioxy moiety;

X is O;

Y is a single bond or —(C$_1$-C$_4$)alkylene- group;

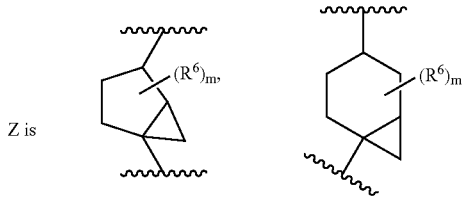

Z is or a C$_4$-C$_8$ cycloalkylene or C$_4$-C$_8$ heterocycloalkylene wherein each of said C$_4$-C$_8$ cycloalkylene or C$_4$-C$_8$ heterocycloalkylene group optionally containing one or two double bonds inside the cyclic ring and optionally substituted with 1 to 4 R$^6$ groups on the ring wherein each R$^6$ is independently selected from the group consisting of alkyl, cycloalkyl, —OH, alkoxy and —OC(O)-alkyl, with the proviso that when R$^6$ is —OH, R$^6$ is not attached to a carbon adjacent to a nitrogen and when two R$^6$ groups are —OH, neither R$^6$ is on the same carbon on Z and further that two R$^6$ groups can be optionally joined together so that Z and said two R$^6$ groups together form a bicycloalkylene or bicycloheteroalkylene group containing from 5 to 12 atoms;

R$^1$ is —NHC(O)(C$_2$-C$_3$)alkyleneN(R$^3$)$_2$, —C(O)NH(C$_2$-C$_3$)alkyleneN(R$^3$)$_2$, —C(O)N(CH$_3$)(C$_2$-C$_3$)alkyleneN (R$^3$)$_2$, -alkyleneC(H)(OH)(C$_1$-C$_2$)alkyleneN(R$^3$)$_2$, —N(CH$_3$)(C$_2$-C$_3$)alkyleneN(R$^3$)$_2$, —N(H)(C$_2$-C$_3$)alkyleneC(O)R$^5$, —N(CH$_3$)(C$_2$-C$_3$)alkyleneN(CH$_3$)S(O$_2$)R$^5$ or —N(CH$_3$)(C$_2$-C$_3$)alkyleneC(O)N(R$^3$)$_2$, wherein each R$^3$ can be the same or different and is independently selected;

R$^2$ is hydrogen or —(C$_1$-C$_6$)alkyl;

each R$^3$ is independently hydrogen, alkyl, cycloalkyl, cycloalkylalkyl, alkoxyalkylene-, aryl, aralkyl, heteroaryl, heterocyclyl, heteroaralkyl, —S(O$_2$)alkyl, —S(O$_2$)aryl, —S(O$_2$)N(H)alkyl, —S(O$_2$)N(alkyl)$_2$, —S(O$_2$)alkyl, —S(O$_2$)heterocycloalkyl, —C(O)alkyl, —C(O)aryl, —C(O)heteroaryl, —C(O)heterocycloalkyl, —C(O)N(H) alkyl, —C(O)N(alkyl)$_2$, —C(O)N(H)aryl, —C(O)Oalkyl, —C(O)Oaryl or alkylene-C(O)Oalkyl, wherein each of said alkyl, alkylene, alkoxy, aralkyl, aryl, heteroaryl, heteroaralkyl or cycloalkyl group can independently be nonsubstituted, halosubstituted or hydroxysubstituted;

R$^4$ is R$^3$, (C$_1$-C$_6$)alkoxy or —N(R$^3$)$_2$, with the proviso that when R$^4$ is attached to a sulfur atom then R$^4$ is not hydrogen;

R$^5$ is hydrogen, —N(R$^3$)$_2$, —(C$_1$-C$_6$)alkyl, —(C$_3$-C$_7$) cycloalkyl, —(C$_3$-C$_7$)cycloalkyl(C$_1$-C$_6$)alkyl, aryl, aralkyl, heteroaralkyl, (C$_1$-C$_6$)alkoxy or (C$_1$-C$_6$)alkoxy(C$_1$-C$_6$)alkylene-, wherein each of said alkyl, alkylene, alkoxy, aralkyl, aryl, heteroaralkyl or cycloalkyl group can independently be nonsubstituted, halosubstituted or hydroxysubstituted;

R$^6$ is —(C$_1$-C$_6$)alkyl, (C$_3$-C$_6$)cycloalkyl, —OH, —O—(C$_1$-C$_6$)alkyl, —OC(O)—(C$_1$-C$_6$alkyl), with the proviso that when R$^6$ is —OH, R$^6$ is not attached to a carbon adjacent to a nitrogen, and when m is 2 and both R$^6$ are —OH, neither R$^6$ is on the same carbon on Z;

R$^8$ is hydrogen, —(C$_1$-C$_6$)alkyl or —(C$_3$-C$_7$)cycloalkyl; with the following provisos that each R$^3$ of —N(R$^3$)$_2$ can be same or different and is independently selected;

that each R$^8$ and R$^9$ of —C(O)N(R$^8$)$_2$, —N(R$^9$)$_2$ and —S(O$_2$)N(R$^8$)$_2$ can be the same or different and is independently selected; and that in the above chemical formulas, each R$^3$ and R$^4$ can be the same or different and is independently selected.

A further preferred group of compounds of formula I are those in which

Ar$^1$ and Ar$^2$ are the same or different and are independently selected from phenyl, pyridyl, (R$^7$)$_p$-substituted aryl or (R$^7$)$_p$-substituted heteroaryl, wherein p is a number from 1 to 3 and when p is more than 1, each R$^7$ can be the same or different and is independently selected from the group consisting of alkyl, cycloalkyl, halo, —CN, alkoxy, —CF$_3$, —OCF$_3$, —C(O)N(R$^8$)$_2$, —N(R$^9$)$_2$, (C$_1$-C$_6$)alkylene-N (R$^9$)$_2$—S-alkyl, —S(O)- alkyl, —S(O$_2$)-alkyl, —S(O$_2$)N (R$^8$)$_2$, —N(R$^8$)C(O)R$^5$, (C$_1$-C$_6$)N(R$^3$)C(O)R$^5$, NO$_2$, —C(O)alkyl, C(O$_2$)R$^8$, C(R$^8$)$_2$OR$^8$ or C=NOR$^8$;

X is O;

Y is a single bond or —CH$_2$—, —CH$_2$CH$_2$—, —CH$_2$CH$_2$CH$_2$— or —CH$_2$CH$_2$CH$_2$CH$_2$—;

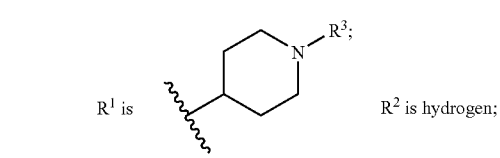

R$^1$ is    R$^2$ is hydrogen;

and

R$^3$ is hydrogen, —(C$_1$-C$_6$)alkyl, —(C$_3$-C$_7$)cycloalkylmethyl, (C$_1$-C$_6$)alkoxy(C$_1$-C$_6$)alkylene— or SO$_2$alkyl.

Another group of preferred compounds are compounds of formula I wherein

Ar$^1$ and Ar$^2$ are the same or different and are independently selected from phenyl, pyridyl; (R$^7$)$_p$-substituted aryl or (R$^7$)$_p$-substituted heteroaryl, wherein p is a number from 1 to 3 and when p is more than 1, each R$^7$ can be the same or different and is independently selected from the group consisting of alkyl, cycloalkyl, halo, —CN, alkoxy, —CF$_3$, —OCF$_3$, —C(O)N(R$^8$)$_2$, —N(R$^9$)$_2$, (C$_1$-C$_6$)alkylene-N(R$^9$)$_2$—S-alkyl, —S(O)- alkyl, —S(O$_2$)-alkyl, —S(O$_2$)N(R$^8$)$_2$, —N(R$^8$)C(O)R$^5$, (C$_1$-C$_6$)N(R$^8$)C(O)R$^5$, NO$_2$, —C(O)alkyl, C(O$_2$)R$^8$, C(R$^8$)$_2$OR$^8$ or C=NOR$^8$;

X is O;

Y is —CH$_2$CH$_2$—, —CH$_2$CH$_2$CH$_2$— or —CH$_2$CH$_2$CH$_2$CH$_2$—;

R$^1$ is —N(R$^3$)$_2$ or —C(O)NH(C$_2$-C$_3$)alkyleneN(R$^3$)$_2$; and

R$^3$ is hydrogen, —(C$_1$-C$_6$)alkyl, -ar(C$_1$-C$_6$)alkyl, heterocyclyl, heteroaryl, heteroarylalkyl, halo-substituted —(C$_1$-C$_6$)alkyl, hydroxy-substituted —(C$_1$-C$_6$)alkyl, —(C$_3$-C$_7$)cycloalkyl, wherein each R$^3$ can be same or different and is independently selected.

Another group of preferred compounds are compounds of formula I wherein

Ar$^1$ and Ar$^2$ are independently phenyl, pyridyl, R$^7$-substituted phenyl or R$^7$-substituted pyridyl, wherein said Ar$^1$ and Ar$^2$ are the same or different and is independently selected, and R$^7$ numbers 1 to 3 which can be the same or different, each being independently selected from the group consisting of alkyl, cycloalkyl, halo, —CN, alkoxy, —CF$_3$, —OCF$_3$, —C(O)N(R$^8$)$_2$, —N(R$^9$)$_2$, —S-alkyl, —S(O)-alkyl, —S(O$_2$)-alkyl, —S(O$_2$)N(R$^8$)$_2$, —N(R$^8$)C(O)R$^5$, —NO$_2$,

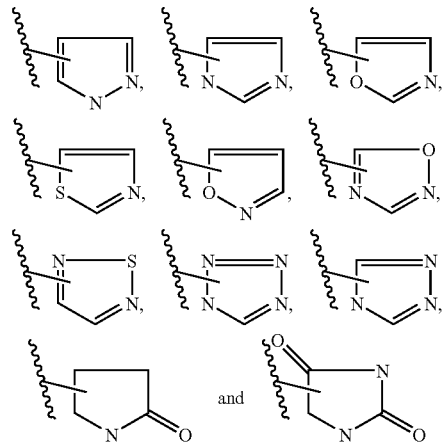

wherein each R$^8$ and R$^9$ can be the same or different and is independently selected, or two adjacent R$^7$ groups can be joined together to form a methylenedioxy or ethylenedioxy group;

X is O;

Y is —CH$_2$CH$_2$—, —CH$_2$CH$_2$CH$_2$— or —CH$_2$CH$_2$CH$_2$CH$_2$—;

R$^1$ is

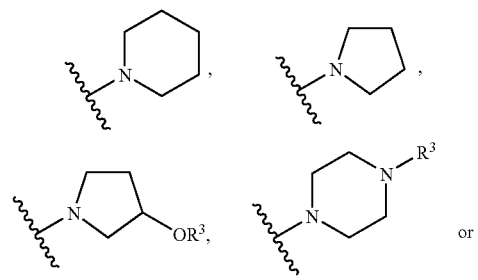

-continued

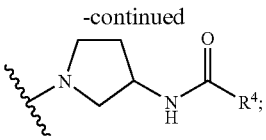

R$^3$ is hydrogen, —(C$_1$-C$_6$)alkyl, —(C$_3$-C$_7$)cycloalkyl, —(C$_3$-C$_7$)cycloalkyl(C$_1$-C$_6$)alkyl, (C$_1$-C$_6$)alkoxy(C$_1$-C$_6$)alkylene-, aryl, aralkyl, heterocyclyl, heteroaryl or heteroaralkyl, wherein each of said alkyl, alkylene, alkoxy, aralkyl, aryl, heteroaryl, heteroaralkyl or cycloalkyl group can independently be nonsubstituted, halosubstituted or hydroxysubstituted;

R$^4$ is R$^3$, (C$_1$-C$_6$)alkoxy or —N(R$^3$)$_2$ wherein each R$^3$ can be same or different and is independently selected, with the proviso that when R$^4$ is attached to a sulfur atom then R$^4$ is not hydrogen;

R$^5$ is hydrogen, —(C$_1$-C$_6$)alkyl, —(C$_3$-C$_7$)cycloalkyl, —(C$_3$-C$_7$)cycloalkyl(C$_1$-C$_6$)alkyl, aryl, aralkyl, heteroaralkyl, (C$_1$-C$_6$)alkoxy or (C$_1$-C$_6$)alkoxy(C$_1$-C$_6$)alkylene-, wherein each of said alkyl, alkylene, alkoxy, aralkyl, aryl, heteroaralkyl or cycloalkyl group can independently be nonsubstituted, halosubstituted or hydroxysubstituted; and R$^8$ is hydrogen, —(C$_1$-C$_6$)alkyl or —(C$_3$-C$_7$)cycloalkyl.

Another group of preferred compounds are compounds of formula I wherein wherein Ar$^1$ is R$^7$-substituted phenyl and said R$^7$ is one group positioned at the 3-position of said substituted phenyl with respect to the linking point to Z.

Another group of preferred compounds are compounds of formula I wherein R$^7$ is —CN, —OCF$_3$, chloro, —C(O)N(R$^8$)$_2$, —N(R$^9$)$_2$, or —N(R$^8$)C(O)R$^5$.

Another group of preferred compounds are compounds of formula I wherein Ar$^1$ is pyridyl and Ar$^2$ is halo-substituted phenyl or (CF$_3$)-substituted phenyl.

Another group of preferred compounds are compounds of formula I wherein Ar$^1$ is pyridyl and Ar$^2$ is halo-substituted pyridyl or —CF$_3$-substituted pyridyl.

A set of preferred compounds are listed below in Tables 1, 1a and 1b.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "alkylamino" etc.

As used above, and throughout the specification, the following terms, unless otherwise indicated, shall be understood to have the following meanings:

"Patient" includes both human and other animals.

"Mammal" means humans and other mammalian animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, -cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. The term "substituted alkenyl" means that the alkenyl group may be substituted by one or more substituents which may be the same or different, each substituent being independently selected from the group consisting of halo, alkyl, aryl, -cycloalkyl, cyano, and alkoxy. Non-limiting examples of suitable alkenyl groups include ethenyl, propenyl, n-butenyl, and 3-methylbut-2-enyl.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means an alkynyl group having about 2 to about 6 carbon atoms in the chain, which may be straight or branched. Non-limiting examples of suitable alkynyl groups include ethynyl, propynyl and 2-butynyl. The term "substituted alkynyl" means that the alkynyl group may be substituted by one or more substituents which may be the same or different, each substituent being independently selected from the group consisting of alkyl, aryl and -cycloalkyl.

"Alkylene" means an alkanedioyl group commonly having free valencies on two carbon atoms. Non-limiting examples include methylene, ethylene, propylene and the like. The term "substituted alkylene" means that the alkylene group may be substituted by one or more substituents which may be the same or different, each substituent being independently selected from the group consisting of halo, alkyl, aryl, -cycloalkyl, cyano, hydroxy, alkoxy, alkylthio, amino, —NH(alkyl), —NH(cycloalkyl), —N(alkyl)$_2$, carboxy and —C(O)O-alkyl.

"Aryl" means an aromatic monocyclic or multicyclic ring system comprising about 6 to about 14 carbon atoms, preferably about 6 to about 10 carbon atoms. The aryl group can be unsubstituted or substituted on the ring with one or more substituents which may be the same or different, each being independently selected from the group consisting of alkyl, aryl, —OCF$_3$, —OCOalkyl, —OCOaryl, —CF$_3$, heteroaryl, aralkyl, alkylaryl, heteroaralkyl, alkylheteroaryl, hydroxy, hydroxyalkyl, alkoxy, aryloxy, aralkoxy, acyl, aroyl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, -cycloalkyl and heterocyclyl. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Arylene" means a bivalent group derived from an aromatic hydrocarbon by removal of a hydrogen atom from two ring carbon atoms. Non-limiting examples include phenylene and the like.

"Alkylenedioxy" means a combination of one or more carbon atoms and one or more oxygen atoms such as the following non-limiting examples that include methylenedioxy, ethylenedioxy, and the like.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, -cycloalkyl, cycloalkenyl and heterocyclyl. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, imidazolyl, and the like.

"Heteroarylene" means a bivalent group derived from a heterocyclic aromatic compound by removal of a hydrogen atom from two ring carbon atoms such as, for example, the bivalent group derived from pyridine, pyrrole and the like.

"Aralkyl" means an aryl-alkyl- group in which the aryl and alkyl are as previously described. Preferred aralkyls comprise a lower alkyl group. Non-limiting examples of suitable aralkyl groups include benzyl, 2-phenethyl and a naphthlenylmethyl. The bond to the parent moiety is through the alkyl. The term "substituted aralkyl" means that the aralkyl group may be substituted by one or more substituents which may be the same or different, each substituent being independently selected from the group consisting of halo, alkyl, aryl, -cycloalkyl, cyano, hydroxy, alkoxy, alkylthio, amino, —NH(alkyl), —NH(cycloalkyl), —N(alkyl)$_2$, carboxy and —C(O)O-alkyl.

"Alkylaryl" means an alkyl-aryl- group in which the alkyl and aryl are as previously described. Preferred alkylaryls comprise a lower alkyl group. Non-limiting example of a suitable alkylaryl groups is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halo" means fluoro, chloro, bromo or iodo groups. Preferred are fluoro, chloro or bromo, and more preferred are fluoro and chloro.

"Halogen" means fluorine, chlorine, bromine or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclyl" or "heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, tetrahydrothiophenyl, morpholinyl and the like.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl. The "heteroaralkyl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, -cycloalkyl, cycloalkenyl and heterocyclyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Alkoxyalkyl" means an alkoxy-alkyl- group in which alkyl and alkoxy are as previously defined. Non-limiting examples of suitable alkoxyalkyl groups include methoxymethyl, ethoxymethyl, methoxyethyl and ethoxyethyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen. The term "substituted alkoxy" means that the alkyl portion of the alkoxy group may be substituted by one or more substituents which may be the same or different, each substituent being independently selected from the group consisting of halo, alkyl, aryl, -cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylamino" means an —NH$_2$ or —NH$_3^+$ group in which one or more of the hydrogen atoms on the nitrogen is replaced by an alkyl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkoxy group defined earlier linked to an adjacent moiety through a carbonyl. Non-limiting examples of alkoxycarbonyl groups include —C(O)—CH$_3$, —C(O)—CH$_2$CH$_3$ and the like.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S(O$_2$)— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

Solvates of the compounds of the invention are also contemplated herein. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

"Effective amount" or "therapeutically effective amount" is meant to describe an amount of compound of the present invention effective to treat a mammal (e.g., human) having a disease or condition mediated by MCH, and thus producing the desired therapeutic effect.

The compound of formula I forms salts which are also within the scope of this invention. Reference to a compound of formula I, herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfoniates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers or may be admixed, for example, as racemates or with all other, or other selected, stereoisomers. The chiral centers of the present invention can have the S or R configuration as defined by the IUPAC 1974 Recommendations. The use of the terms "salt", "solvate" and the like, is intended to equally apply to the salt and solvate of enantiomers, stereoisomers, rotamers, tautomers or racemates of the inventive compounds.

When any variable (e.g., aryl, heterocycle, $R^2$, etc.) occurs more than one time in any constituent or in formula I, its definition on each occurrence is independent of its definition at every other occurrence. Also, combinations of substituents and/or variables are permissible only if such combinations result in stable compounds.

Compounds of formula I can be highly selective, high affinity Melanin Concentrating Hormone (MCH) receptor antagonists useful for the treatment of obesity.

Another aspect of this invention is a method of treating a mammal (e.g., human) having a disease or condition mediated by MCH by administering a therapeutically effective amount of at least one compound of formula I, or a pharmaceutically acceptable salt or solvate of said compound to the mammal.

A preferred dosage is about 0.001 to 100 mg/kg of body weight/day of the compound of formula I. An especially preferred dosage is about 0.01 to 25 mg/kg of body weight/day of a compound of formula I, or a pharmaceutically acceptable salt or solvate of said compound.

Another aspect of this invention is directed to a method of treating obesity comprising administering to a mammal in need of such treatment a therapeutically effective amount of at least one compound of formula I, or a pharmaceutically acceptable salt or solvate of said compound.

Another aspect of this invention is directed to a method for treating eating and metabolic disorders such as bulimia and anorexia comprising administering to a mammal a therapeutically effective amount of at least one compound of formula I, or a pharmaceutically acceptable salt or solvate of said compound.

Another aspect of this invention is directed to a method for treating hyperlipidemia comprising administering to a mammal a therapeutically effective amount of at least one compound of formula I, or a pharmaceutically acceptable salt or solvate of said compound.

Another aspect of this invention is directed to a method for treating cellulite and fat accumulation comprising administering to a mammal a therapeutically effective amount of at least one compound of formula I, or a pharmaceutically acceptable salt or solvate of said compound.

Another aspect of this invention is directed to a method for treating type II diabetes comprising administering to a mammal a therapeutically effective amount of at least one compound of formula I, or a pharmaceutically acceptable salt or solvate of said compound.

In addition to the "direct" effect of the compounds of this invention on the MCH subtype, there are diseases and conditions that will benefit from the weight loss such as insulin resistance, impaired glucose tolerance, Type II Diabetes, hypertension, hyperlipidemia, cardiovascular disease, gall stones, certain cancers, and sleep apnea.

Another aspect of this invention is directed to a method for treating mental disorders such as major depression, manic depression, anxiety, schizophrenia and sleep disorders, comprising administering to a mammal a therapeutically effective amount of at least one compound of formula I, or a pharmaceutically acceptable salt or solvate of said compound.

This invention is also directed to pharmaceutical compositions which comprise at least one compound of formula I, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of formula I, or a pharmaceutically acceptable salt or solvate of said compound and at least one pharmaceutically acceptable carrier.

Compounds of formula I, can be produced by processes known to those skilled in the art using either solution phase or solid phase synthesis as shown in the following reaction schemes, in the preparations and examples below.

Compounds of this invention of type 1a and 1b can be prepared as shown below in Scheme 1.

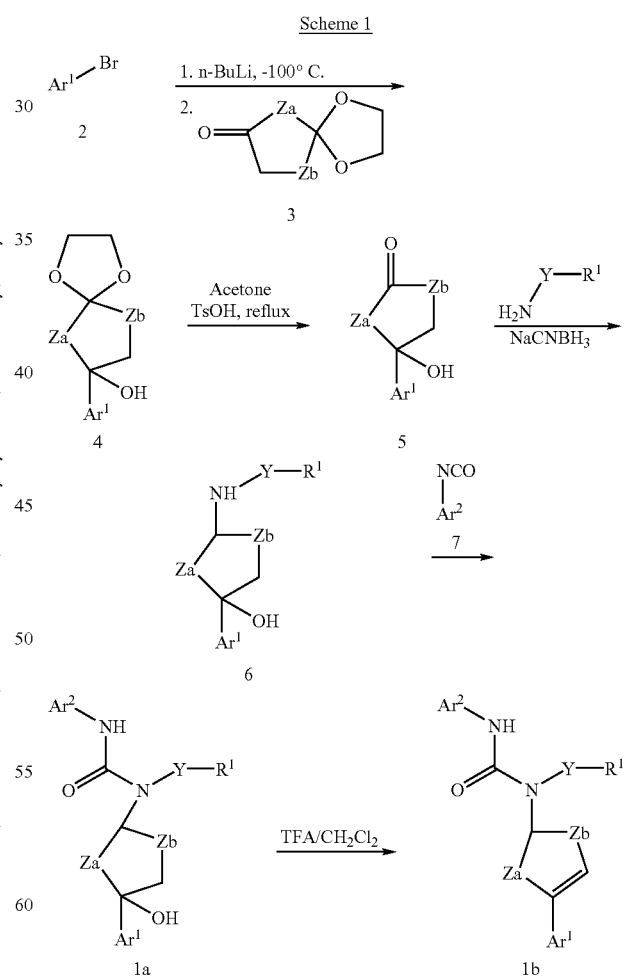

Scheme 1

An aryl bromide 2 is treated with an organolithium reagent such as n-butyllithium in a solvent such as THF or ether at a temperature from −100° C. to 0° C. followed by reaction with a dione monoketal 3, where Za and Zb together with the carbons to which they are attached form a cycloalkyl group Z as previously defined. The ketal of the resulting diol 4 is removed under acidic conditions and the ketone is subjected to reductive amination followed by urea formation to give compounds of type 1a. These can be converted to compounds of type 1b by treatment with strong acid.

Compounds of type 1c can be prepared as shown in Scheme 2:

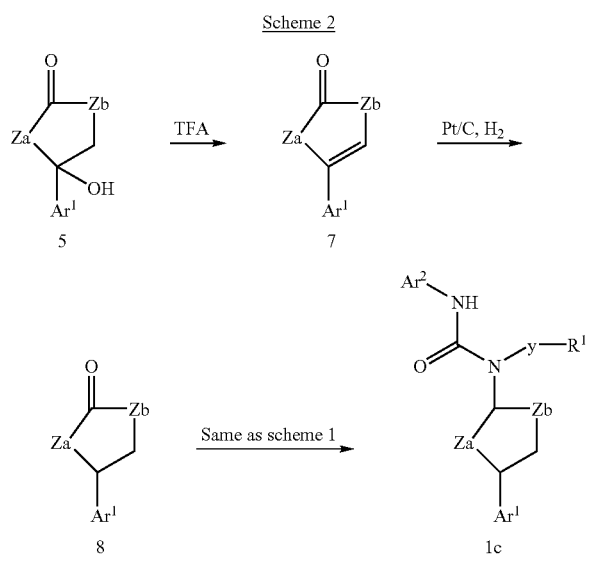

Intermediate 5 from Scheme 2 is treated with strong acid to give olefin 7. This is reduced using hydrogen and a suitable catalyst such as platinum on carbon to give compound 8. Using conditions analogous to those shown for compound 5 in Scheme 1, compound 8 is transformed to compounds of type 1c.

Compounds of type 1d can be prepared as shown in Scheme 3:

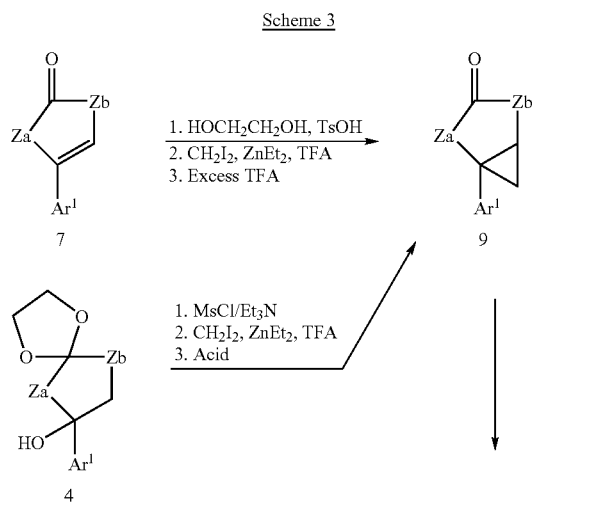

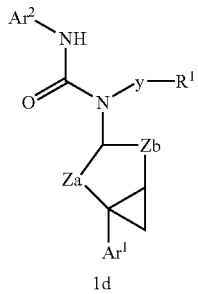

Intermediate 7 from Scheme 2 is protected as its ketal under standard conditions. The resulting olefin is cyclopropanated under known conditions, such as by treatment with methylene diiodide and diethylzinc in the presence of acid such as TFA. After work-up, the crude product is treated with a strong acid such as TFA to give ketone 9. Alternatively, intermediate 4 from Scheme 1 can dehydrated, such as with methanesulfonyl chloride in the presence of triethylamine, and then converted to ketone 9 in a manner similar to 7. The ketone is converted to products of type 1d using the methods outlined in Scheme 1.

Compounds of this invention of type 1b can also be prepared as shown below in Scheme 4:

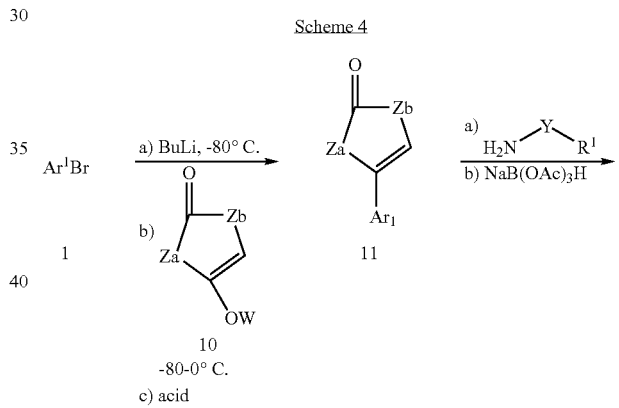

An aryl bromide 1 is treated with an organolithium reagent such as n-butyllithium in a solvent such as THF or diethyl ether at −80° C. followed by reaction with an enone 10, where Za and Zb with the carbons to which they are attached constitute a Z group as previously defined and W is any alkyl group. Quenching with a solution of acid such as hydrochloric acid provides enone 11. Reductive amination and treatment with an isocyanate under standard conditions provides compounds of type 1b. The starting aryl bromide 1 and enone 10 are either commercially available or are prepared by well-known procedures.

Compounds of this invention of type 1d can also be prepared as shown below in Scheme 5:

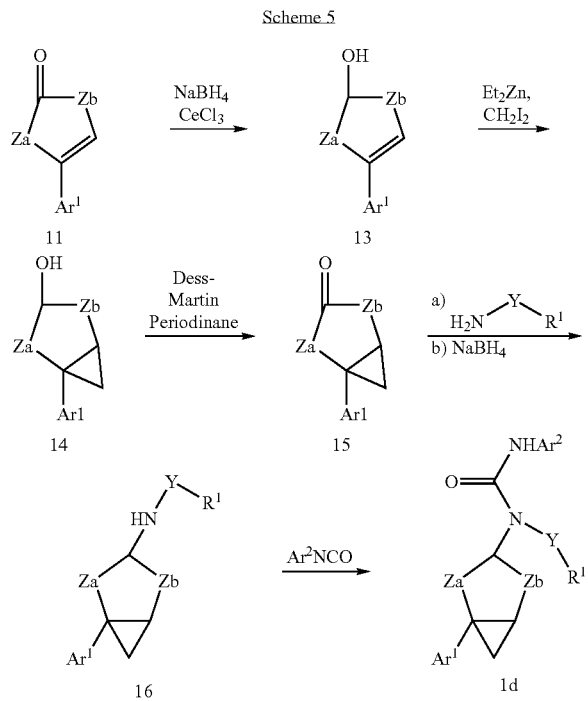

Enone 11 is reduced to the allylic alcohol 13 with a reducing agent such as sodium borohydride. Cyclopropanation of 13 occurs upon treatment with $Et_2Zn$ and $CH_2I_2$ to afford cyclopropyl alcohol 14. Oxidation proceeds under standard conditions, such as by treatment with Dess-Martin periodinane to give ketone 15. Reductive amination and treatment with an isocyanate under standard conditions provides compounds of type 1d.

Still another method of preparation of compounds of type 1d proceeds according to Scheme 6.

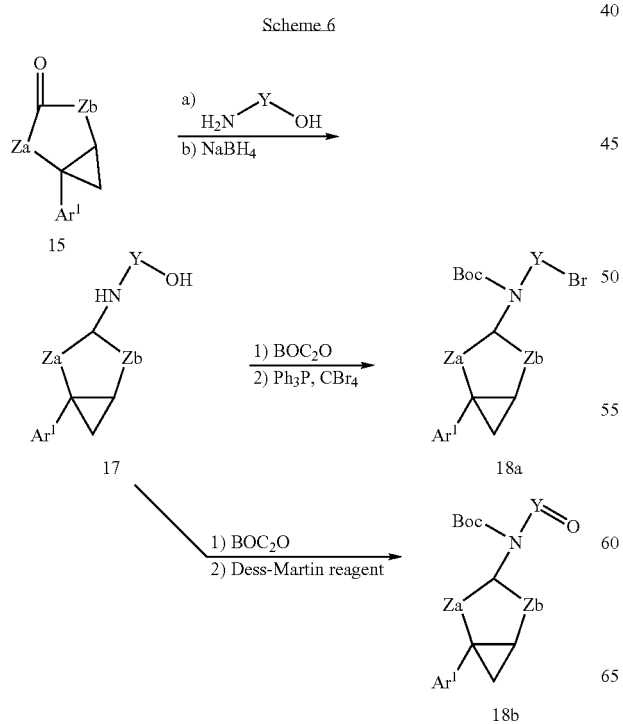

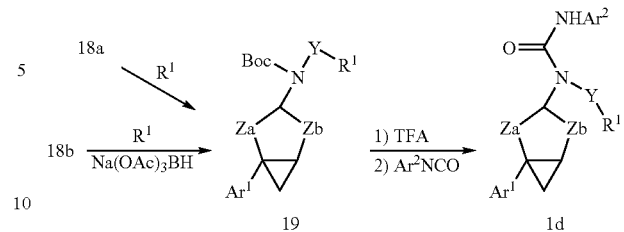

Ketone 15 undergoes reductive amination to provide amino-alcohol 17. The basic nitrogen of 17 is protected using standard methods, such as carbamate formation. The hydroxyl group of 17 can be activated using a variety of methods, such conversion to a bromide 18a or by oxidation to aldehyde or ketone 18b. Treatment of 18a with an amine (herein defined as $R^1$) or 18b with an amine in the presence of a reducing agent such as sodium triacetoxyborohydride gives 19. Deprotection, such as by acid removal of the carbamate, and treatment of the resultant amine with an isocyanate provides compounds of type 1d.

Compounds of type 1e are prepared according to Scheme 7:

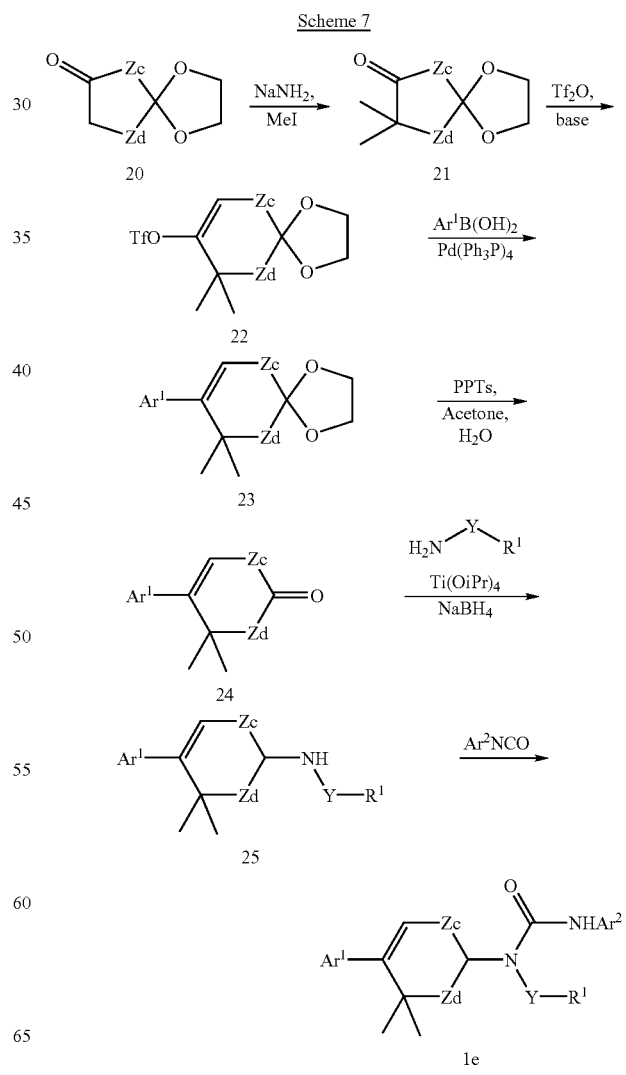

A ketone 20, where Zc and Zd together with attached carbons and the C=O group form a ring which constitute a Z group as previously defined, is treated with an base such as sodamide in a solvent such as THF, followed by reaction with an alkyl halide such as methyl iodide. The resultant ketone 21 is then treated with a base and a sulfonic anhydride, and the enol triflate 22 is coupled to an aryl boronic acid with a catalyst such as Pd(Ph$_3$P)$_4$ to give 23. The ketal is removed under acidic conditions and the resultant ketone is subjected to reductive amination followed by urea formation as described earlier to provide compounds of type 1e.

A method of preparation of compounds of type 1f proceeds according to Scheme 8:

Scheme 8

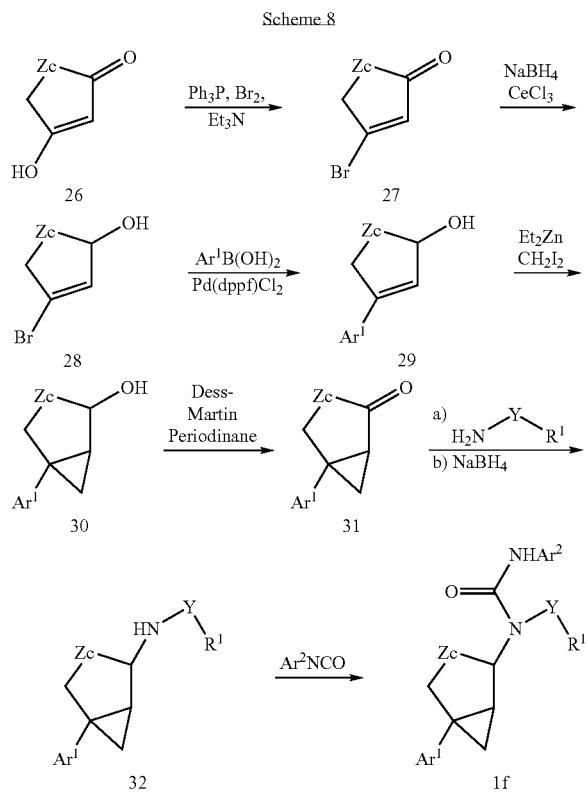

Enol ether 26, where Zc is as previously defined, is brominated to provide vinyl bromide 27. Enone 27 is reduced to the allylic alcohol 28 with a reducing agent such as sodium borohydride. Cross-coupling of 28 with a boronic acid provides arylated enol 29. Cyclopropanation of 29 occurs upon treatment with Et$_2$Zn and CH$_2$I$_2$ to afford cyclopropyl alcohol 30. Oxidation proceeds under standard conditions, such as by treatment with Dess-Martin periodinane to give ketone 31. Reductive amination and treatment with an isocyanate under standard conditions provides compounds of type 1f.

Still another method of preparation of compounds of type 1d proceeds according to Scheme 9.

Scheme 9

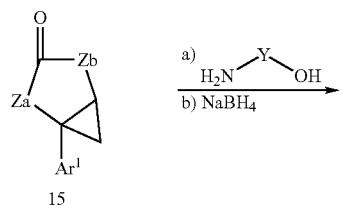

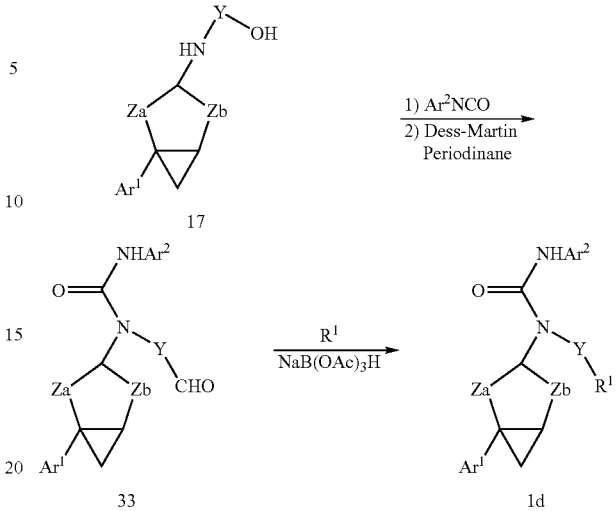

Ketone 15, where Za and Zb are as previously defined, undergoes reductive amination to provide amino-alcohol 17. Treatment of the resultant amine with an isocyanate followed by oxidation of the hydroxyl with a suitable oxidant affords aldehyde 33. Reductive amination of 33 with an amine (herein defined as R$^1$) provides compounds of type 1d.

Compounds of type 1g can be prepared according to

Scheme 10

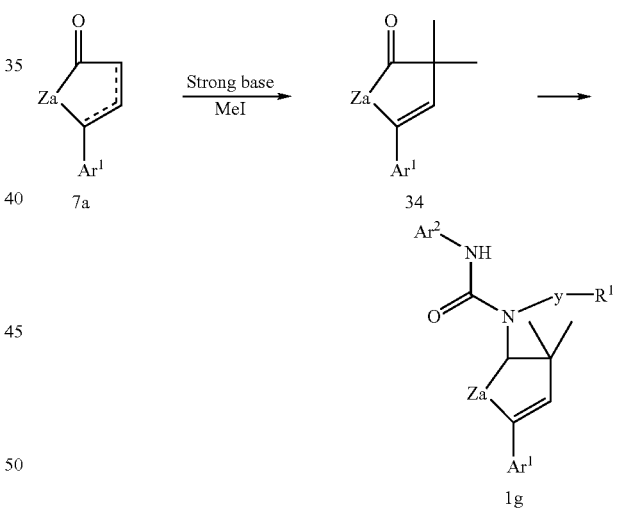

Enone 7a, prepared as described in Scheme 2, is treated with a strong base such as sodium hydride, optionally in the presence of a silylating agent such as trimethylsilyl chloride, followed by treatment with an alkylating agent such as methyl iodide to give, is after purification, compound 34. This can be converted to compound 1g by methods analogous to those described above.

In some cases the procedures described in Scheme 1-Scheme 10 may optionally be carried out in library or parallel synthesis format using resin bound reagents either as reactant or to aid in purification, such as for instance, resin-bound isocyanate to scavenge excess amines or trisamine resin to scavange excess isocyanate.

In some cases, one compound of this invention can be converted to another compound of this invention by well-known functional group transformations. For instance, an $R^1$ group of this invention can be converted to another $R^1$ group of this invention using standard methods known by those skilled in the art, including for instance alkylation, reductive alkylation, acylation, sulfonylation, or hydrolysis reactions. In further example, compounds wherein $R^7$ is a sulfide can be oxidized to the corresponding sulfoxide and sulfone and compounds where $R^7$ is a nitrile can be converted to, among others, the analogous imidazole, oxazole, tetrazole, aldehyde, carboxylic acid, carboxamide or methylamine derivatives. Other possible transformations of one compound of this invention to another will be apparent to those skilled in the art.

Yet another aspect of this invention are combinations of at least one compound of formula I, or a pharmaceutically acceptable salt or solvate of said compound and at least one compound from the compounds as illustrated below.

Accordingly, another aspect of this invention is a method for treating obesity comprising administering to a mammal (e.g., a female or male human)

a. an amount of a first compound, said first compound being a compound of formula I, or a pharmaceutically acceptable salt or solvate of said compound; and b. an amount of a second compound, said second compound being an antiobesity and/or anorectic agent such as a $\beta_3$ agonist, a thyromimetic agent, an anoretic agent, or an NPY antagonist wherein the amounts of the first and second compounds result in a therapeutic effect.

This invention is also directed to a pharmaceutical combination composition comprising: a therapeutically effective amount of a composition comprising at least one first compound, said first compound being a compound of formula I, or a pharmaceutically acceptable salt or solvate of said compound a second compound, said second compound being an antiobesity and/or anorectic agent such as a $\beta_3$ agonist, a thyromimetic agent, an anoretic, or an NPY antagonist; and/or optionally a pharmaceutical carrier, vehicle or diluent.

Another aspect of this invention is a kit comprising:

a. an amount of a compound of formula I, or a pharmaceutically acceptable salt or solvate of said compound and a pharmaceutically acceptable carrier, vehicle or diluent in a first unit dosage form;

b. an amount of an antiobesity and/or anorectic agent such as a $\beta_3$ agonist, a thyromimetic agent, an anoretic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method of treating diabetes comprising administering to a mammal (e.g., a female or male human)

a. an amount of a first compound, said first compound being a compound of formula I, or a pharmaceutically acceptable salt or solvate of said compound; and, b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of formula I, or a pharmaceutically acceptable salt or solvate of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, mefformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a compound of formula I, or a pharmaceutically acceptable salt or solvate of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, mefformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

This invention is also directed to pharmaceutical compositions for the treatment of metabolic disorders such as obesity, and eating disorders such as hyperphagia.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences,* 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents and reagents may be referred to by their abbreviations in parenthesis:
Thin layer chromatography (TLC);
ethyl acetate (AcOEt or EtOAc);
sodium triacetoxyborohydride (NaBH(OAc)$_3$));
di-t-butyl carbonate (BOC$_2$O);
trifluoroacetate (TFA);
ammonia chloride (NH$_4$Cl);
titanium tetraisoproposice (Ti(O-iPr)$_4$;
N,N'-diisopropylethylamine (iPr$_2$NEt);
triethylamine (Et$_3$N or TEA);
butoxycarbonyl (n-Boc or Boc);
nuclear magnetic resonance spectroscopy (H NMR);
liquid chromatography mass spectrometry (LCMS);
high resolution mass spectrometry (HRMS);
hexane (hex);
is milliliters (mL);
millimoles (mmol);
microliters (μl);
grams (g);
milligrams (mg);
room temperature (ambient) about 25° C. (rt).

EXAMPLES

The following examples illustrate the preparation of some of the compounds of the invention and are not to be construed as limiting-the scope of the invention disclosed herein.

Method 1

Example 1

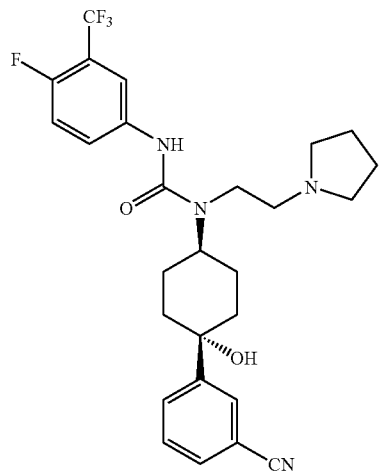

Step 1

3-bromobenzonitrile (20 g, 0.11 mole) was dissolved in 500 ml dry THF and the solution was cooled to −100° C. n-Butyllithium (1.6 M in hexane, 68 ml, 0.11 mole) was added over one hour via an addition funnel. During this time, the temperature inside the reaction flask was kept under −95° C. After n-butyllithium was added, the reaction was stirred at −95° C. for 10 minutes. 1,4-Dioxaspiro[4,5]decan-8-one (17.1 g, 0.11 mole) in 100 ml dry THF was added via another addition funnel over one hour. During this time the reaction temperature was kept under −75° C. The reaction was stirred for 30 minutes, and the temperature was slowly raised to −25° C. The reaction was then quenched by adding 200 ml water and one liter of ethyl acetate was added. The organic layer was washed with water (3×400 ml), dried over sodium sulfate and solvent was removed by vacuum. The residue was recrystallized from ethyl acetate/hexane mixture to give rise to 15.5 g pure product. The crude product from mother liquor was purified by flash chromatography using hexane/ethyl acetate (70/30) as the eluent. An additional 8.0 g pure product was obtained from the column. (Total yield: 23.5 g, 82%).

Step 2

The product from step 1 (1.5 g, 5.8 mmole) was dissolved in 100 ml acetone and toluenesulfonic acid monohydrate (0.2 g) was added. The reaction was refluxed for one hour. Acetone was removed and residue was dissolved in 100 mL ethyl acetate. The organic layer was washed with water (3×100 ml), dried over sodium sulfate. After the solvent was removed, the residue (1.2 g, 100%) was used in next step without further purification. Alternatively, the product of step 1 can be treated with TFA as described in Example 91 to eliminate the hydroxyl group yielding the corresponding olefin.

Step 3

The product from step 2 (1.4 g, 6.5 mmole), 1-(2-aminoethyl)pyrrolidine (1.5 g, 13 mmole) and sodium cyanoborohydride (0.8 g, 13 mmole) were stirred in 100 ml methylene chloride at room temperature overnight. The organic layer was washed with water (3×50 ml), dried over sodium sulfate and the solvent was removed by vacuum. The residue was purified by column chromatography using ethyl acetate/methanol/triethylamine (65/34/1) as the eluent. Two isomers were obtained from the column; trans-1-[2-(1-pyrrolidinyl)ethylamino]-4-(3-cyanophenyl)-4-hydroxycyclohexane, (0.91 g, 45%). 1 H NMR (300 MHz, CDCl3) δ 7.82 (s, 1 H), 7.75 (d, J=7.69 Hz, 1 H), 7.50 (d, J=7.69 Hz, 1 H), 7.40 (t, J=7.69 Hz, 1 H), 2.80 (m, 1 H), 2.68 (t, J=6.04 Hz, 2 H), 2.57 (t, J=6.04 Hz, 2 H), 2.48 (s, 4 H), 2.22 (s, 2 H), 1.93 (s, 2 H), 1.73 (s, 4 H), 1.51 (m, 4 H) and cis-1-[2-(1-pyrrolidinyl)ethylamino]-4-(3-cyanophenyl)-4-hydroxycyclohexane (0.40 g, 20%). 1H NMR (300 MHz, CDCl3) δ 7.82 (s, 1 H), 7.74 (d, J=7.69 Hz, 1 H), 7.53 (d, J=7.69 Hz, 1 H), 7.43 (t, J=7.69 Hz, 1 H), 2.78 (t, J=6.04 Hz, 2 H), 2.59 (t, J=6.04 Hz, 2 H), 2.49 (m, 5 H), 1.56-1.96 (m, 8 H).

Step 4

Trans-1-[2-(1-pyrrolidinyl)ethyl]-4-(3-cyanophenyl )-4-hydroxycyclohexane (25 mg, 0.08 mmole) and 3-trifluoro-4-fluorophenylisocyanate (15 mg, 0.08 mmole) were stirred in 3 ml methylene chloride at room temperature overnight. The reaction solution was loaded directly onto a preparative TLC plate and the plate was developed with ethyl acetate. The major compound is the desired product, N'-(3-trifluoro-4-fluorophenyl)-N-[trans-4-(3-cyanophenyl)-4-hydroxycyclohexyl]-N-[2-(1-pyrrolidinyl)ethyl]urea (21 mg HCl salt, 49%). 1H NMR (300 MHz, CDCl3) δ 11.2 (s, 1 H), 7.84 (s, 1 H), 7.82 (d, J=6.9 Hz, 1 H), 7.50-7.64 (m, 3 H), 7.41 (dd, J=6.2 and 2.5 Hz 1 H), 7.06 (t, J=9.3 Hz, 1 H), 4.36 (tt, J=12, 3.7 Hz, 1 H), 3.06 (t, J=4.0 Hz, 2 H), 2.50-2.70 (m, 8 H), 1.77-2.05 (m, 8 H), 1.28 (q, J=12.4 Hz, 2 H).

Following procedures similar to those described in Example 1, the following compounds were prepared. Example 2 was prepared from commercially available 4-phenylcyclohexanone using the procedures described in Example 1, steps 3 and 4.

| Ex. | STRUCTURE | HRMS Mass (M + 1) | NMR |
|---|---|---|---|
| 2 | (3,5-dichlorophenyl urea, 4-phenylcyclohexyl, 2-(1-pyrrolidinyl)ethyl) | 459 | |
| 3 | (3,5-dichlorophenyl urea, 4-(3-cyanophenyl)-4-hydroxycyclohexyl, 2-(dimethylamino)ethyl) | 474 | 475.166 |

-continued

| Ex. | STRUCTURE | HRMS Mass (M + 1) | NMR |
|---|---|---|---|
| 4 | 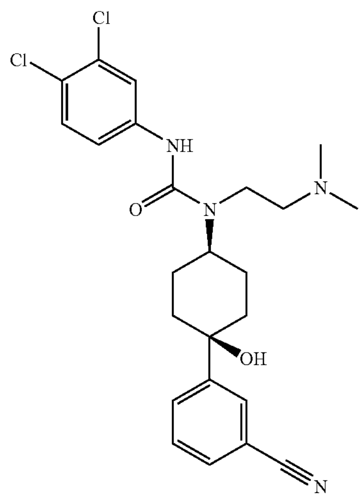 | 474 475.166 | |
| 5 | 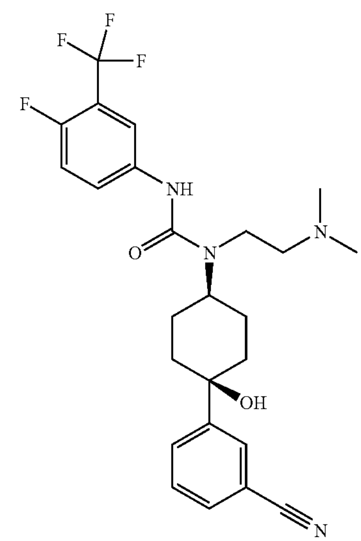 | 492 463.2222 | |
| 6 | 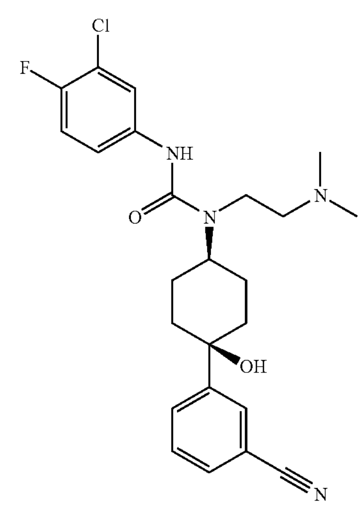 | 458 459.1968 | |

-continued

| Ex. | STRUCTURE | HRMS Mass (M + 1) | NMR |
|---|---|---|---|
| 7 | 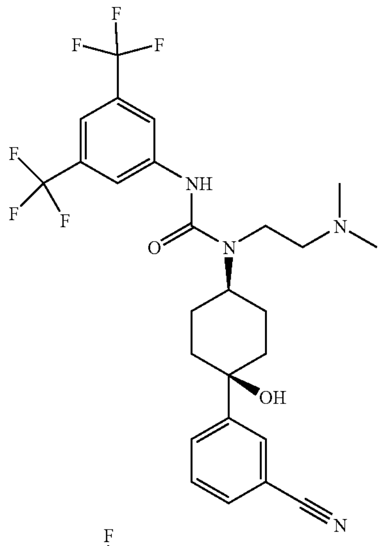 | 542  543.2198 | |
| 8 | 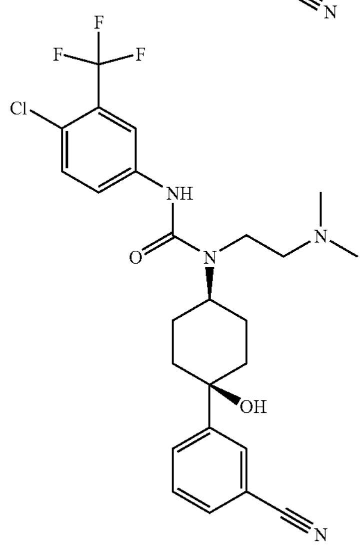 | 508  509.1923 | |
| 9 | 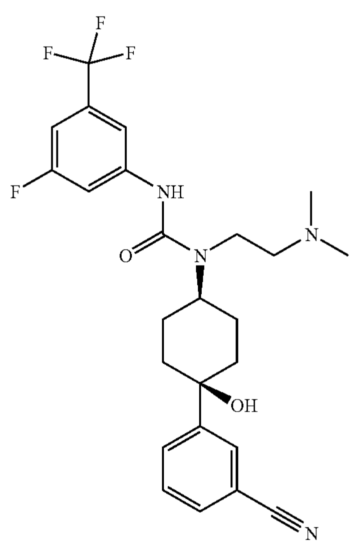 | 492  493.2236 | |

-continued

| Ex. | STRUCTURE | HRMS Mass (M + 1) | NMR |
|---|---|---|---|
| 10 | (structure) | 442  443.2262 | |
| 11 | (structure) | 442  443.2266 | |
| 12 | (structure) | 500  501.1831 | |

-continued

| Ex. | STRUCTURE | HRMS Mass (M + 1) | | NMR |
|---|---|---|---|---|
| 13 | (3,4-dichlorophenyl)-NH-C(=O)-N(CH₂CH₂-pyrrolidinyl)-cyclohexyl(OH)(3-cyanophenyl) | 500 | 501.1831 | |
| 14 | (4-fluoro-3-trifluoromethylphenyl)-NH-C(=O)-N(CH₂CH₂-pyrrolidinyl)-cyclohexyl(OH)(3-cyanophenyl) | 518 | 519.2373 | 1H NMR (300 MHz, CDCl3) 11.2(s, 1H), 7.84(m, 2H), 7.42-7.70(m, 5H), 7.08(t, J=9.2Hz, 1H), 4.30(br, 1H), 3.40(t,J=3.7Hz, 2H), 2.81(t, J=3.7Hz, 2H), 2.73(br, 4H), 1.70-2.00(m, 12H). |
| 15 | (3-chloro-4-fluorophenyl)-NH-C(=O)-N(CH₂CH₂-pyrrolidinyl)-cyclohexyl(OH)(3-cyanophenyl) | 484 | 485.2113 | |

| Ex. | STRUCTURE | HRMS Mass (M + 1) | NMR |
|---|---|---|---|
| 16 | 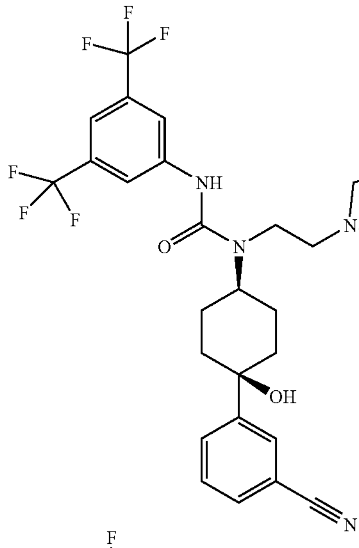 | 568 569.2343 | |
| 17 | 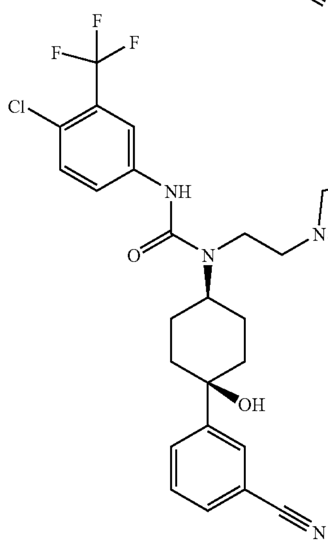 | 534 535.2081 | |
| 18 | 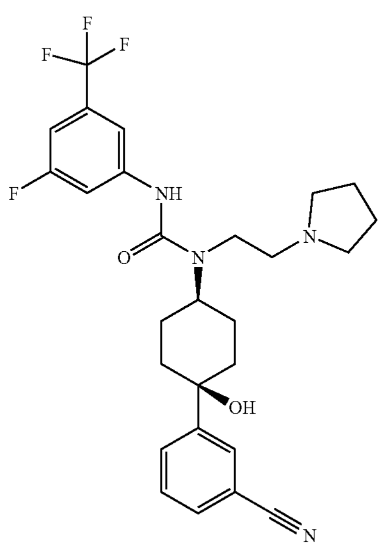 | 518 519.2373 | |

-continued

| Ex. | STRUCTURE | HRMS Mass (M + 1) | NMR |
|---|---|---|---|
| 19 | 3,4-difluorophenyl-NH-C(=O)-N(CH₂CH₂-pyrrolidinyl)-(trans-4-hydroxy-4-(3-cyanophenyl)cyclohexyl) | 468  469.241 | |
| 20 | 3,5-difluorophenyl-NH-C(=O)-N(CH₂CH₂-pyrrolidinyl)-(trans-4-hydroxy-4-(3-cyanophenyl)cyclohexyl) | 468  469.241 | |
| 21 | 3,5-dichlorophenyl-NH-C(=O)-N(CH₂CH₂-pyrrolidinyl)-(trans-4-hydroxy-4-(3-cyanophenyl)cyclohexyl) | 500  501.1831 | |

-continued

| Ex. | STRUCTURE | HRMS Mass (M + 1) | | NMR |
|---|---|---|---|---|
| 22 | (3,4-dichlorophenyl)-NH-C(O)-N(CH₂CH₂-pyrrolidinyl)-(cyclohexyl with OH)-(3-cyanophenyl) | 500 | 501.1831 | |
| 23 | (3-chloro-4-fluorophenyl)-NH-C(O)-N(CH₂CH₂-pyrrolidinyl)-(cyclohexyl with OH)-(3-cyanophenyl) | 484 | 485.2125 | |
| 24 | (3,5-bis(trifluoromethyl)phenyl)-NH-C(O)-N(CH₂CH₂-pyrrolidinyl)-(cyclohexyl with OH)-(3-cyanophenyl) | 568 | 569.2354 | |

| Ex. | STRUCTURE | HRMS Mass (M + 1) | NMR |
|---|---|---|---|
| 25 | 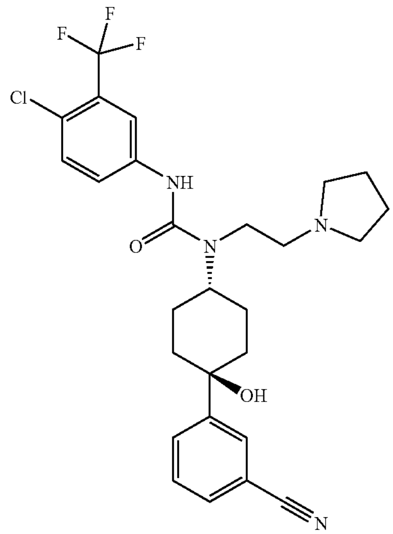 | 534 535.2094 | |
| 26 | 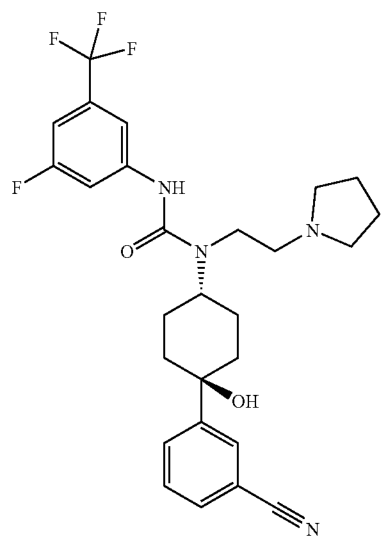 | 518 519.2376 | |
| 27 | 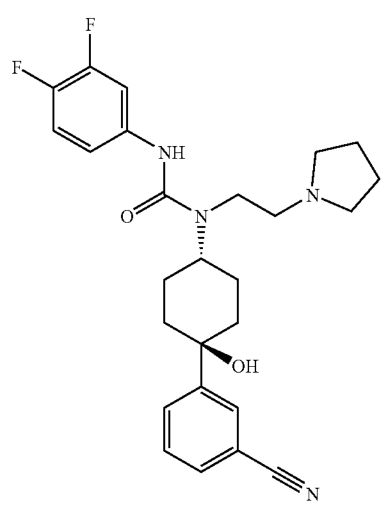 | 468 469.2423 | |

| Ex. | STRUCTURE | HRMS Mass (M + 1) | NMR |
|---|---|---|---|
| 28 | 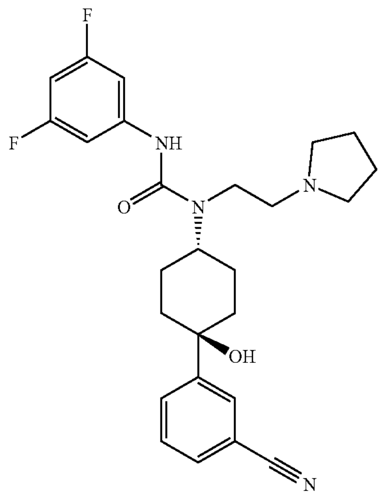 | 468 | 469.2419 |
| 29 | 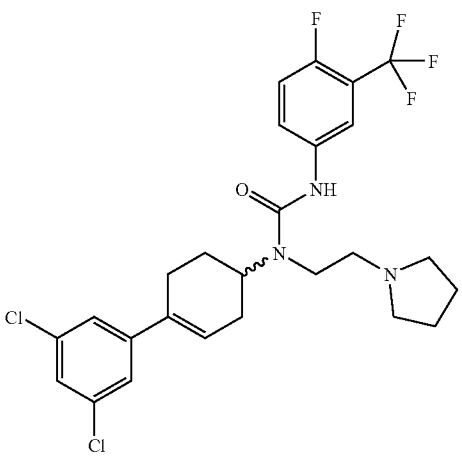 | 543 | LCMS(544.1) |
| 30 | 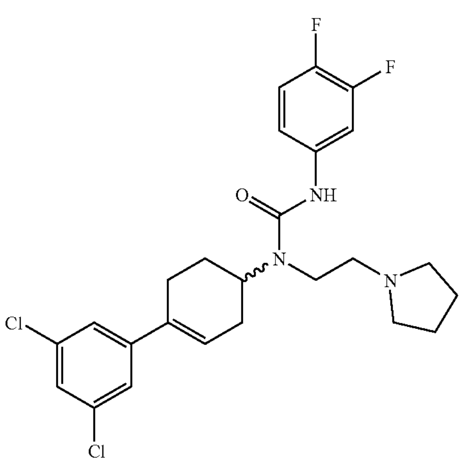 | 493 | 493.1(LCMS) |

-continued
| Ex. | STRUCTURE | HRMS Mass (M + 1) | NMR |
|---|---|---|---|
| 31 | 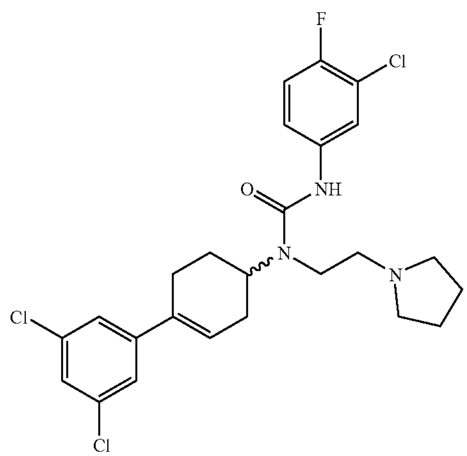 | 509 | 510.1(LCMS) |
| 32 | 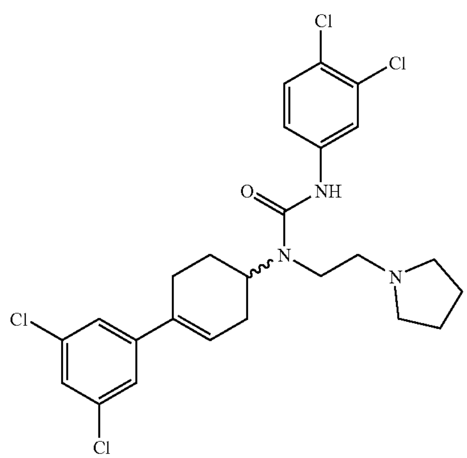 | 525 | 526.1(LCMS) |
| 33 | 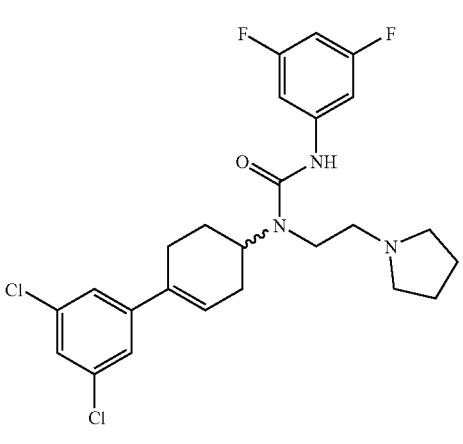 | 493 | 494.1(LCMS) |

-continued
| Ex. | STRUCTURE | HRMS Mass (M + 1) | | NMR |
|---|---|---|---|---|
| 34 | 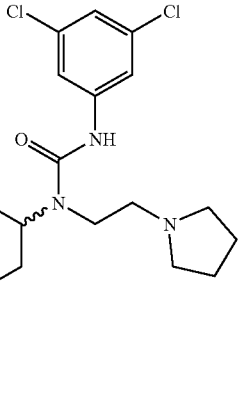 | 525 | 526.1(LCMS) | |
| 35 | 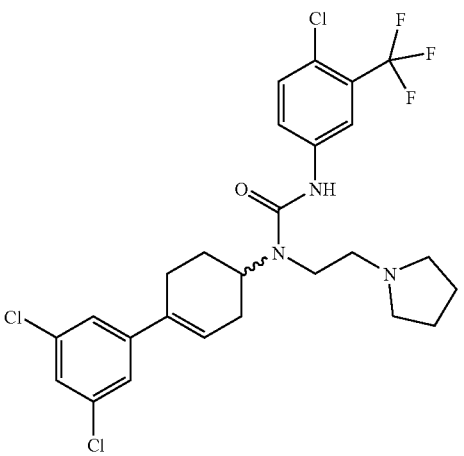 | 559 | 560.1(LCMS) | |
| 36 | 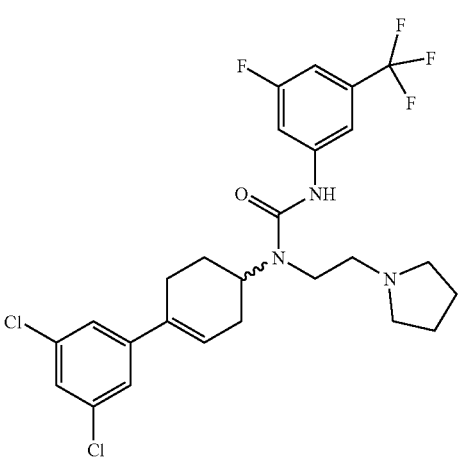 | 543 | 544.1(LCMS) | |

-continued

| Ex. | STRUCTURE | HRMS Mass (M + 1) | NMR |
|---|---|---|---|
| 37 | (3,4-difluorophenyl)-NH-C(=O)-N(CH2CH2-pyrrolidinyl)-(cyclohex-3-enyl)-(4-cyanophenyl) | 450 451.2303 | |
| 38 | (3-chloro-4-fluorophenyl)-NH-C(=O)-N(CH2CH2-pyrrolidinyl)-(cyclohex-3-enyl)-(4-cyanophenyl) | 466 467.2021 | |
| 39 | (3,4-dichlorophenyl)-NH-C(=O)-N(CH2CH2-pyrrolidinyl)-(cyclohex-3-enyl)-(4-cyanophenyl) | 482 483.1747 | |

| Ex. | STRUCTURE | HRMS Mass (M + 1) | NMR |
|---|---|---|---|
| 40 | 3,5-difluorophenyl-NH-C(=O)-N(CH2CH2-pyrrolidinyl)-(cyclohex-3-enyl)-(4-cyanophenyl) | 450  451.2317 | |
| 41 | 3,5-dichlorophenyl-NH-C(=O)-N(CH2CH2-pyrrolidinyl)-(cyclohex-3-enyl)-(4-cyanophenyl) | 482  483.1785 | |
| 42 | 4-chloro-3-(trifluoromethyl)phenyl-NH-C(=O)-N(CH2CH2-pyrrolidinyl)-(cyclohex-3-enyl)-(4-cyanophenyl) | 516  517.1988 | |

| Ex. | STRUCTURE | HRMS Mass (M + 1) | NMR |
|---|---|---|---|
| 43 | 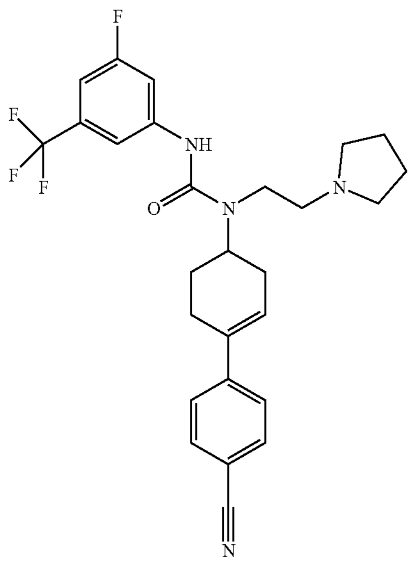 | 500 501.2267 | |
| 44 | 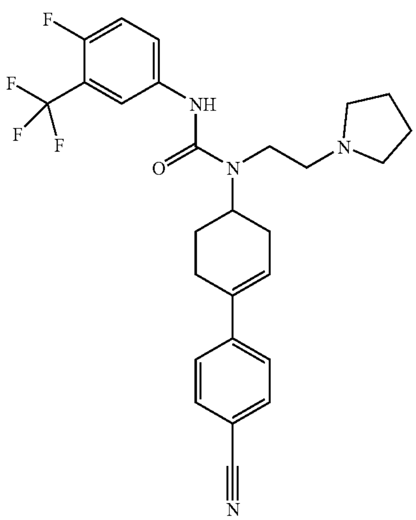 | 500 501.2267 | |
| 45 | 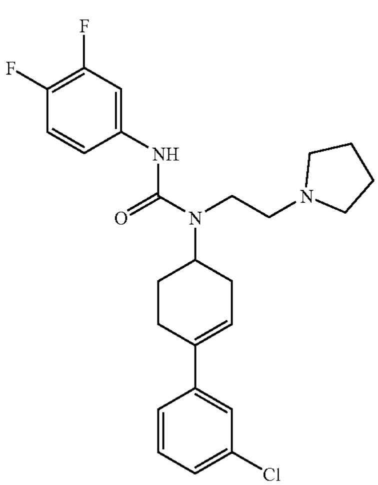 | 459 460.1914 | |

-continued

| Ex. | STRUCTURE | HRMS Mass (M + 1) | NMR |
|---|---|---|---|
| 46 | 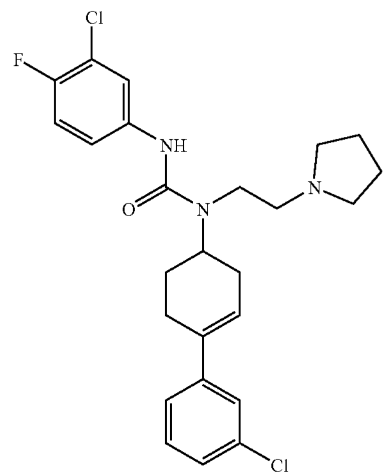 | 475 476.1665 | |
| 47 | 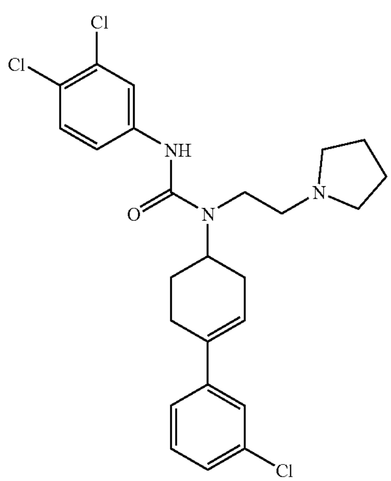 | 491 492.1379 | |
| 48 | 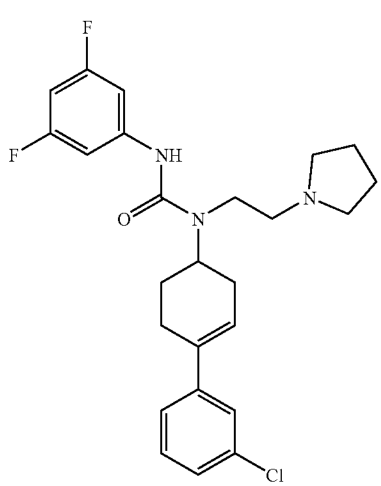 | 459 460.1959 | |

-continued
| Ex. | STRUCTURE | HRMS Mass (M + 1) | NMR |
|---|---|---|---|
| 49 | 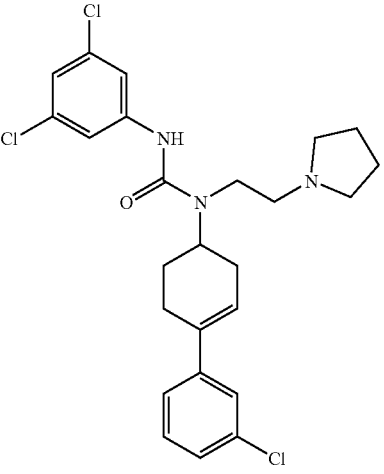 | 491 492.1374 | |
| 50 | 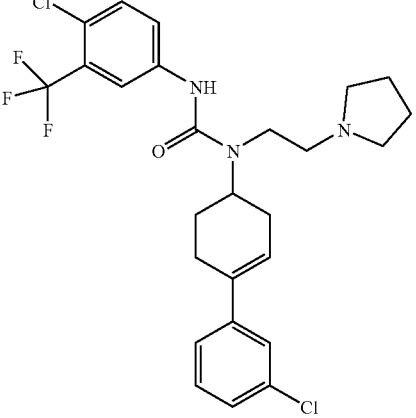 | 525 526.1652 | |
| 51 | 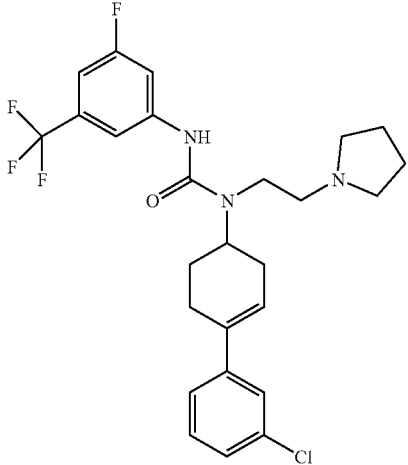 | 509 510.1931 | |

| Ex. | STRUCTURE | HRMS Mass (M + 1) | NMR |
|---|---|---|---|
| 52 | F, F, F, NH, O, N, N (pyrrolidine), cyclohexene, Cl-phenyl | 509 510.1926 | |

Method 2

Example 53a

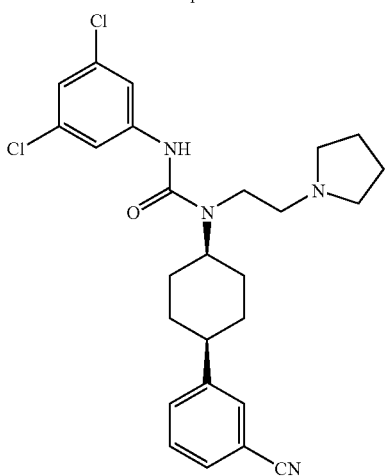

Example 53b

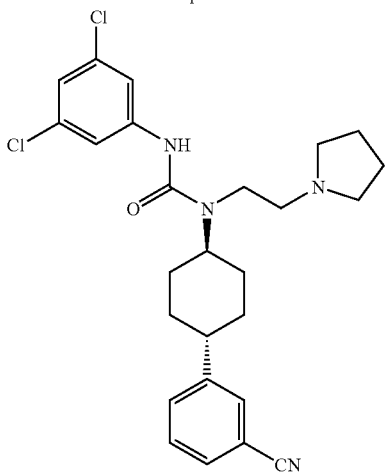

Step 1

4-(3-cyanophenyl)-4-hydroxycyclohexane-1-one ethylene ketal (from step 1 of method 1, 10 g, 39 mmole) was dissolved in 80 ml trifluoroacetic acid. The mixture was heated to 50° C. for four hours. Trifluoroacetic acid was removed under vacuum and the residue was partitioned between 200 ml ethyl acetate and 100 ml saturated sodium bicarbonate solution. The organic layer was washed with water (2×100 ml) dried over sodium sulfate. The product was purified by column using hexane/ethyl acetate (85/15) as the eluent. Two products were obtained; 4-(3-cyanophenyl)-3-cyclohexene-1-one (3.1 g, 41%) and 4-(3-cyanophenyl)-2-cyclohexene-1-one (4.0 g, 53%).

Step 2

The mixture of 4-(3-cyanophenyl)-3-cyclohexene-1-one and 4-(3-cyanophenyl)-2-cyclohexene-1-one (total 1.8 g, 9.1 mmole) was dissolved in 50 ml ethyl acetate. The catalyst, Pt/C (10%, 0.5 g) was then added and mixture was shaken overnight under 45 psi hydrogen gas. The catalyst was filtered off and solvent was removed under vacuum. The residue is a mixture of cis and trans 4-(3-cyanophenyl)-1-hydroxycyclohexane (1.8 g, 98%).

Step 3

The mixture of cis and trans 4-(3-cyanophenyl)-1-hydroxycyclohexane (1.8 g, 9 mmole) was dissolved in 100 ml methylene chloride and Dess-Martin reagent(4.2 g, 10 mmole) was added. The mixture was stirred at room temperature for five hours. The reaction solution was washed with water (3×100 mL) and dried over sodium sulfate. The product was purified by column chromatography using hexane/ethyl acetate (85/15) as the eluent to afford 4-(3-cyanophenyl)-cyclohexane-1-one (1,1 g, 63%).

Step 4

4-(3-cyanophenyl)-cyclohexane-1-one (0.32 g, 1.6 mmole), 2-aminoethylpyrrolidine (0.36 g, 3.2 mmole) and sodium cyanoborohydride (0.2 g, 3.2 mmole) were stirred in 20 ml methylene chloride at room temperature for two hours. 50 ml methylene chloride was added. The organic layer was washed with water (3×50 ml), dried over sodium sulfate and the solvent was removed by vacuum. The residue was purified by column chromatography using ethyl acetate/methanol/triethylamine (89/10/1) as the eluent. The product is a mixture of cis and trans-1-[2-(1-pyrrolidinyl)ethylamino]-4-(3-cyanophenyl)-cyclohexane (0.2 g, 48%)

Step 5

The mixture of cis and trans-1-[2-(1-pyrrolidinyl)ethylamino]-4-(3-cyanophenyl)-cyclohexane (20 mg, 0.067 mmole) and 3,5-dichloro phenylisocyanate (20 mg, 0.11 mmole) were stirred in 5 ml methylene chloride at room temperature overnight. The reaction solution was loaded directly onto a preparative silica gel TLC plate and the plate was developed in ethyl acetate/hexane(70/30). Two products were isolated from the plate; N'-(3,5-dichlorophenyl)-N-[cis-4-(3-cyanophenyl)-cyclohexyl]-N-[2-(1-pyrrolidinyl)ethyl]urea (6.5 mg HCl salt, 19%). 1H NMR (300 MHz, CDCl3) δ 11.3 (s, 1 H), 7.65 (s, 1 H), 7.62 (d, J=8.5 Hz, 1 H), 7.45-7.55 (m, 2 H), 7.29 (s, 2 H), 6.91(s, 1 H), 4.30 (tt, J=12 and 3.7 Hz, 1 H), 3.12 (m, 3 H), 2.68 (m, 6 H), 1.70-2.36 (m, 12 H), and N'-(3,5-dichlorophenyl)-N-[trans-4-(3-cyanophenyl)-cyclohexyl]-N-[2-(1-pyrrolidinyl)ethyl]urea (15.5 mg HCl salt, 46%). 1H NMR (300 MHz, CDCl3) δ 11.3 (s, 1 H), 7.38-7.52 (m, 4 H), 7.31 (s, 2 H), 6.92(s, 1 H), 4.25 (tt, J=12 and 3.7 Hz, 1 H), 3.35 (t, J=4.0 Hz, 2 H), 2.79 (t, J=4.0 Hz, 2 H), 2.73 (b, 4 H), 2.50 (tt, J=12 and 3.7 Hz, 1 H), 1.48-2.02 (m, 12 H).

Following procedures similar to those described in Example 53, the following compounds were prepared.

| Ex | STRUCTURE | HRMS Mass (M + 1) | NMR |
|---|---|---|---|
| 54 | 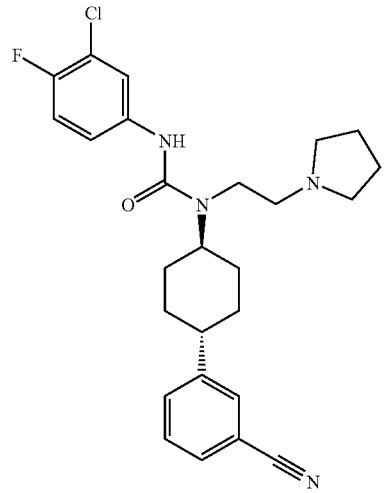 | 468 469.2175 | |
| 55 | 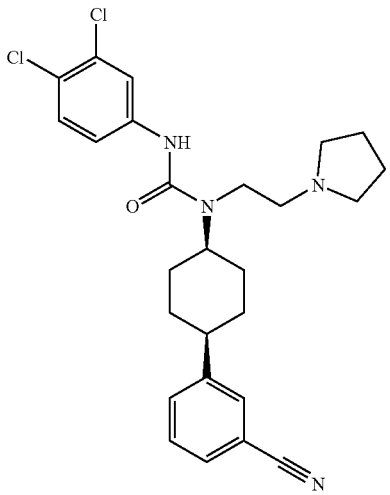 | 484 485.1875 | |

-continued
| Ex | STRUCTURE | HRMS Mass (M + 1) | NMR |
|---|---|---|---|
| 56 | 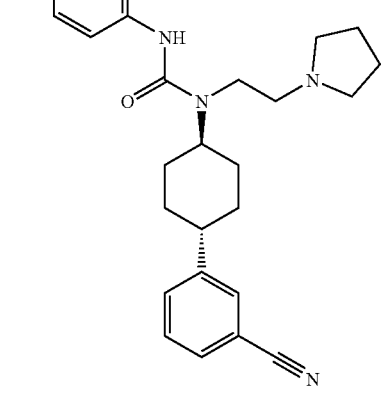 | 484  485.188 | |
| 57 | 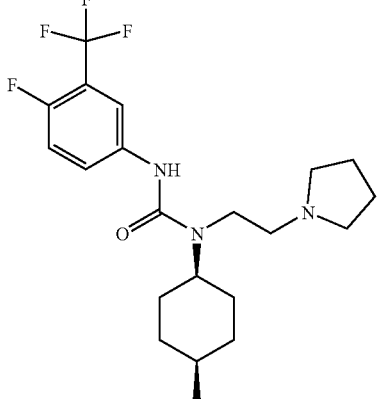 | 502  503.2443 | 1H NMR (300 MHz, CDCl3) 11.2(s, 1H), 7.60-7.68(m, 3H), 7.42-7.54(m, 3H), 7.07(t, J=9.3Hz, 1H), 4.33(tt, J=12.1 and 4.0Hz, 1H), 3.13(t, J=3.6Hz, 2H), 3.10(br, 1H), 2.68(br. 6H), 2.33(m, 2H), 2.01(tt, J=14 and 4.1Hz, 2H), 1.60-1.90(m, 6H), 1.30-1.45(m, 2H). |
| 58 | 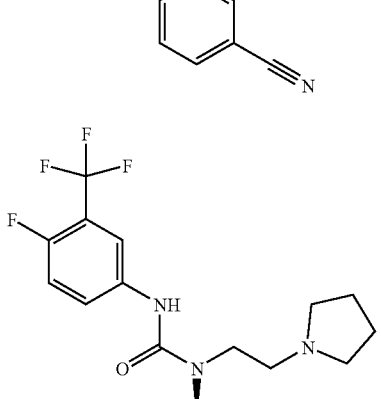 | 502  503.2438 | 1H NMR (300 MHz, CDCl3) 11.2(s, 1H), 7.62-7.70(m, 1H), 7.36-7.52(m, 5H), 7.08(t, J=9.5Hz), 4.28(tt, J=12 and 3.7Hz, 1H), 3.36(t, J=4.2Hz, 2H), 2.80(t, J=4.2Hz, 2H), 2.74(br, 4H), 2.51(tt, J=12 and 3.7Hz, 1H), 1.48-2.01(m, 12H). |

| Ex | STRUCTURE | HRMS Mass | (M + 1) | NMR |
|---|---|---|---|---|
| 59 | 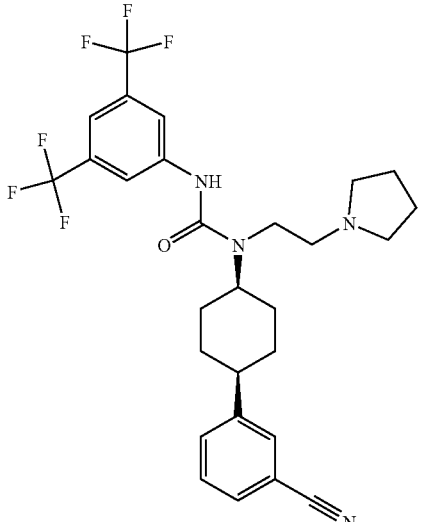 | 552 | 553.2399 | |
| 60 | 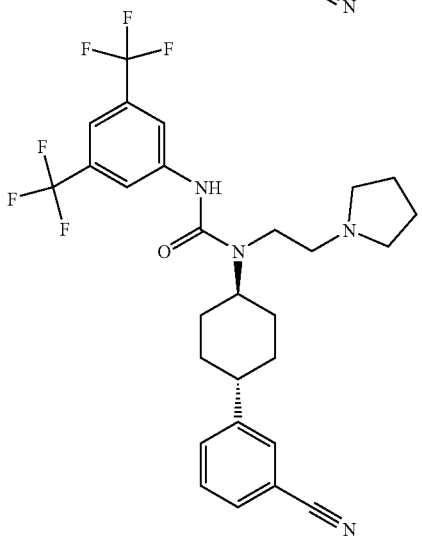 | 552 | 553.2404 | |
| 61 | 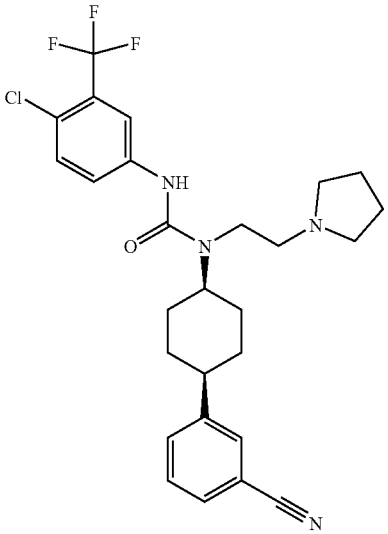 | 518 | 519.2137 | |

| Ex | STRUCTURE | HRMS Mass (M + 1) | NMR |
|---|---|---|---|
| 62 | 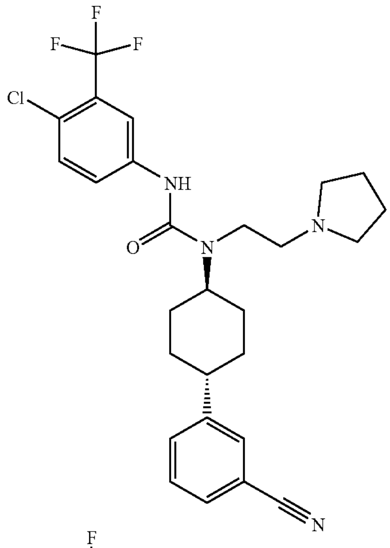 | 518 519.2132 | |
| 63 | 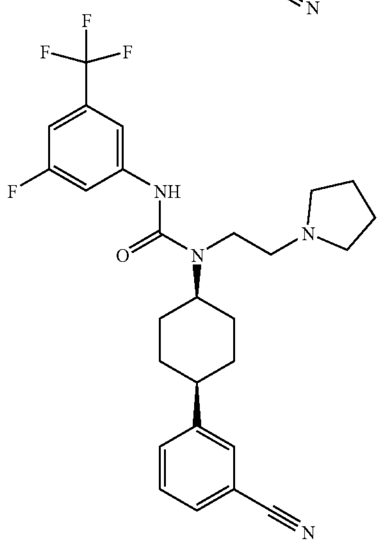 | 502 503.2438 | |
| 64 | 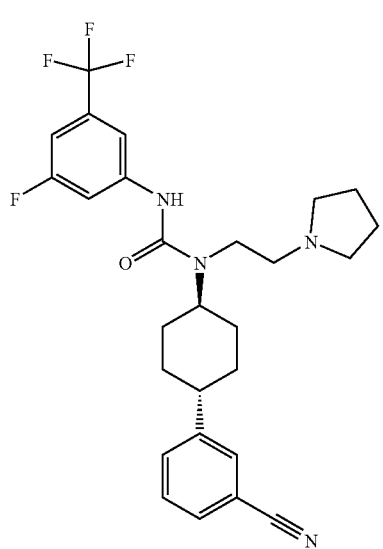 | 502 503.2438 | |

| Ex | STRUCTURE | HRMS Mass (M + 1) | NMR |
|---|---|---|---|
| 65 | 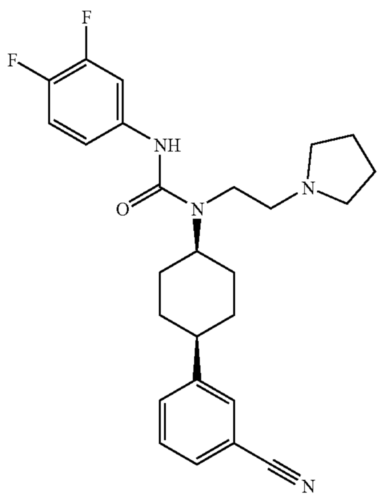 | 452 453.246 | |
| 66 | 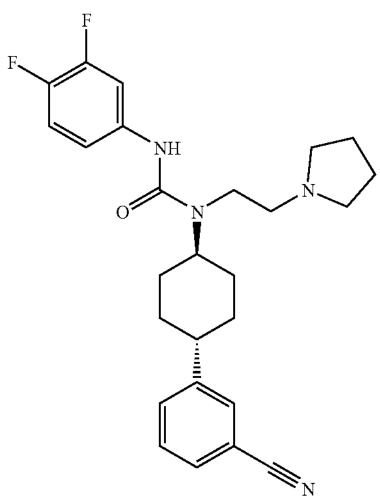 | 452 453.2465 | |
| 67 | 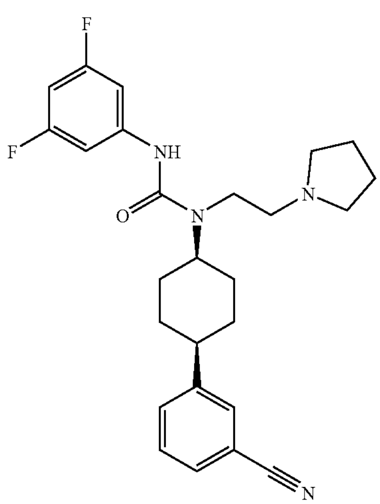 | 452 453.2465 | |

-continued
| Ex | STRUCTURE | HRMS Mass (M + 1) | | NMR |
|---|---|---|---|---|
| 68 | 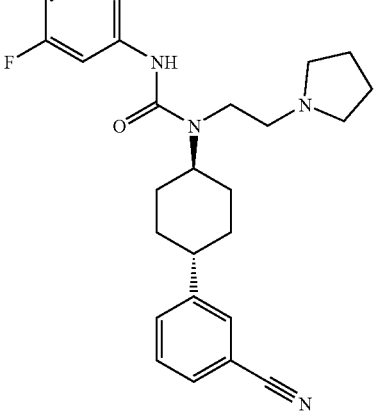 | 452 | 453.246 | |
| 69 | 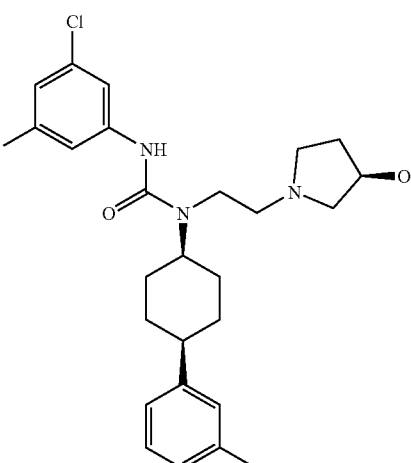 | 500 | 501.1827 | |
| 70 | 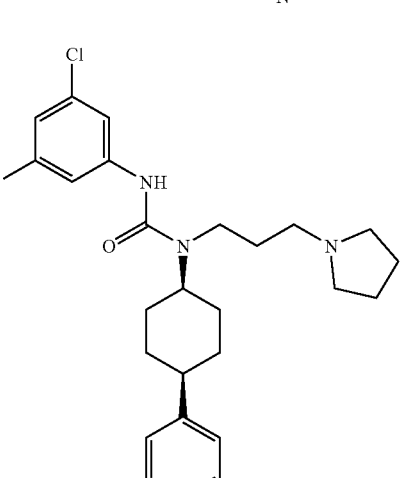 | 498 | 499.2041 | |

-continued

| Ex | STRUCTURE | HRMS Mass (M + 1) | | NMR |
|---|---|---|---|---|
| 71 | (3,5-dichlorophenyl)-NH-C(=O)-N(CH₂CH₂CH₂-pyrrolidin-1-yl)-(trans-cyclohexyl)-3-cyanophenyl | 498 | 499.2036 | |
| 72 | (3,4-dichlorophenyl)-NH-C(=O)-N(CH₂CH₂CH₂-pyrrolidin-1-yl)-(trans-cyclohexyl)-3-cyanophenyl | 498 | 499.2036 | |
| 73 | (3,4-dichlorophenyl)-NH-C(=O)-N(CH₂CH₂CH₂-pyrrolidin-1-yl)-(trans-cyclohexyl)-3-cyanophenyl | 498 | 499.2041 | |

| Ex | STRUCTURE | HRMS Mass (M + 1) | NMR |
|---|---|---|---|
| 74 | 4-fluoro-3-(trifluoromethyl)phenyl NH-C(=O)-N(CH₂CH₂CH₂-pyrrolidinyl)-trans-cyclohexyl-(3-cyanophenyl) | 516  517.2599 | |
| 75 | 4-fluoro-3-(trifluoromethyl)phenyl NH-C(=O)-N(CH₂CH₂CH₂-pyrrolidinyl)-trans-cyclohexyl-(3-cyanophenyl) | 516  517.2599 | |
| 76 | 3-chloro-4-fluorophenyl NH-C(=O)-N(CH₂CH₂CH₂-pyrrolidinyl)-trans-cyclohexyl-(3-cyanophenyl) | 516  483.2334 | |

-continued
| Ex | STRUCTURE | HRMS Mass (M + 1) | NMR |
|---|---|---|---|
| 77 | 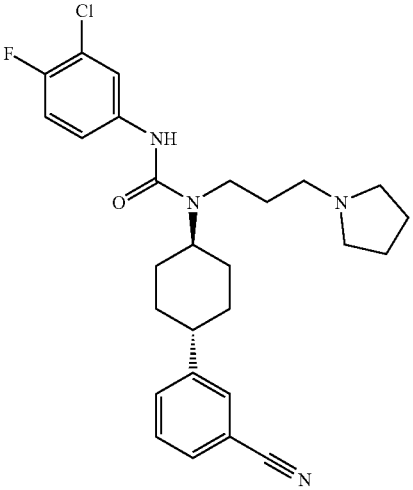 | 482 483.2339 | |
| 78 | 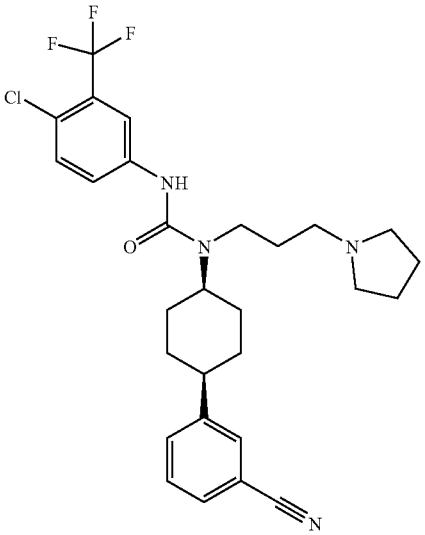 | 532 533.2303 | |
| 79 | 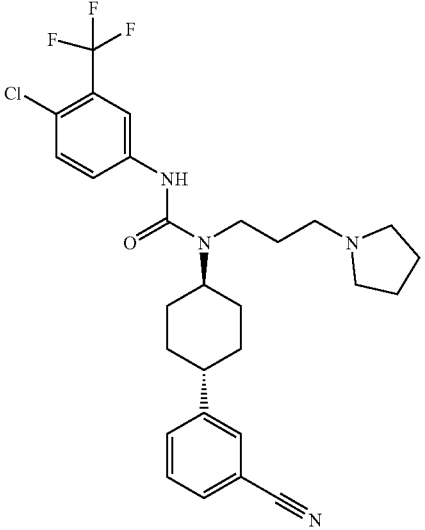 | 532 533.2299 | |

-continued

| Ex | STRUCTURE | HRMS Mass (M + 1) | | NMR |
|---|---|---|---|---|
| 80 | 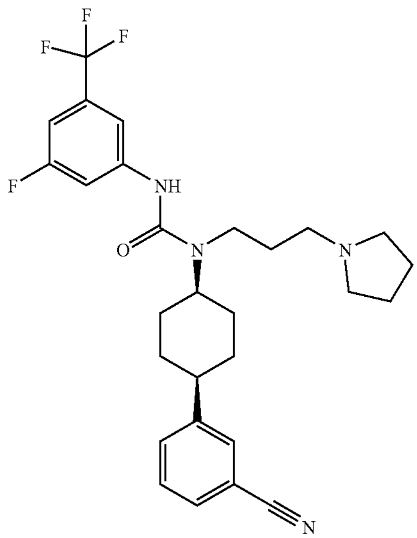 | 516 | 517.2599 | |
| 81 | 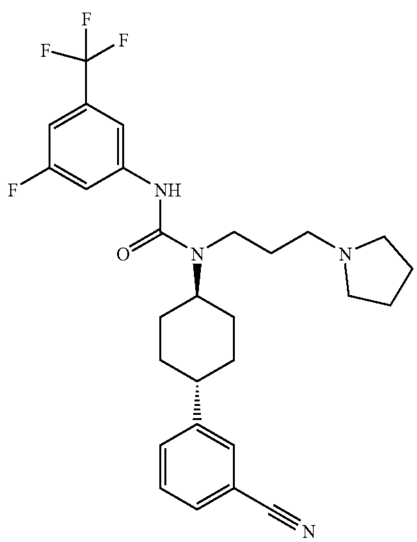 | 516 | 517.2599 | |
| 82 | 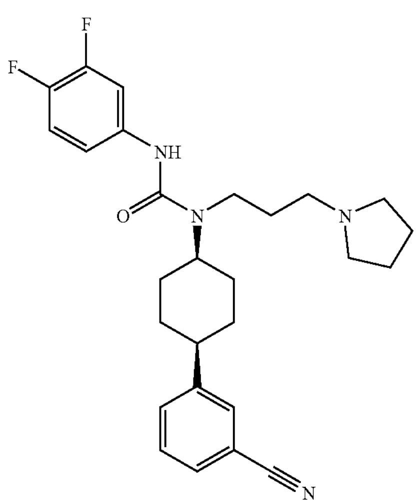 | 466 | 467.2615 | |

-continued
| Ex | STRUCTURE | HRMS Mass (M + 1) | NMR |
|---|---|---|---|
| 83 | 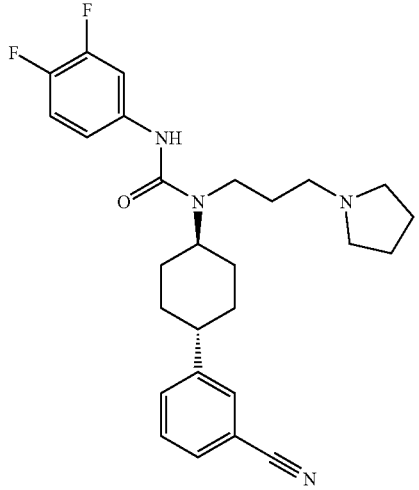 | 466 467.2619 | |
| 84 | 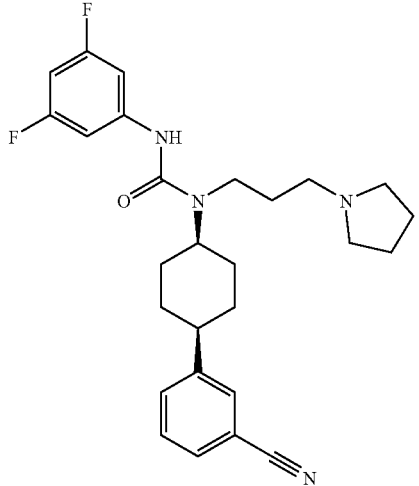 | 466 467.2619 | |
| 85 | 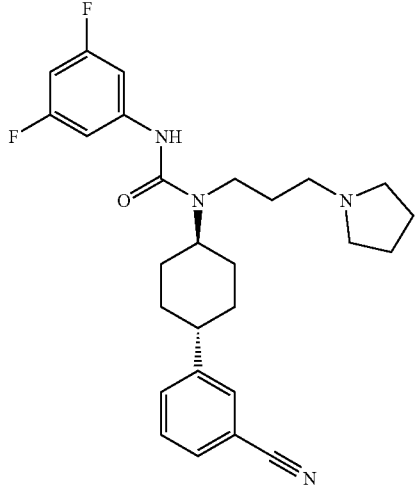 | 466 467.2619 | |

| Ex | STRUCTURE | HRMS Mass (M + 1) | NMR |
|---|---|---|---|
| 86 | 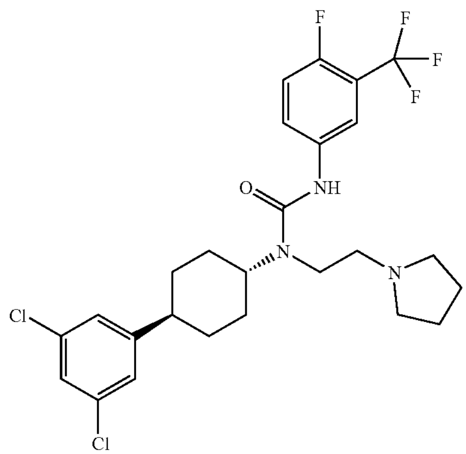 | 545 546.1(LCMS) | |
| 87 | 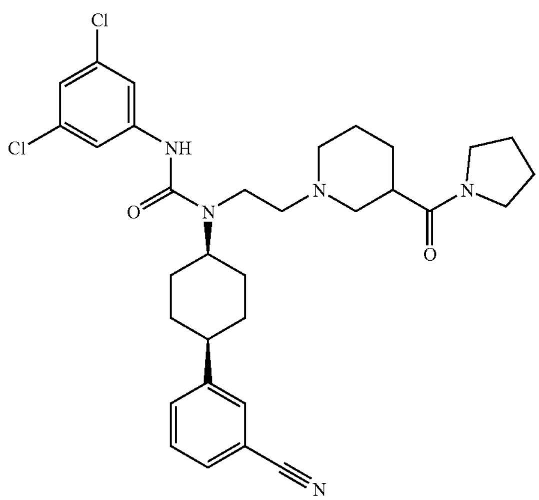 | 595 596.2565 | |
| 88 | 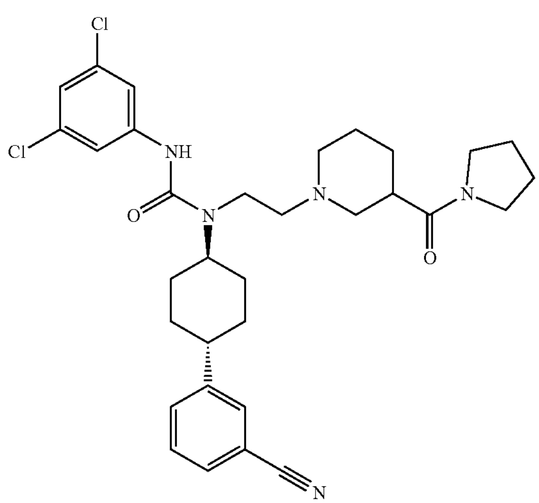 | 595 596.2565 | |

-continued

| Ex | STRUCTURE | HRMS Mass (M + 1) | NMR |
|---|---|---|---|
| 89 | 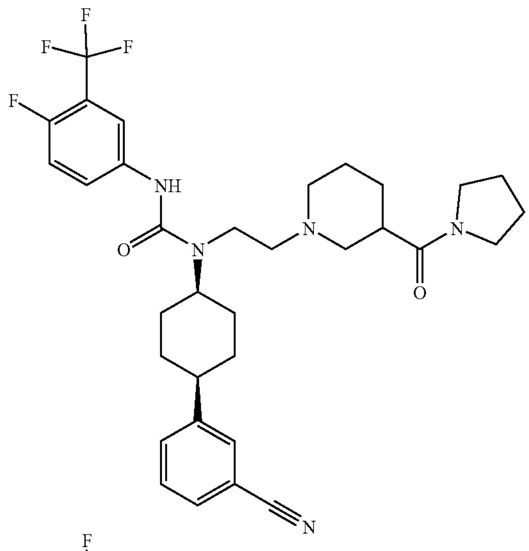 | 613  614.3108 | |
| 90 | 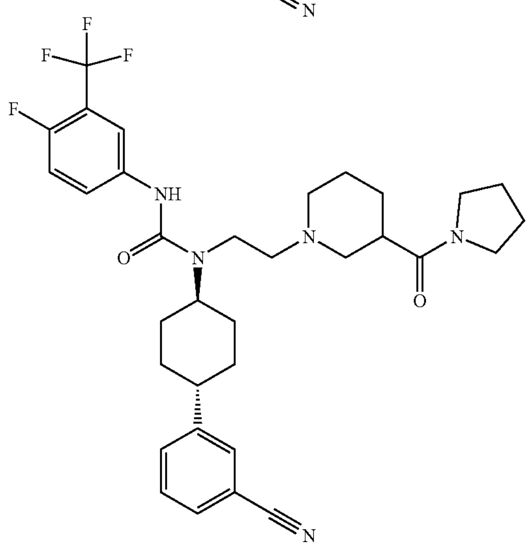 | 613  614.3108 | |

Method 3
Example 91

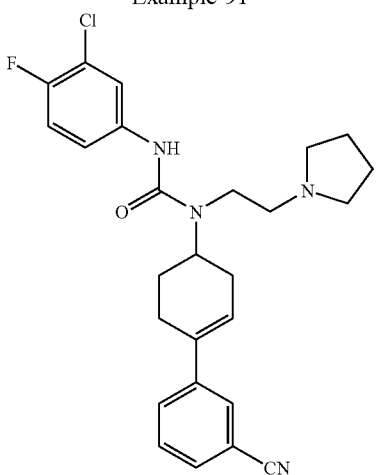

N'-(3-chloro-4-fluorophenyl)-N-[trans-4-(3-cyanophenyl)-4-hydroxycyclohexyl]-N-[2-(1-pyrrolidinyl)ethyl]urea (from step 4 of method 1, 0.12 g, 0.26 mmole), 15 ml trifluoroacetic acid were heated to 80° C. for eight hours, then room temperature overnight. Trifluoroacetic acid was removed and residue was partitioned between 60 ml ethyl acetate and 60 ml saturated sodium bicarbonate solution. The organic layer was washed with water (2×50 mL) and dried over sodium sulfate. The final product from organic layer was purified by column chromatography using ethyl acetate as the eluent (93 mg, 82%). 1H NMR (300 MHz, CDCl3) δ 11.09 (s, 1H), 7.62 (s, 1 H), 7.58 (d, J=7.8 Hz, 1 H), 7.38-7.52 (m, 3 H), 7.15 (m, 1H), 7.01 (t, J=8.9 Hz, 1H), 6.11 (t, J=2.8 Hz, 1 H), 4.50 (m, 1 H), 3.32 (t, J=4.1 Hz, 2 H), 1.70-2.82 (m, 16 H).

Following procedures similar to those described in Example 91, the following compounds were prepared.

| Ex | STRUCTURE | HRMS Mass (M + 1) | NMR |
|---|---|---|---|
| 92 | (structure) | 456 457.1555 | |
| 93 | (structure) | 490 LCMS(491.1) | |
| 94 | (structure) | 482 483.1726 | 1H NMR (300 MHz, CDCl3) 11.1(br, 1H), 7.63(s, 1H), 7.58(d, J=7.8Hz, 1H), 7.52(d, J=7.7Hz, 1H) 7.37-7.44(m, 3H), 6.94(s, 1H), 6.11(br, 1H), 4.50(m, 1H), 3.38(t, J=4.1Hz, 2H), 1.70-2.82(m, 16H). |

| Ex | STRUCTURE | HRMS Mass (M + 1) | NMR |
|---|---|---|---|
| 95 | 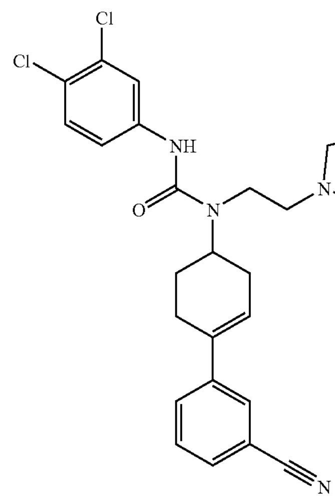 | 482 483.1726 | |
| 96 | 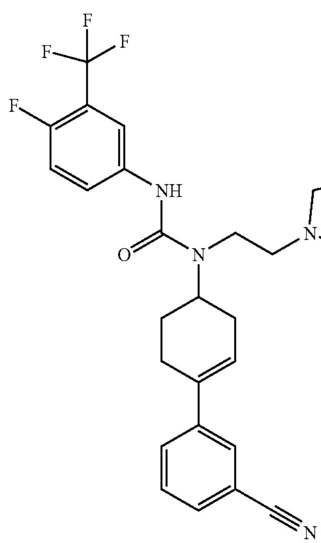 | 500 501.2268 | |
| 97 | 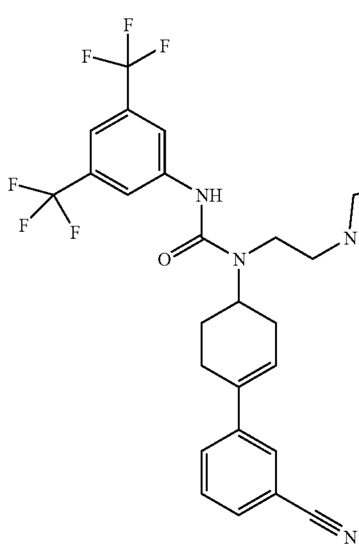 | 550 551.2239 | |

-continued
| Ex | STRUCTURE | HRMS Mass (M + 1) | | NMR |
|---|---|---|---|---|
| 98 | 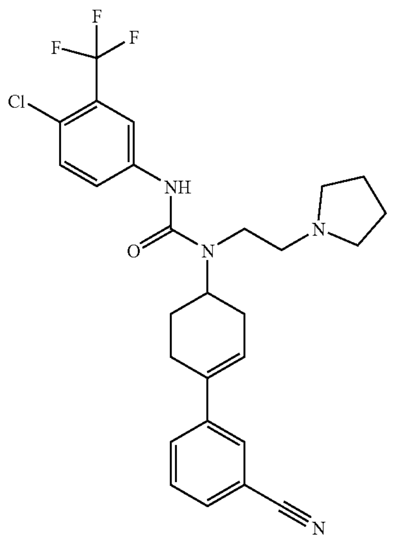 | 516 | 517.1987 | |
| 99 | 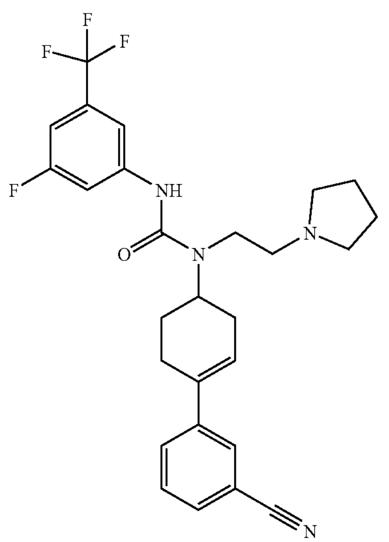 | 500 | 501.2272 | |
| 100 | 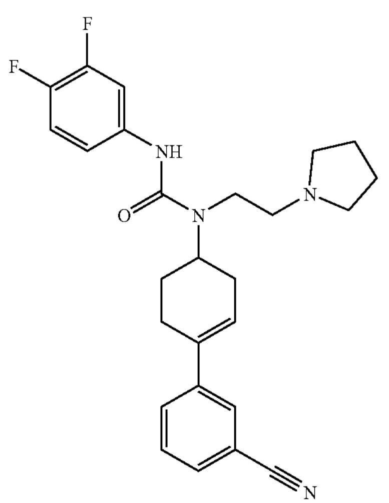 | 450 | 451.2312 | |

| Ex | STRUCTURE | HRMS Mass (M + 1) | | NMR |
|---|---|---|---|---|
| 101 | 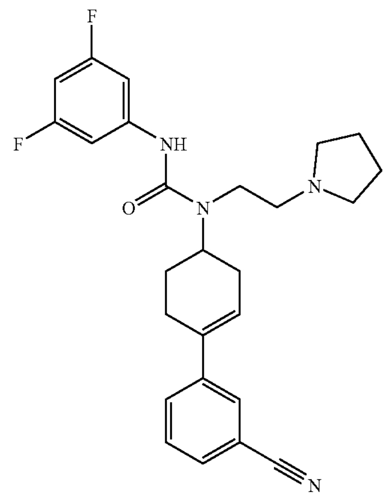 | 450 | 451.2317 | |

Method 4

Example 102

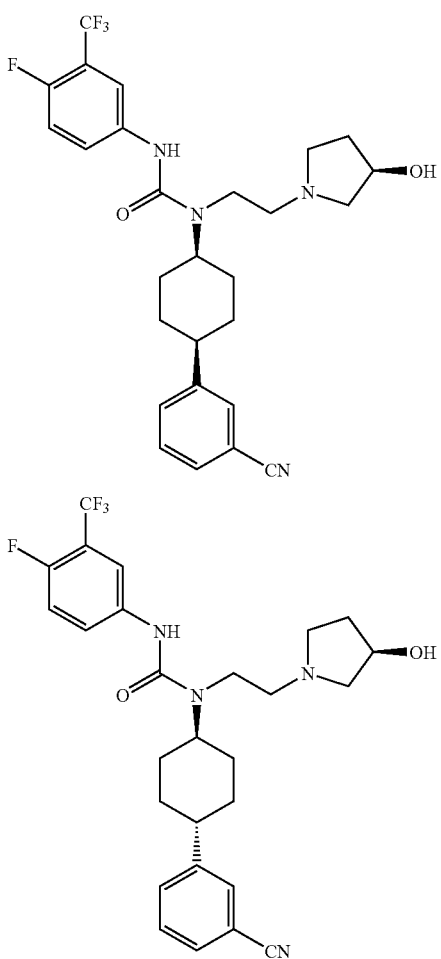

Step 1

4-(3-cyanophenyl)-cyclohexane-1-one (from step 3 of method 2, 0.7 g, 3.5 mmole), aminoethanol (0.64 g, 10.5 mmole) and sodium triacetoxylborohydride (2.2 g, 10.5 mmole) were refluxed in 50 ml methylene chloride for 24 hours. 50 ml water was added to quench the reaction. The organic layer was washed with water (3×50 ml), dried over sodium sulfate and the solvent was removed by vacuum. The residue was used in the next step without further purification. The product is a mixture of cis and trans-1-[2-hydroxyethylamino]-4-(3-cyanophenyl)-cyclohexane.

Step 2

The mixture of cis and trans-1-(2-hydroxy-ethylamino)-4-(3-cyanophenyl)-cyclohexane (from Step 1) was suspended in 50 ml ether and 50 ml 1N sodium hydroxide solution. Di-tert-butyl dicarbonate (1.8 mg, 10.5 mmole) was added and the reaction was stirred at room temperature for 5 hours. 3 ml of ammonium hydroxide solution was added to quench excess di-tert-butyl dicarbonate. The ether layer was washed with water (2×50 mL) and dried over sodium sulfate. The residue was purified by column using ethyl acetate/hexane (35/65) as the eluent. The product is a mixture of cis- and trans-1-(N-Boc-2-hydroxy-ethylamino)-4-(3-cyanophenyl)-cyclohexane (0.85 g, 71% for two steps).

Step 3

The mixture of cis- and trans-1-(N-Boc-2-hydroxy-ethylamino)-4-(3-cyanophenyl)-cyclohexane (0.85 g, 2.5 mmole) and Dess-Martin reagent (1.15 g, 2.7 mmole) were stirred in 50 ml methylene chloride overnight. The reaction solution was washed with water (2×50 mL), dried over sodium sulfate. The residue from organic layer was purified by column chromatography using hexane/ethyl acetate (85/15) as the eluent. The product is the mixture of cis and trans-1-(N-Boc-2-oxo-ethylamino)-4-(3-cyanophenyl)-cyclohexane (0.67 g, 79%).

Step 4

The mixture of cis and trans-1-(N-Boc-2-oxo-ethylamino)-4-(3-cyanophenyl)-cyclohexane (0.27 g, 0.79 mmole), (R)-3-hydroxypyrrolidine (0.2 g, 2.4 mmole) and sodium triacetoxylborohydride (0.67 g, 3.2 mmole) were stirred in 50 ml methylene chloride for 5 hours. 50 ml water was added to quench the reaction. The organic layer was washed with water (3×50 ml), dried over sodium sulfate and the solvent was removed via vacuum. The residue was purified by column chromatography using ethyl acetate/methanol (90/10) as the eluent. The product is the mixture of cis and trans-1-[N-Boc-2-(3-(R)-hydroxy-1-pyrrolidinyl)-ethylamino]-4-(3-cyanophenyl)-cyclohexane (0.25 g, 77%).

Step 5

The mixture of cis and trans-1-[N-Boc-2-(3-(R)-hydroxy-1-pyrrolidinyl)-ethylamino]-4-(3-cyanophenyl)-cyclohexane (0.25 g, 0.61 mmole) was dissolved in 15 ml 4N hydrogen chloride in dioxane. The solution was stirred at room temperature for one hour. The solvent was removed and the residue was partitioned between 50 ml methylene chloride and 50 ml saturated sodium bicarbonate. The organic layer was washed with water (2×50 ml) and dried over sodium sulfate. After the solvent was removed, the residue was used in the next step without further purification. The product is the mixture of cis and trans-1-[2-(3-(R)-hydroxy-1-pyrrolidinyl)-ethylamino]-4-(3-cyanophenyl)-cyclohexane (0.18 g, 95%)

Step 6

The mixture of cis and trans-1-[2-(3-(R)-hydroxy-1-pyrrolidinyl)-ethylamino]-4-(3-cyanophenyl)-cyclohexane (60 mg, 0.19 mmole) and 3-chloro-4-fluoro phenylisocyanate (50 mg, 0.29 mmole) was stirred in 5 ml methylene chloride at room temperature overnight. The reaction solution was loaded directly onto a preparative TLC plate and the plate was developed in ethyl acetate/hexane(85/15). Two products were isolated from the plate; N'-(3-chloro-4-fluorophenyl)-N-[cis-4-(3-cyanophenyl)-cyclohexyl]-N-[2-(3-(R)-hydroxy-1-pyrrolidinyl)ethyl]urea (35.9 mg HCl salt, 36%) 10H NMR (300 MHz, CDCl3) δ 10.73 (s, 1H), 7.58-7.71 (m, 4 H), 7.42-7.53 (m, 2 H), 7.03 (t, J=9.8 Hz, 1 H), 4.48 (m, 1 H), 4.29 (tt, J=12.0 and 4.0 Hz, 1 H), 3.00-3.17 (m, 4 H), 2.66-2.85 (m, 4 H), 1.76-2.52 (m, 8 H), 1.60-1.70 (m, 2 H0, 1.30-1.45 (m, 2 H) and N'-(3-chloro-4-fluorophenyl)-N-[trans-4-(3-cyanophenyl)-cyclohexyl]-N-[2-(R-3-hydroxy-1-pyrrolidinyl)ethyl]urea (38.6mg HCl salt, 39%). 1H NMR (300 MHz, CDCl3) δ 10.73 (s, 1 H), 7.67-7.73 (m, 2 H), 7.36-7.51 (m, 4H), 7.03 (t, J=9.8 Hz, 1 H), 4.51 (m, 1 H), 4.24 (tt, J=12.0 and 4.0 Hz, 1 H), 3.35 (t, J=4.0 Hz, 2 H), 3.10 (m, 1 H), 2.75-2.90 (m, 4 H), 2.52 (m, 2 H), 2.22 (m, 1 H), 1.80-2.00 (m, 6 H), 1.45-1.70 (m, 4 H).

Following procedures similar to those described in Example 102, the following compounds were prepared.

| Ex | STRUCTURE | HRMS Mass (M + 1) | | NMR |
|---|---|---|---|---|
| 103 | 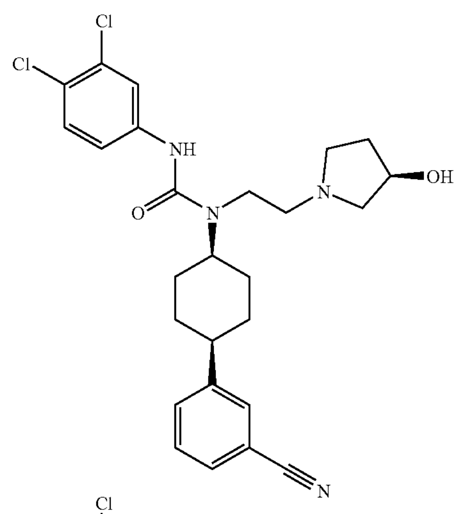 | 500 | 501.1837 | |
| 104 | 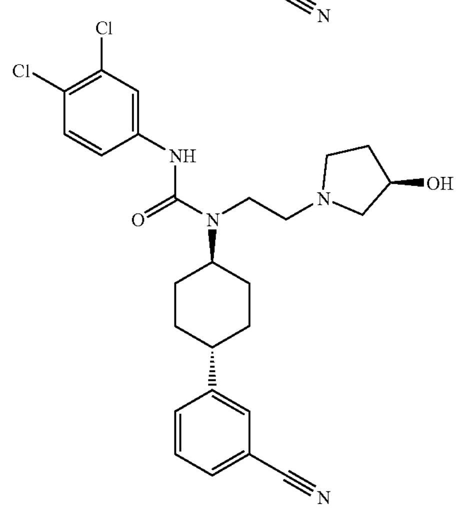 | 500 | 501.1832 | |

-continued
| Ex | STRUCTURE | HRMS Mass (M + 1) | NMR |
|---|---|---|---|
| 105 | 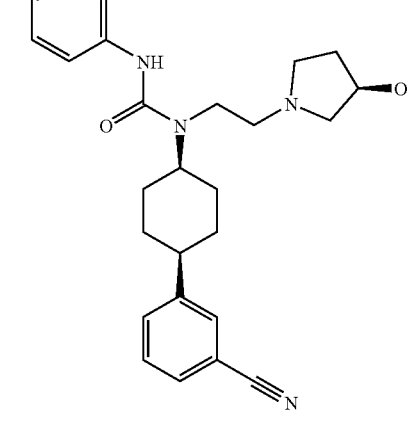 | 484 485.2125 | |
| 106 | 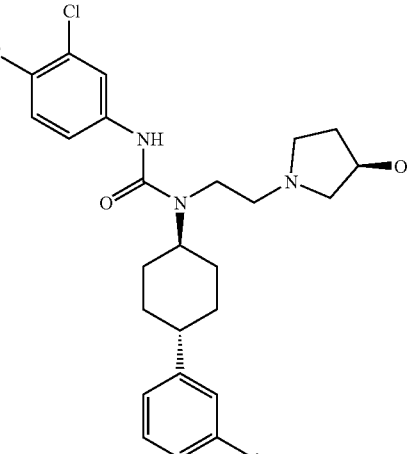 | 484 485.2125 | |
| 107 | 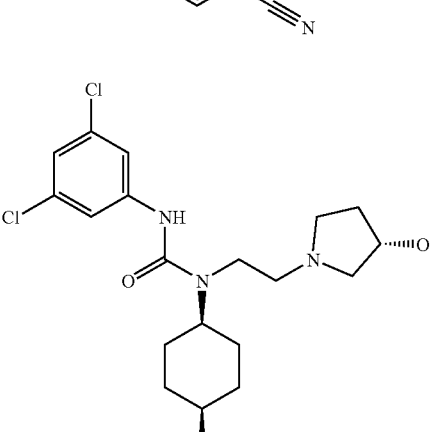 | 500 501.1832 | |

-continued

| Ex | STRUCTURE | HRMS Mass (M + 1) | NMR |
|---|---|---|---|
| 108 | 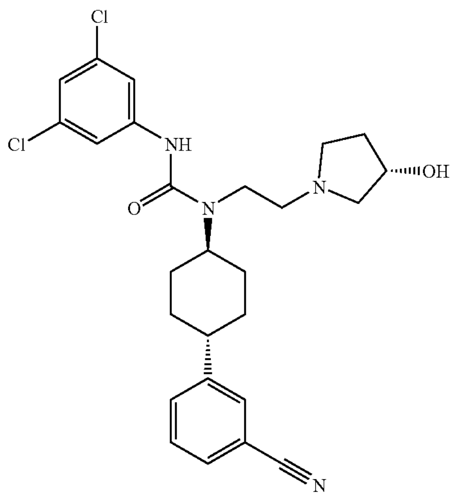 | 500 501.1827 | |
| 109 | 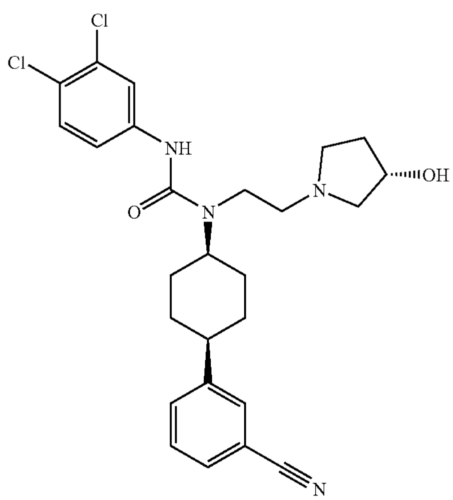 | 500 501.1832 | |
| 110 | 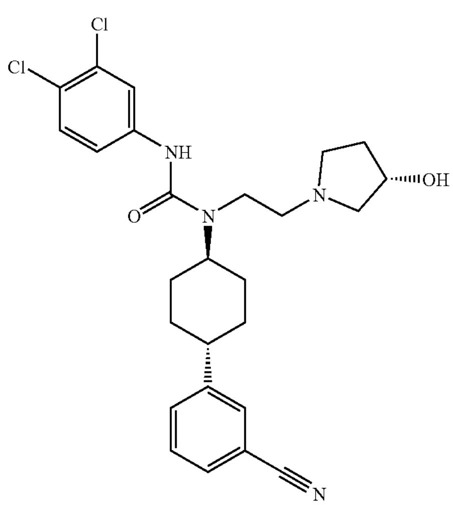 | 500 501.1832 | |

-continued

| Ex | STRUCTURE | HRMS Mass (M + 1) | NMR |
|---|---|---|---|
| 111 | 3,5-dichlorophenyl-NH-C(O)-N(CH₂CH₂-[(3R)-3-hydroxypyrrolidin-1-yl])-(trans-cyclohexyl)-3-cyanophenyl | 108 500 | |
| 112 | 4-fluoro-3-(trifluoromethyl)phenyl-NH-C(O)-N(CH₂CH₂-[(3R)-3-hydroxypyrrolidin-1-yl])-(trans-cyclohexyl)-3-cyanophenyl | 518 519.2377 | |
| 113 | 3-chloro-4-fluorophenyl-NH-C(O)-N(CH₂CH₂-[(3R)-3-hydroxypyrrolidin-1-yl])-(trans-cyclohexyl)-3-cyanophenyl | 484 485.2125 | |

| Ex | STRUCTURE | HRMS Mass (M + 1) | NMR |
|---|---|---|---|
| 114 | (3-chloro-4-fluorophenyl)-urea with cyclohexyl-3-cyanophenyl and N-ethyl-(3-hydroxypyrrolidinyl) | 484  485.2121 | |
| 115 | (4-chloro-3-trifluoromethylphenyl)-urea with cyclohexyl-3-cyanophenyl and N-ethyl-(3-hydroxypyrrolidinyl) | 534  535.2091 | |
| 116 | (4-chloro-3-trifluoromethylphenyl)-urea with cyclohexyl-3-cyanophenyl and N-ethyl-(3-hydroxypyrrolidinyl) | 534  535.2085 | |

|    |              | HRMS        |     |
|----|--------------|-------------|-----|
| Ex | STRUCTURE    | Mass (M + 1)| NMR |
| 117 | | 518 | 519.1(LCMS) |
| 118 | | 518 | 519.2389 |
| 119 | | 468 | 469.1(LCMS) |

-continued

| Ex | STRUCTURE | HRMS Mass (M + 1) | NMR |
|---|---|---|---|
| 120 | (3,4-difluorophenyl urea derivative) | 468  469.2414 | |
| 121 | (3,5-difluorophenyl urea derivative) | 468  469.241 | |
| 122 | (3,5-difluorophenyl urea derivative) | 468  469.241 | |

Method 5

Example 123

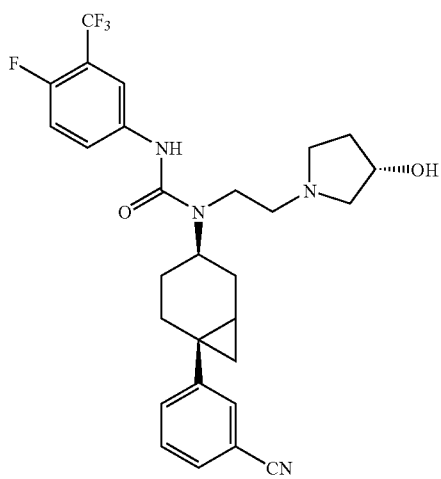

123a

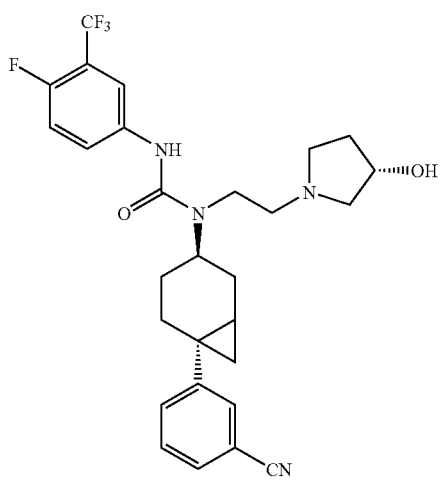

123b a. Preparation of N-(2-aminoethyl)-3-(S)-hydroxy-pyrrolidine

Step 1

3-(S)-hydroxypyrrodine(0.5 g, 5.7 mmole), 1.0 g of iodoacetonitrile (1.0 g, 6.0 mmole) and potassium carbonate (2.4 g, 17.4 mmole were stirred in 20 ml methylene chloride at room temperature overnight. The reaction mixture was filtered and the solid was washed with methylene chloride. The combined organic solution was rotavaped to dryness to afford an oil which is N-(cyanomethyl)-3-(S)-hydroxy-pyrrolidine (0.60 g, yield 84%). This product was used in the step without further purification.

Step 2

The nitrile intermediate obtained from Step 1 was dissolved in 20 ml dry THF and the solution cooled to −20° C. Lithium aluminum hydride (1.0 M in THF, 10 mL) was added dropwise to the above solution. After the lithium aluminum hydride was added, the reaction solution was heated at 75° C. for 2 hrs. The reaction was cooled to −78° C. and quenched with 5 ml of MeOH. The reaction was warmed to room temperature and filtered through a celite cake. The filtrate was concentrated to dryness and 80 ml of methylene chloride was added. The solution was filtered through celite again and the filtrate was concentrated. The desired product N-(2-aminoethyl)-3-(S)-hydroxy-pyrrolidine (0.24 g, 39%) was used in the next step without further purification.

b. Preparation of 6-(3-cyanophenyl)bicyclo[4.1.0]heptane-3-one

Step 1

4-(3-cyanophenyl)-3-cyclohexene-1-one (from step 1 of method 2, 1.8 g, 9.0 mmole), ethylene glycol (2.8 g, 45 mmole) and p-toluenesulfonic acid monohydrate (0.1 g, 0.5 mmole) were dissolved in 50 ml toluene. The reaction was refluxed for 2 hours. The organic layer was washed with water (2×50 mL) and dried over sodium sulfate. The residue from the organic layer was purified by column chromatography using ethyl acetate/hexane (15/85) as the eluent to afford 4-(3-cyanophenyl)-3-cyclohexene-1-one ethylene ketal(1.9 g, 87%).

Alternate Step 1:

4-(3-Cyanophenyl)-4-hydroxycyclohexane-1-one ethylene ketal (from step 1 of method 1, 20 g, 77 mmole) and Triethylamine (15.6 g, 154 mmole) were dissolved in 500 ml methylene chloride. Mesyl chloride (9.7 g, 85 mmole) in 100 ml methylene chloride was then added dropwise in one hour. The mixture was stirred at room temperature for five hours. Additional triethylamine and mesyl chloride (same amount as the first time) were added, and the reaction was stirred at room temperature for 1 more hour. 200 ml saturated sodium bicarbonate solution was added to quench the reaction. The organic layer was washed with water (2×200ml), dried over sodium sulfate and solvent was removed. The residue was recrystallized from ethyl acetate/hexane to give rise to 9.1 g pure product. Column purification of the compound in filtrate with ethyl acetate/hexane (80/20) give rise to additional 7.8 g pure product, 4-(3-Cyanophenyl)-3-cyclohexene-1-one ethylene ketal (total yield:16.9 g, 91%).

Step 2

Diethylzinc(1 M in hexane, 19 ml, 19 mmole) was mixed with 50 ml methylene chloride and the mixture was cooled to 0° C. Trifluoroacetic acid (2.1 g, 19 mmole) in 20 mL methylene chloride was added. The mixture was stirred at 0° C. for 20 minutes. Diiodomethane (5 g, 19 mmole) in 10 ml methylene chloride was then added, followed by 4-(3-cyanophenyl)-3-cyclohexene-1-one ethylene ketal (1.5 g, 6.2 mmole) in 20 mL methylene chloride. The mixture was stirred at room temperature overnight. 50 ml 1N hydrogen chloride solution was added to quench the reaction. The organic layer was separated, washed with water (2×50 mL) and dried over sodium sulfate. The product was purified by column using ethyl acetate/hexane (10/90) as the eluent to afford 6-(3-cyanophenyl)bicyclo[4.1.0]heptane-3-one ethylene ketal (0.8 g, 50%).

Step 3

6-(3-cyanophenyl)bicyclo[4.1.0]heptane-3-one ethylene ketal (0.8 g, 3.1 mmole) was stirred in 20 ml methylene chloride/trifluoroacetic acid (1/1) for 30 minutes. The solvent was removed and the residue was partitioned between 100 ml ethyl acetate and 100 ml saturated sodium carbonate solution. The organic layer was washed with water (2×50 mL), dried with sodium sulfate and the solvent was removed by vacuum. The product was purified by column using ethyl acetate/hexane (10/90) as the eluent. (0.56 g, 85%).

Step 4

The products from procedure (a) and (b) are converted to the title compounds using the same procedure as steps 4 and 5 of method 2, 123a: 1H NMR (300 MHz, CDCl3) δ 10.75 (s, 1 H), 7.67-7.73 (m, 2H), 7.33-7.53 (m, 4 H), 7.05 (t, J=9.3 Hz), 4.53 (m, 1 H), 4.15 (tt, J=11.5 and 3.8 Hz, 1 H), 3.35 (m, 2 H), 3.11 (m, 1 H), 2.75-2.92 (m, 4 H), 2.55 (m, 1 H), 1.36-2.30 (m, 9 H), 1.08 (dd, J=9.3 and 4.9 Hz, 1 H), 0.84 (t, J=5.5 Hz, 1 H).

123b: 1H NMR (300 MHz, CDCl3) δ 10.71 (s, 1 H), 7.67-7.78 (m, 2 H), 7.34-7.53 (m, 4 H), 7.05 (t, J=9.3 Hz), 4.53 (m, 1 H). 4.21 (m, 1 H), 3.27 (m, 2 H), 3.10 (m, 1 H), 2.72-2.92 (m, 4 H), 2.55 (m, 1 H), 1.36-2.30 (m, 9 H), 0.99 (dd, J=9.3 and 4.9 Hz, 1 H), 0.76 (t, J=5.5 Hz, 1 H).

Following procedures similar to those described in Example 123, the following compounds were prepared.

| Ex | STRUCTURE | HRMS Mass (M + 1) | | NMR |
|---|---|---|---|---|
| 124 | 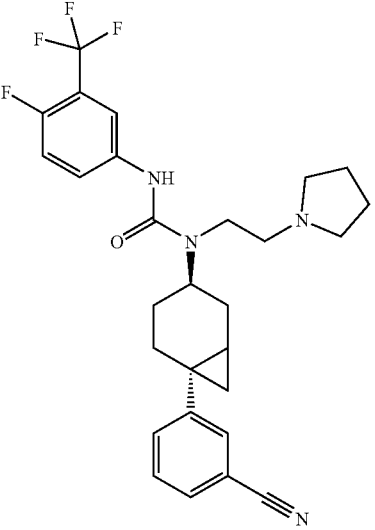 | 514 | 515.2427 | 1H NMR (300 MHz, CDCl3) 11.2(s, 1H), 7.62-7.68(m, 1H), 7.34-7.56(m, 5H), 7.08(t, J=9.5 Hz), 4.24(m, 1H), 3.27(m, 2H), 2.72-2.81(m, 6H), 2.24-2.44(m, 2H), 2.08-2.18(m, 1H), 1.90(br, 4H), 1.52-1.64(m, 2H), 1.26-1.44(m, 2H), 0.99(dd, J=9.3 and 4.8Hz, 1H), 0.76(t, J=4.8Hz, 1H). |
| 125 | 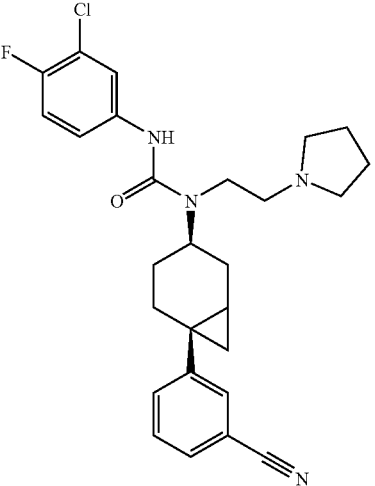 | 480 | 497.1882 | |

| 126 | 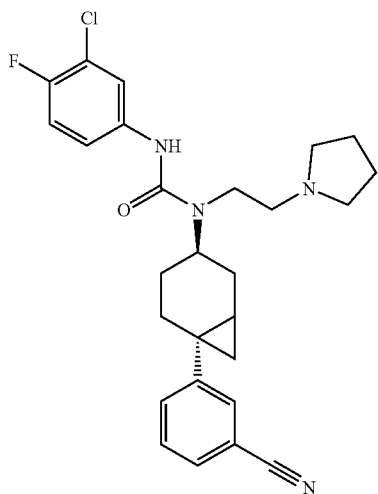 | 480 | 497.1882 | |
|---|---|---|---|---|
| 127 | 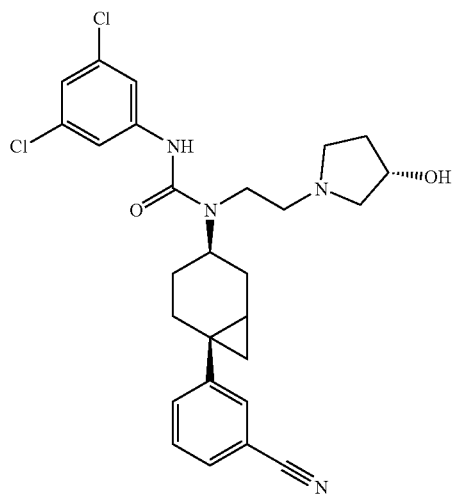 | 512 | 513.1828 | 1H NMR (300 MHz, CDCl3) 10.74(s, 1H), 7.62-7.68(m, 1H), 7.33-7.54(m, 5H), 6.91(t, J=1.65 Hz), 4.55(m, 1H), 4.13(tt, J=11.5 and 3.9Hz, 1H), 3.36(t, J=4.4Hz, 2H), 3.12(q, J=7.7Hz, 1H), 2.70-2.94(m, 4H), 2.57(q, J=7.7Hz, 1H), 2.20-2.32(m, 2H), 1.84-2.16(m, 4H), 1.36-1.56(m, 3H), 1.08(dd, J=9.3 and 4.9Hz, 1H), 0.84(t, J=5.5Hz, 1H). |
| 128 | 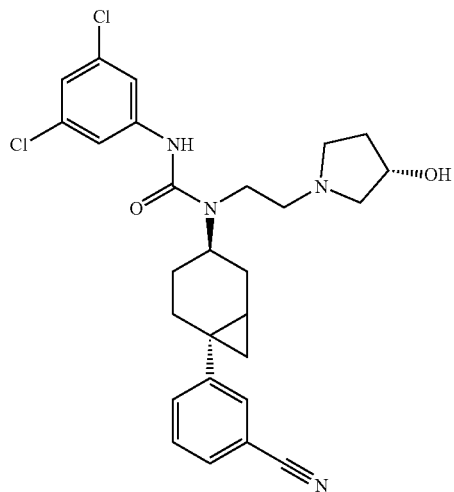 | 512 | 513.1828 | 1H NMR (300 MHz, CDCl3) 10.74(d, J=7.7Hz, 1H), 7.34-7.53(m, 6H), 6.91(t, J=1.7 Hz), 4.5(m, 1H), 4.19(m, 1H), 3.24(m, 2H), 3.09(m, 1H), 2.72-2.94(m, 4H), 2.46-2.62(m, 1H), 1.84-2.40(m, 5H), 1.51-1.70(m, 2H), 1.26-1.43(m, 2H), 0.99(dd, J=9.3 and 4.9Hz, 1H), 0.84(t, J=5.5Hz, 1H). |

-continued
| 129 | 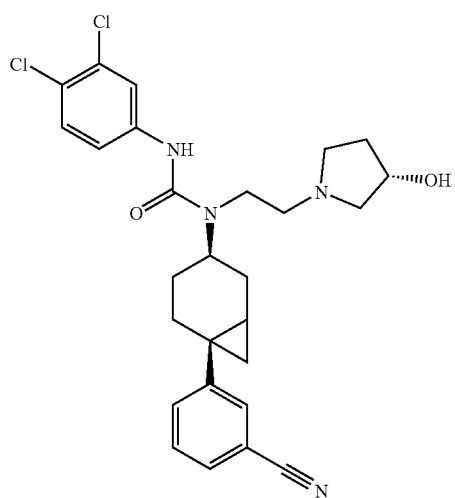 | 512 | 513.1833 |
| 130 | 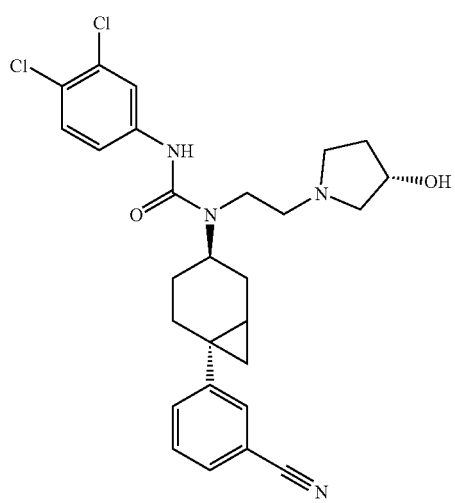 | 512 | 513.1833 |
| 131 | 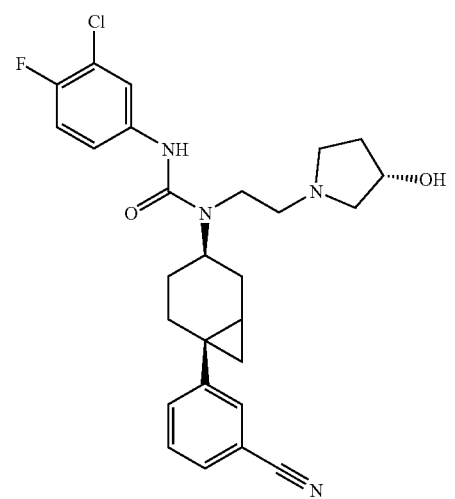 | 496 | 497.2123 |

-continued
| 132 | 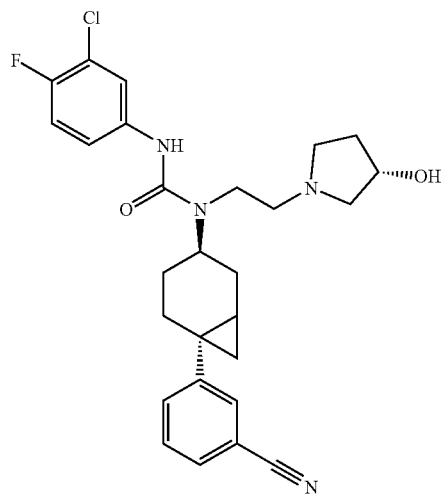 | 496 | 497.2123 |
| 133 | 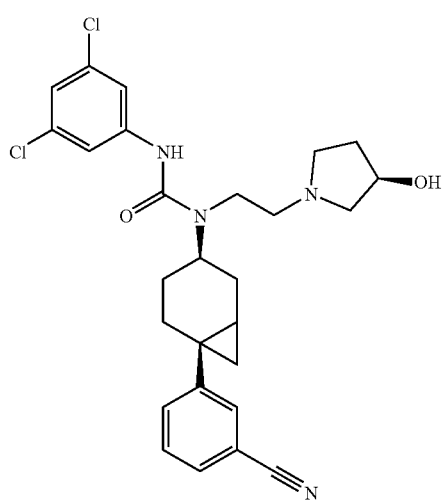 | 513 | 513.1833 |
| 134 | 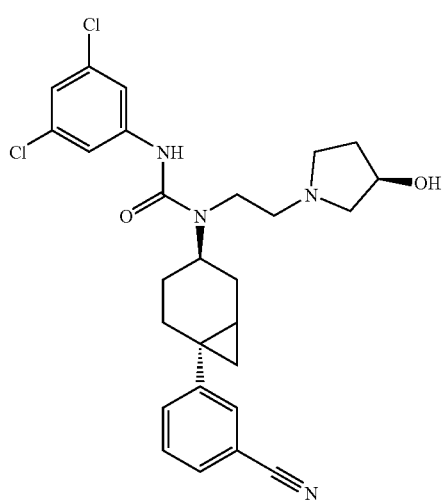 | 513 | 513.816 |

| | | | |
|---|---|---|---|
| 135 | 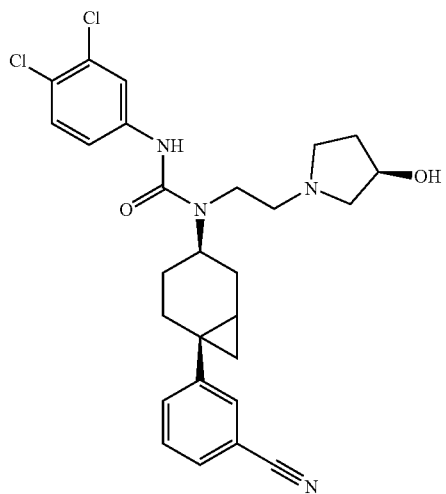 | 513 | 513.1833 |
| 136 | 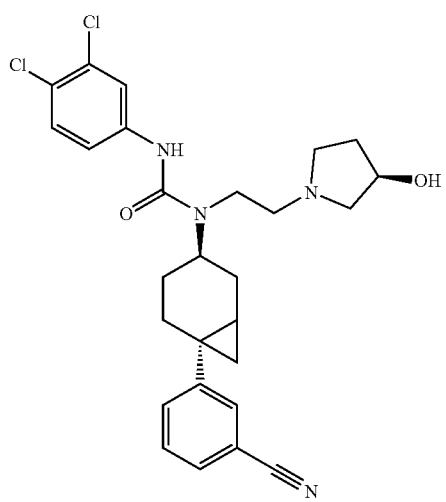 | 513 | 513.1828 |
| 137 | 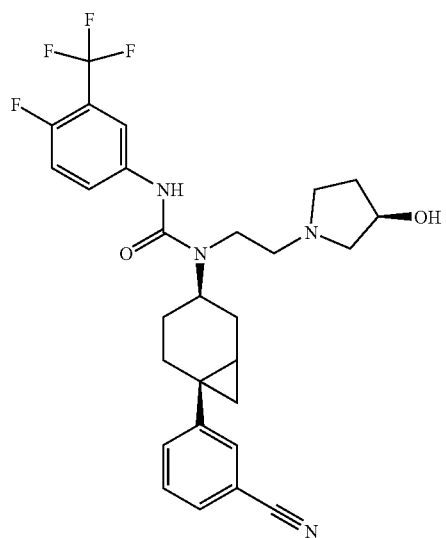 | 531 | 531.2373 |

-continued
| | | | |
|---|---|---|---|
| 138 | 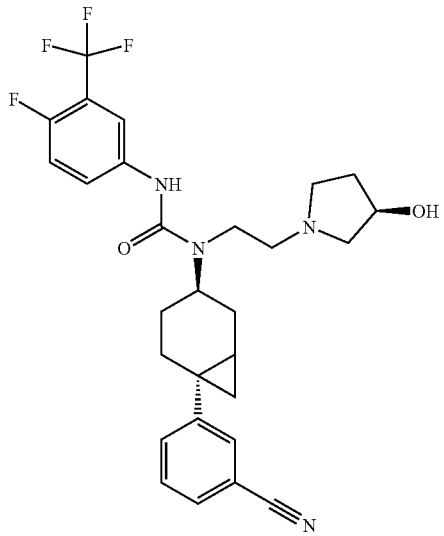 | 531 | 531.2373 |
| 139 | 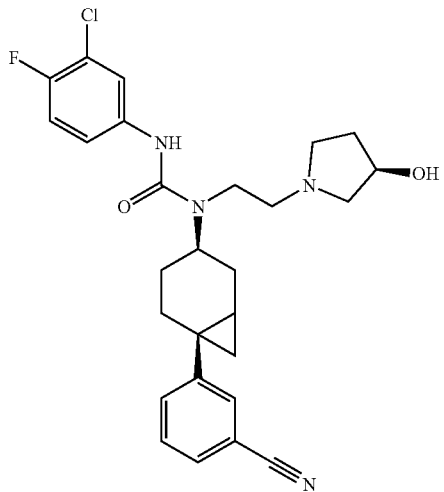 | 497 | 497.2126 |
| 140 | 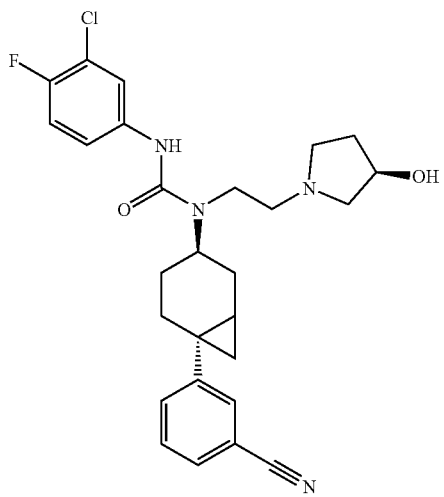 | 497 | 497.2125 |

|     |     | HRMS | LCMS |
| --- | --- | --- | --- |
| 141 | 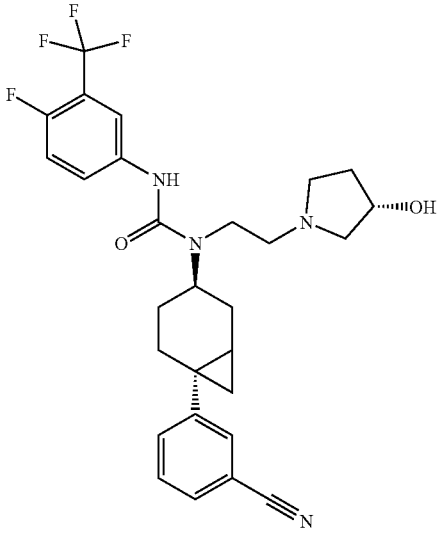 | | LC rt = 5.94 min.<br>Spec. rotation = −35.16 Deg. |
| 142 | 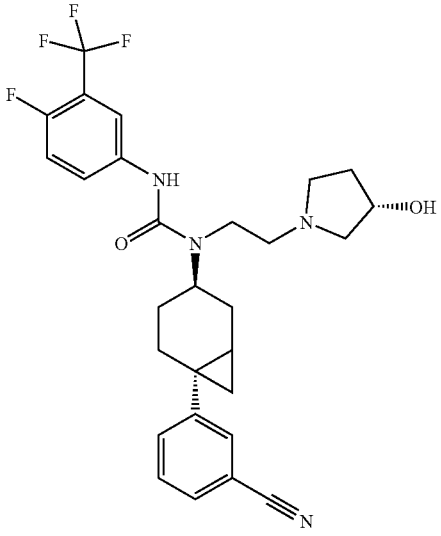 | | LC rt = 5. min.<br>Spec. rotation = 38.5 Deg. |
| 143 | 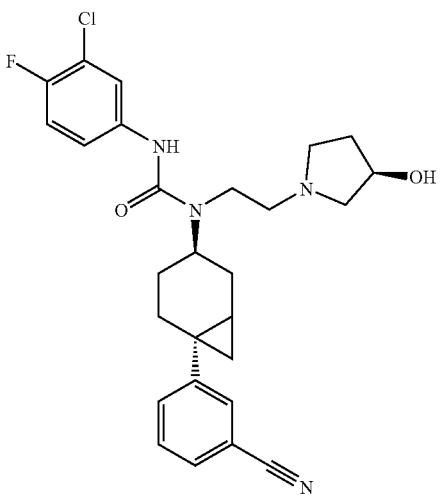 | | 497.10<br>rt = 5.11 min.<br>Spec. rotation = −43.77 Deg. |

-continued
| 144 | 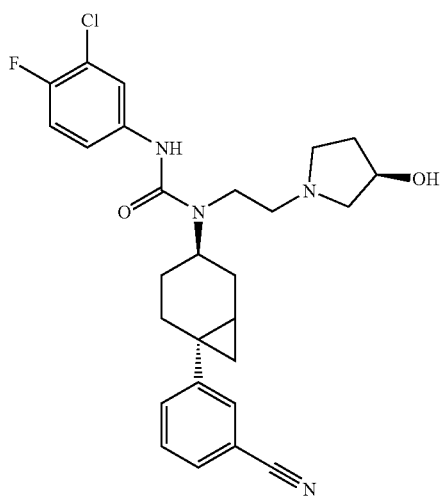 | | 497.10<br>rt = 5.16 min.<br>Spec. rotation = 41.51 Deg. |
|---|---|---|---|
| 145 | 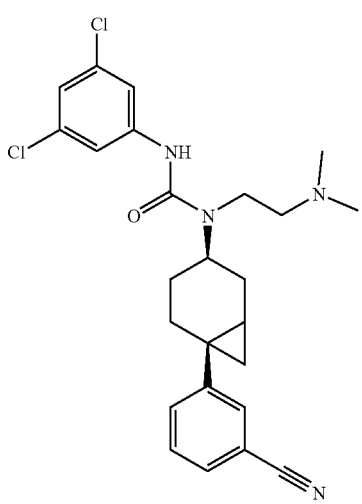 | 471.1721 | 471.1<br>rt = 5.31 min. |
| 146 | 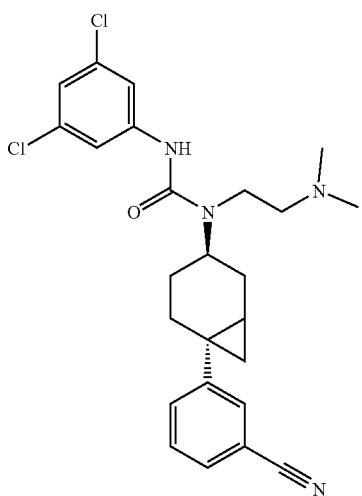 | 471.1721 | 471.1<br>rt = 5.35 min. |

-continued
| | | | |
|---|---|---|---|
| 147 | 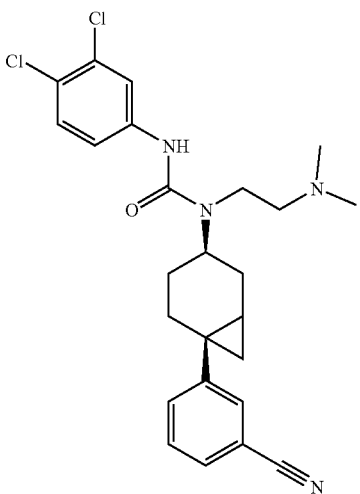 | 471.1721 | 471.1<br>rt = 5.21 min. |
| 148 | 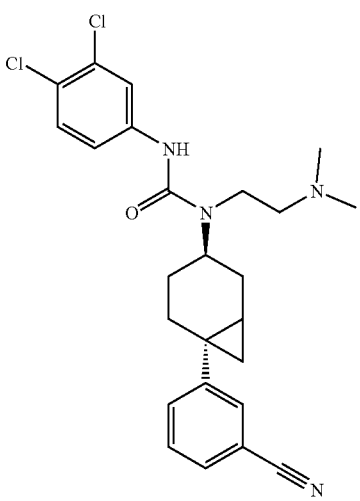 | 471.1721 | 471.1<br>rt = 5.21 min. |
| 149 | 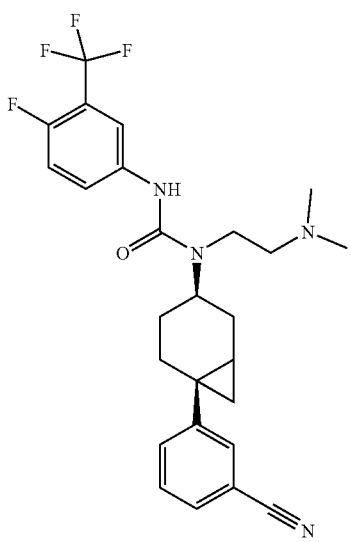 | 489.2289 | 489.1<br>rt = 5.08 min. |

| | | | |
|---|---|---|---|
| 150 | 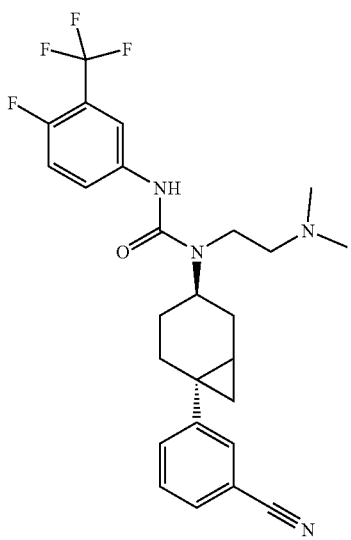 | 489.2289 | 489.1<br>rt = 5.08 min. |
| 151 | 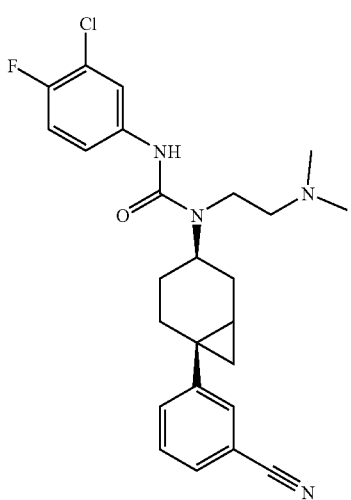 | 455.2009 | 455.1<br>rt = 4.95 min. |
| 152 | 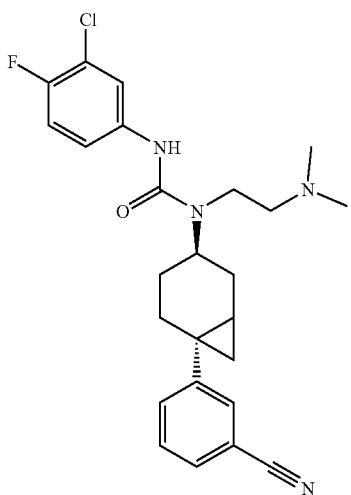 | 455.1998 | 455.1<br>rt = 4.98 min. |

-continued
| | | | |
|---|---|---|---|
| 153 | 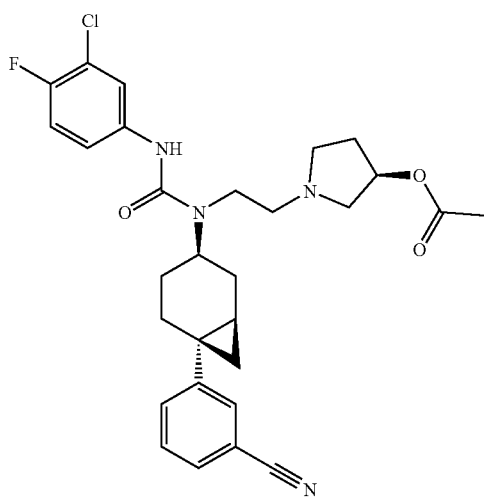 | 539.223 | 539.1 rt = 5.08 min. |
| 154 | 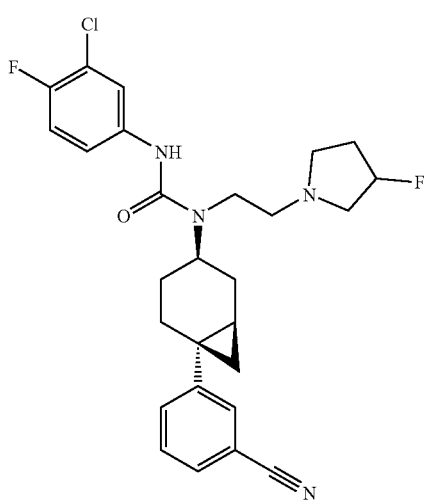 | | 499.1 rt = 5.28 min. |
| 155 | 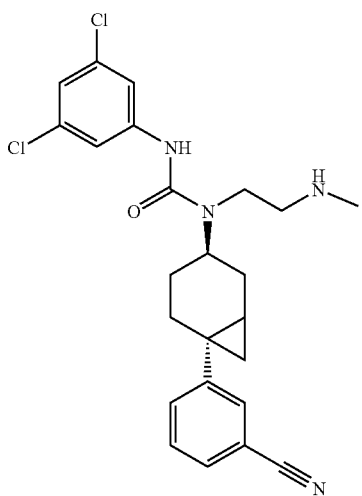 | | 457.1 rt = 5.28 min. |

| | | -continued | |
|---|---|---|---|
| 156 | 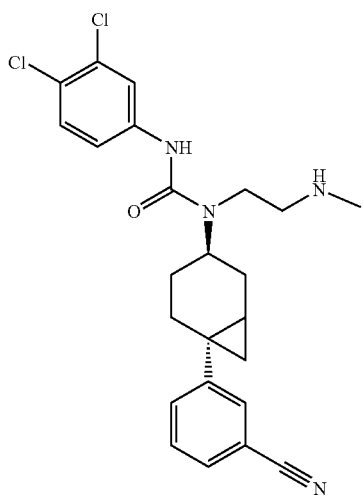 | | 457.1<br>rt = 5.29 min. |
| 157 | 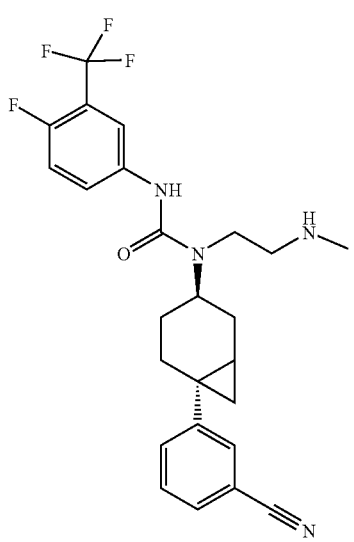 | | 475.1<br>rt = 5.05 min. |
| 158 | 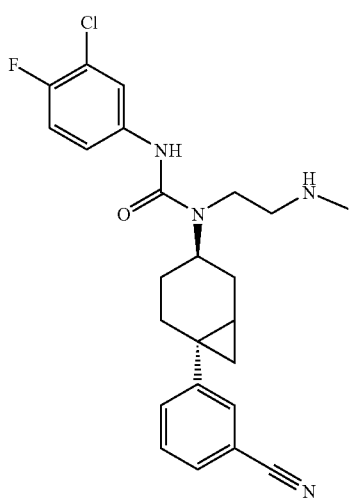 | | 441.1<br>rt = 5.01 min. |

-continued
| | | | |
|---|---|---|---|
| 159 | 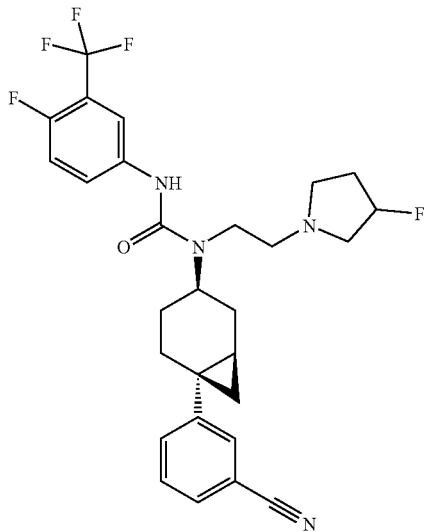 | 533.2338 | 533.1 rt = 5.25 min. |
| 160 | 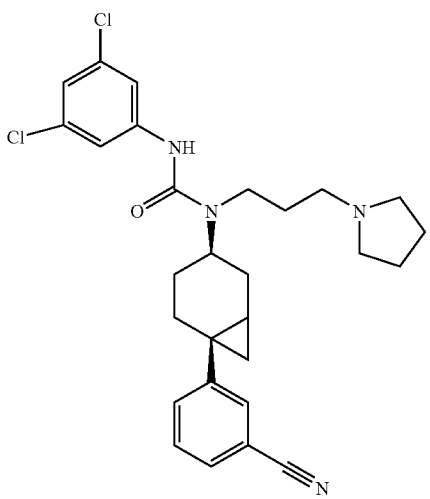 | 511.2024 | 511.1 rt = 5.85 min. |
| 161 | 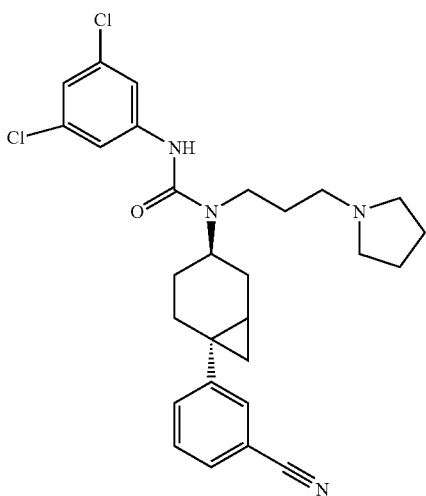 | 511.2024 | 511.1 rt = 6.02 min. |

-continued
| | | | |
|---|---|---|---|
| 162 | 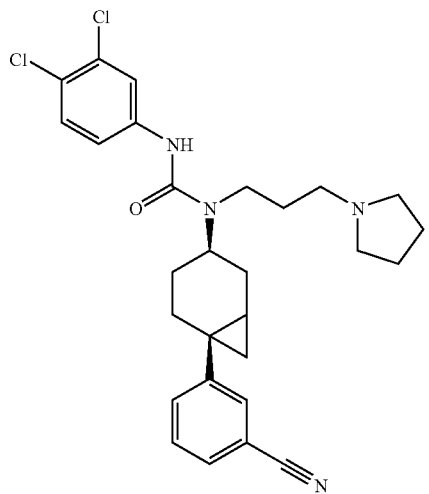 | 511.2024 | 511.1 rt = 5.78 min. |
| 163 | 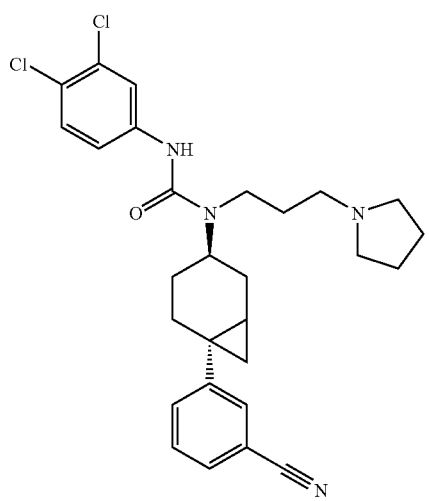 | 511.2024 | 511.1 rt = 6.02 min. |
| 164 | 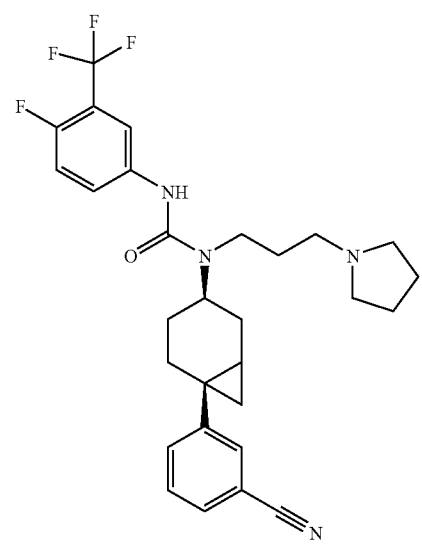 | 529.26 | 529.1 rt = 5.85 min. |

| | | | |
|---|---|---|---|
| 165 | 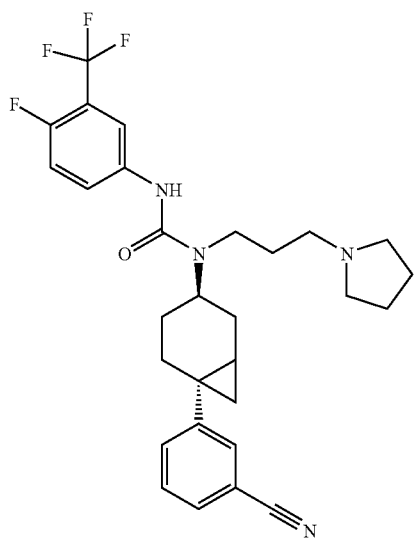 | 529.26 | 529.1 rt = 5.85 min. |
| 166 | 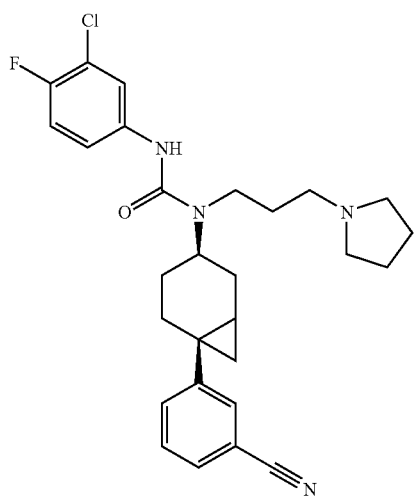 | 495.2331 | 495.1 rt = 5.55 min. |
| 167 | 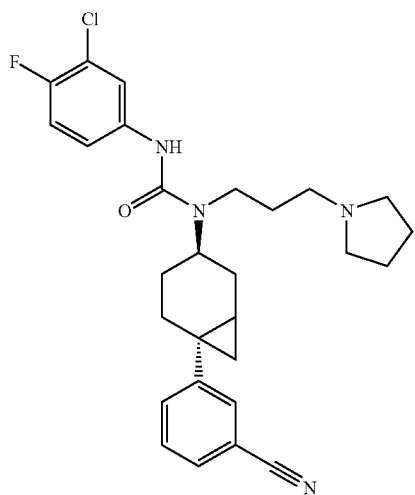 | 495.2331 | 495.1 rt = 5.72 min. |

-continued
| | | | |
|---|---|---|---|
| 168 | 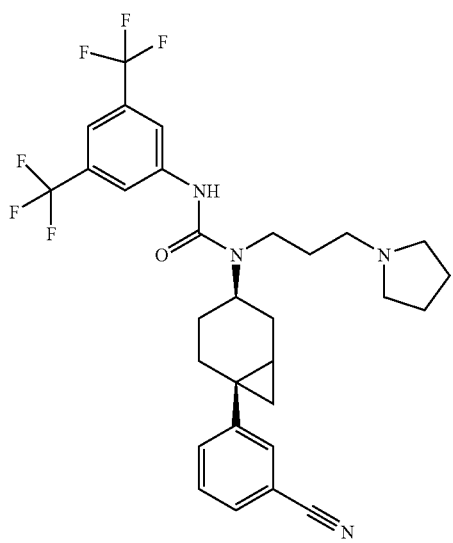 | 579.255 | 579.1 rt = 5.98 min. |
| 169 | 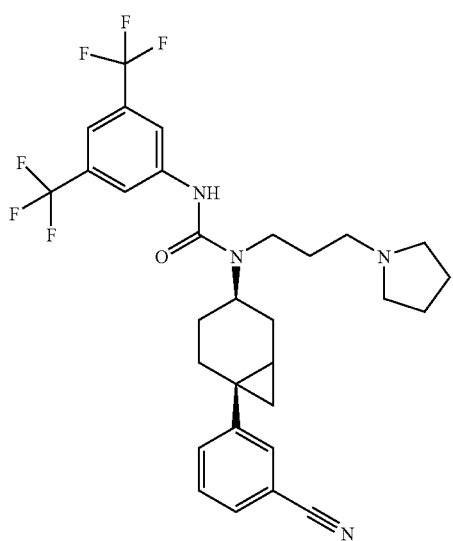 | 579.255 | 579.1 rt = 6.08 min. |
| 170 | 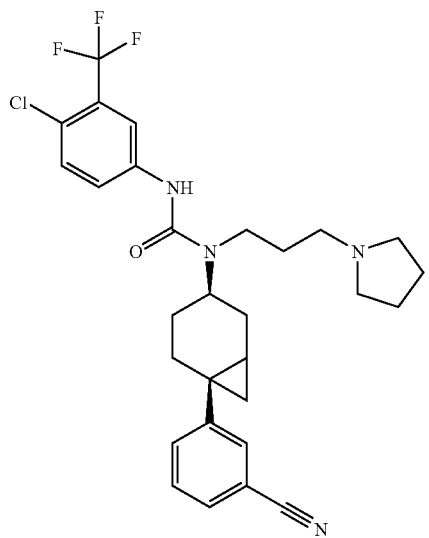 | 545.2303 | 545.1 rt = 5.88 min. |

-continued
| | | | |
|---|---|---|---|
| 171 | 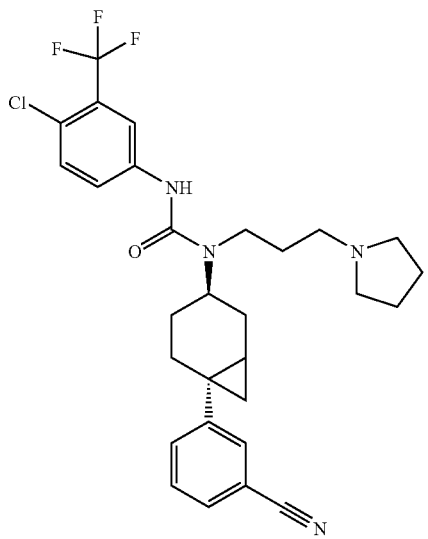 | 545.2295 | 545.1<br>rt = 6.05 min. |
| 172 | 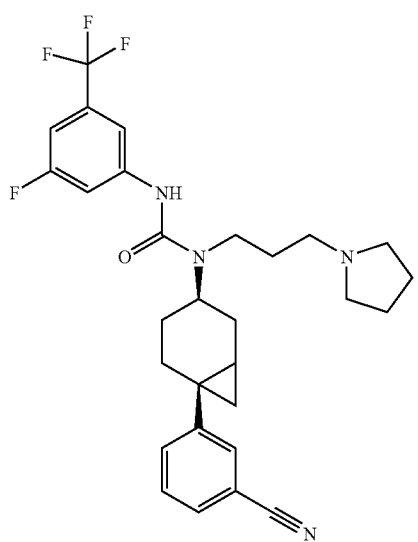 | 529.259 | 529.1<br>rt = 5.88 min. |
| 173 | 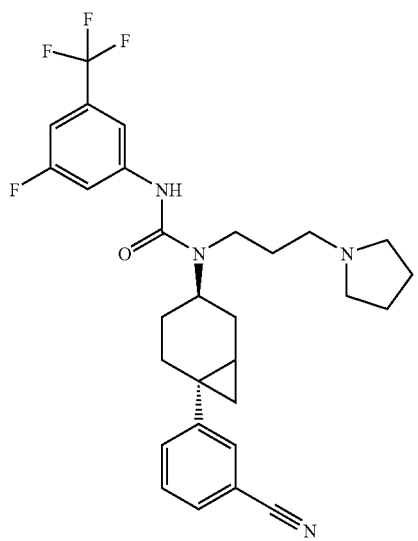 | 529.259 | 529.1<br>rt = 5.92 min. |

| | | | |
|---|---|---|---|
| 174 | 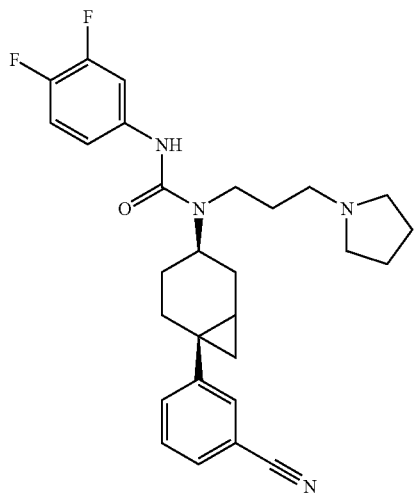 | 479.2622 | 479.1<br>rt = 5.52 min. |
| 175 | 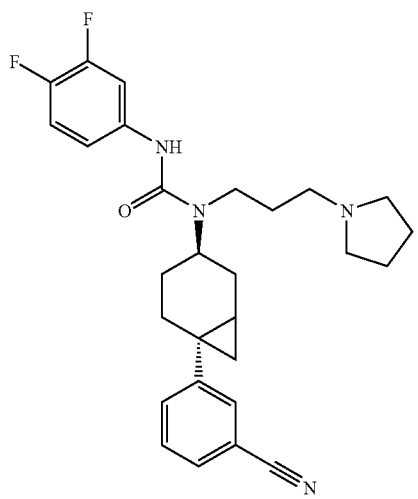 | 479.2622 | 479.1<br>rt = 5.72 min. |
| 176 | 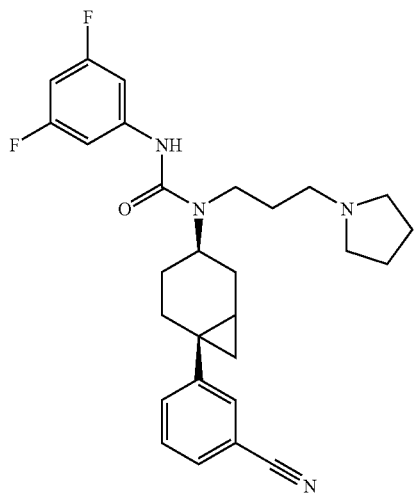 | 479.26 | 479.1<br>rt = 5.65 min. |

| | | | |
|---|---|---|---|
| 177 | 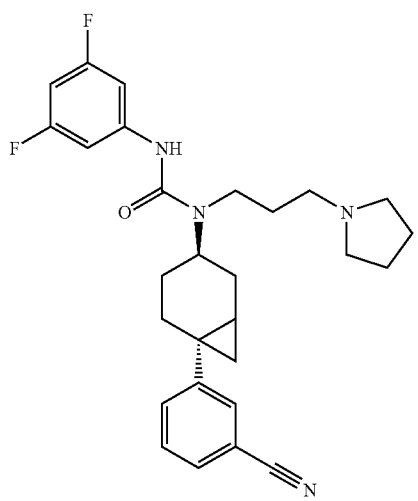 | 479.2622 | 479.1 rt = 5.72 min. |
| 178 | 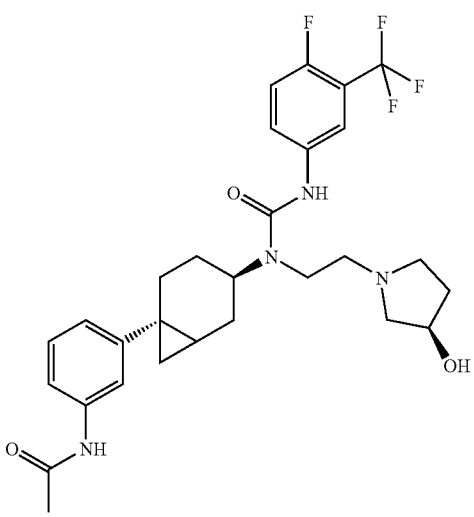 | RT = 5.05 min M/e = 563.1 | 563.2664 |
| 179 | 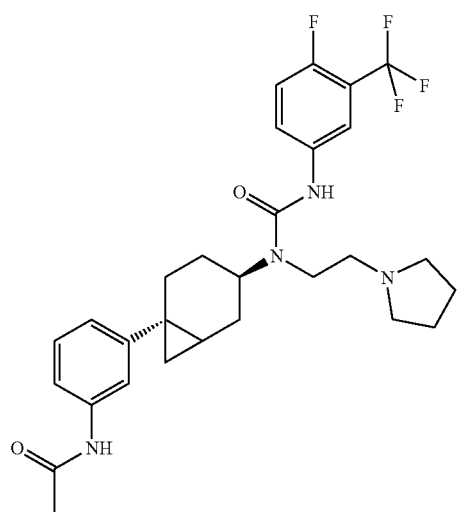 | RT = 5.3 min M/e = 547.1 | 547.2693 |

-continued
| 180 | 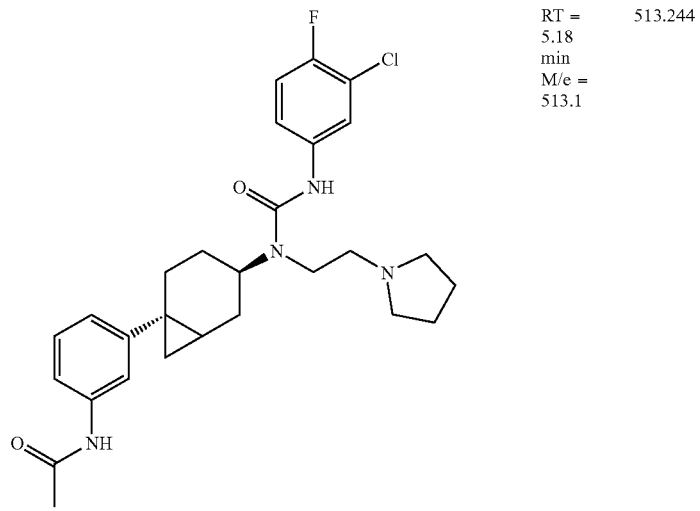 | RT = 5.18 min M/e = 513.1 | 513.244 |
| 181 | 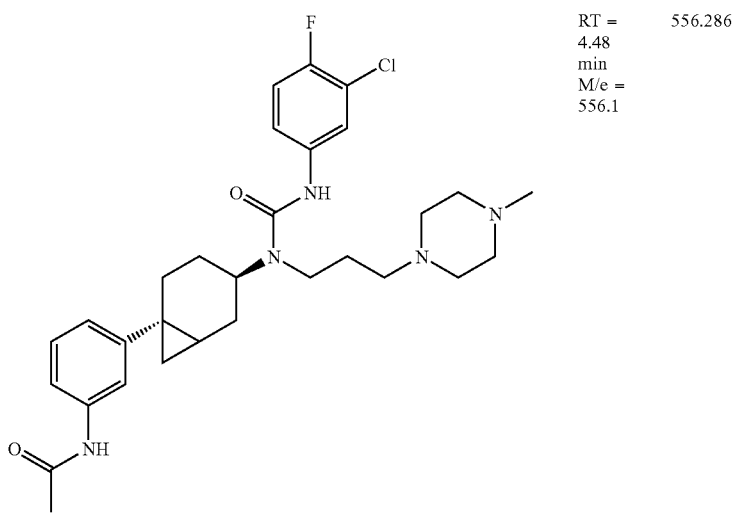 | RT = 4.48 min M/e = 556.1 | 556.286 |
| 182 | 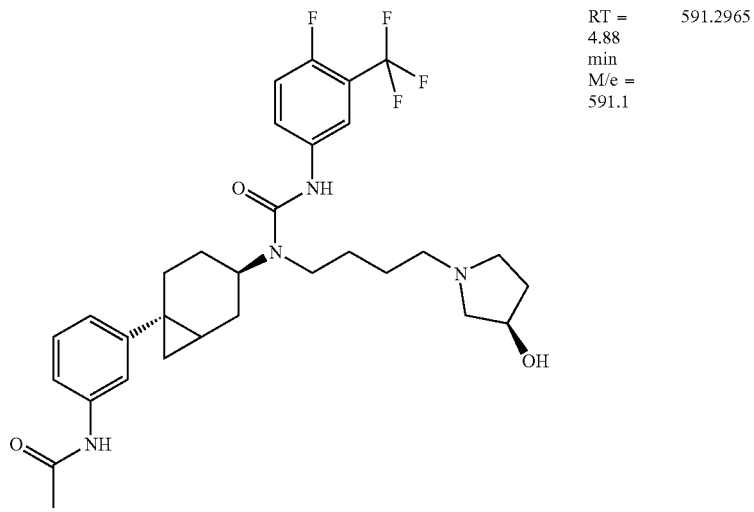 | RT = 4.88 min M/e = 591.1 | 591.2965 |

-continued
| 183 | 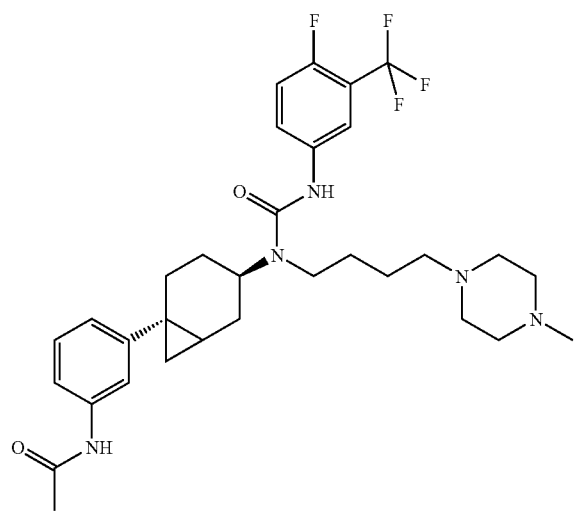 | RT = 4.85 min M/e = 604.1 | 604.3269 |
| --- | --- | --- | --- |
| 184 | 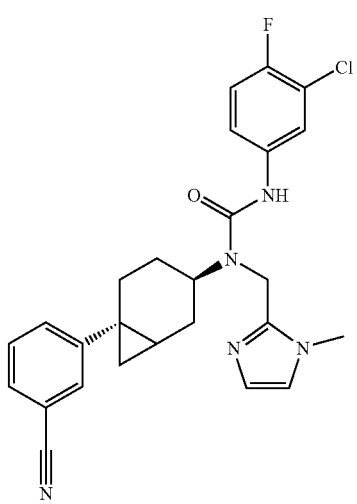 | RT = 5.28 min M/e = 478.1 | 478.1805 |
| 185 | 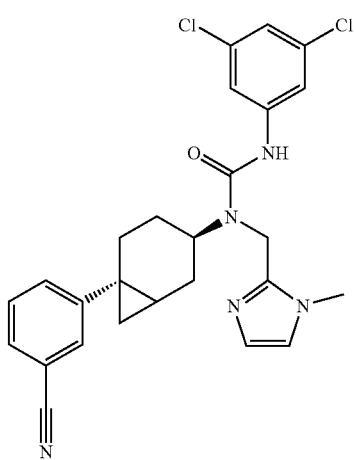 | RT = 5.48 min M/e = 494.1 | 494.152 |

Experimental Procedures:

Example 186

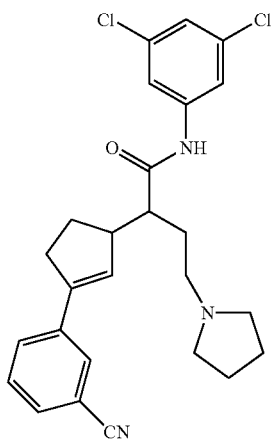

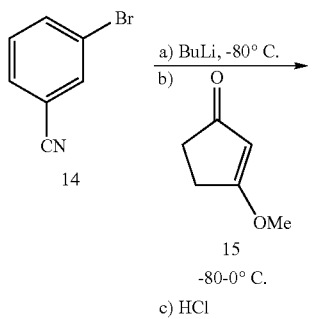

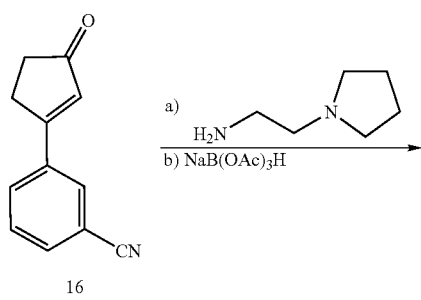

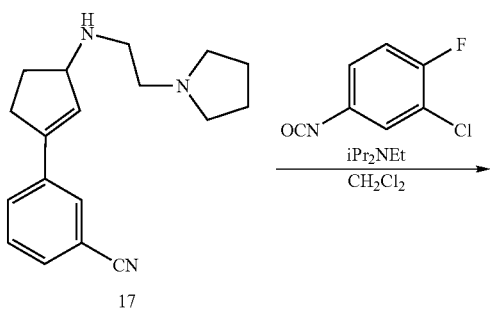

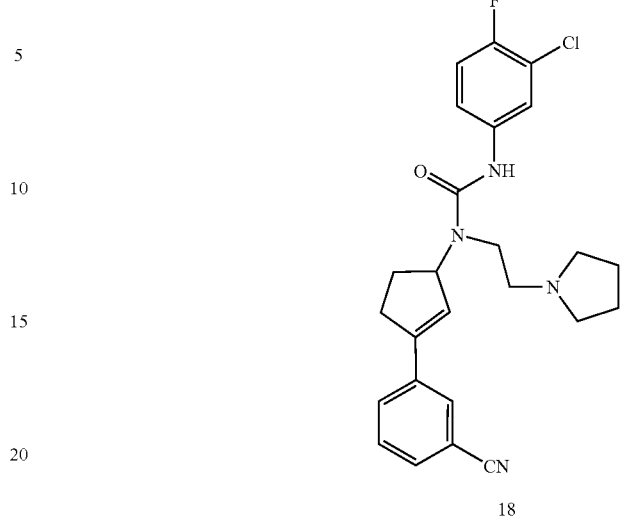

Step 1:

A solution of 3-bromobenzonitrile (26.8 g, 147.1 mmol) in THF (1000 mL) at −80° C. was treated with a solution of n-butyllithium (2.5 M in hexanes; 61.0 mL, 155 mmol) such that the reaction temperature remained ≦−78° C. After 15 min, a solution of 3-methoxy-2-cyclopenten-1-one (15 g, 134 mmol) in THF (80 mL) was added such that the reaction temperature remained ≦−78° C. The reaction mixture was warmed to −20° C. over 1.5 h, quenched with a solution of 1N HCl and concentrated in vacuo to remove THF. A solution of 1N HCl (100 mL) was added, the solution was stirred for 45 min. and extracted with EtOAc (3×). The combined organic extracts were washed with saturated aqueous $NaHCO_3$, brine, dried over $MgSO_4$, filtered and concentrated in vacuo. The residue was crystallized at 0° C. from a solution of 1N HCl, filtered, rinsed with cold 1N HCl, $H_2O$ and ether to provide 16 (14.4 g, 59%) as a pale yellow solid.

Step 2:

A solution of ketone 16 (120 mg, 0.66 mmol) in $CH_2Cl_2$ (7 mL) was treated with 1-(2-aminoethyl)pyrrolidine (110 μL, 0.86 mmol) followed by sodium triacetoxyborohydride (212 mg, 1.00 mmol). After 18 h, the reaction mixture was diluted with a solution of saturated $NaHCO_3$ and extracted with EtOAc (2×). The combined organic phases were dried and concentrated in vacuo. The crude product 17 was dissolved in dichloroethane (5 mL) and treated with diisopropylethyl amine (350 μL, 2.00 mmol) followed by 3,5-dichlorophenyl isocyanate (250 mg, 1.32 mmol). After 6 days, the reaction mixture was diluted with saturated aqueous $NaHCO_3$ and extracted with EtOAc. The organic phase was dried and concentrated in vacuo. Flash chromatography (95:4.5:0.5 $CH_2Cl_2$, MeOH, $NH_4OH$), followed by preparative thin layer chromatography (TLC) (5% MeOH/$CH_2Cl_2$) furnished 18 (11.5 mg, 3.7% over 2 steps) as a white solid: $^1$H NMR (300 MHz, $CDCl_3$) δ 11.46 (s, 1H), 7.71–7.44 (m, 4H), 7.33 (s, 2 H), 6.95 (s, 1 H), 6.12 (s, 1 H), 5.67 (m, 1 H) 3.41–3.17 (m, 2 H), 2.96–2.45 (m, 6 H), 2.10–1.77 (m, 4 H), 1.75–1.48 (m, 2 H), 1.30–1.25 (m, 2 H). 469.3, rt.=5.62 min (M+1), HRMS m/z 469.1568 [(M+H)$^+$].

Example 187

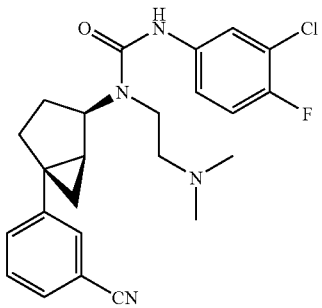

Step 1:
A solution of 16 (7.88 g, 43.0 mmol) in methanol (100 mL) at 0° C. was treated with $CeCl_3.7H_2O$ (20.5 g, 55.0 mmol) followed portionwise by $NaBH_4$ (2.10 g, 55.0 mmol). The reaction was warmed to ambient temperature over 12 h, quenched with saturated aqueous $NH_4Cl$ and concentrated to remove MeOH. The concentrate was diluted with $H_2O$ and extracted with EtOAc (3×). The combined organic extracts were washed with saturated aqueous $NaHCO_3$, brine, dried and concentrated in vacuo. Trituration (10% EtOAc/Hex) at 0° C. and filtration afforded 19 (6.39 g, 80%) as a white powder.

Step 2:
A solution of allylic alcohol 19 (0.50 g, 2.7 mmol) in $CH_2Cl_2$ (75 mL) was treated with $Et_2Zn$ (1.0 M in hexanes; 14 mL, 14 mmol). After 10 min, the reaction mixture was cooled to 0° C., treated with a solution of $CH_2I_2$ (1.13 mL, 14 mmol) in $CH_2Cl_2$ (10 mL) drop-wise over 10 min and allowed to warm to ambient temperature. After 48 h, the reaction mixture was quenched slowly with saturated aqueous $NH_4Cl$ and stirred 10 min. The reaction mixture was extracted with $CH_2Cl_2$ (2×), and the combined organic phases were washed with saturated aqueous $NaHCO_3$, dried and concentrated in vacuo. Flash chromatography (40% EtOAc/Hex) gave 20 (500 mg, 93%) as a clear oil.

Step 3:
A solution of alcohol 20 (0.50 g, 2.51 mmol) in $CH_2Cl_2$ (25 mL) at 0° C. was treated with pyridine (445 μL, 5.50 mmol) followed by Dess-Martin periodinane (2.12 g, 5.0 mmol) and warmed to ambient temperature. After 2 h, 3 drops of $H_2O$ were added. After 30 min further, the reaction was quenched with saturated aqueous $NaHCO_3$, saturated aqueous $Na_2SO_3$, and extracted with $CH_2Cl_2$ (3×). The combined organic phases were dried and concentrated in vacuo. Flash chromatography (25% EtOAc/Hex) gave 21 (440 mg, 89%) as a clear oil.

Step 4:
A solution of ketone 21 (65 mg, 0.33 mmol) in $CH_2Cl_2$ (1 mL) was treated with N,N-dimethylethylenediamine (55 μL, 0.494 mmol) followed by titanium tetraisopropoxide (118 μL, 0.396 mmol). After 18 h, the reaction mixture was diluted with MeOH (1 mL) and sodium borohydride (25 mg, 0.396 mmol) was added. After 2h further, the reaction mixture was diluted with a solution of saturated aqueous sodium/potassium tartrate and extracted with $CH_2Cl_2$ (4×). The combined organic phases were dried and concentrated in vacuo. The crude product 22 was dissolved in $CH_2Cl_2$ (1 mL) and treated with diisopropylethyl amine (122 μL, 0.70 mmol) followed by 3-chloro-4-fluorophenyl isocyanate (62 μL, 0.50 mmol). After 18 h, the reaction mixture was diluted with saturated aqueous $NaHCO_3$ and extracted with $CH_2Cl_2$ (3×). The combined organic phases were dried and concentrated in vacuo. Preparative thin layer chromatography (5% MeOH/$CH_2Cl_2$) furnished 23 (96 mg, 66% over 2 steps) as a clear oil: $^1H$ NMR (300 MHz, $CDCl_3$) δ 11.17 (s, 1 H), 7.51 (dd, J=6.6, 2.7 Hz, 1 H), 7.47–7.41 (m, 4 H), 7.11–6.96 (m, 2 H), 5.07 (ddd, J=11.0, 7.1, 3.9 Hz, 1 H), 3.47 (dd, J=14.8, 7.7 Hz, 1 H), 3.35 (dd, J=14.3, 4.4 Hz, 1 H), 2.70 (dd, J=13.7, 7.7 Hz, 1 H), 2.58 (dd, J=13.7, 4.9 Hz, 1 H), 2.42 (s, 6 H), 2.20–1.91 (m, 3 H), 1.71 (m, 1 H), 1.30–1.19 (m, 2 H), 0.94 (dd, J=7.1, 6.0 Hz, 1 H). LCMS: 441.1, rt.=4.65 min (M+1), HRMS m/z 441.1855 [(M+H)$^+$].

Following procedures similar to those described in Example 187, the following compounds were prepared:

| EX. | STRUCTURE | Mass | LCMS (M + 1) | HRMS (M + H)$^+$ |
|---|---|---|---|---|
| 188 | 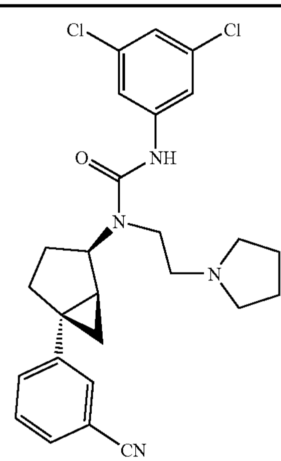 | 483.43 | 483.3, rt. = 5.52 min | 483.1722 |

| | | | | |
|---|---|---|---|---|
| 189 | 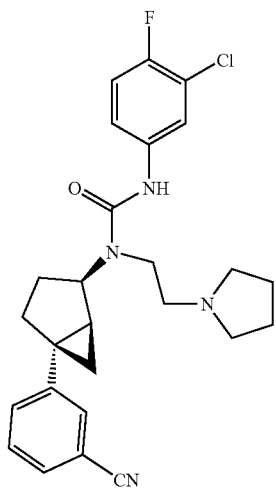 | 466.98 | 467.3, rt. = 5.25 min | 467.2020 |
| 190 | 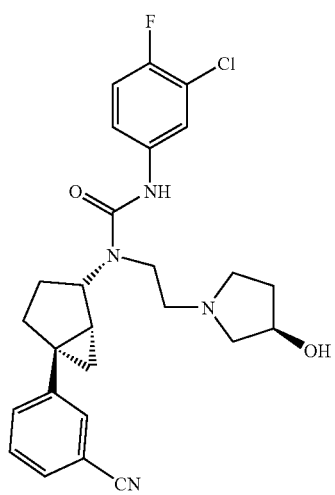 | 482.98 | 483.1, rt = 4.85 min. | 483.1960 |
| 191 | 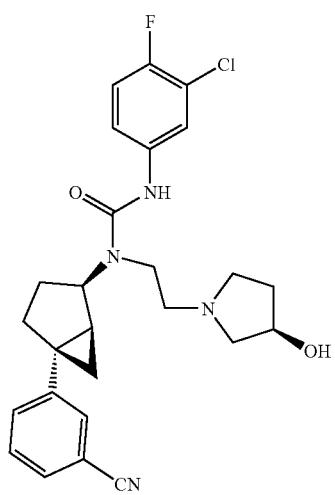 | 482.98 | 483.1, rt = 4.85 min. | 483.1960 |

| | | | | |
|---|---|---|---|---|
| 192 | 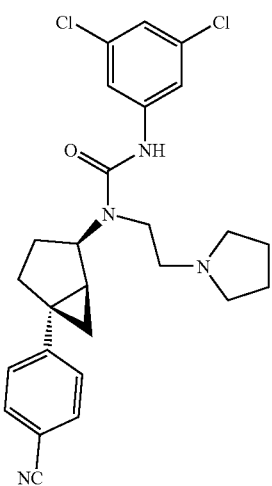 | 483.43 | 483.1, rt. = 5.28 min. | 483.1725 |
| 193 | 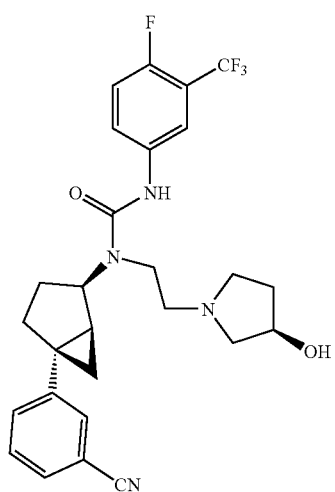 | 516.53 | 517.1, rt. = 4.51 min. | 517.2250 |
| 194 | 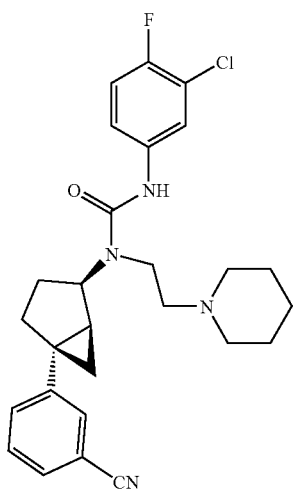 | 481.00 | 481.1, rt. = 4.88 min. | 481.2173 |

| | | | | |
|---|---|---|---|---|
| 195 | 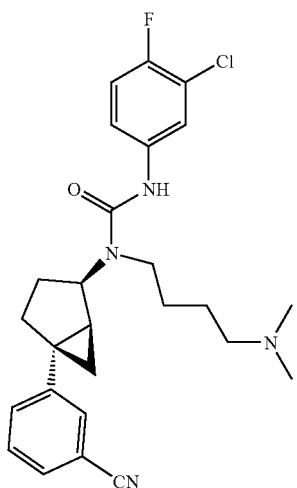 | 468.99 | 469.1, rt. = 4.71 min. | 469.2171 |
| 196 | 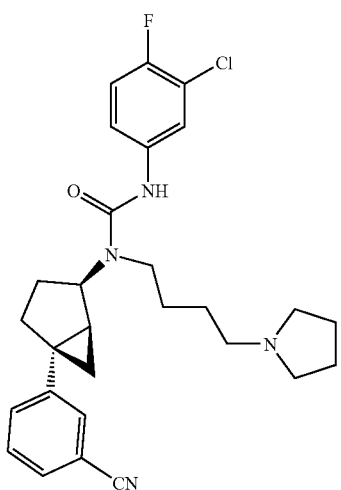 | 495.03 | 495.1, rt. = 4.81 min. | 495.2330 |
| 197 | 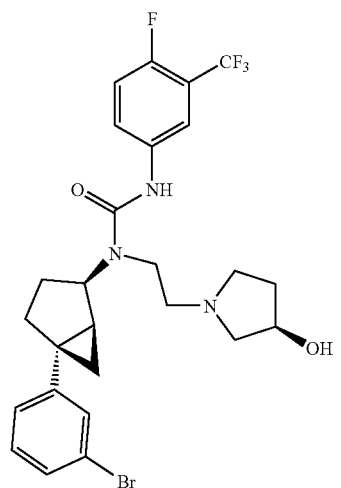 | 570.42 | 572.1, rt. = 5.52 min. | 572.1372 |

-continued
| EX. | STRUCTURE | LCMS (M + 1) | HRMS (M + H)+ |
|---|---|---|---|
| 198 | 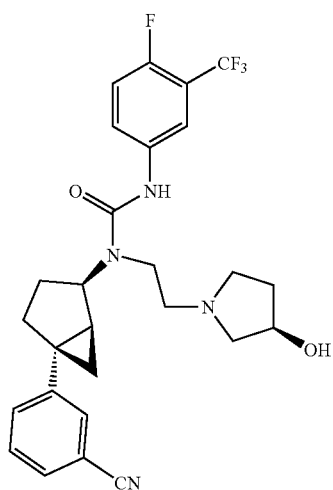 | 516.2148 517.1, rt = 5.25 min. | 517.2236 |
| 199 | 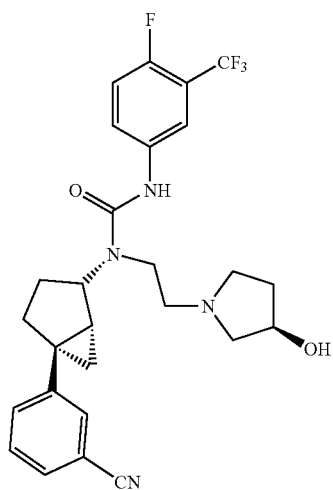 | 516.2148 517.1, rt = 5.15 min. | 517.2236 |
| EX. | STRUCTURE | LCMS (M + 1) | HRMS (M + H)+ |
|---|---|---|---|
| 200 | 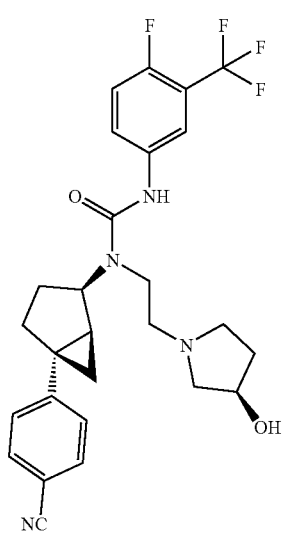 | 517.1, rt. = 5.52 min | 517.2232 |

-continued
| | | | |
|---|---|---|---|
| 201 | 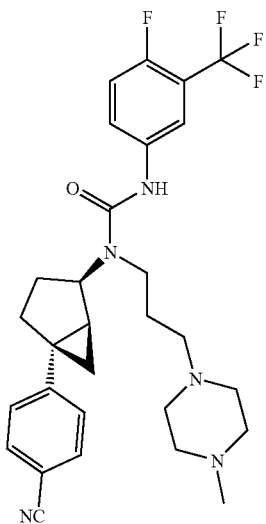 | 544.3 rt. = 4.44 min | |
| 202 | 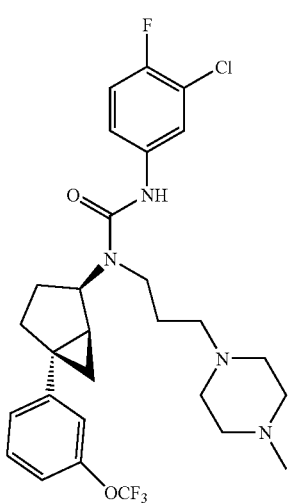 | 569.1 rt. = 5.05 min | 569.2306 |
| 203 | 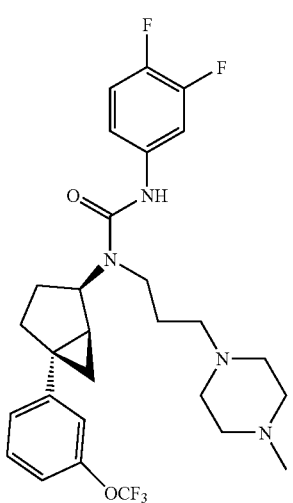 | 553.1 rt. = 4.88 min | 553.2602 |

| 204 | 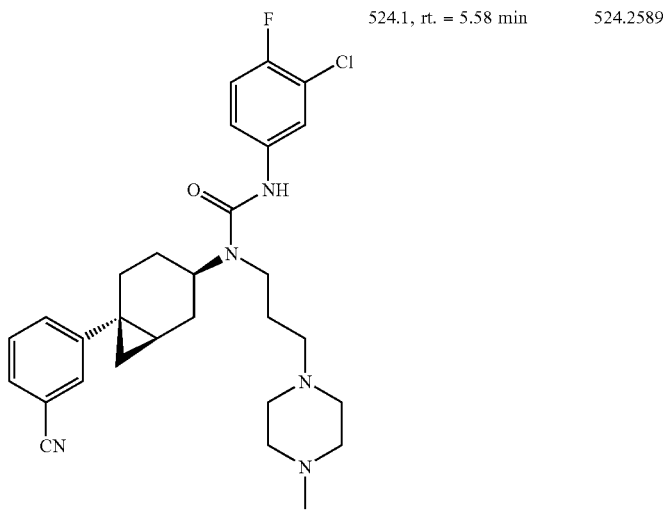 | 524.1, rt. = 5.58 min | 524.2589 |
|---|---|---|---|
| 205 | 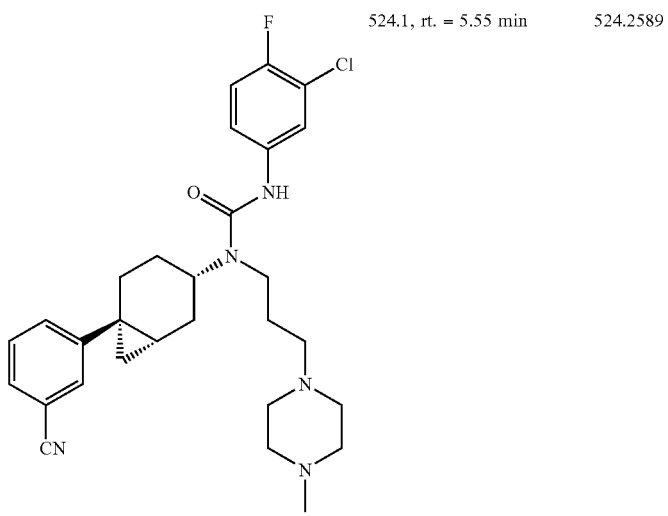 | 524.1, rt. = 5.55 min | 524.2589 |
Example 206
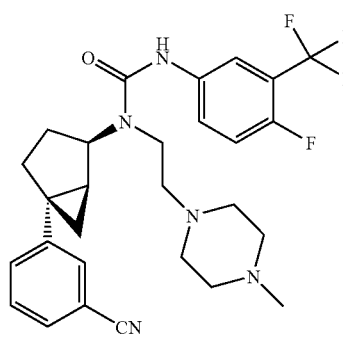 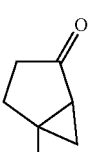 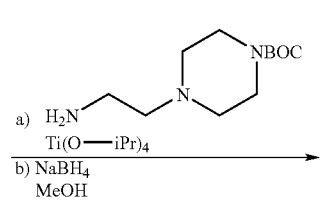

-continued

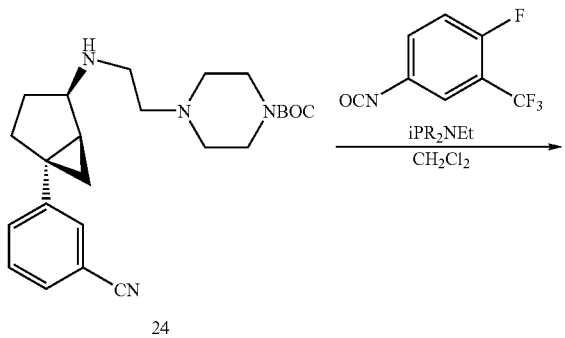

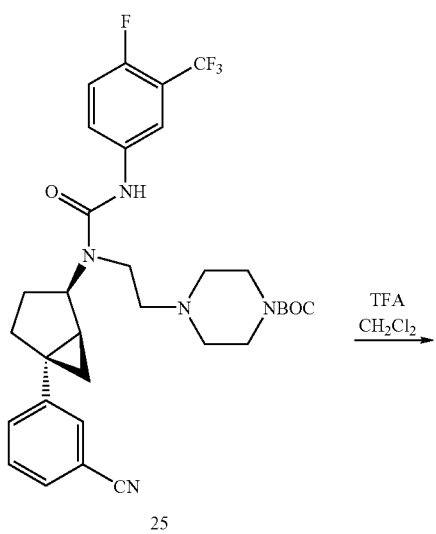

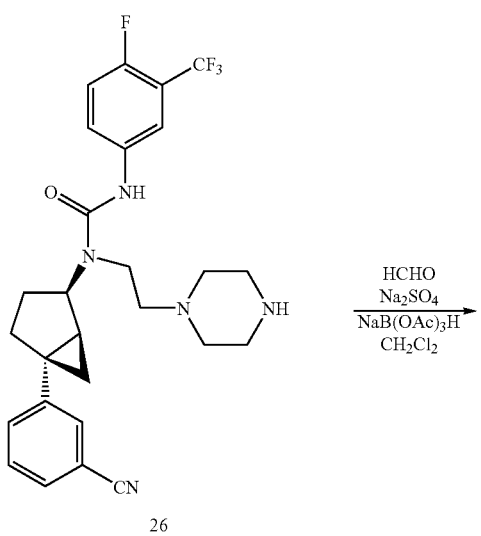

-continued

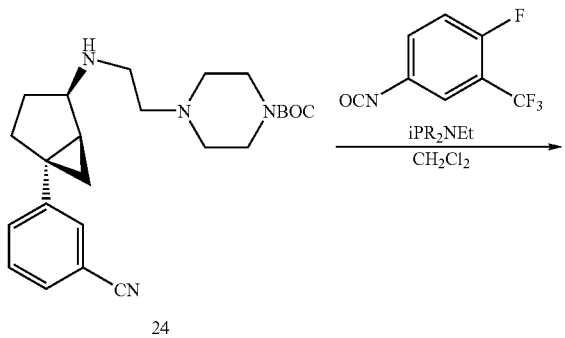

27

Step 1:

A solution of ketone 21 (500 mg, 2.54 mmol) in CH$_2$Cl$_2$ (1 mL) was treated 4-N-(2-Aminoethyl)-1-N-(t-butoxycarbonyl)-piperazine (756 mg, 3.30 mmol) followed by titanium tetraisopropoxide (987 μL, 3.30 mmol). After 12 h, the reaction mixture was diluted with MeOH (1 mL) and sodium borohydride (192 mg, 5.10 mmol) was added. After 2 h further, the reaction mixture was diluted with a solution of saturated aqueous NaHCO$_3$ and extracted with CH$_2$Cl$_2$ (4×). The combined organic phases were dried and concentrated in vacuo. The crude product (820 mg) was dissolved in CH$_2$Cl$_2$ (20 mL) and treated with N,N'-diisopropylethylamine (870 μL, 5.0 mmol) followed by 3-trifluoromethyl-4-fluorophenyl isocyanate (430 μL, 3.0 mmol). After 12 h, the reaction mixture was diluted with saturated aqueous NaHCO$_3$ and extracted with CH$_2$Cl$_2$ (2×). The combined organic phases were dried and concentrated in vacuo. Flash chromatography (gradient 40%→60% EtOAc/Hex) furnished 25 (450 mg, 29% over 2 steps) as a clear oil.

Step 2:

A solution of 25 (450 mg, 0.731 mmol) in CH$_2$Cl$_2$ (6 mL) at 0° C. was treated with TFA (1.4 mL) and warmed ambient temperature. After 12 h, the reaction mixture was concentrated in vacuo, diluted with saturated aqueous NaHCO$_3$ and extracted with CH$_2$Cl$_2$ (3×). The combined organic phases were dried and concentrated in vacuo to provide 26 (370 mg, 98%) as a yellow oil.

Step 3:

A solution of amine 26 (80 mg, 0.155 mmol) in CH$_2$Cl$_2$ (2 mL) was treated with Na$_2$SO$_4$ (350 mg, 2.5 mmol), formaldehyde (37% in H$_2$O; 50 μL, 0.6 mmol) and NaB(OAc)$_3$H (160 mg, 0.75 mmol). After 12 h, the reaction mixture was diluted with saturated aqueous NaHCO$_3$ and extracted with CH$_2$Cl$_2$ (3×). The combined organic phases were dried and concentrated in vacuo. Preparative thin layer chromatography (5% MeOH/CH$_2$Cl$_2$) furnished 27 (47 mg, 57%) as a clear oil: $^1$H NMR (300 MHz, CDCl$_3$) δ 10.34 (s, 1 H), 7.76 (m, 1 H), 7.61 (d, J=5.5 Hz, 1H), 7.49–7.42 (m, 2 H), 7.40–7.34 (m, 2 H), 7.11 (dd, J=9.9, 9.3 Hz, 1 H), 5.07 (ddd, J=11.0, 6.6, 4.4 Hz, 1 H), 3.53 (dd, J=15.9, 7.1 Hz, 1 H), 3.40 (dd, J=15.4, 4.9 Hz, 1 H), 2.79–2.55 (m, 1 H), 2.33 (s, 3 H), 2.20–1.92 (m, 3 H), 1.71 (m, 1 H), 1.37–1.17 (m, 2 H), 0.96 (dd, J=6.6, 6.6 Hz, 1 H). LCMS: 530.1, rt.=4.85 min (M+1), HRMS m/z 530.2538 [(M+H)$^+$].

Following procedures similar to those described in Example 206, the following compounds were prepared:
| EX. | STRUCTURE | Mass | LCMS (M + 1) | HRMS (M + H)+ |
|---|---|---|---|---|
| 207 | 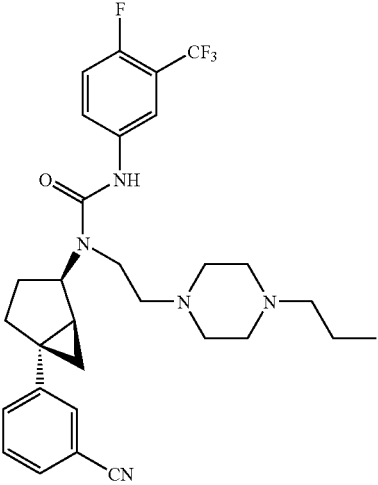 | 557.63 | 558.1, rt. = 5.22 min | 558.2863 |
| 208 | 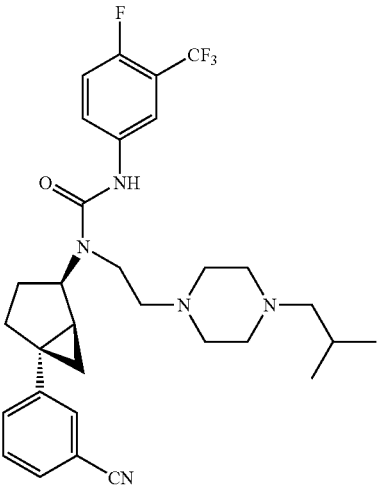 | 571.65 | 572.1, rt. = 5.12 min | 572.3020 |
| 209 | 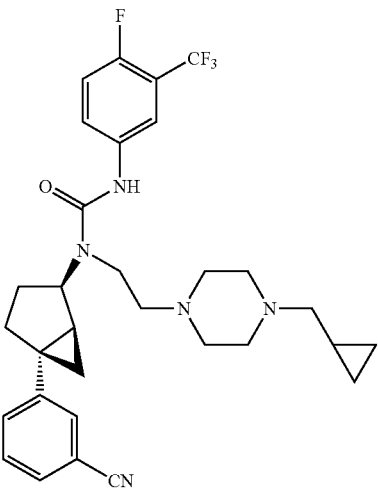 | 569.64 | 570.1, rt. = 4.95 min. | 570.2850 |

| | | | | |
|---|---|---|---|---|
| 210 | 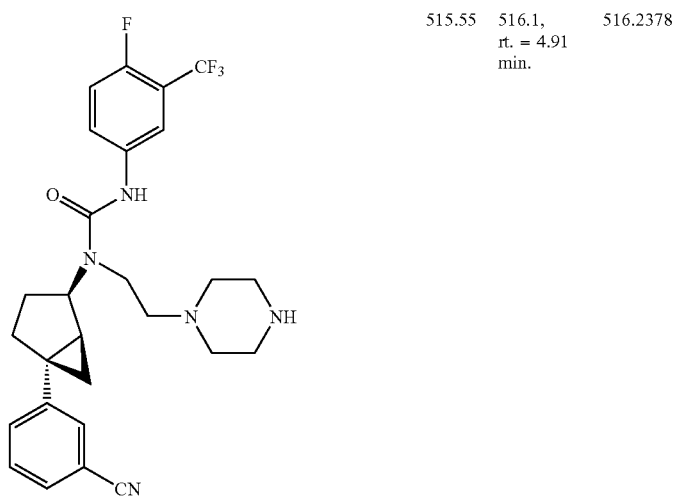 | 515.55 | 516.1, rt. = 4.91 min. | 516.2378 |
| 211 | 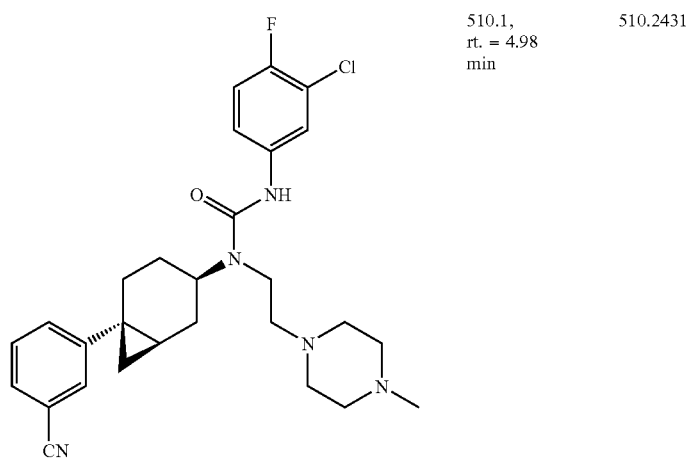 | | 510.1, rt. = 4.98 min | 510.2431 |
| 212 | 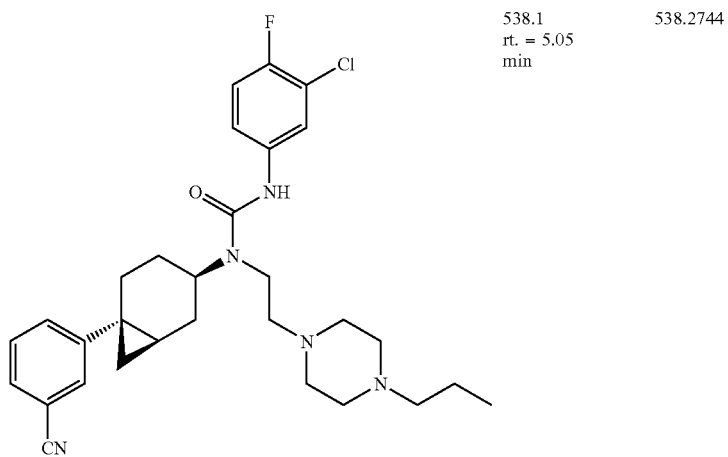 | | 538.1 rt. = 5.05 min | 538.2744 |

| | | | |
|---|---|---|---|
| 213 | 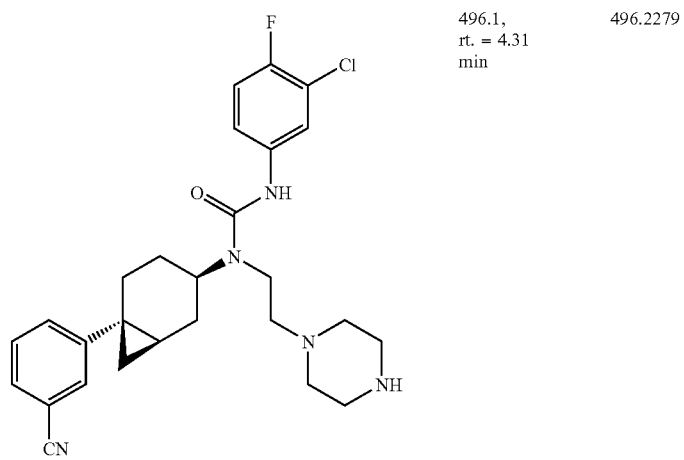 | 496.1, rt. = 4.31 min | 496.2279 |
| 214 | 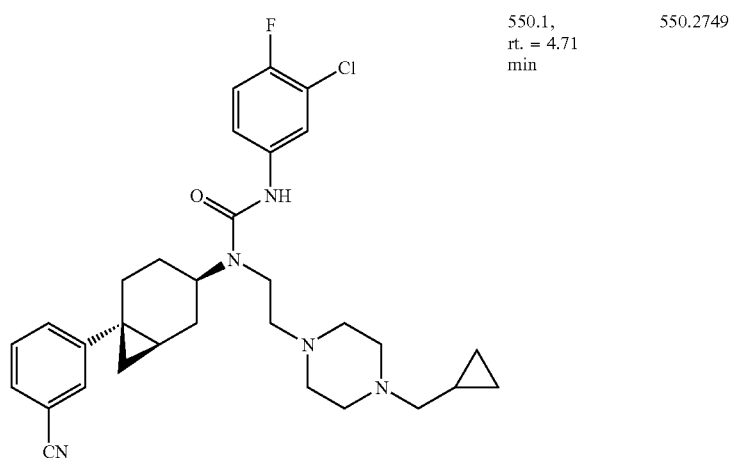 | 550.1, rt. = 4.71 min | 550.2749 |
| 215 | 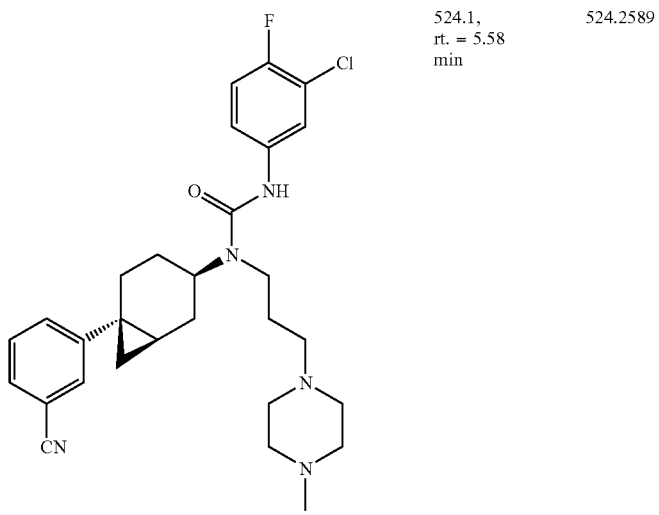 | 524.1, rt. = 5.58 min | 524.2589 |

-continued
| 216 | 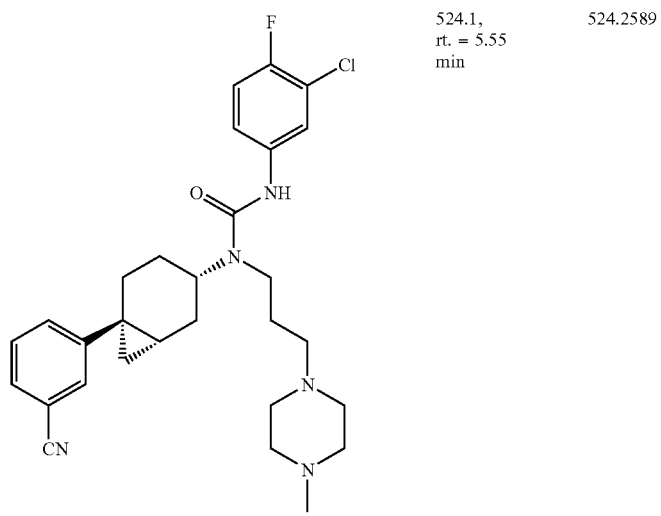 | 524.1, rt. = 5.55 min | 524.2589 |
| 217 | 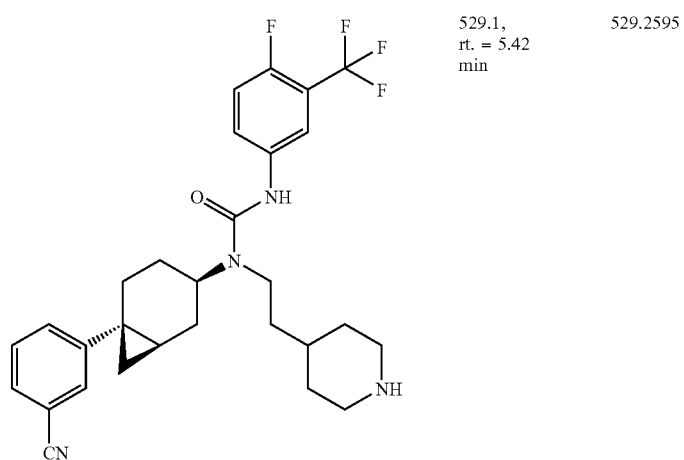 | 529.1, rt. = 5.42 min | 529.2595 |
| 218 | 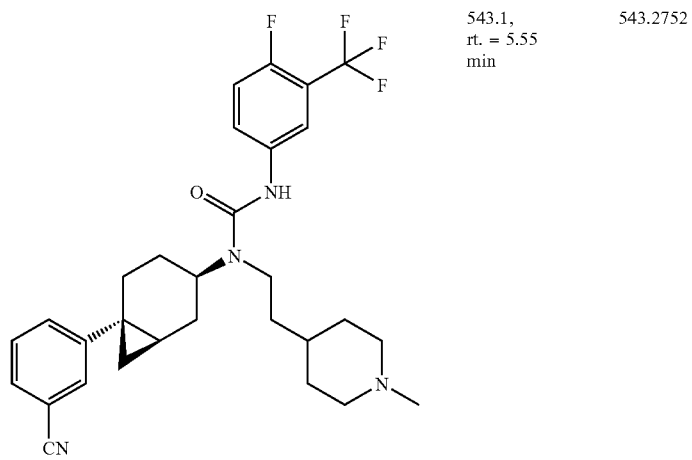 | 543.1, rt. = 5.55 min | 543.2752 |

| | | | |
|---|---|---|---|
| 219 | 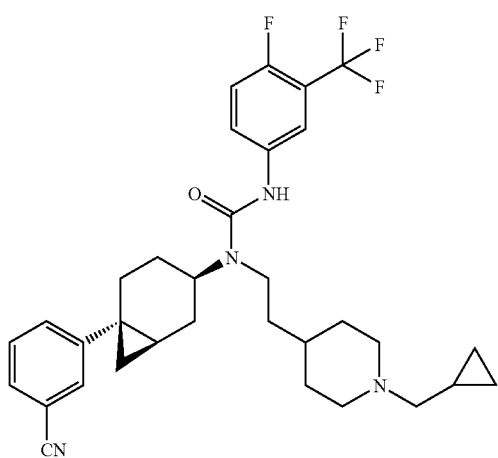 | 583.1, rt. = 5.65 min | 583.3065 |
| 220 | 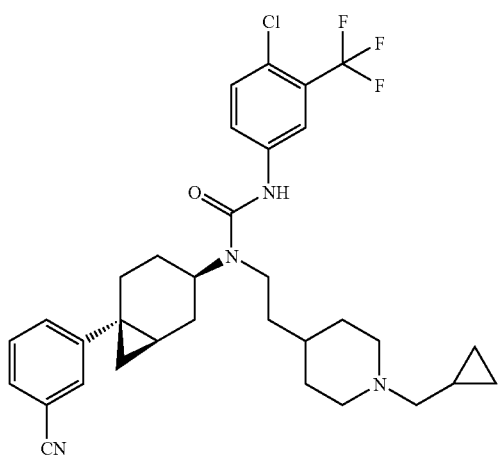 | 600.1, rt. = 5.75 min | 600.2717 |
| 221 | 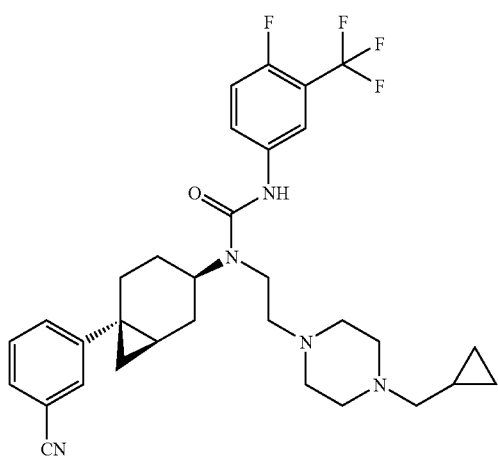 | 584.1, rt. = 5.48 min | 584.3012 |

-continued
| | | | |
|---|---|---|---|
| 222 | 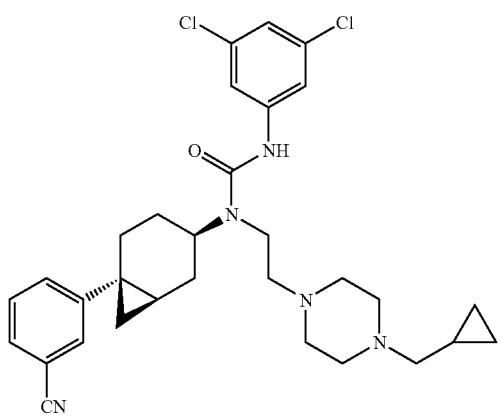 | 566.1, rt. = 5.78 min | 566.2453 |
| 223 | 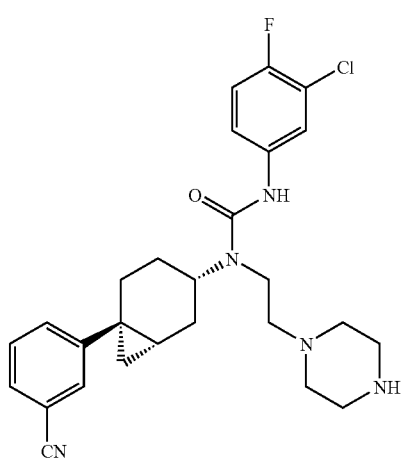 | 496.1, rt. = 5.15 min | 496.2279 |
| 224 | 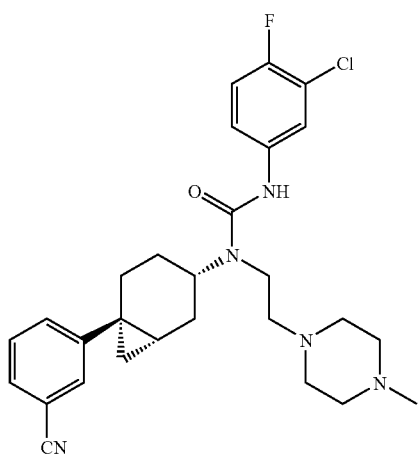 | 510.1, rt. = 5.45 min | 510.2436 |

Example 225

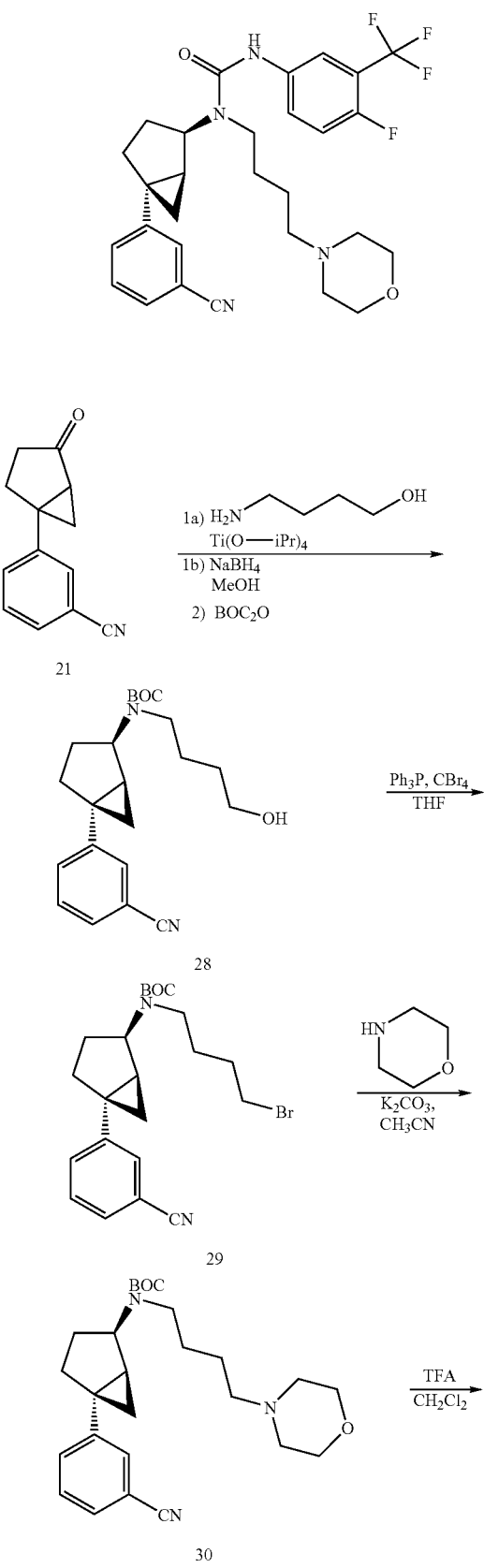

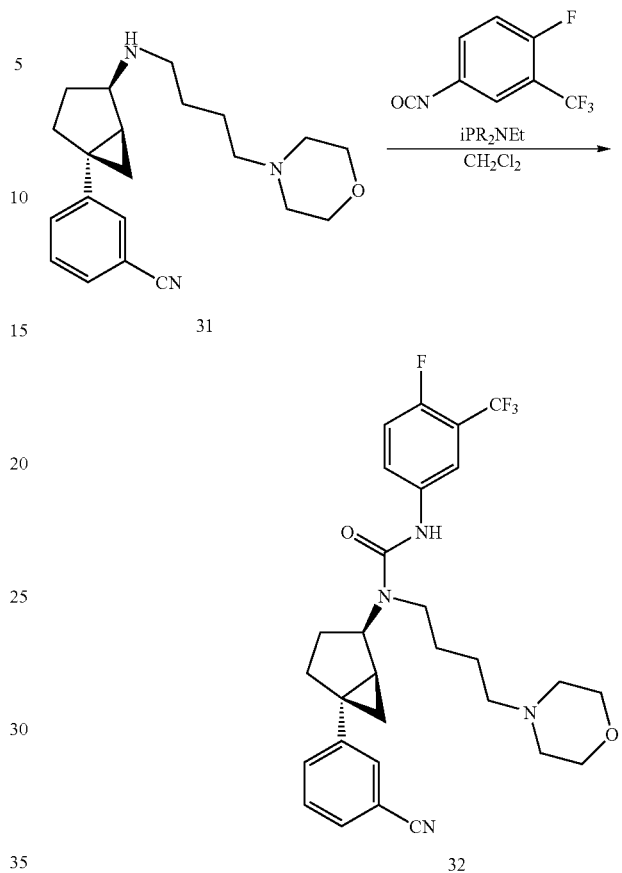

Step 1:

A solution of ketone 21 (440 mg, 2.23 mmol) in $CH_2Cl_2$ (2 mL) was treated with 4-amino-1-butanol (247 µL, 2.68 mmol) followed by titanium tetraisopropoxide (800 µL, 2.68 mmol). After 18 h, the reaction mixture was diluted with MeOH (2 mL) and sodium borohydride (130 mg, 3.40 mmol) was added. After 1.5 h further, the reaction mixture was diluted with a solution of saturated aqueous sodium/potassium tartrate, $CH_2Cl_2$ and stirred vigorously. After 12 h, the solution was extracted with $CH_2Cl_2$ (4×). The combined organic phases were dried and concentrated in vacuo. The crude product (560 mg) was dissolved in $CH_2Cl_2$ (4 mL) and treated with triethylamine (TEA or $Et_3N$) (280 µL, 2.0 mmol) followed by di-t-butyl carbonate (437 mg, 2.0 mmol). After 12 h, the reaction mixture was diluted with EtOAc, washed with saturated aqueous $NH_4Cl$, $NaHCO_3$, brine, dried and concentrated in vacuo. Flash chromatography (50% EtOAc/Hex) gave 28 (700 mg, 80% over 2 steps) as a clear oil.

Step 2:

A solution of alcohol 28 (700 mg, 1.81 mmol) in THF (9 mL) at 0° C. was treated with carbon tetrabromide (1.2 g, 3.6 mmol) followed by triphenylphosphine (1.05 g, 4.0 mmol) and warmed to ambient temperature. After 45 min, the reaction mixture was diluted with diethyl ether, filtered through celite, rinsed and concentrated in vacuo. Flash chromatography (10% EtOAc/Hex) gave 29 (770 mg, 95%) as a clear oil.

Step 3:

A solution of 29 (150 mg, 0.333 mmol) in CH$_3$CN was treated with K$_2$CO$_3$ (70 mg, 0.50 mmol), morpholine (32 µL, 0.367 mmol) and heated to 70° C. After 12 h, the reaction mixture was cooled to ambient temperature, diluted with saturated aqueous NH$_4$Cl and extracted with EtOAc (3×). The combined organic extracts were washed with NaHCO$_3$, brine, dried and concentrated in vacuo to provide crude 30 as a clear oil.

Step 4:

A solution of crude 30 (≦0.333 mmol) in 20% TFA/CH$_2$Cl$_2$ (3.6 mL) was stirred at ambient temperature. After 12 h, the reaction mixture was poured into saturated aqueous NaHCO$_3$ and extracted with CH$_2$Cl$_2$ (2×). The combined organic phases were dried and concentrated in vacuo to provide 31 as a yellow oil.

Step 5:

A solution of 31 (≦0.333 mmol) in CH$_2$Cl$_2$ (3 mL) was treated with diisopropylethyl amine (87 µL, 0.50 mmol) followed by 3-(trifluoromethyl)-4-fluorophenyl isocyanate (57 µL, 0.40 mmol). After 12 h, the reaction mixture was diluted with saturated aqueous NaHCO$_3$ and extracted with CH$_2$Cl$_2$ (2×). The combined organic phases were dried and concentrated in vacuo. Preparative thin layer chromatography (5% MeOH/CH$_2$Cl$_2$) furnished 32 (136 mg, 75% over 3 steps) as a clear oil: $^1$H NMR (300 MHz, CDCl$_3$) δ 7.59–7.54 (m, 2H), 7.48–7.44 (m, 2H), 7.39–7.37 (m, 2 H), 7.11 (dd, J=9.9, 9.3 Hz, 1 H), 6.95 (s, 1 H), 5.00 (ddd, J=10.4, 6.6, 3.5 Hz, 1 H), 3.80–3.60 (m, 4 H), 3.50–3.26 (m, 2 H), 2.62–2.32 (m, 6 H), 2.16 (dd, J=11.0, 7.1 Hz, 1 H), 2.10-2.94 (m, 2 H), 1.87–1.72 (m, 3 H), 1.67–1.56 (m, 2 H), 1.42–1.27 (m, 2 H), 0.99 (dd, J=7.1, 6.0 Hz, 1 H). LCMS: 545.1, rt.=5.38 min (M+1), HRMS m/z 544.2543 [(M+H)$^+$].

Following procedures similar to those described in Example 225, the following compounds were prepared:

| EX. | STRUCTURE | Mass | LCMS (M + 1) | HRMS (M + H)$^+$ |
|---|---|---|---|---|
| 226 | 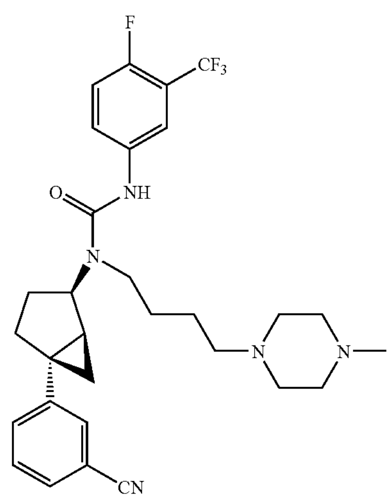 | 557.63 | 558.1, rt. = 4.85 min | 558.2851 |
| 227 | 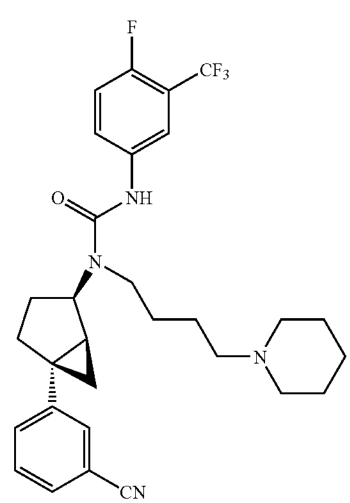 | 542.61 | 544.1, rt. = 5.55 min | 543.2757 |

-continued

| EX. | STRUCTURE | LCMS (M + 1) | HRMS (M + H)+ |
|---|---|---|---|
| 228 | 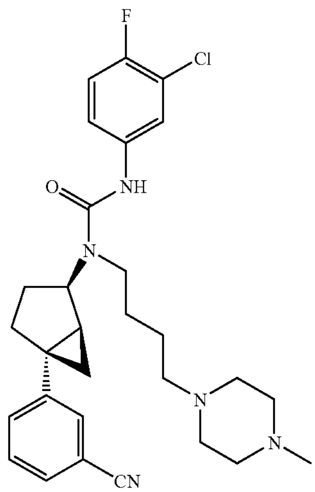 | 524.1, rt. = 4.38 min | 524.2599 |
| 229 | 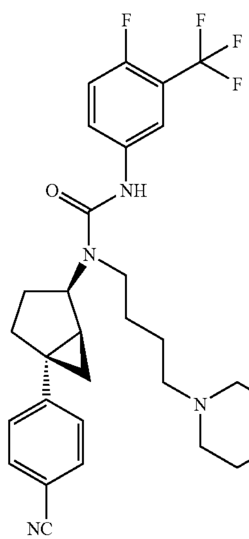 | 558.1 rt. = 4.71 min | 558.2856 |
| 230 | 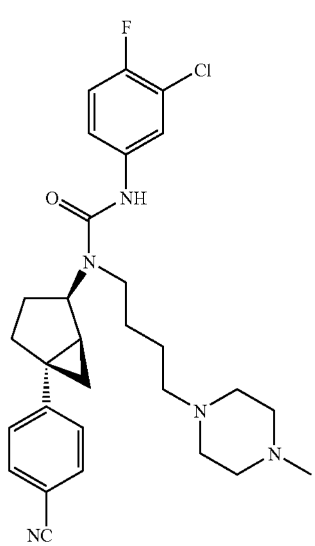 | 524.1 rt. = 4.75 min | |

-continued

| 231 | 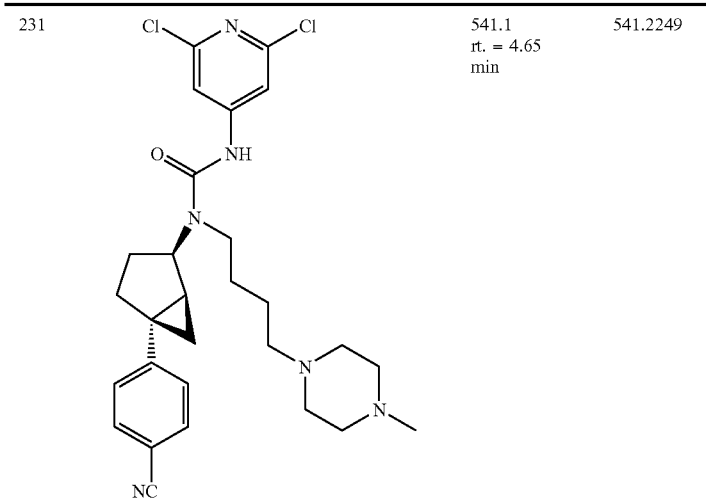 | 541.1 rt. = 4.65 min | 541.2249 |

Examples 232

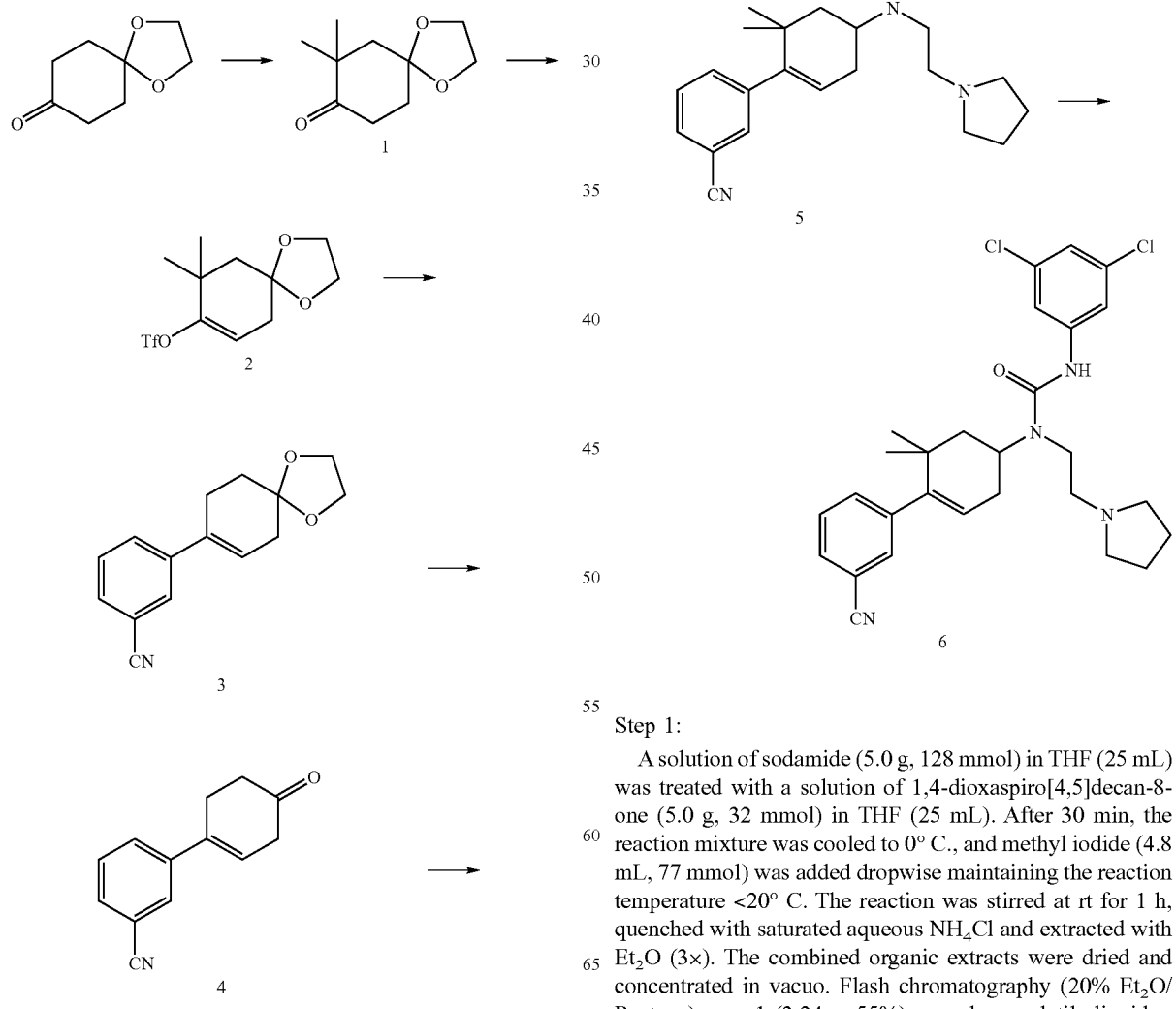

Step 1:

A solution of sodamide (5.0 g, 128 mmol) in THF (25 mL) was treated with a solution of 1,4-dioxaspiro[4,5]decan-8-one (5.0 g, 32 mmol) in THF (25 mL). After 30 min, the reaction mixture was cooled to 0° C., and methyl iodide (4.8 mL, 77 mmol) was added dropwise maintaining the reaction temperature <20° C. The reaction was stirred at rt for 1 h, quenched with saturated aqueous $NH_4Cl$ and extracted with $Et_2O$ (3×). The combined organic extracts were dried and concentrated in vacuo. Flash chromatography (20% $Et_2O$/Pentane) gave 1 (3.24 g, 55%) as a clear, volatile liquid:

Step 2:

A solution of ketone 1 (3.24 g, 17.6 mmol) in CH₂Cl₂ (170 mL) at 0° C. was treated with 2,6-di-tert-butyl-4-methylpyridine (5.4 g, 26.4 mmol) followed by Tf₂O (3.55 mL, 21.1 mmol) and warmed to ambient temperature. After 60 h, the reaction was quenched with 1M citric acid and extracted with Et₂O (2×). The combined organic extracts were washed with saturated aqueous NaHCO₃, brine, dried and concentrated in vacuo. The crude product 2 was dissolved in DME/H₂O (4:1, 65 mL), and treated with Na₂CO₃ (6.75 g, 63.4 mmol), LiCl (2.7 g, 63.4 mmol), 3-cyanophenylboronic acid (4.65 g, 31.7 mmol) and Pd(Ph₃P)₄ (1.0 g, 0.9 mmol). The reaction mixture was evacuated, purged with nitrogen (2×) and heated to 80° C. After 18 h, the reaction mixture was cooled to ambient temperature, diluted with saturated aqueous NaHCO₃ and extracted with EtOAc (3×). The combined organic extracts were dried and concentrated in vacuo. Flash chromatography (10% EtOAc/Hex) gave 3 (2.80 g, 59% over 2 steps) as a yellow liquid:

Step 3:

A solution of ketal 3 (1.0 g, 3.71 mmol) in acetone/H₂O (4:1, 20 mL) was treated with PPTs (1.4 g, 5.57 mmol) and heated to 60° C. After 18 h, the reaction mixture was cooled to ambient temperature and concentrated. The reaction mixture was quenched with saturated aqueous NaHCO₃ and extracted with EtOAc (2×). The combined organic extracts were washed with brine, dried and concentrated in vacuo. Flash chromatography (10% EtOAc/Hex) gave 4 (520 mg, 62%) as a yellow solid:

Step 4:

A solution of ketone 4 (150 mg, 0.666 mmol) in CH₂Cl₂ (1 mL) was treated with 1-(2-aminoethyl)pyrrolidine (127 μL, 1.0 mmol) followed by titanium tetraisopropoxide is (300 μL, 1.0 mmol). After 18 h, the reaction mixture was diluted with MeOH (1 mL) and sodium borohydride (50 mg, 1.3 mmol) was added. After 2 h further, the reaction mixture was diluted with saturated aqueous NaHCO₃ and extracted with CH₂Cl₂ (4×). The combined organic extracts were dried and concentrated in vacuo to provide crude 5 (250 mg) as a yellow oil.

Step 5:

A solution of crude 5 (100 mg, <0.309 mmol) in CH₂Cl₂ (1 mL) was treated with diisopropylethyl amine (108 μL, 0.618 mmol) followed by 3,5-dichlorophenyl isocyanate (87 mg, 0.464 mmol). After 18 h, the reaction mixture was diluted with saturated aqueous NaHCO₃ and extracted with EtOAc (2×). The combined organic extracts were dried and concentrated in vacuo. Preparative thin layer chromatography (75% EtOAc/Hex) afforded 6 (41 mg, 26% over 2 steps) as a white solid: ¹H NMR (300 MHz, CDCl₃) d 11.33 (s, 1 H), 7.54 (d, J=7.1 Hz, 1 H), 7.41–7.34 (m, 3 H), 7.36 (s, 2 H), 6.92 (s, 1 H), 5.40 (dd, J=5.6, 2.1 Hz, 1 H), 4.72 (m, 1 H), 3.35–3.30 (m, 2 H), 2.81–2.65 (m, 6 H), 2.36 (ddd, J=17.1, 5.0, 5.0 Hz, 1 H), 2.14 (ddd, J=16.8, 11.4, 2.1 Hz, 1 H), 2.00–1.95 (m, 4 H), 1.71 (dd, J=24.7, 12.1 Hz, 1 H), 1.64 (dd, J=11.4, 2.0 Hz, 1 H), 1.25 (s, 3 H), 0.92 (s, 3 H). LCMS: 511.3, rt.=5.56 min (M+1), HRMS m/z 511.2019 [(M+H)⁺].

Following procedures similar to those described in Example 232, the following compounds were prepared:

| EX. | STRUCTURE | LCMS (M + 1) | HRMS (M + H)⁺ |
|---|---|---|---|
| 233 | 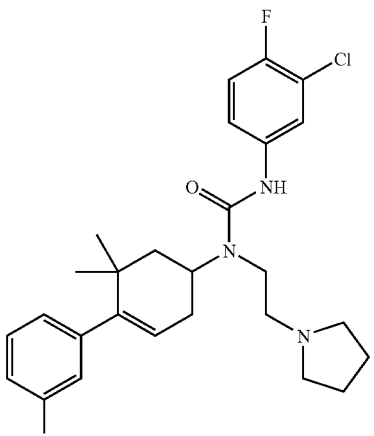 | 495.3, rt. = 5.48 min | 495.2328 |

| EX. | STRUCTURE | LCMS (M + 1) | HRMS (M + H)+ |
|---|---|---|---|
| 234 | 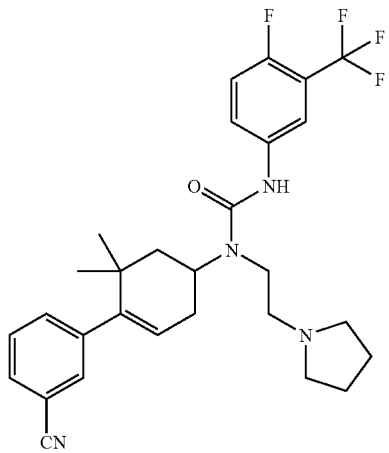 | 529.3, rt. = 5.52 min | 529.2600 |
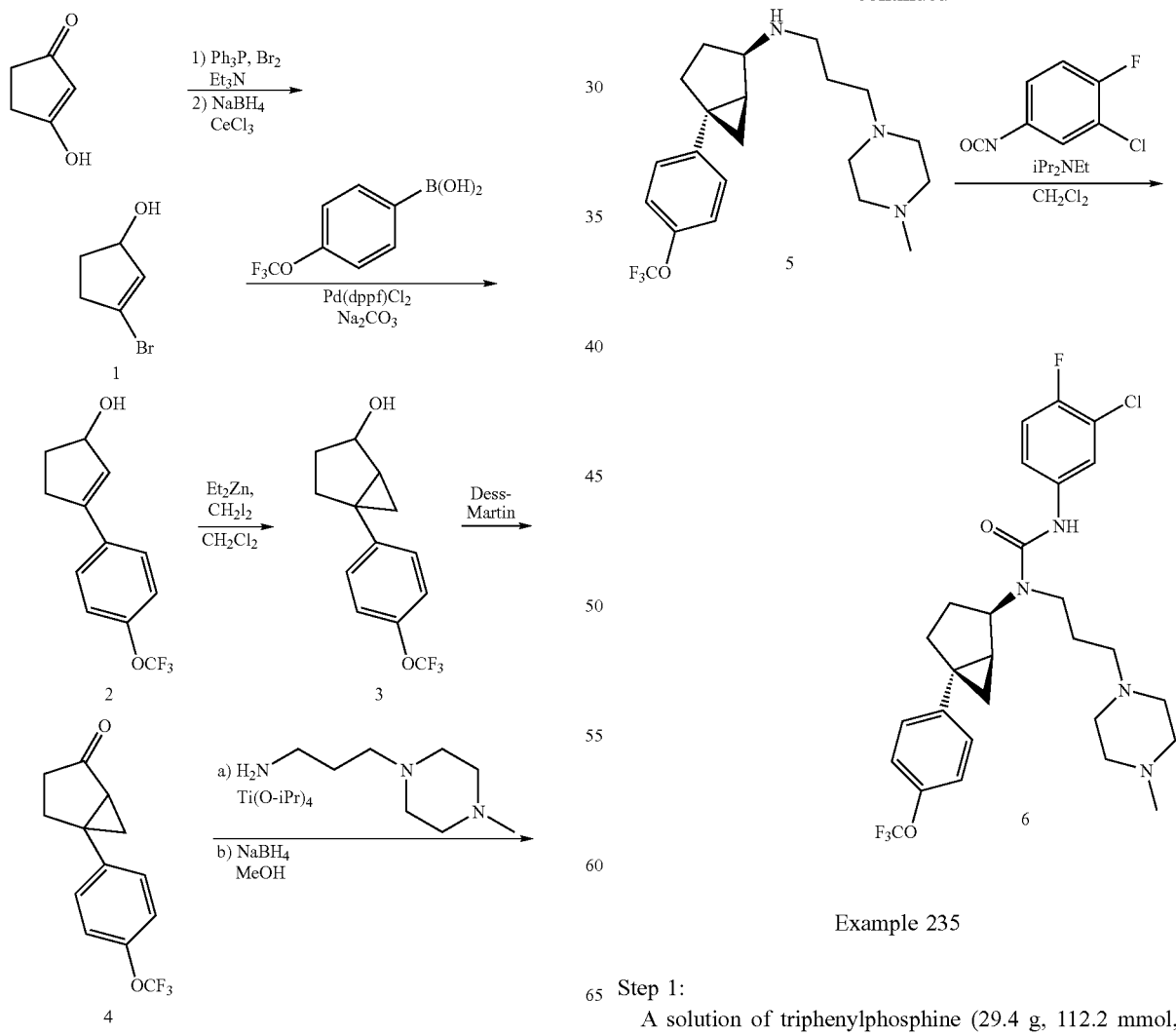
Example 235
Step 1:
A solution of triphenylphosphine (29.4 g, 112.2 mmol, recrystallized from benzene) in benzene (700 mL) at 0° C.

was treated with a solution of bromine (5.8 mL, 112.2 mmol) in benzene (100 mL) over 15 min. Triethylamine (15.6 mL) was added slowly followed by 1,3-cyclopentanedione (10 g, 102 mmol) and the reaction mixture was warmed to ambient temperature. After 4 h, the reaction was filtered through silica gel, rinsed with Et$_2$O and concentrated to a volume of ~150 mL. The residue was diluted with Et$_2$O, filtered through silica gel and concentrated. The crude product (21 g) was diluted with MeOH (200 mL), cooled to 0° C. and treated with CeCl$_3$.7H$_2$O (56.6 g, 152 mmol) followed by NaBH$_4$ (5.75 g, 152 mmol) portionwise over 10 min. After 12 h, the reaction was quenched with saturated aqueous NH$_4$Cl and concentrated in vacuo. The concentrate was diluted with saturated aqueous NaHCO$_3$ and extracted with CH$_2$Cl$_2$ (3×). The combined organic extracts were dried and concentrated in vacuo. Flash chromatography (10% Et$_2$O/Hex) gave 1 (11.8 g, 70% over 2 steps) as a clear oil.

Step 2:

A solution of 1 (530 mg, 3.24 mmol) in 4:1 DME/H$_2$O (35 mL) was treated with Na$_2$CO$_3$ (520 mg, 4.90 mmol), 4-trifluoromethoxyphenyl boronic acid (1.00 g, 4.86 mmol), Pd(dppf)Cl$_2$ (250 mg, 0.30 mmol) and heated to 80° C. After 1 h, the reaction mixture was cooled to ambient temperature, diluted with saturated aqueous NaHCO$_3$ and extracted with EtOAc (2×). The combined organic extracts were washed with brine, dried and concentrated in vacuo. Flash chromatography (33% EtOAc/Hex) afforded 2 (380 mg, 48%) as a white solid.

Step 3:

A solution of 2 (380 mg, 1.55 mmol) in CH$_2$Cl$_2$ (40 mL) was treated with diethylzinc (7.75 mL, 1.0 M in hex). After 10 min, the reaction mixture was cooled to 0° C., treated with a solution of CH$_2$I$_2$ (624 µL, 7.75 mmol) in CH$_2$Cl$_2$ (5 mL) and warmed to ambient temperature overnight. After 12 h, the reaction mixture was quenched with saturated aqueous NH$_4$Cl and extracted with CH$_2$Cl$_2$ (2×). The combined organic extracts were washed with saturated aqueous NaHCO$_3$, dried and concentrated in vacuo. Flash chromatography (33% EtOAc/Hex) gave 3 (270 mg, 67%) as a clear oil.

Step 4

A solution of alcohol 3 (270 mg, 1.05 mmol) in CH$_2$Cl$_2$ (10 mL) was treated with pyridine (160 µL, 2.00 mmol) followed by Dess-Martin periodinane (640 mg, 1.50 mmol. After 18 h, the reaction mixture was quenched with saturated aqueous NaHCO$_3$, saturated aqueous Na$_2$S$_2$O$_3$, extracted with CH$_2$Cl$_2$ (2×). The combined organic extracts were concentrated in vacuo. Flash chromatography (25% EtOAc/Hex) provided 4 (248 mg, 92%) as clear oil.

Step 5:

A solution of 4 (123 mg, 0.478 mmol) in CH$_2$Cl$_2$ (1 mL) was treated with 1-(3-aminopropyl)-4-methylpiperazine (106 µL, 0.622 mmol) followed by titanium tetraisopropoxide (186 µL, 0.622 mmol). After 18 h, the reaction mixture was diluted with EtOH (1 mL) and sodium borohydride (31 mg, 0.813 mmol) was added. After 2 h further, the reaction mixture was diluted with water (2 mL) and stirred for 1 h. The reaction mixture was diluted with saturated aqueous NaHCO$_3$ and extracted with CH$_2$Cl$_2$ (3×). The combined organic extracts were dried and concentrated in vacuo to provide crude 5 (184 mg) as a clear oil.

Step 6:

A solution of crude 5 (184 mg, <0.461 mmol) in CH$_2$Cl$_2$ (5 mL) was treated with diisopropylethyl amine (226 µL, 1.30 mmol) followed by 3-chloro, 4-fluorophenyl isocyanate (119 µL, 1.00 mmol). After 18 h, the reaction mixture was diluted with saturated aqueous NaHCO$_3$ and extracted with CH$_2$Cl$_2$ (2×). The combined organic extracts were dried and concentrated in vacuo. Preparative thin layer chromatography (5% MeOH/CH$_2$Cl$_2$) afforded 6 (188 mg, 69% over 2 steps) as a clear oil: $^1$H NMR (300 MHz, CDCl$_3$) 9.26 (s, 1 H), 7.53 (dd, J=6.6, 2.1 Hz, 1 H), 7.36 (m, 1 H), 7.18 (d, J=8.9 Hz, 2 H), 7.11 (d, J=8.9 Hz, 2 H), 7.05 (t, J=8.9 Hz, 1 H), 5.06 (ddd, J=11.1, 6.5, 3.9 Hz, 1 H), 3.47 (m, 1 H), 3.33 (ddd, J=15.4, 4.9, 4.9 Hz, 1 H), 2.26 (s, 3 H), 2.68–1.85 (m, 14 H), 1.65 (ddd, J=7.8, 3.8, 3.8 Hz, 2 H), 1.36-1.20 (m, 2 H), 0.92 (dd, J=7.7, 5.7 Hz, 1 H). LCMS: 569.1, rt.=4.37 min (M+1), HRMS m/z 569.2298 [(M+H)$^+$].

Following procedures similar to those described in Example 235, the following compounds were prepared:

| EX. | STRUCTURE | LCMS (M + 1) | HRMS (M + H)$^+$ |
|---|---|---|---|
| 236 | (structure: urea linking 3-chloro-4-fluorophenyl to bicyclic core bearing 4-trifluoromethoxyphenyl and N-(2-(3-hydroxypyrrolidin-1-yl)ethyl)) | 542.1, rt. = 5.35 min | 542.1828 |
| 237 | (structure: urea linking 3-chloro-4-fluorophenyl to bicyclic core bearing 3,5-dichlorophenyl and N-(3-(4-methylpiperazin-1-yl)propyl)) | 555.1, rt. = 5.58 min | 553.1701 |

-continued
| EX. | STRUCTURE | LCMS (M + 1) | HRMS (M + H)+ |
|---|---|---|---|
| 238 | 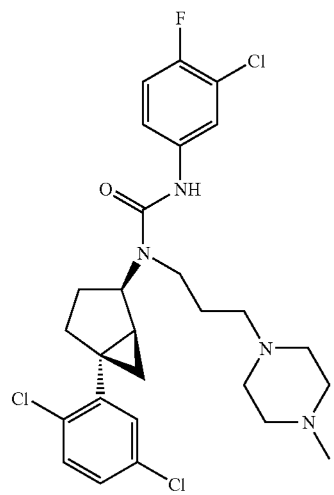 | 555.1, rt. = 5.55 min | 553.1701 |
| 239 | 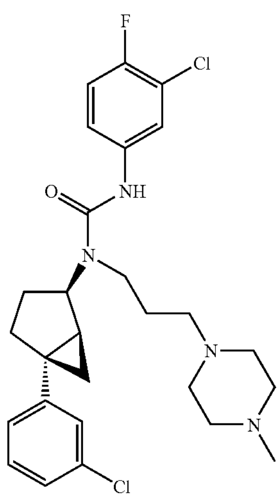 | 519.3, rt. = 4.51 min | 519.2086 |
| 240 | 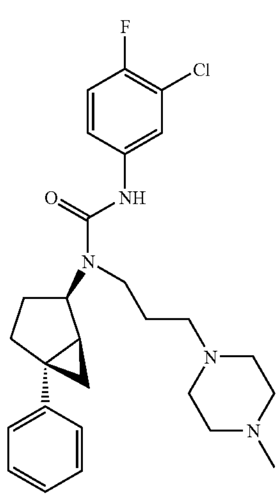 | 485.1, rt. = 4.95 min | 485.2478 |
Example 241
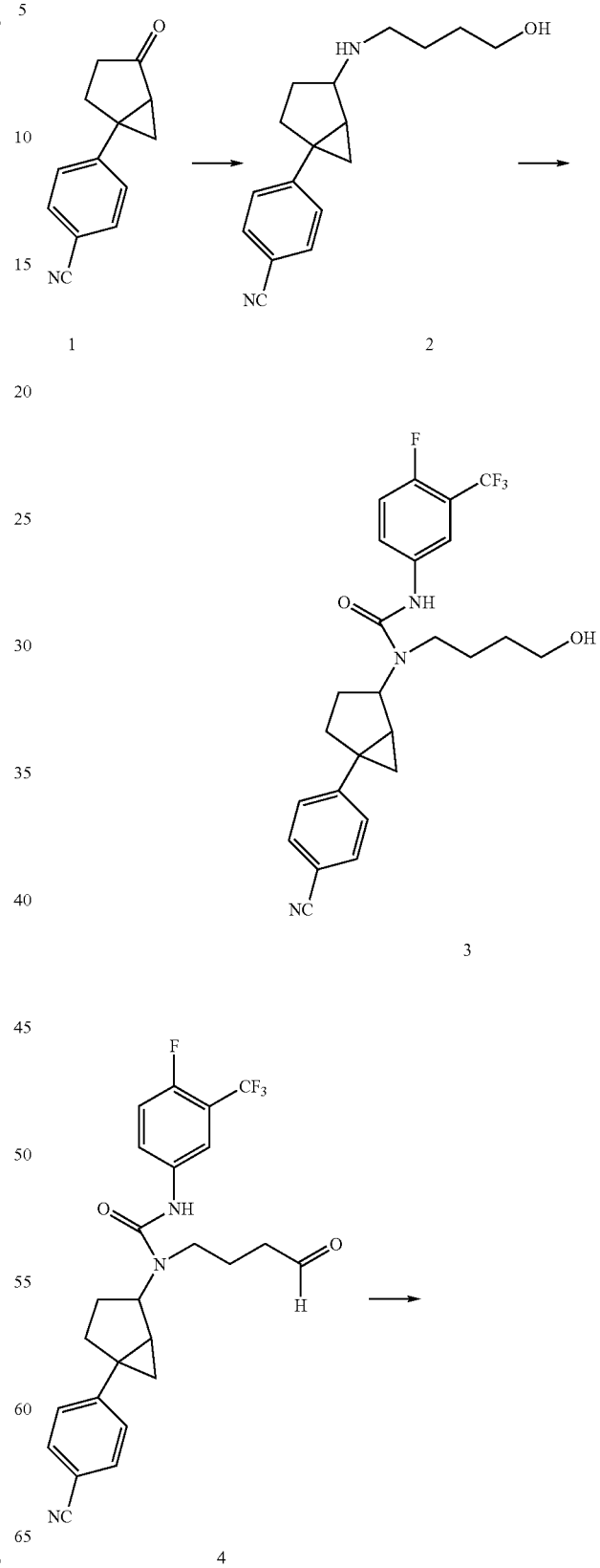

-continued

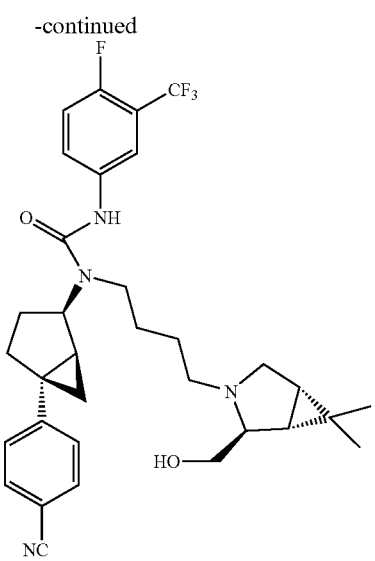

Step 1

A solution of ketone 1 (1.0 g, 5.07 mmol) in CH₂Cl₂ (4 mL) was treated with 4-amino-1-butanol (560 μL, 6.08 mmol) followed by titanium tetraisopropoxide (1.80 ml, 6.08 mmol). After 18 h, the reaction mixture was diluted with EtOH (4 mL) and sodium borohydride (290 mg, 7.60 mmol) was added. After 2 h further, the reaction mixture was diluted with water and stirred vigorously. After 3 h, the reaction mixture was filtered through celite, rinsed with EtOH (4×) and concentrated in vacuo. The resulting solid was diluted with CH₂Cl₂, saturated aqueous NaHCO₃ and extracted with CH₂Cl₂ (4×). The combined organic extracts were dried and concentrated in vacuo to provide crude 2 (1.24 g). Crude amino-alcohol 2 (1.24 g) was dissolved in CH₂Cl₂ (40 mL) and treated with diisopropylethyl amine (780 μL, 4.50 mmol) followed by 3-(trifluoromethyl)-4-fluorophenyl isocyanate (640 μL, 4.50 mmol). After 60 h, the reaction mixture was diluted with saturated aqueous NaHCO₃ and extracted with CH₂Cl₂ (2×). The combined organic phases were dried and concentrated in vacuo. Trituration (CH₂Cl₂) at 0° C. and filtration furnished 3 (1.44 g, 60% over 2 steps) as a white solid.

Step 2

A solution of alcohol 3 (1.44 g, 3.04 mmol) in CH₂Cl₂ (30 mL) at 0° C. was treated with pyridine (490 μL, 6.00 mmol) followed by Dess-Martin periodinane (1.90 g, 4.50 mmol) and warmed to ambient temperature. After 1.5 h, the reaction mixture was quenched with saturated aqueous NaHCO₃, saturated aqueous Na₂S₂O₃, extracted with CH₂Cl₂ (3×). The combined organic extracts were concentrated in vacuo. Flash chromatography (2% MeOH/CH₂Cl₂) provided 4 (1.21 g, 84%) as an orange solid.

Step 3

A solution of aldehyde 4 (150 mg, 0.318 mmol) in CH₂Cl₂ was treated with (6,6-dimethyl-3-aza-bicyclo[3.1.0]hex-2-yl)-methanol (55 mg, 0.381 mmol) followed by NaB(OAc)₃H (157 mg, 0.740 mmol). After 18 h, the reaction mixture was diluted with saturated aqueous NaHCO₃ and extracted with CH₂Cl₂ (3×). The combined organic phases were dried and concentrated in vacuo. Flash chromatography (EtOAc) afforded 5 (40 mg, 21%) as a clear oil: ¹H NMR (300 MHz, CDCl₃) δ 7.72-7.55 (m, 2 H), 7.57 (d, J=8.2 Hz, 2 H), 7.24 (d, J=8.2 Hz, 2 H), 7.11 (dd, J=9.9, 9.3 Hz, 1 H), 6.90 (s, 1 H), 4.99 (m, 1 H), 3.59(s, 2 H), 3.44 (dd, J=9.9, 6.7 Hz, 1 H), 3.37 (m, 1 H), 3.25 (m, 1 H), 2.71-2.62 (m, 2 H), 2.57 (m, 1 H), 2.29 (d, J=10.0 Hz, 1 H), 2.23-1.95 (m, 3 H), 1.86-1.22 (m, 10 H), 1.03 (s, 3H), 0.92 (s, 3H), 0.93-0.88 (m, 1H). LCMS: 599.1, rt.=5.38 min (M+1), HRMS m/z 599.3004 [(M+H)⁺].

Following procedures similar to those described in Example 241, the following compounds were prepared:

| EX. | STRUCTURE | LCMS (M + 1) | HRMS (M + H)⁺ |
|---|---|---|---|
| 242 | 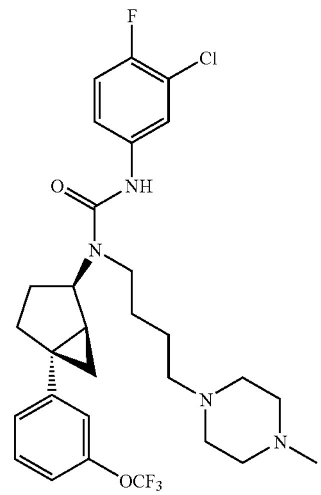 | 583.3, rt. = 4.88 min | 583.2463 |
| 243 | 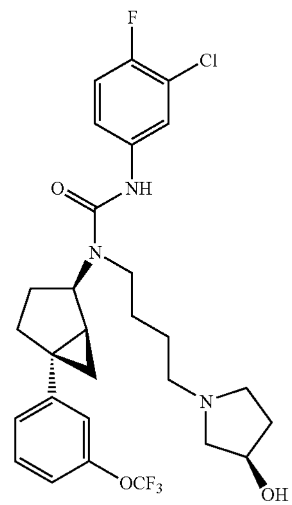 | 570.3, rt. = 5.01 min | 570.2147 |
| 244 | 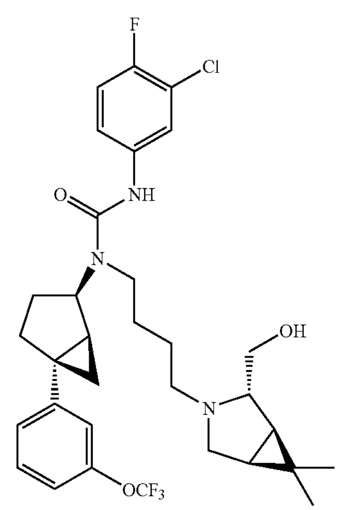 | 624.1, rt. = 5.65 min | 624.2616 |

-continued

| EX. | STRUCTURE | LCMS (M + 1) | HRMS (M + H)+ |
|---|---|---|---|
| 245 | 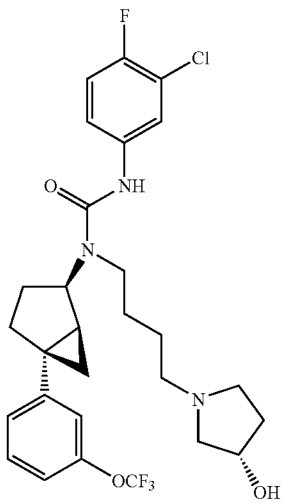 | 570.1, rt. = 5.55 min | 570.2147 |
| 246 | 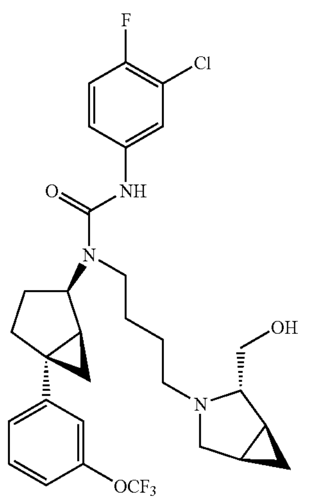 | 596.3, rt. = 5.21 min | 596.2303 |
| 247 | 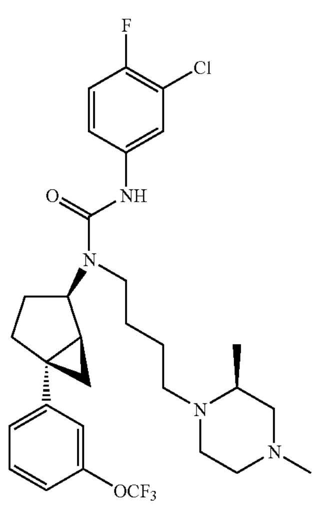 | 597.3, rt. = 4.85 min | 597.2610 |

Example 248

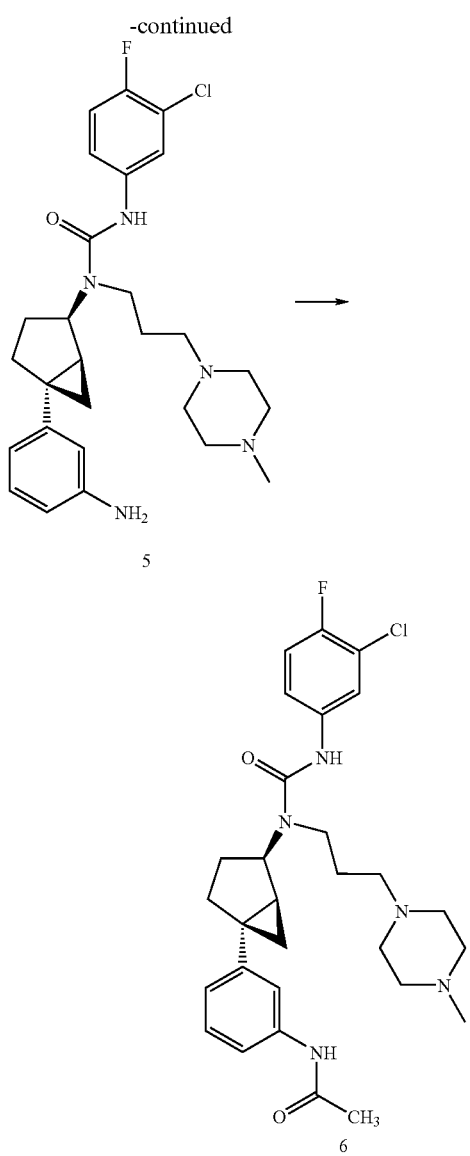

Example 248

Step 1

A tube was purged with Argon and charged with CuI (34 mg, 0.18 mmol), bromide 1 (875 mg, 3.48 mmol), prepared by methods previously described, and t-butyl carbamate (490 mg, 4.18 mmol), and $K_2CO_3$ (962 mg, 6.96 mmol). The tube was evacuated and backfilled with Argon. N,N'-Dimethyl-ethylenediamine (37 L, 0.35 mmol) and toluene (3 mL) were added and the tube was sealed and heated to 110° C. After 18 h, the reaction mixture was cooled to ambient temperature, filtered through celite, rinsed with EtOAc and concentrated in vacuo. Flash chromatography (20% EtOAc/Hex) gave 2 (450 mg, 45%) as a clear oil.

Step 2:

A solution of ketone 2 (450 mg, 1.57 mmol) in $CH_2Cl_2$ (3 mL) was treated with 1-(3-aminopropyl)-4-methylpiperazine (347 μL, 2.04 mmol) followed by titanium tetraisopropoxide (610 μL, 2.04 mmol). After 18 h, the reaction mixture was diluted with EtOH (2 mL) and sodium borohydride (101 mg, 2.67 mmol) was added. After 1.5 h further, the reaction mixture was diluted with water (2 mL) and stirred for 30 min. The reaction mixture was filtered through celite, rinsed with MeOH and concentrated in vacuo. The residue was diluted with saturated aqueous $NaHCO_3$ and extracted with $CH_2Cl_2$ (5×). The combined organic extracts were dried and concentrated in vacuo to provide crude 3 (560 mg) as a yellow oil. The crude product was dissolved in $CH_2Cl_2$ (10 mL) and treated with diisopropylethyl amine (685 μL, 3.93 mmol) followed by 3-chloro, 4-fluorophenyl isocyanate (325 μL, 2.61 mmol). After 18 h, the reaction mixture was diluted with saturated aqueous $NaHCO_3$ and extracted with $CH_2Cl_2$ (2×). The combined organic extracts were dried and concentrated in vacuo. Flash chromatography (3% MeOH/$CH_2Cl_2$) afforded 4 (640 mg, 68% over 2 steps) as a white solid.

Step 3

A solution of carbamate 4 (640 mg, 1.07 mmol) in $CH_2Cl_2$ (8 mL) at 0° C. was treated with trifluoroacetic acid (2 mL) and warmed to ambient temperature. After 24 h, the reaction mixture was concentrated in vacuo, quenched with saturated aqueous $NaHCO_3$ and extracted with $CH_2Cl_2$ (3×). The combined organic extracts were dried and concentrated in vacuo to provide 5 (470 mg, 88%) as a yellow solid.

Step 4

A solution of aniline 5 (52 mg, 0.104 mmol) in $CH_2Cl_2$ (2 mL) and treated with diisopropylethyl amine (44 L, 0.250 mmol), acetyl chloride (12 μL, 0.160 mmol) and DMAP (5 mg, 0.04 mmol). After 18 h, the reaction mixture was diluted with saturated aqueous $NaHCO_3$ and extracted with $CH_2Cl_2$ (23×). The combined organic extracts were dried and concentrated in vacuo. Preparative thin layer chromatography (10% MeOH/$CH_2Cl_2$) furnished 6 (25 mg, 44%) as a white solid: $^1$H NMR (300 MHz, $CDCl_3$) δ 9.30 (s, 1 H), 7.53 (dd, J=6.6, 1.7 Hz, 1 H), 7.40-7.27 (m, 3H), 7.21 (dd, J=7.7, 7.6 Hz, 1 H), 7.05 (t, J=8.9 Hz, 1 H), 6.92 (d, J=7.7 Hz, 1 H), 5.03 (m, 1 H), 3.44 (ddd, J=16.5, 9.3, 4.4 Hz, 1 H), 3.35 (ddd, J=15.4, 5.0, 4.6 Hz, 1 H), 2.69-2.29 (m, 9 H), 2.26 (s, 3 H), 2.16 (s, 3 H), 2.11-1.83 (m, 5 H), 1.68-1.62 (m, 2 H), 1.26-1.21 (m, 2 H), 0.92 (dd, J=6.5, 6.2 Hz, 1 H). LCMS: 542.1, rt.=4.67 min (M+1), HRMS m/z 542.2690 [(M+H)$^+$].

Following procedures similar to those described in Example 248, the following compounds were prepared:

| EX. | STRUCTURE | LCMS (M + 1) | HRMS (M + H)$^+$ |
|---|---|---|---|
| 249 | 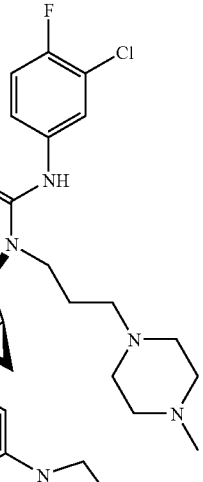 | 568.1, rt. = 4.85 min | 568.2849 |

-continued
| EX. | STRUCTURE | LCMS (M + 1) | HRMS (M + H)+ |
|---|---|---|---|
| 250 | 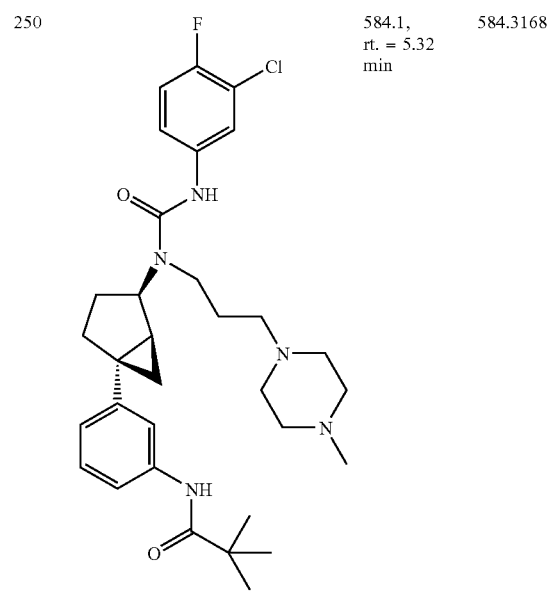 | 584.1, rt. = 5.32 min | 584.3168 |
| 251 | 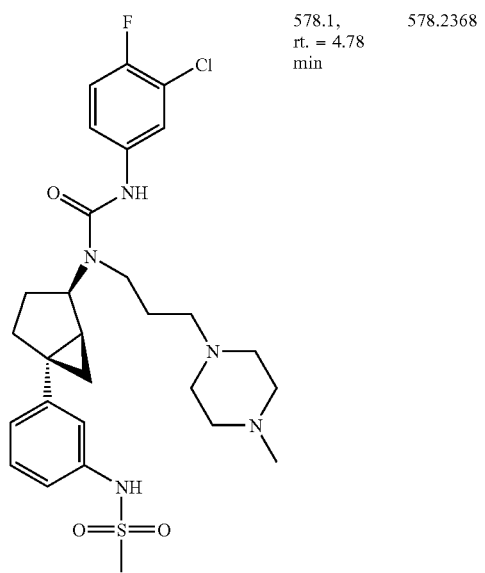 | 578.1, rt. = 4.78 min | 578.2368 |
-continued
| EX. | STRUCTURE | LCMS (M + 1) | HRMS (M + H)+ |
|---|---|---|---|
| 252 | 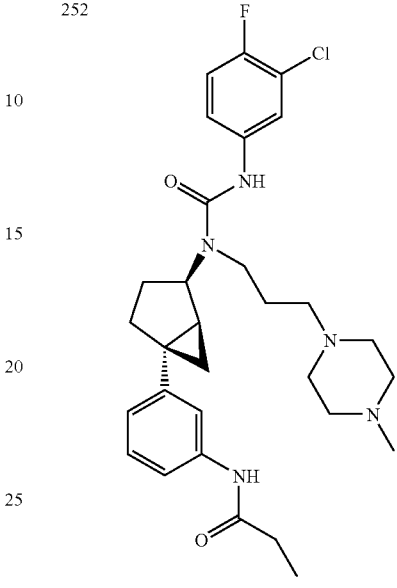 | 556.1, rt. = 4.71 min | 556.2855 |
| 253 | 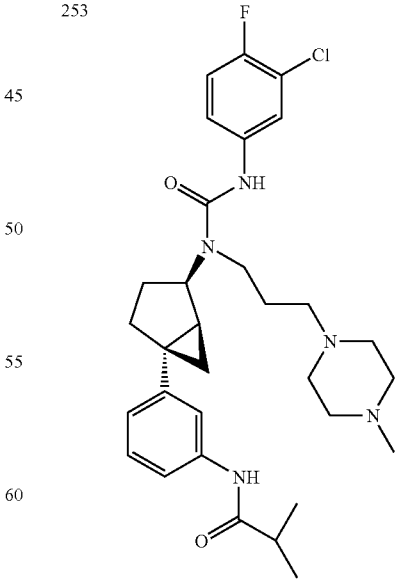 | 570.1, rt. = 4.85 min | 570.3011 |

-continued

| EX. | STRUCTURE | LCMS (M + 1) | HRMS (M + H)+ |
|---|---|---|---|
| 254 | 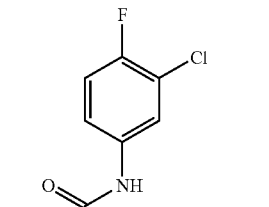 | 500.1, rt. = 4.01 min | 500.2592 |

Example 255

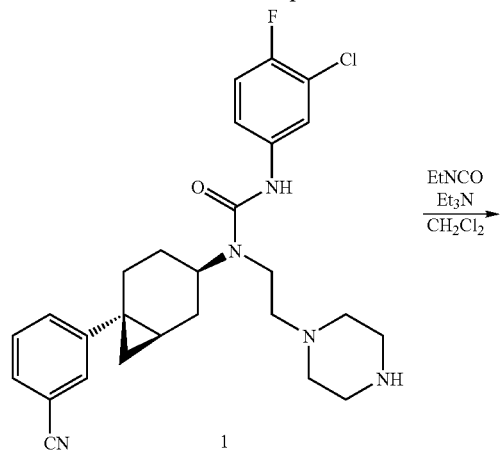

-continued

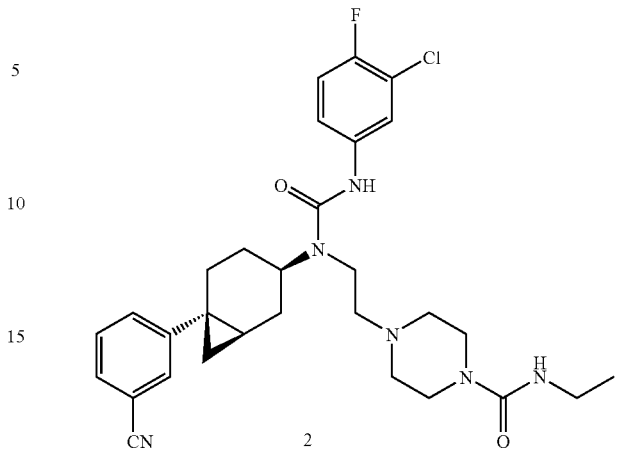

Step 1:

A solution of 1 (75 mg, 0.15 mmol), prepared according to the methods previously described, in CH$_2$Cl$_2$ (2 mL) was treated with triethylamine (42 μL, 0.30 mmol) followed by ethyl isocyanate (16 μL, 0.20 mmol). After 18 h, the reaction mixture was diluted with saturated aqueous NaHCO$_3$ and extracted with CH$_2$Cl$_2$ (3×). The combined organic extracts were dried and concentrated in vacuo. Preparative thin layer chromatography (5% MeOH/CH$_2$Cl$_2$) afforded 2 (85 mg, 99%) as a white solid: $^1$H NMR (300 MHz, CDCl$_3$) δ 9.92 (s, 1 H), 7.61 (dd, J=6.6, 2.8 Hz, 1 H), 7.53-7.44 (m, 3 H), 7.37 (dd, J=7.7, 7.6 Hz, 1 H), 7.12 (m, 1 H), 7.05 (t, J=8.9 Hz, 1 H), 7.02 (t, J=8.8 Hz, 1 H), 4.46 (s, 1 H), 4.20 (m, 1 H), 3.42 (s, 4 H), 3.31-3.22 (m, 4 H), 2.62 (s, 6 H), 2.40-2.25 (m, 2 H), 2.10 (ddd, J=12.9, 12.8,4.9 Hz, 1 H), 1.58 (t, J=12.6 Hz, 2 H), 1.43-1.22 (m, 2 H), 1.14 (t, J=7.1 Hz, 3 H), 1.00 (dd, J=9.3, 4.9 Hz, 1 H), 0.76 (dd, J=5.5, 4.9 Hz, 1 H). LCMS: 567.1, rt.=5.05 min (M+1), HRMS m/z 567.2647 [(M+H)$^+$].

Following procedures similar to those described in example 255, the following compounds were prepared:

| EX. | STRUCTURE | LCMS (M + 1) | HRMS (M + H)+ |
|---|---|---|---|
| 256 | 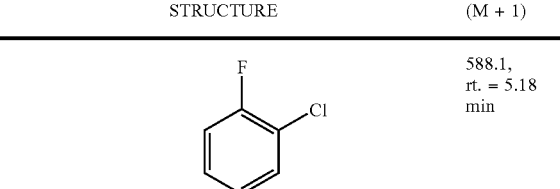 | 588.1, rt. = 5.18 min | 588.2216 |

Example 257

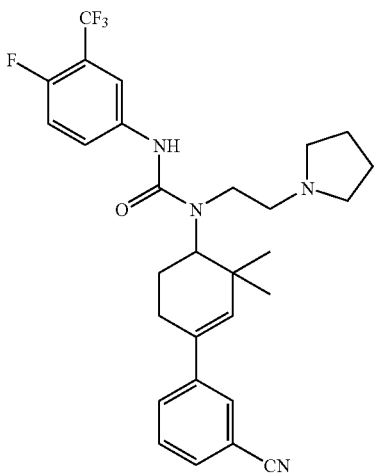

Step 1

4-(3-Cyanophenyl)-2-cyclohexene-1-one(step 2 of method 1, 0.5 g, 2.5 mmole) was dissolved in 15 ml THF and sodium hydride (60% in oil, 0.2 g 5 mmole) was added. The reaction was stirred in at 0° C. for half-hour. Trimethylsilyl chloride (0.27 g, 2.5 mmole) was then added, and the mixture was stirred for another hour at 0° C. Iodomethane was added, the reaction was warmed to room temperature slowly overnight. 50 ml ethyl acetate was added and the organic layer was washed with water (3×50 ml), dried over sodium sulfate. The reaction was very messy, but after purification by preparative TLC plates, one pure compound was obtained with very low yield (33 mg, 6%). The compound is 4-(3-cyanophenyl)-2,2-dimethyl-3-cyclohexene-1-one.

The product from above procedure can be converted to the title compounds using the same procedure as steps 4 and 5 of Example 53.

: 1H NMR (300 MHz, CDCl3) δ 11.41 (s, 1 H), 7.74-7.79 (m, 2 H), 7.37-7.62 (m, 4 H), 7.08 (t, J=9.3 Hz), 5.8(s, 1 H), 4.67 (m, 1 H), 3.42 (m, 2 H), 2.88 (m, 2 H), 2.46-2.74 (m, 6 H), 1.80-1.96 (m, 6 H), 1,17(s, 3 H), 1.07(s, 3 H).

The following compounds were prepared by similar methods:

|   |   | LCMS | HRMS |
|---|---|------|------|
| 258 | (structure) | 495.1, rt = 5.31 min | 495.2325 |

Example 259

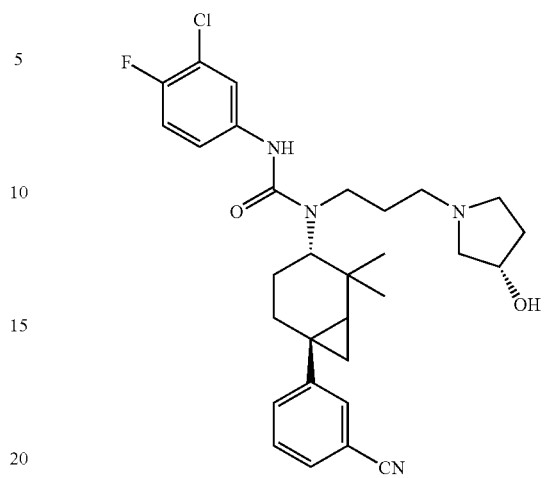

Step 1

6-(3-Cyanophenyl)bicyclo[4.1.0]heptane-3-one (procedure b of method 5, 8 g, 38 mmole), 3-amino-1-propanol (5.7 g, 76 mmole) and titanium(IV) isopropoxide (5 ml) were stirred in 200 ml methylene chloride at room temperature overnight. Sodium borohydride (2.8 g, 76 mmole) was then added and a little methanol (about 10 ml) was also added to dissolve everything. The reaction was stirred at room temperature for three hours. 200 ml 1 N HCl solution was added to quench the reaction, and the aqueous layer was washed with methylene chloride (2×100 ml). The aqueous layer was then basified with 50% sodium hydroxide solution to pH 14, and 200 ml methlene chloride was added. The mixture was filtered though a Celite cake and organic layer was separated and washed with water (2×100 ml). To the above organic solution was added 100 ml 1N sodium hydroxide solution. With vigorous stirring, di-t-butyl carbonate (8 g, 36.7 mmole) was added. The mixture was stirred at room temperature overnight. The organic layer was separated, dried over sodium sulfate and the solvent was removed by vacuum. The product was purified by column using ethyl acetate/hexane(50/50) as the eluent. It is the 10 to 1 mixture of trans and cis-3-(N-Boc-3-hydroxy-propylamino)-6-(3-Cyanophenyl)-bicyclo[4.1.0]heptane (yield: 7 g, 50%).

Step 2

The 10 to 1 mixture of trans and cis-3-(3-hydroxypropylamino)-6-(3-Cyanophenyl)-bicyclo[4.1.0]heptane (7 g, 19 mmole) was dissolved in 150 ml methylene chloride. Dess-Martin reagent (8.8 g, 21 mmole) was added and the reaction was stirred at room temperature for two hours. White precipitate was filtered and discarded. The filtrate was concentrated to dryness and purified by a silica plug using ethyl acetate/hexane (35/65) as the eluent. The product is 10 to 1 mixture of trans- and cis-3-(N-Boc-3-one-propylamino)-6-(3-Cyanophenyl)-bicyclo[4.1.0]heptane (6.4 g, 92%).

Step 3

The 10 to 1 mixture of trans- and cis-3-(N-Boc-3-one-propylamino)-6-(3-Cyanophenyl)-bicyclo[4.1.0]heptane (2.3 g, 6.25 mmole), S-3-hydroxypyrrolidine (1 g, 11.5 mmole) and titanium(IV) isopropoxide (5 ml) were stirred in 100 ml methylene chloride at room temperature for two hours. Sodium triacetoxylborohydride (2.65 g, 12.5 mmole) was added and the reaction was stirred at room temperature overnight. 100 ml 1N sodium hydroxide solution was added and the mixture was filtered though a celite cake. The organic layer was washed with water (3×50 ml), dried over sodium sulfate and the solvent was removed via vacuum. The residue was purified by column using ethylacetate/methanol (gradient from 100/0 to 50/50 in 40 minutes) as the eluent. The product is a 10 to 1 mixture of trans- and cis-3-[N-Boc-3-(S-3-hydroxypyrrolidinyl)-propylamino)-6-(3-Cyanophenyl)-bicyclo[4.1.0]heptane (1.14 g, 42%).

Step 4

The 10 to 1 mixture of trans- and cis-3-[N-Boc-3-(S-3-hydroxypyrrolidinyl)-propylamino)-6-(3-Cyanophenyl)-bicyclo[4.1.0]heptane (0.4 g, 0.91 mmole) was dissolved in 25 ml methylene chloride and 25 ml trifluoroacetic acid was then added. The reaction was stirred at room temperature for 2 hours. Solvent was removed and the residue was partitioned between 100 ml methylene chloride and 100 ml saturated sodium bicarbonate solution. The organic layer was washed with water (2×50 ml), dried over sodium sulfate. The product was purified by a column with ethylacetate/0.5N methanol as the eluent (gradient from 100/0 to 0/100 in 40 minutes). The product is the 10 to 1 mixture of trans- and cis-3-[3-(S-3-hydroxypyrrolidinyl)-propylamino)-6-(3-Cyanophenyl)-bicyclo[4.1.0]heptane (0.20 g 65%).

Step 5

The 10 to 1 mixture of trans- and cis-3-[3-(S-3-hydroxypyrrolidinyl)-propylamino)-6-(3-Cyanophenyl)-bicyclo[4.1.0]heptane (26 mg, 0.077 mmole) and 3-chloro-4-fluoro phenylisocyanate (13.1 mg, 0.077 mmole) were stirred in 5 ml methylene chloride at room temperature for half hour. The reaction solution was loaded directly onto a preparative TLC plate and the plate was developed in pure ethylacetate. The trans isomer was isolated from the plate as the product: N'-(3-chloro-4-fluorophenyl)-N-[trans-6-(3-Cyanophenyl)-bicyclo[4.1.0]hept-3-yl]-N-[3-(s-3-hydroxy-1-pyrrolidinyl) propyl]urea (31.6 mg HCl salt, 75%). 1H NMR (300 MHz, CDCl3) 9.51 (d, J=25.3 Hz, 1 H), 7.32-7.67 (m, 6 H), 6.99 (t, J=8.8 Hz, 1 H), 4.44 (m, 1 H), 3.88 (m, 1 H), 3.19-3.45 (m, 2 H), 1.56-2.84 (m,16H), 1.28 (m, 1H), 0.97 (m, 1 H), 0.84 (m, 1 H).

The following compounds were prepared by similar methods

| | | LCMS | HRMS |
|---|---|---|---|
| 260 | 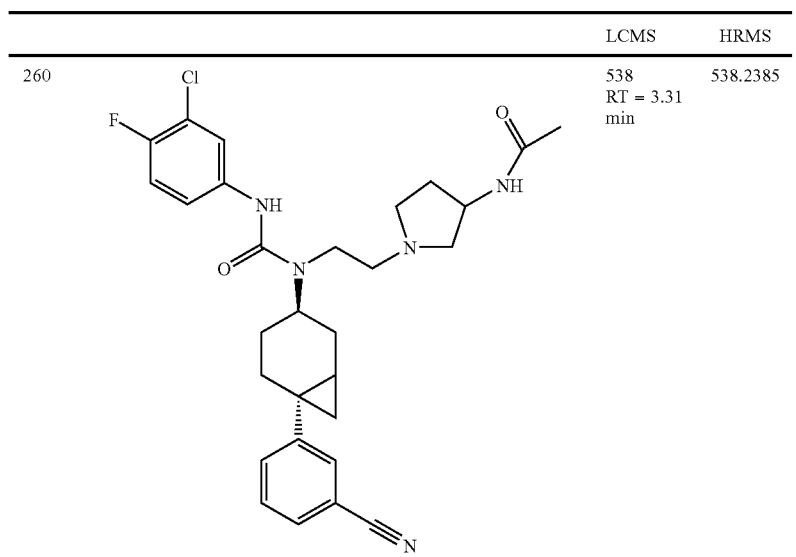 | 538 RT = 3.31 min | 538.2385 |
| 261 | 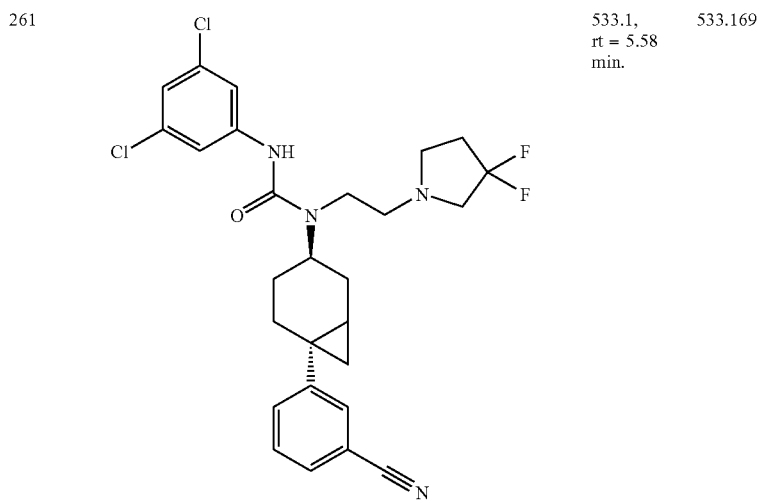 | 533.1, rt = 5.58 min. | 533.169 |

| | | LCMS | HRMS |
|---|---|---|---|
| 262 | 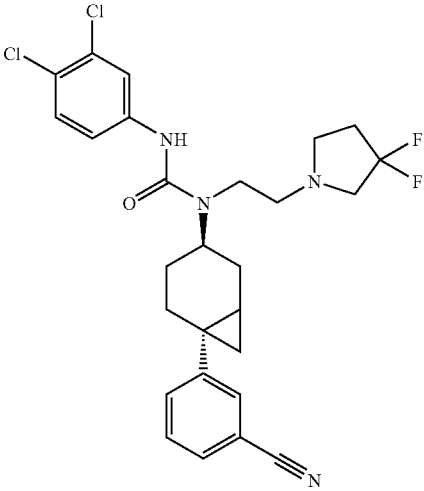 | 533.1, rt = 5.42 min. | 533.169 |
| 263 | 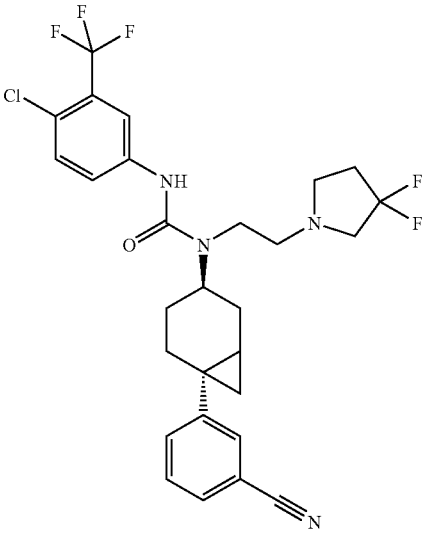 | 551.1, rt = 5.32 min. | 551.2241 |
| 264 | 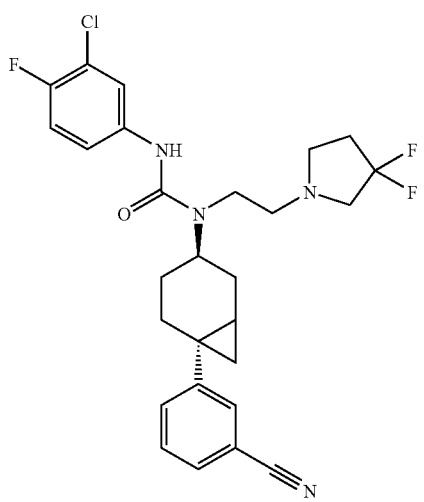 | 517.1, rt = 5.32 min. | 517.1977 |

-continued
| | | LCMS | HRMS |
|---|---|---|---|
| 265 | 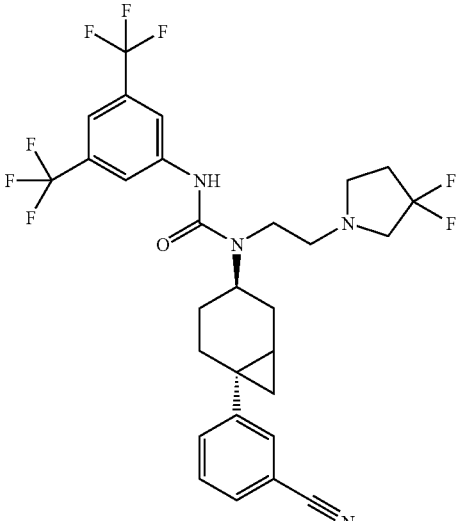 | 601.1, rt = 5.58 min. | 601.2226 |
| 266 | 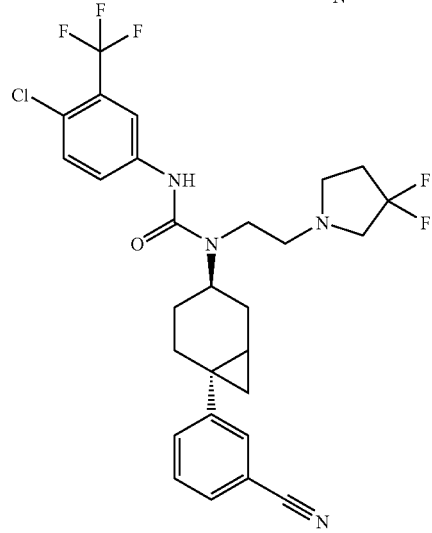 | 567.1, rt = 5.45 min. | 567.1956 |
| 267 | 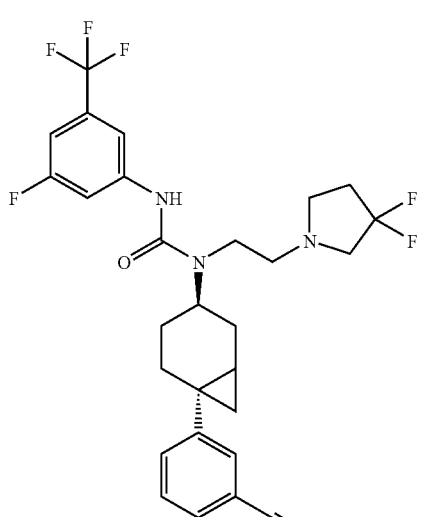 | 551.1, rt = 5.35 min. | 551.2241 |

-continued
|     |     | LCMS | HRMS |
|-----|-----|------|------|
| 268 | 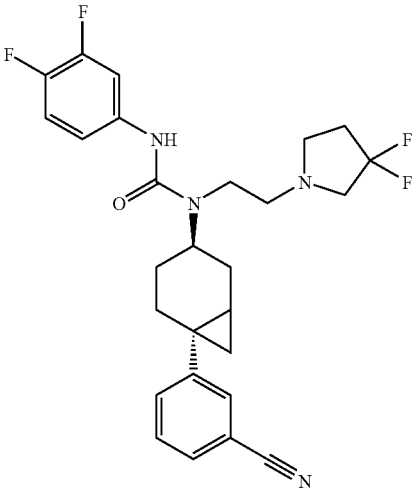 | 501.1, rt = 5.15 min. | 501.2282 |
| 269 | 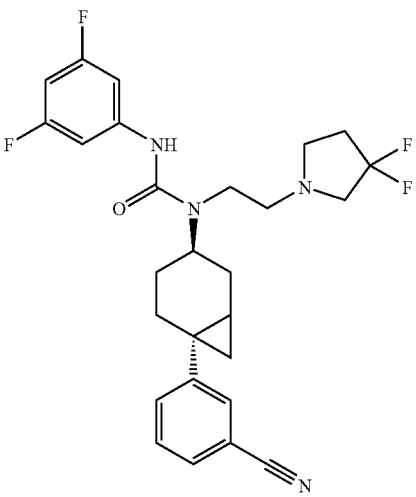 | 501.1, rt = 5.22 min. | 501.2282 |
| 270 | 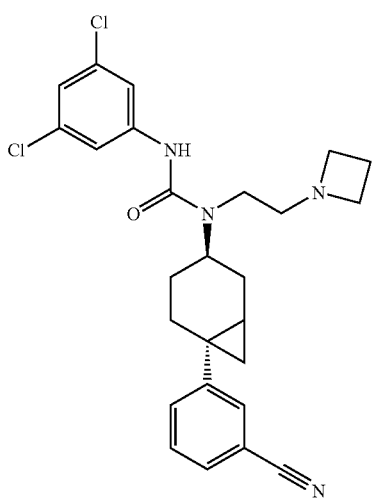 | 483.1, rt = 5.82 min. | 483.1725 |

-continued
| | | LCMS | HRMS |
|---|---|---|---|
| 271 | 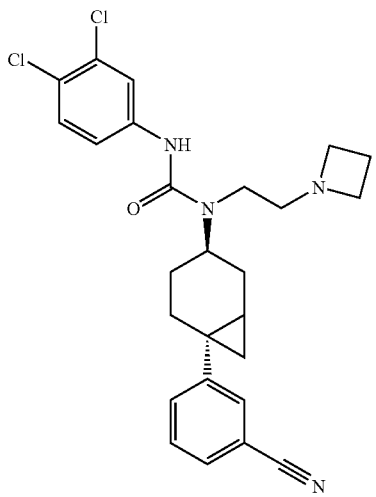 | 483.1, rt = 5.75 min. | 483.1725 |
| 272 | 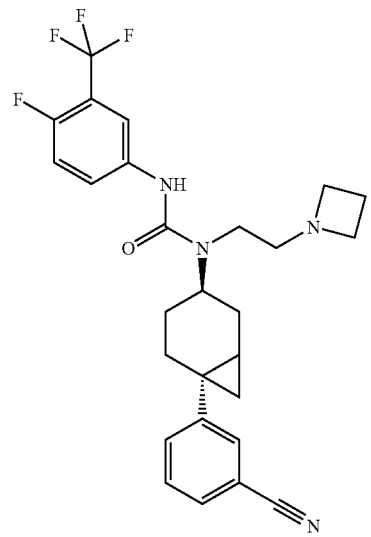 | 501.1, rt = 5.58 min. | 501.2272 |
| 273 | 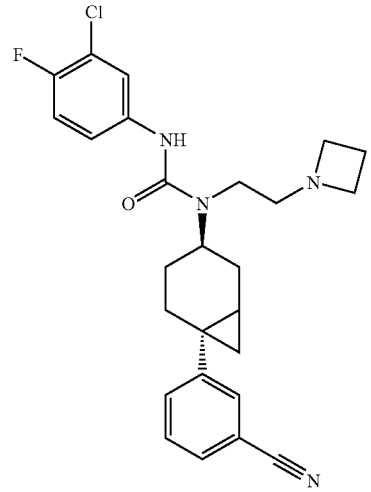 | 467.1, rt = 5.52 min. | 467.2007 |

| | | LCMS | HRMS |
|---|---|---|---|
| 274 | 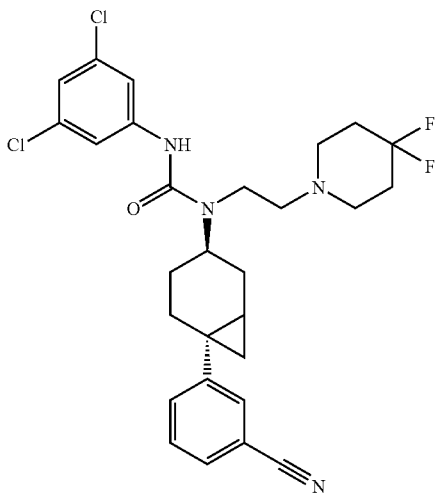 | 547.1, rt = 5.82 min. | 547.1837 |
| 275 | 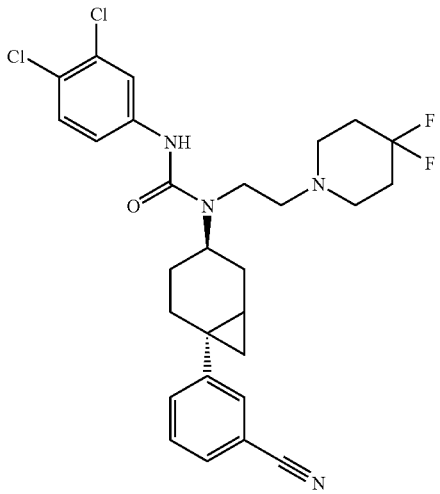 | 547.1, rt = 5.75 min. | 547.1837 |
| 276 | 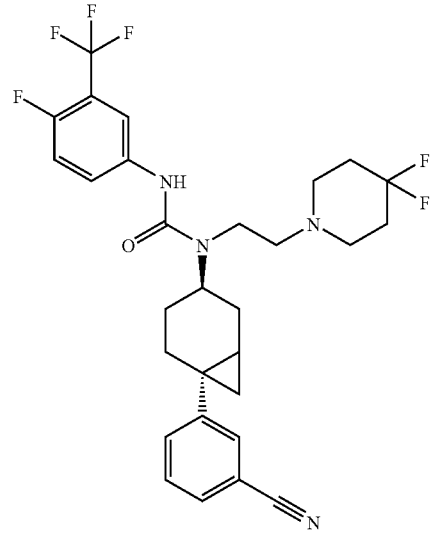 | 565.1, rt = 5.65 min. | 565.2391 |

-continued
| | | LCMS | HRMS |
|---|---|---|---|
| 277 | 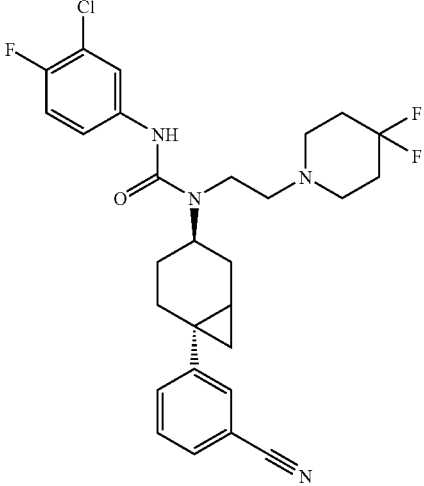 | 531.1, rt = 5.52 min. | 531.213 |
| 278 | 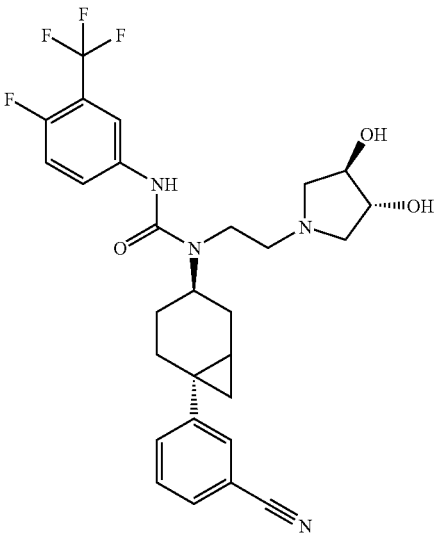 | 547.1, rt = 5.85 min. | 547.234 |
| 279 | 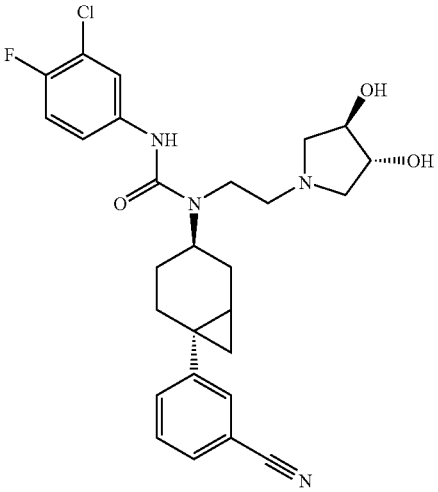 | 513.1, rt = 5.78 min. | 513.2073 |

-continued
| | | LCMS | HRMS |
|---|---|---|---|
| 280 | 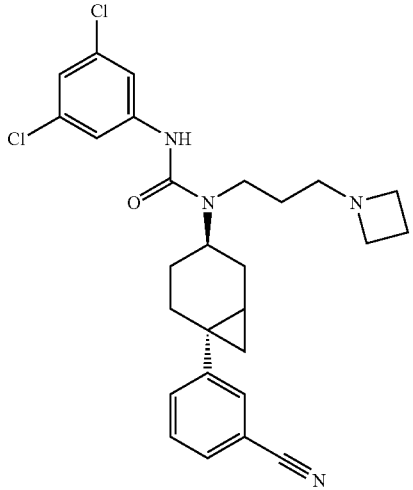 | 497.1, rt = 6.29 min. | 497.1879 |
| 281 | 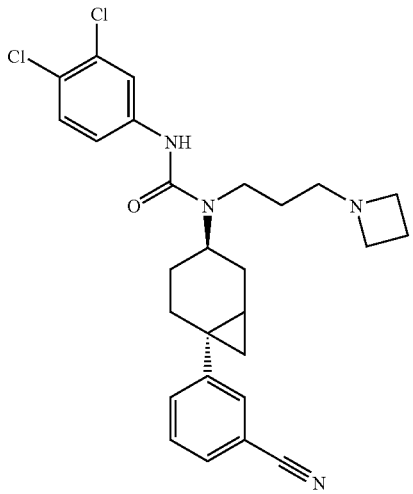 | 497.1, rt = 6.22 min. | 497.1879 |
| 282 | 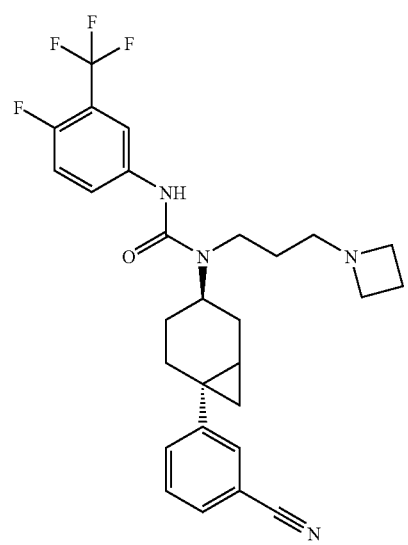 | 515.1 rt = 6.09 min. | 515.2426 |

-continued
| | | LCMS | HRMS |
|---|---|---|---|
| 283 | 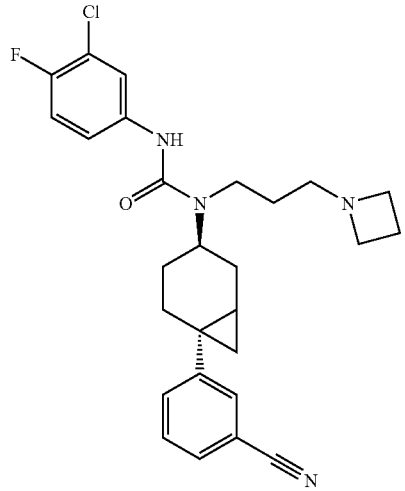 | 481.1, rt = 6.06 min. | 481.2175 |
| 284 | 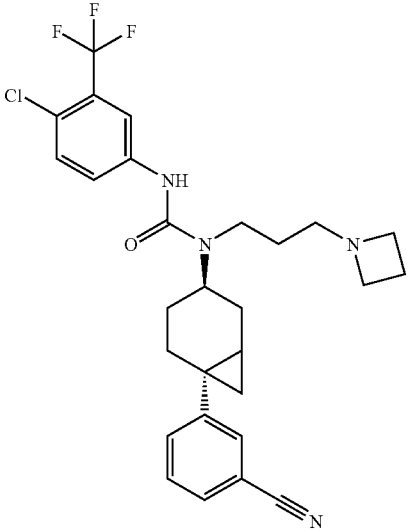 | 531.1, rt = 6.25 min. | 531.2137 |
| 285 | 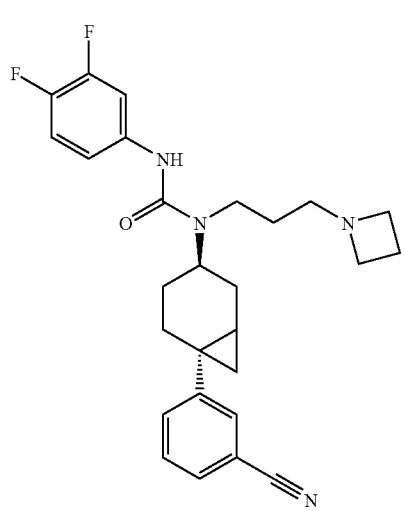 | 465.1, rt = 4.97 min. | 465.2471 |

-continued
| | | LCMS | HRMS |
|---|---|---|---|
| 286 | 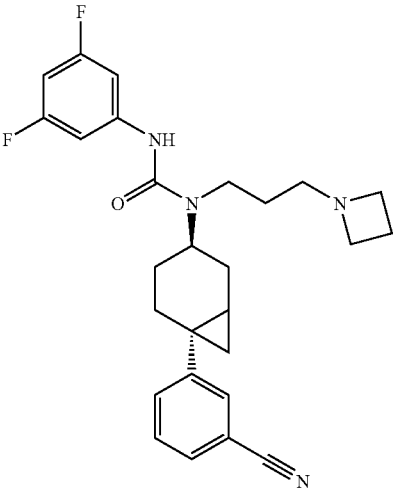 | 465.1, rt = 6.09 min. | 465.2471 |
| 287 | 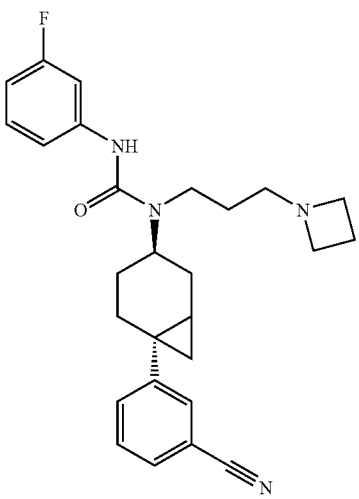 | 447.1, rt = 6.02 min. | 447.2566 |
| 288 | 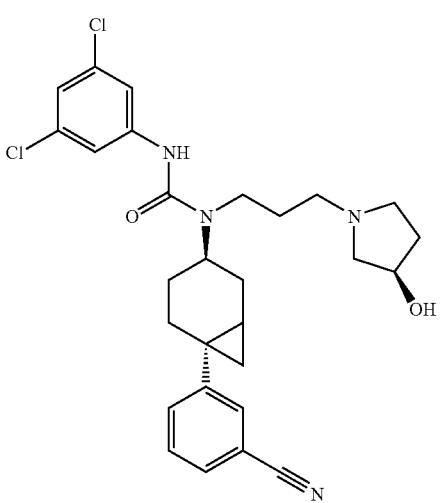 | 527.1 rt = 5.58 min. | 527.1974 |

-continued
|     |     | LCMS | HRMS |
|-----|-----|------|------|
| 289 | 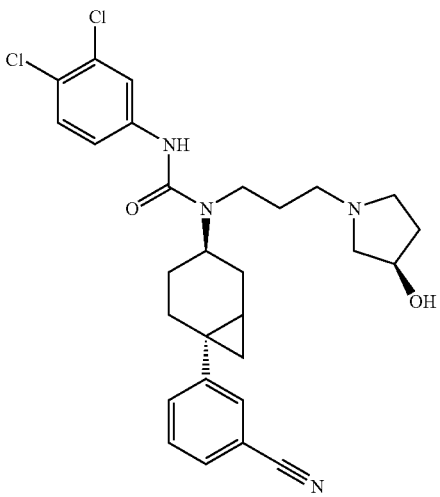 | 527.1 rt = 5.38 min. | 527.1974 |
| 290 | 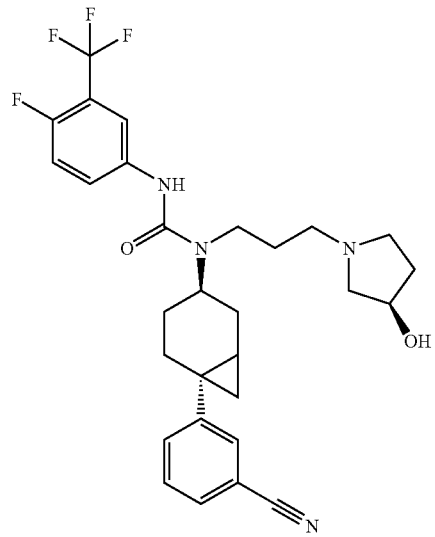 | 545.1 rt = 5.38 min. | 545.2535 |
| 291 | 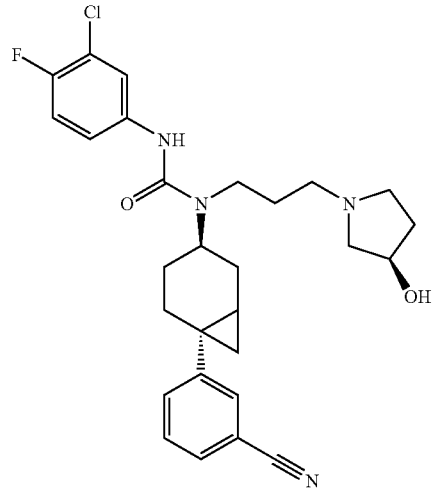 | 511.1 rt = 5.18 min. | 511.2283 |

|     |     | LCMS | HRMS |
| --- | --- | --- | --- |
| 292 | 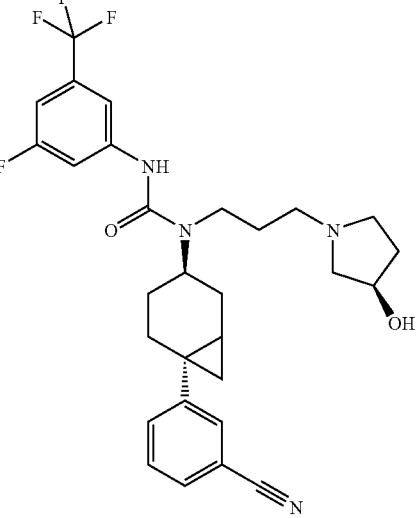 | 545.1 rt = 5.48 min. | 545.2534 |
| 293 | 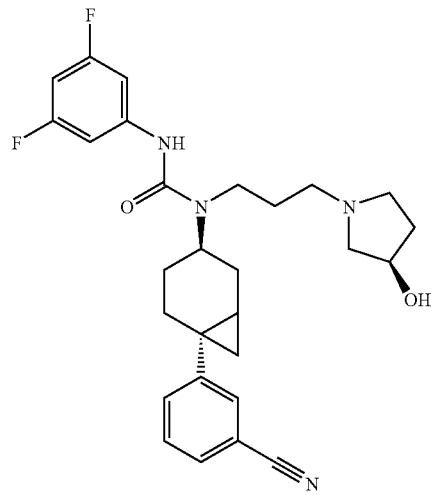 | 495.1 rt = 5.22 min. | 495.2579 |
| 294 | 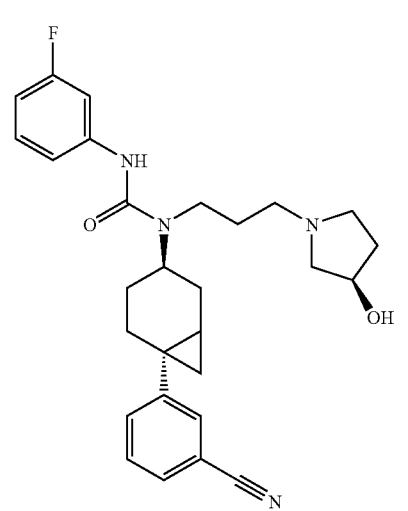 | 477.1 rt = 4.91 min. | 477.267 |

|     |     | LCMS | HRMS |
| --- | --- | --- | --- |
| 295 | 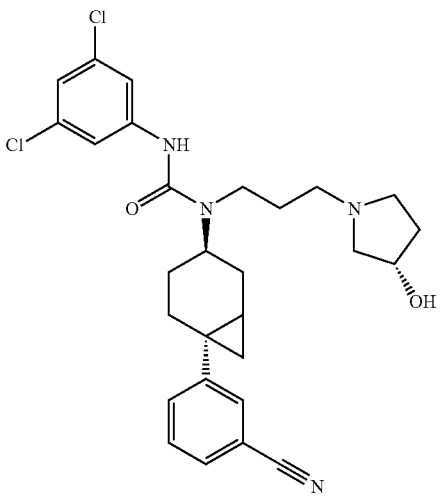 | 527.1 rt = 5.58 min. | 527.1974 |
| 296 | 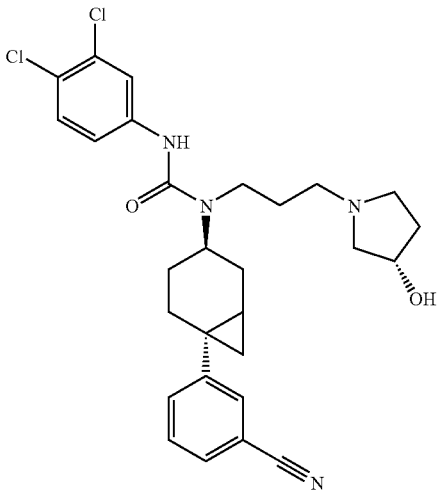 | 527.1 rt = 5.38 min. | 527.1974 |
| 297 | 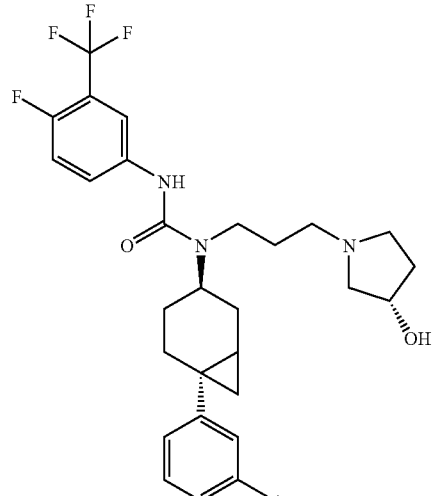 | 545.1 rt = 5.18 min. | 545.2534 |

-continued

|     |     | LCMS | HRMS |
| --- | --- | --- | --- |
| 298 | | 495.1 rt = 4.95 min. | 495.2564 |
| 299 | | 495.1 rt = 5.05 min. | 495.2564 |
| 300 | | 477.1 rt = 4.92 min. | 477.2671 |

-continued
| | | LCMS | HRMS |
|---|---|---|---|
| 301 | 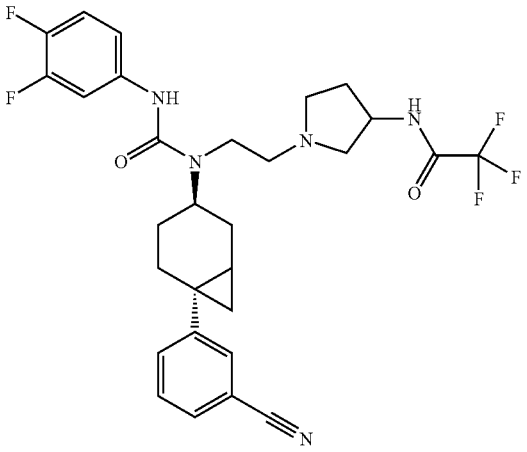 | 576.1 rt = 5.42 min. | 576.2388 |
| 302 | 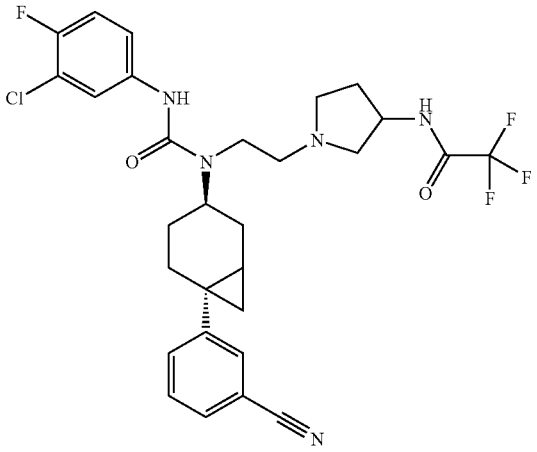 | 591.2 rt = 5.42 min. | 591.2108 |
| 303 | 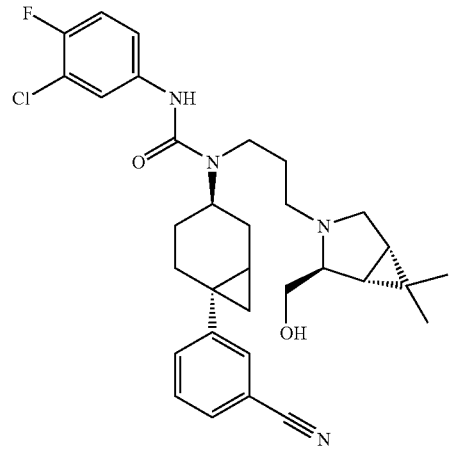 | 565.1 rt = 5.32 min. | 565.2754 |

-continued
| | | LCMS | HRMS |
|---|---|---|---|
| 304 | 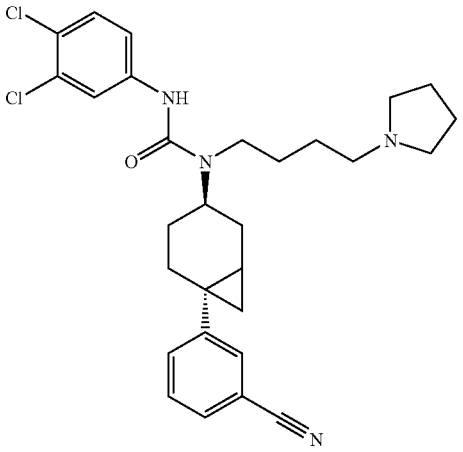 | 525.1 rt = 5.82 min. | 525.2188 |
| 305 | 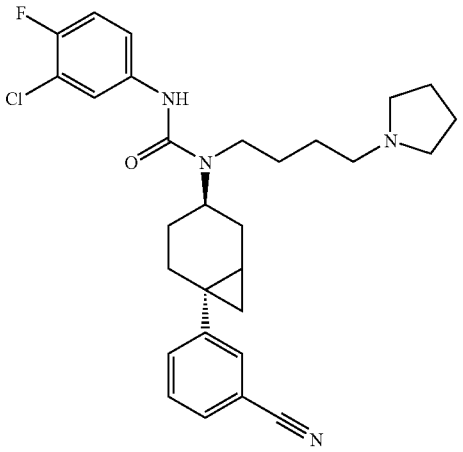 | 509.1 rt = 5.65 min. | 509.2483 |
| 306 | 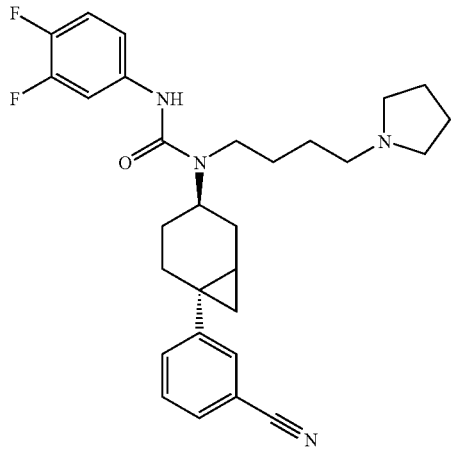 | 493.1 rt = 5.62 min. | 493.2779 |

-continued

| | | LCMS | HRMS |
|---|---|---|---|
| 307 | 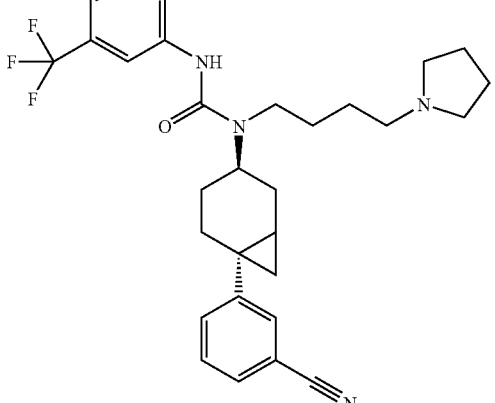 | 543.1 rt = 5.62 min. | 543.2741 |
| 308 | 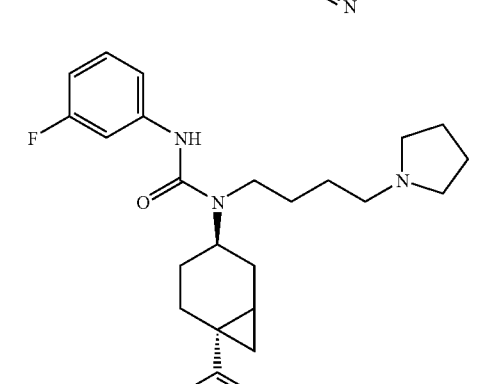 | 475.1 rt = 5.35 min. | 475.2873 |

Example 309

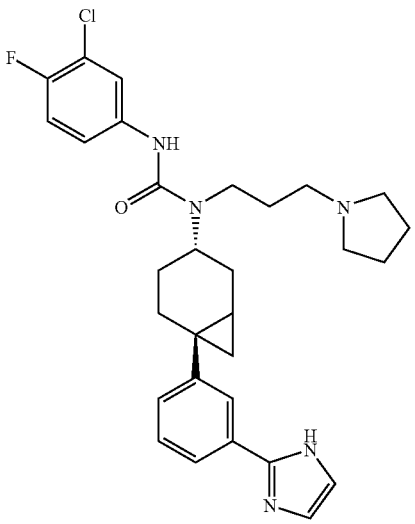

Step 1

6-(3-Cyanophenyl)bicyclo[4.1.0]heptane-3-one ethylene ketal (The product from procedure b of method 5, step 2. 3 g, 11.8 mmole) was dissolved in 10 ml dry toluene. This solution was added to the solution of aminoacetaldehyde diethyl acetal (2.3 g, 17.3 mmole) and trimethyl aluminum (8.8 ml 2M solution in toluene) in 100 ml toluene. The reaction was heated to 80° C. overnight. Additional aminoacetaldehyde diethyl acetal (2.3 g, 17.3 mmole) and trimethyl aluminum (8.8 ml 2M solution in toluene) were added and reaction heated to 80° C. for 25 more hours. The reaction was quenched by adding 1N sodium hydroxide (100 ml). The organic layer was washed with water (2×100 ml), dried over sodium sulfate and solvent was removed by vacuum. The product was purified by column using ethylacetate/hexane (gradient from 0/100 to 40/60 in 40 minutes). The product is 6-[3-(2-one-diethyl ketal amino imino)phenyl]bicyclo[4.1.0]heptane-3-one ethylene ketal (2.1 g, 48%).

Step 2

6-[3-(2-one-diethyl ketal amino imino)phenyl]bicyclo[4.1.0]heptane-3-one ethylene ketal (2.1 g, 5.6 mmole) was dissolved in 100 ml methanol. 10 ml 5N hydrochloride acid was then added and the mixture was refluxed for three hours. Solvent was removed and residue was partitioned between 100 ml ethylacetate and 100 ml saturated sodium bicarbonate solution. The organic layer was washed with water (2×100 ml) dried over sodium sulfate. The product was purified by column using hexane/ethylacetate(gradient from 80/20 to 0/100 in 40 minutes). The product is 6-[3-(1H-imidazol-2-yl)phenyl]bicyclo[4.1.0]heptane-3-one(0.67 g, 47%).

Step 3

6-[3-(1H-imidazol-2-yl)phenyl]bicyclo[4.1.0]heptane-3-one (0.24 g, 0.95 mmole), 1-pyrrolidinepropanamine (0.48 g, 3.7 mmole) and titanium(IV) isopropoxide (2 ml) were stirred in 50 ml methylene chloride at room temperature for 2 hours. Sodium borohydride (0.14 g, 3.7 mmole) was then added. The reaction was stirred at room temperature for two hours. 50 ml 1 N HCl solution was added to quench the reaction, and the aqueous layer was washed with methylene chloride (2×50ml). The aqueous layer was then basified with 50% sodium hydroxide solution to pH 14, and 100 ml methylene chloride was added. The mixture was filtered though a Celite cake. The organic layer was washed with water (2×100 ml), dried over sodium sulfate. The product was purified by column using methylene chloride/0.5N ammonium in methanol (gradient from 100/0 to 0/100 in 40 minutes). The product is N-trans-6-[3-(1H-imidazol-2-yl)phenyl]bicyclo[4.1.0]hept-3-yl]-1-pyrrolidinepropanamine (0.19 g, 55%).

Above compound can be transferred to final product according step 5 of example 270. Title compound: N'-(3-chloro-4-fluorophenyl)-N-[trans-6-(3-1H-imidazol-2-yl)phenyl)-bicyclo[4.1.0]hept-3-yl]-N-[3-(1-pyrrolidinyl)propyl]urea. 1H NMR (300 MHz, CDCl3) δ 10.04 (s, 1H), 7.80(d, J=7.69 Hz, 1H), 7.68(s, 1H), 7.50 (dd, J=6.59 and 2.75 Hz, 1 H), 7.36 (m, 1 H), 7.09-7.27 (m, 4 H), 7.02 (t, J=8.79 Hz, 1 H), 3.82 (m, 1 H), 3.29 (m, 2 H), 2.56 (m, 6H), 2.08(m, 2H), 1.59-1.87 (m, 8H), 1.45 (m, 2H), 1.04(m, 1 H), 0.80 (dd, J=9.34 and 4.94 Hz, 1 H), 0.60 (t, J=4.94 Hz, 1 H).

The following compounds were prepared by similar methods:

| | | LCMS | HRMS |
|---|---|---|---|
| 310 | 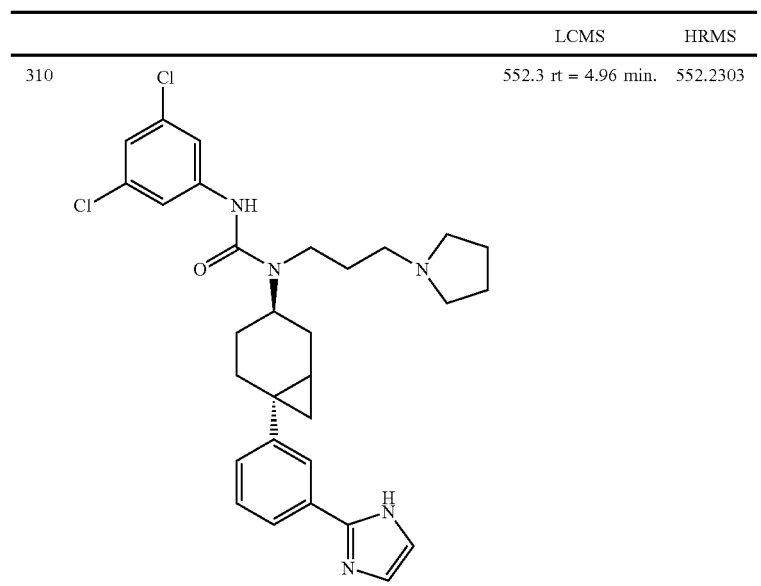 | 552.3 rt = 4.96 min. | 552.2303 |
| 311 | 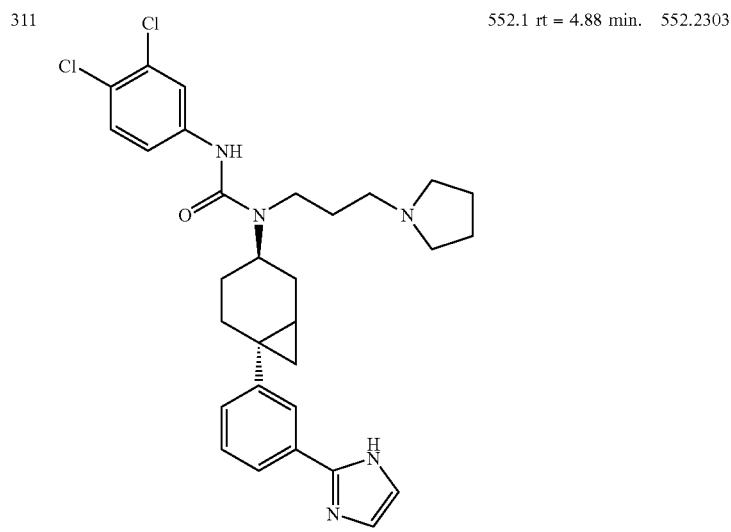 | 552.1 rt = 4.88 min. | 552.2303 |

|   |   | LCMS | HRMS |
|---|---|---|---|
| 312 | | 570.1 rt = 4.81 min. | 570.2862 |
| 313 | | 520.1 rt = 4.38 min. | 520.2898 |
| 314 | | 502.1 rt = 4.75 min. | 502.2988 |

Example 315

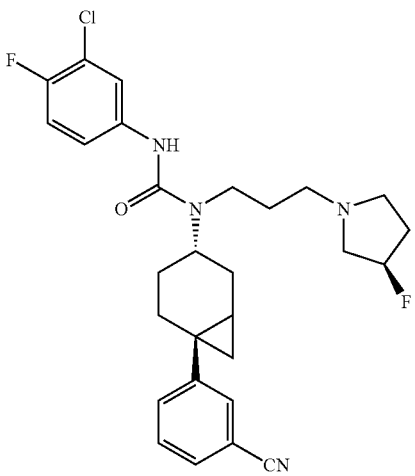

Step 1

The 10 to 1 mixture of trans- and cis-3-[N-Boc-3-(S-3-hydroxypyrrolidinyl)-propylamino)-6-(3-Cyanophenyl)-bicyclo[4.1.0]heptane (The product of step 3 of method 7, 0.74 g, 1.7 mmole) was dissolved in 100 ml methylene chloride. Diethylaminosulfur trifluoride (0.93 g, 5.8 mmole) was then added and the mixture was stirred at room temperature for three hours. 100 ml water was added to quench the reaction. Organic layer was separated, dried over sodium sulfate and solvent was then removed. The residue was purified by column using methylene chloride/methanol (gradient from 100/0 to 50/50 in 30 minutes) as the eluent. The product is the 10 to 1 mixture of trans- and cis-3-[N-Boc-3-(R-3-fluoropyrrolidinyl)-propylamino)-6-(3-Cyanophenyl)-bicyclo[4.1.0]heptane (0.55 g, 74%).

Above product can be converted to title compound using steps 4 and 5 of method 7. N'-(3-chloro-4-fluorophenyl)-N-[trans-6-(3-Cyanophenyl)-bicyclo[4.1.0]hept-3-yl]-N-[3-(R-3-fluoropyrrolidinyl)propyl]urea. 1H NMR (300 MHz, CDCl3) δ 9.40 (d, J=26.4 Hz, 1 H), 7.28-7.64 (m, 6 H), 7.00 (t, J=8.79 Hz, 1 H), 5.24 (dt, J=54.4 and 4.9 Hz, 1 H), 3.90 (m, 1 H), 1.58-3.48 (m, 18 H), 1.30 (m,1 H), 0.99 (m, 1H), 0.86 (m, 1H).

The following compounds were prepared by similar methods

|  |  | LCMS | HRMS |
|---|---|---|---|
| 316 | | 529.3<br>rt = 5.38 min. | 529.1945 |
| 317 | | 529.3<br>rt = 5.31 min. | 529.1945 |

-continued
| | | LCMS | HRMS |
|---|---|---|---|
| 318 | 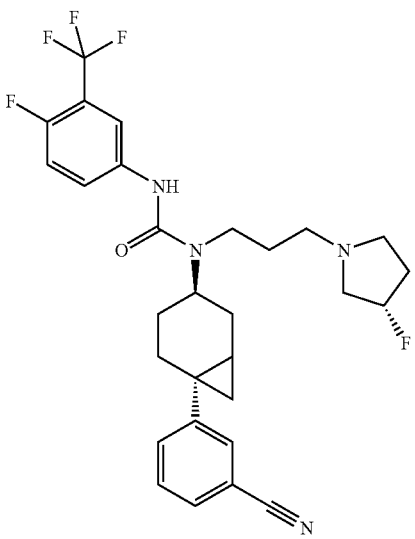 | 547.3 rt = 5.11 min. | 547.2489 |
| 319 | 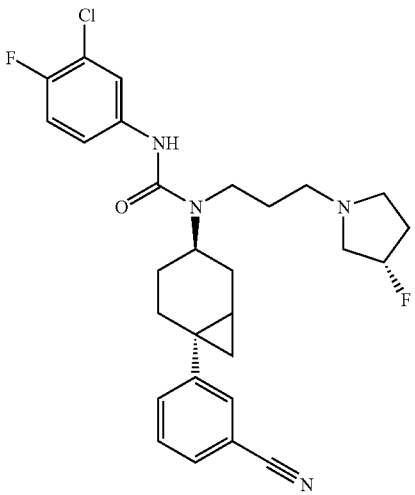 | 513.3 rt = 5.01 min. | 513.2238 |
| 320 | 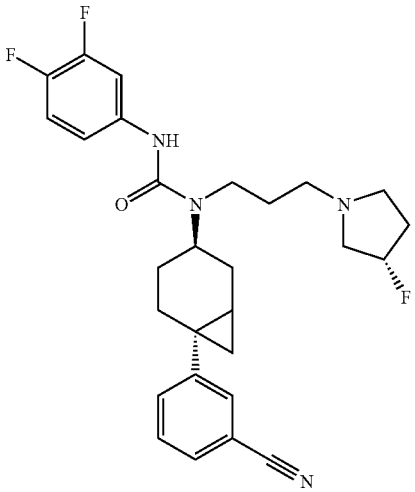 | 497.1 rt = 4.98 min. | 497.2519 |

|     |     | LCMS | HRMS |
| --- | --- | --- | --- |
| 321 | 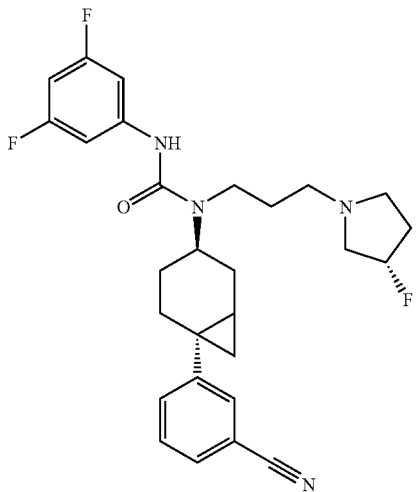 | 597.3<br>rt = 4.98 min. | 497.2519 |
| 322 | 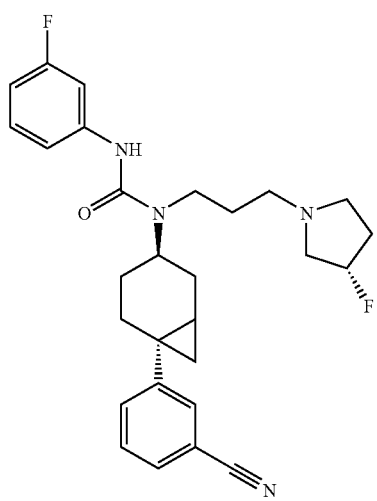 | 479.3<br>rt = 4.91 min. | 479.2615 |
| 323 | 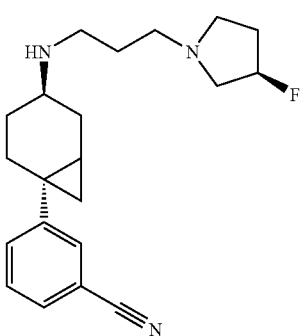 | 342.1<br>rt = 3.61 min. | 342.2344 |

| | | LCMS | HRMS |
|---|---|---|---|
| 324 | | 497.1 rt = 5.26 min. | 497.2524 |
| 325 | | 479.1 rt = 5.28 min. | 479.2629 |

Example 326

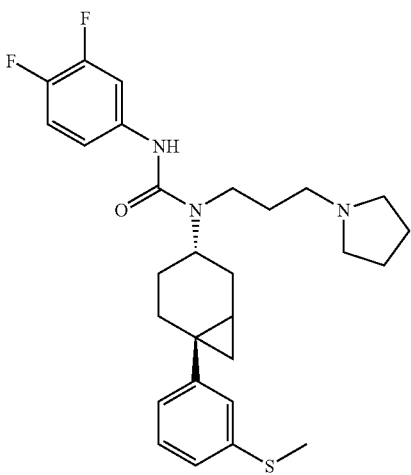

Step 1

3-bromothioanisole (15 g, 74 mmole) was dissolved in 200 ml dry THF and the solution was cooled to −78° C. n-Butyllithium (2.0 M in hexane, 37 ml, 74 mmole) was added via an additional funnel in half an hour. After n-butyllithium was added, the reaction was stirred at −78° C. for 30 minutes. 1,4-Dioxaspiro[4,5]decan-8-one (11.5 g, 74 mmole) in 100 ml dry THF was added via another additional funnel in 30 minutes. The reaction was stirred overnight and the temperature was slowly raised to −25° C. The reaction was then quenched by adding 200 ml water and 200 ml of ethylacetate was added. The organic layer was washed with water (3×400 ml), dried over sodium sulfate and solvent was removed by vacuum. The product was purified by column using hexane/ethylacetate (gradient from 100/0 to 50/50 in 50 Min.) as the eluent. The product is 4-(3-(Methylthio) phenyl)-4-hydroxycyclohexane-1-one ethylene is ketal (Yield: 14.5 g, 70%).

Step 2

4-(3-(Methylthio)phenyl)-4-hydroxycyclohexane-1-one ethylene ketal (14.5 g, 52 mmole) and Triethylamine (10.4 g, 103 mmole) were dissolved in 200 ml methylene chloride.

Mesyl chloride (8.8 g, 77 mmole) in 100 ml methylene chloride was then added dropwise in one hour. The mixture was stirred at room temperature for two hours. Additional triethylamine and mesyl chloride (same amount as the first time) were added, and the reaction was stirred at room temperature for 1 more hour. 200 ml saturated sodium bicarbonate solution was added to quench the reaction. The organic layer was washed with water (2×200 ml), dried over sodium sulfate and solvent was removed. The residue was purified by column with ethyl acetate/hexane as the eluent. The product is 4-(3-(Methylthio)phenyl)-3-cyclohexene-1-one ethylene ketal (Yield: 12.5 g, 92%).

Step 3

Diethylzinc(1 M in hexane, 108 ml, 108 mmole) was mixed with 400 ml methylene chloride and the mixture was cooled to −20° C. Trifluoroacetic acid (12.4 g, 108 mmole) in 100 ml methylene chloride was added in 15 minutes. The mixture was stirred at −20° C. for 5 minutes. Diiodomethane (29 g, 108 mmole) in 70 ml methylene chloride was then added in 20 minutes and the mixture was stirred for 5 minutes. 4-(3-(Methylthio)phenyl)-3-cyclohexene-1-one ethylene ketal (9.5 g, 36.6 mmole) in 100 ml methylene chloride was added dropwise in 10 minutes. The mixture was stirred overnight at −5° C. 300 ml 1N sodium hydroxide solution was added to quench the reaction. The organic layer was separated, washed with water (2×200 ml) and dried over sodium sulfate. The product was purified by column using ethylacetate/hexane (gradient from 0/100 to 40/60 in 1 hour) as the eluent. The product is 6-(3-(Methylthio)phenyl)bicyclo[4.1.0]heptane-3-one ethylene ketal (8.8 g, 88%).

Step 4

6-(3-(Methylthio)phenyl)bicyclo[4.1.0]heptane-3-one ethylene ketal (0.6 g, 2.2 mmole), and toluenesulfonic acid(0.5 g) were heated to 60° C. in 50 ml acetone for three hours. The solvent was removed and the residue was partitioned between 100 ml ethylacetate and 100 ml saturated sodium carbonate solution. The organic layer was washed with water (2×50 ml), dried with sodium sulfate and the solvent was removed by vacuum. The product was purified by column using ethylacetate/Hexane as the eluent. The product is 6-(3-(Methylthio)phenyl)bicyclo[4.1.0]heptane-3-one (Yield:0.43 g, 86%).

Step 5

6-[3-(Methylthio)phenyl]bicyclo[4.1.0]heptane-3-one (0.43 g, 1.9 mmole), 1-pyrrolidinepropanamine (0.71 g, 5.5 mmole) and newly activated molecular sieves (2 g) were stirred in 50 ml methylene chloride at room temperature overnight. Sodium borohydride (0.14 g, 3.7 mmole) was then added. The reaction was stirred at room temperature for two hours. 50 ml 1 N HCl solution was added to quench the reaction. The molecular sieves were removed and the aqueous layer was washed with methylene chloride (2×50 ml). The aqueous layer was then basified with 50% sodium hydroxide solution to pH 14, and 100 ml methylene chloride was added. The organic layer was washed with water (2×100 ml), dried over sodium sulfate. The product was purified by column using methylene chloride/0.5N ammonium in methanol (gradient from 100/0 to 0/100 in 40 minutes). The product is predominantly N-trans-6-[3-(methylthio)phenyl] bicyclo[4.1.0]hept-3-yl]-1-pyrrolidinepropanamine, which was used in next step without further purification (0.31 g, 49%).

Step 6

N-trans-6-[3-thiomethoxyl phenyl]bicyclo[4.1.0]hept-3-yl]-1-pyrrolidinepropanamine(80 mg, 0.24 mmole) and 3,4-Difluoro phenylisocyanate (74 mg, 0.48 mmole) were stirred in 5 ml CH2CL2 for two hours. The reaction solution was loaded on a preparative TLC plate. The plate was developed by EtOAc/MeOH (95/5) solution and the product was isolated off the plate. The product is SCH 643212 (17.4HCl salt, 14%). N'-(3,4-Difluorophenyl)-N-[trans-6-(3-(methylthio) phenyl)-bicyclo[4.1.0]hept-3-yl]-N-[3-(s-3-hydroxy-1-pyrrolidinyl)propyl]urea. 1H NMR (300 MHz, CDCl3) δ 9.73 (s, 1 H), 7.46 (m, 1 H), 7.18 (m, 2 H), 7.02 (m, 4H), 3.93 (m, 1H), 3.34 (m, 2H), 2.61 (m, 6 H), 2.47 (s, 3 H), 1.58-2.38 (m, 12H), 1.28 (m, 1H), 0.97 (m, 1H), 0.75 (m, (m, 1 H).

The following compounds were made using similar procedures:

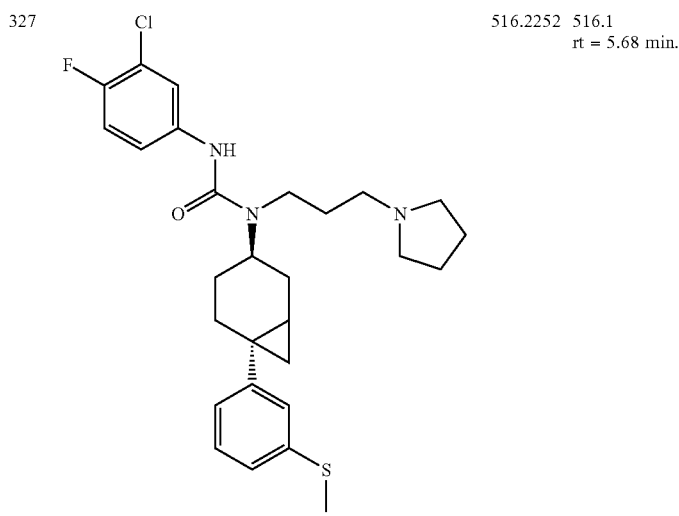

327     516.2252 516.1
rt = 5.68 min.

-continued
| 328 | 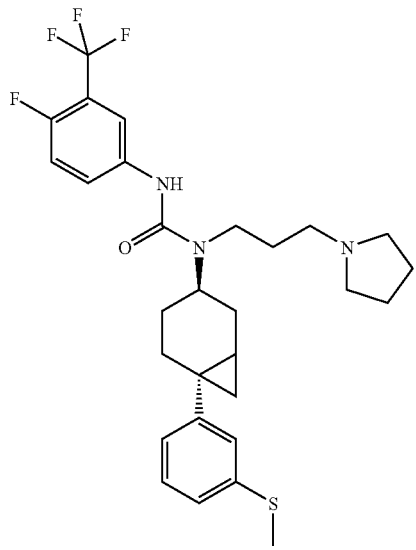 | 550.2515 | 550.1 rt = 5.82 min. |
| 329 | 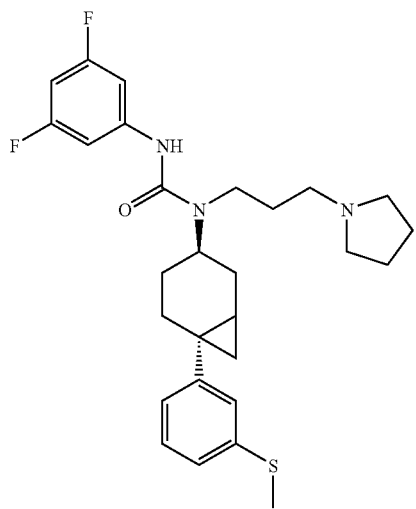 | 500.2547 | 500.1 rt = 5.68 min. |
| 330 | 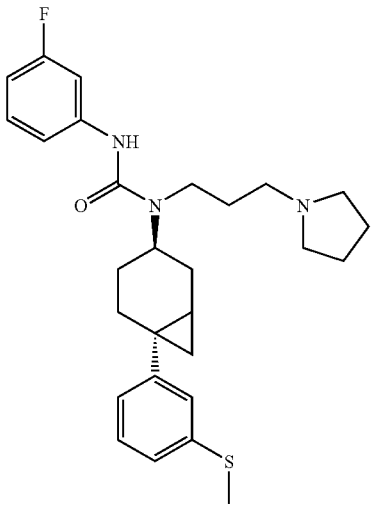 | 482.2641 | 482.1 rt = 5.62 min. |

Example 331

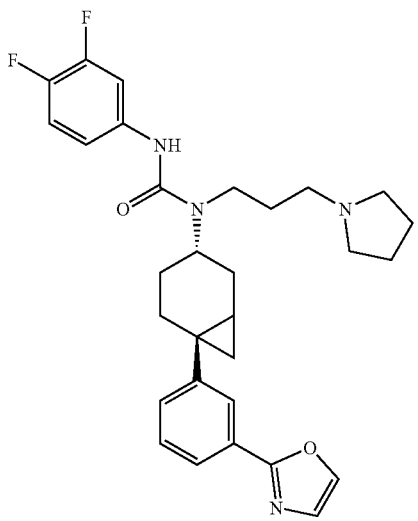

Step 1

6-(3-Cyanophenyl)bicyclo[4.1.0]heptane-3-one ethylene ketal (The product from procedure b of method [[Example 123 in P case]]), step 2. 2 g, 3.9 mmole) was dissolved in 10 ml dry ethanol. Zinc chloride(0.5 N in hexane, 1 ml) was added and the mixture was irradiated in a microwave oven for 10 minutes at 200W. After the reaction vessel was cooled to room temperature, 100 ml ethylacetate was added. The organic layer was washed with water(2×100 ml), dried over sodium sulfate and solvent was removed by vacuum. The product was purified by column using ethylacetate/hexane (gradient from 0/100 to 55/45 in one hour) as the eluent. The product is 6-[3-(oxazolino-2-yl) phenyl]bicyclo[4.1.0]heptane-3-one ethylene ketal (0.9 g, 38%).

Step 2

6-[3-(oxazolino-2-yl) phenyl]bicyclo[4.1.0]heptane-3-one ethylene ketal (0.9 g, 3 mmole) and DDQ (1.37 g, 6 mmole) were refluxed in 100 ml toluene for two hours. The reaction was cooled to room temperature and 100 ml 1N sodium hydroxide solution was then added. The organic layer was washed with water (2×100 ml) dried over sodium sulfate. The product was purified by column using hexane/ethylacetate(gradient from 100/0 to 40/60 in 50 minutes). The product is 6-[3-(2-oxazolyl)phenyl]bicyclo[4.1.0]heptane-3-one ethylene ketal (0.30 g, 34%).

Above compound can be converted to title compound according the steps 4-6 of method 10. N'-(3,4-Difluorophenyl)-N-[trans-6-(3-(2-oxazolyl)phenyl)-bicyclo[4.1.0]hept-3-yl]-N-[3-(1-pyrrolidinyl)propyl]urea. 1H NMR (300 MHz, CDCl3) δ 9.43 (b, 1H), 7.97(s, 1H), 7.84 (m, 1H), 7.71 (s, 1H), 7.49 (m, 1H), 7.38 (m, 2H), 7.23 (s, 1H), 7.02 (m, 2 H), 3.91 (m, 1H), 3.39 (m, 2H), 2.2 (m, 6H), 1.60-2.4 (m, 12H), 1.34 (m, 1H), 1.04 (m, 1H), 0.60 (m, 1H).

The following compounds were prepared via similar methods

|  |  | LCMS | HRMS |
|---|---|---|---|
| 332 | (structure) | 521.3<br>rt = 5.21 min. | 521.2728 |

Example 333

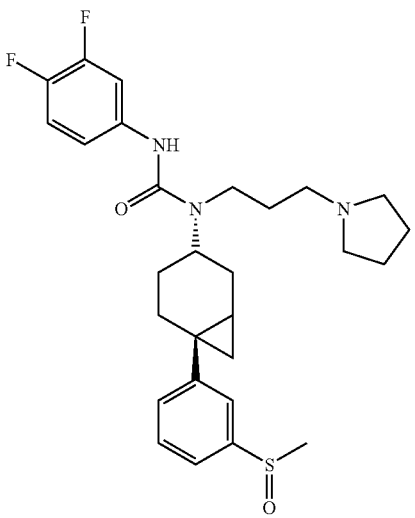

Step 1

6-(3-(Methylthio)phenyl)bicyclo[4.1.0]heptane-3-one ethylene ketal (From step 3 of To method 10, 1.0 g, 3.6 mmole) was dissolved in 100 ml methylene chloride. m-chloroperbenzoic acid (77%, 0.81 g, 3.6 mmole) was then added and the reaction was stirred at room temperature for one hour. The reaction was washed with 1N sodium hydroxide solution (50 ml), dried over sodium sulfate and solvent was removed via vacuum. The product was purified by silica plug using ethylacetate/hexane as the eluent. The product is 6-(3-(Methylsulfinyl)phenyl)bicyclo[4.1.0]heptane-3-one ethylene ketal (0.67 g, 63%).

Above compound can be converted to title compound according the steps 4-6 of method 10. N'-(3,4-Difluorophenyl)-N-[trans-6-(3-(methylsulfinyl)phenyl)-bicyclo[4.1.0]hept-3-yl]-N-[3-(s-3-hydroxy-1-pyrrolidinyl)propyl]urea.
1H NMR (300 MHz, CDCl3) δ 9.08 (b, 1H), 7.35-7.60 (m, 5H), 7.02 (m, 2 H), 3.90 (m, 1H), 3.35 (m, 2H), 2.82 (m, 6H), 2.70 (s, 3H), 1.60-2.34 (m, 12H), 1.30 (m, 1H), 1.00 (m, 1H), 0.82 (m, 1H).

The following compounds were prepared via similar methods:

|   |   | LCMS | HRMS |
|---|---|------|------|
| 334 |   | 548.1<br>rt = 5.45 min. | 548.1905 |
| 335 |   | 566.1<br>rt = 5.18 min. | 566.2664 |

|     |            | LCMS                  | HRMS     |
|-----|------------|-----------------------|----------|
| 336 | 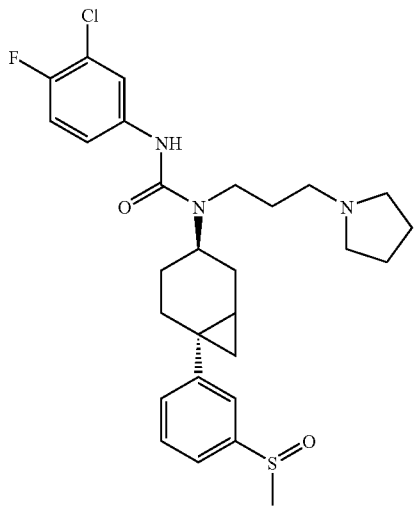 | 532.1 rt = 5.12 min. | 532.2201 |
| 337 | 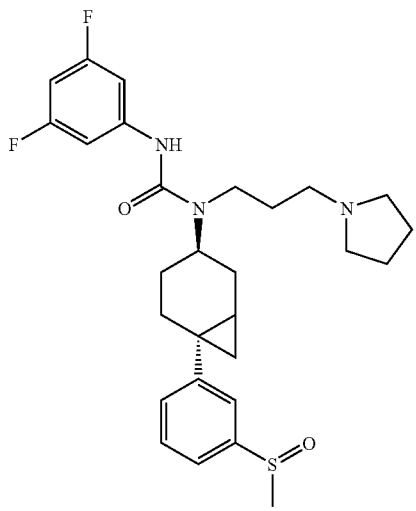 | 516.1 rt = 4.95 min. | 516.2496 |

|     |     | LCMS | HRMS |
|-----|-----|------|------|
| 338 | 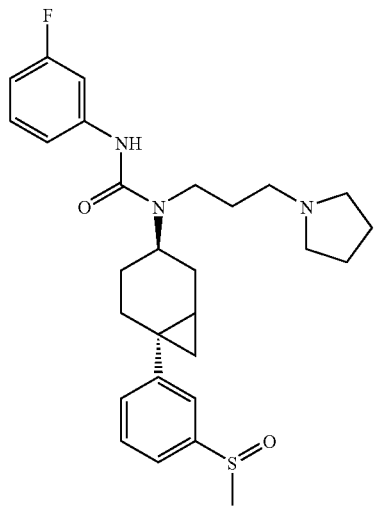 | 498.1 rt = 4.81 min. | 498.2591 |
| 339 | 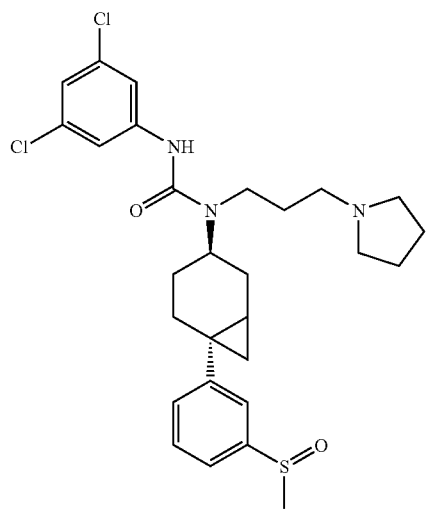 | 548.1 rt = 5.52 min. | 548.1905 |

Example 340

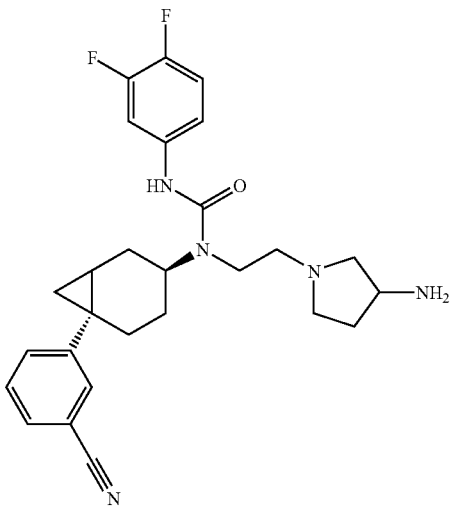

Example 342

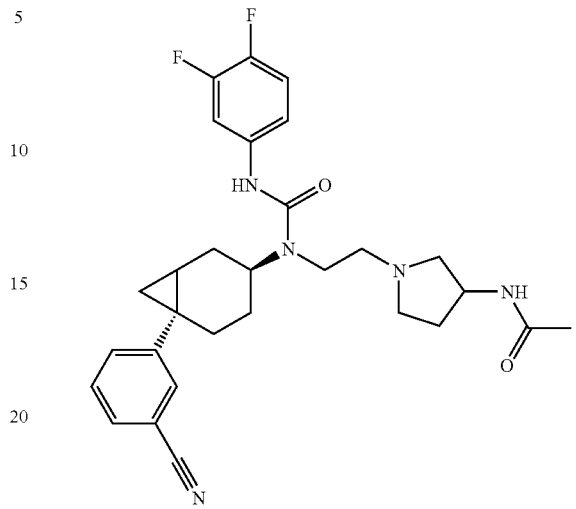

N-[1-[2-[[trans-6-(3-cyanophenyl)bicyclo[4.1.0]hept-3-yl][[(3,4-difluorophenyl)amino]carbonyl]amino]ethyl]-3-pyrrolidinyl]-2,2,2-trifluoroacetamide (as prepared by the method described herein) (120 mg, 0.21 mmol) was dissolved in 10 mL MeOH. $K_2CO_3$ (250 mg, 1.81 mmol) was then added. 5 ml water was added to dissolve all $K_2CO_3$. The reaction mixture was stirred overnight. Solvents were then removed by vacuum. The oily residue was then partitioned in 30 mL of $CH_2Cl_2$ and 20 ml water. The organic was washed with water (2×20 ml), dried over sodium sulfate and solvent was removed by vacuum. The crude product was purified by column chromatography using $CH_2Cl_2$/MeOH (0.35 $NH_3$) (gradient from 100% $CH_2Cl_2$ to 100% MeOH). The product is N-[2-(3-amino-1-pyrrolidinyl)ethyl]-N-[trans-6-(3-cyanophenyl)bicyclo[4.1.0]hept-3-yl]-N'-(3,4-difluorophenyl)urea (Total yield: 75 mg, 75%).

Using similar procedures the following compounds were prepared:

N-[2-(3-amino-1-pyrrolidinyl)ethyl]-N-[trans-6-(3-cyanophenyl)bicyclo[4.1.0]hept-3-yl]-N'-(3,4-difluorophenyl)urea, prepared according to Method (60 mg, 0.13 mmol) was dissolved in 5 mL of $CH_2Cl_2$. Triethylamine (53 mg, 0.52 mmol) was then added followed by acetic anhydride (27 mg, 0.26 mmol). Reaction mixture was stirred at room temperature for 2 hours. Reaction mixture was then poured into 30 ml saturated sodium bicarbonate solution and additional 20 mL of $CH_2Cl_2$ were added. Organic layer was washed with water (2×20 ml), dried over sodium sulfate and solvent was removed by vacuum. The crude product was purified by preparative TLC using 5% MeOH, 95% ethylacetate. Yield: 40 mg, 62%.

Starting with the appropriate anhydride, sulfonyl chloride, sulfamoyl chloride, carbonyl chloride, or isocyanate, the following compounds were prepared via an analogous procedure:

| Example | Structure | LC/MS | HRMS |
|---|---|---|---|
| 341 | (structure shown) | 496.1 rt = 4.71 min. | 496.2279 |

| | Structure | LC/MS | HRMS |
|---|---|---|---|
| 343 | 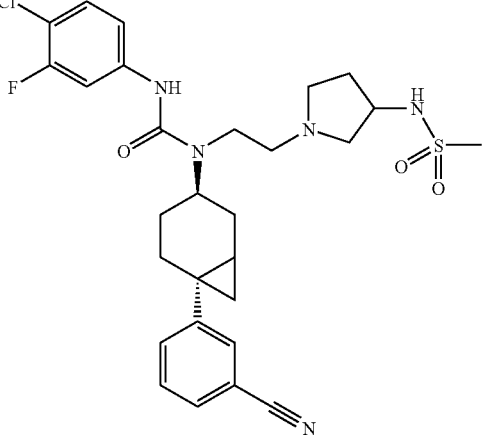 | 574.1 rt = 5.18 min. | 574.2055 |
| 344 | 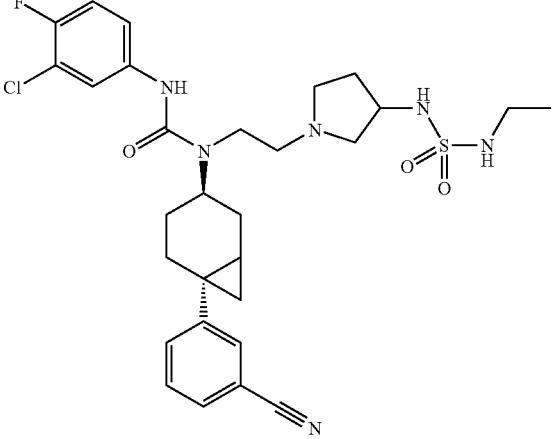 | 603.1 rt = 5.12 min. | 603.2315 |
| 345 | 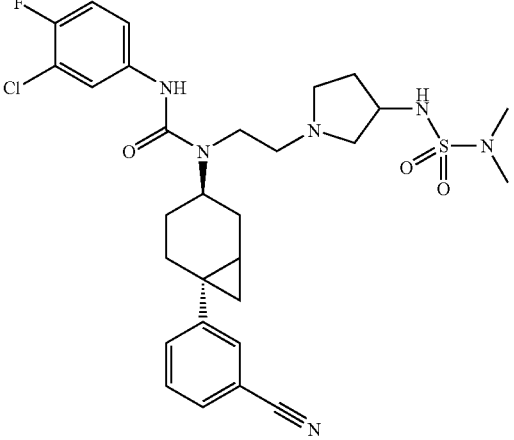 | 603.1 rt = 5.32 min. | 603.2315 |

-continued

| | Structure | LC/MS | HRMS |
|---|---|---|---|
| 346 | 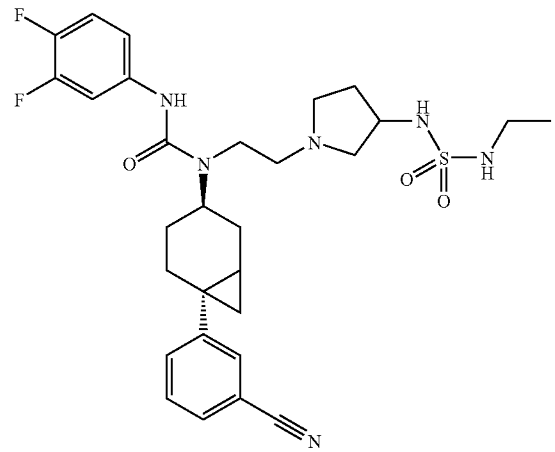 | 587.3 rt = 4.65 min. | 587.2607 |
| 347 | 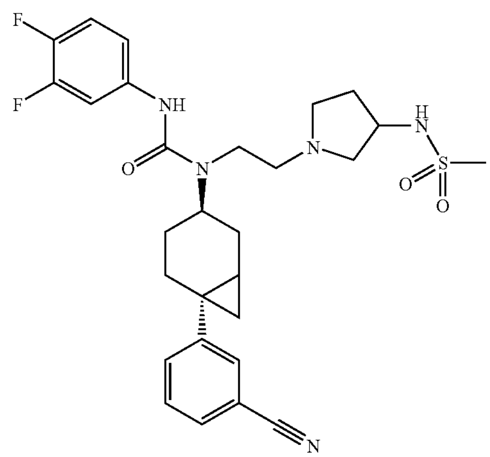 | 558.3 rt = 4.58 min. | 558.2347 |
| 348 | 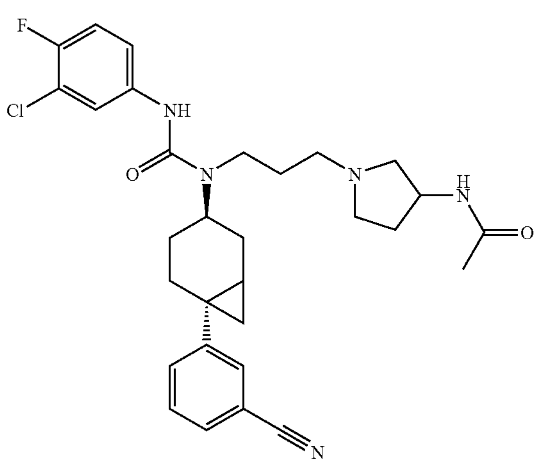 | 552.3 rt = 4.78 min. | 552.2536 |

-continued

| | Structure | LC/MS | HRMS |
|---|---|---|---|
| 349 | 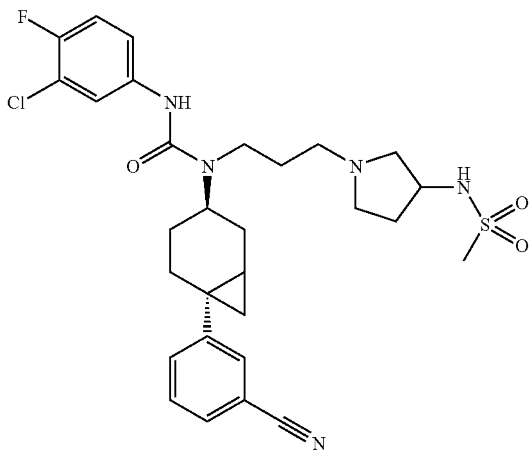 | 588.3 rt = 4.61 min. | 588.2216 |
| 350 | 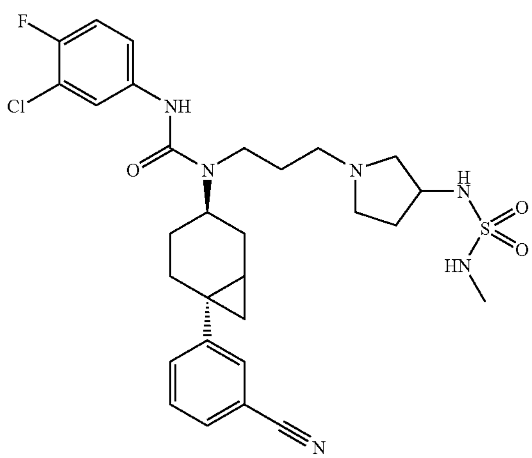 | 603.3 rt = 4.61 min. | 603.2327 |
| 351 | 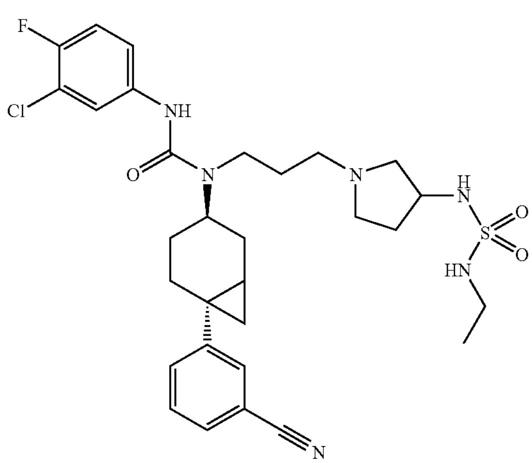 | 617.1 rt = 5.75 min. | 617.2487 |

-continued
| | Structure | LC/MS | HRMS |
|---|---|---|---|
| 352 | 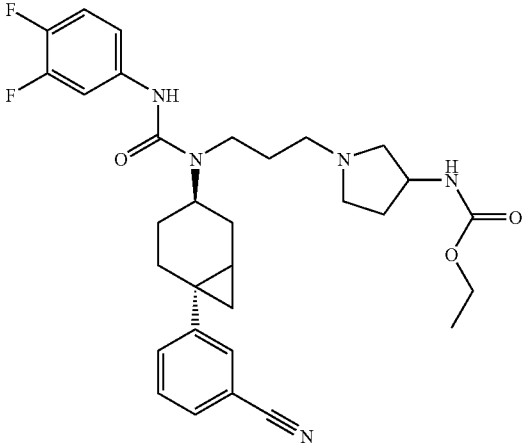 | 566.1 rt = 5.32 min. | 566.295 |
| 353 | 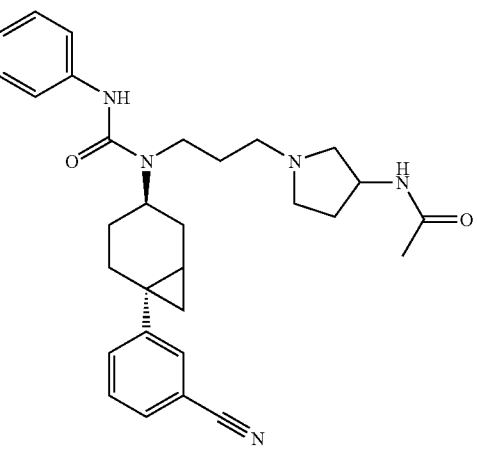 | 536.1 rt = 5.32 min. | 536.2843 |
| 354 | 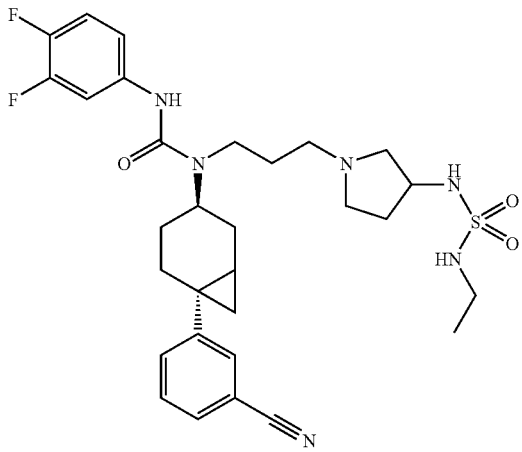 | 601.1 rt = 5.38 min. | 601.2759 |

| | Structure | LC/MS | HRMS |
|---|---|---|---|
| 355 | 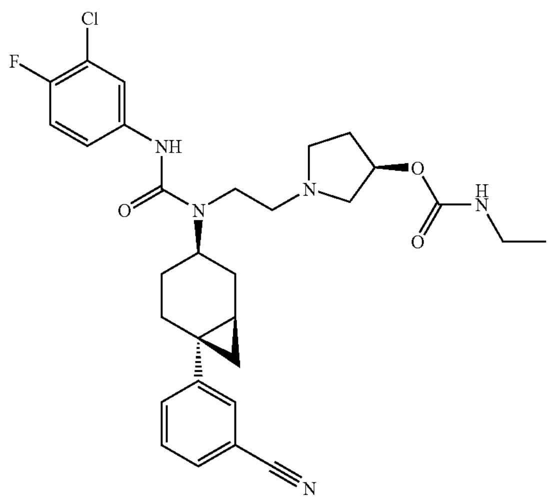 | 568.1 rt = 5.05 min. | 568.2508 |

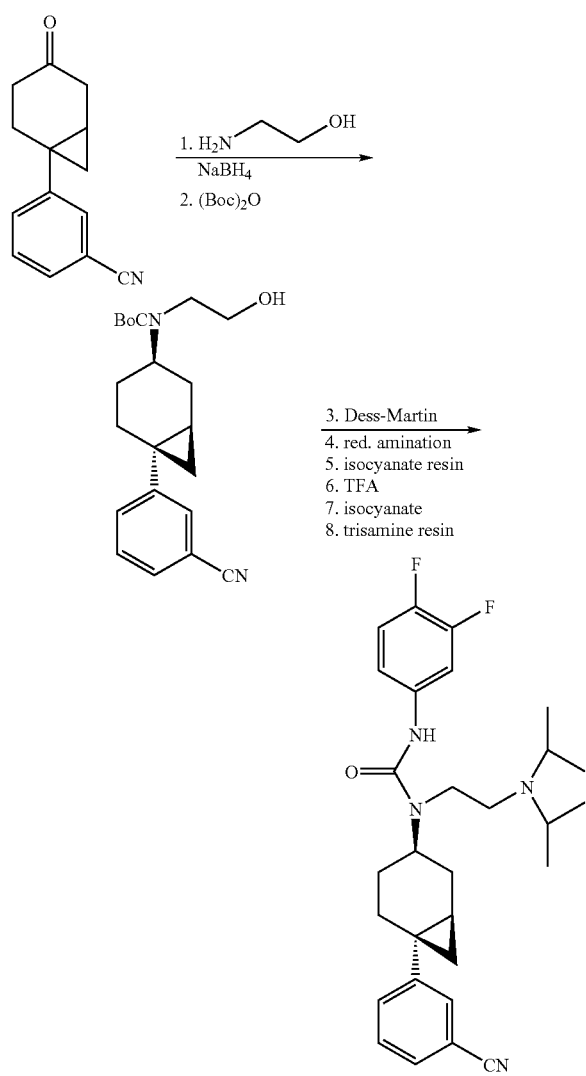

Example 356

Preparation of N'-(3,4-DIFLUOROPHENYL)-N-[TRANS-6-(3-CYANOPHENYL)BICYCLO[4.1.0]HEPT-3-YL]-N-[1,2-DI-(1-METHYLETHYL)AMINO]ETHYL]UREA Step 1

The ketone (from Step 3 of Method 5, 0.97 g, 4.6 mmol) was mixed with 2-aminoethanol (0.31 g, 6 mmol, 1.1 eq), Ti(OiPr)$_4$ (1.44 g, 1.1 eq) in 20 mL of DCM under nitrogen for overnight. The solution was cooled with ice bath and NaBH$_4$ (0.18 g, 1 eq) was added. 30 min later the ice bath was removed and after another 3.5 hr, the reaction was quenched by methanol. The solvent was removed and EtOAc was added. After washing with 1 N NaOH, the crude was chromatographed (EtOAc: hexane=1:3 to 1:1) to give the desired product (0.56 g, 48%).

$^1$H NMR (300 MHz, CDCl3) δ 0.88 (m, 1H) 0.98 (m, 1H) 1.05 (m, 1H) 1.20-1.38 (m, 2H) 1.78 (m, 1H) 1.95 (m, 1H) 2.22 (m, 1H) 2.20-2.76 (m, 4H) 2.80 (m, 2H), 3.40 (m, 2H) 7.30-7.58 (m, 4H).

Steps 2 and 3

The above product (0.42 g, 1.64 mmol) was treated with di-tert-butyl carbonate (0.42 g, 1.12 eq), NaHCO$_3$ (0.2 g, 1 eq), 8 mL THF, 5 mL water and stirred at room temperature for 2 h. Extraction with EtOAc and removal of the solvent gave 0.7 g of the which was directly treated with Dess-Martin reagent (1 g, 1.2 eq) in 10 mL DCM. After stirring at room temperature for 2 hr, the solvent was removed and EtOAc was added. The organic layer was washed with saturated NaHCO$_3$ several times until no solid was found after removal of the solvent. Chromatography (EtOAc: hexane=1:3) gave the desired product aldehyde (0.48 g, 83% yield in two steps).

$^1$H NMR (400 MHz, CDCl3) δ 0.70 (m, 1 H) 0.98 (m, 1H) 1.00 (m, 1H) 1.20 (m, 2 H), 1.40 (s, 9 H) 1.60 (m, 2 H) 2.00 (m, 1 H) 2.22 (m, 2 H) 3.80 (m, 2 H) 4.10 (m, 1 H), 7.30-7.58 (m, 4 H) 9.50 (s, 1 H).

Steps 4 and 5

The above aldehyde (280 mg, 0.79 mmol) was mixed with N,N-diisopropylamine (Fluka, 0.57 g, 4 eq) and NaBH(OAc)$_3$ (0.84 g, 5 eq) in 8 mL DCM and stirred for 24 hr. The reaction was quenched with MeOH and the solvent was removed. The crude was redissolved in DCM and washed with 1 N NaOH. The organic layer was treated with resin-bound isocyanate (Argonaut, 3.1 g, 6 eq) for 4 h. The crude was filtered and the filtrate was dried.

Steps 6 to 8

The above compound was treated with 50% TFA/DCM over night. The solvent was removed and 2 N NH$_3$/MeOH was added and removed completely to give the free amine quantitatively. The free amine was dissolved in DCM and filtered through cotton ball to get rid of the salt. Then it was treated with 3,4-difluorophenylisocyanate (0.18 g, 1.5 eq) in 5 mL DCM at room temperature for 1 h. Resin-bound trisamine (Argonaut, 0.36 g, 2 eq) was added and stirred for 3 h. After filtration, the filtrate was collected to afford 156 mg of the desired product (40% yield).

$^1$H NMR (400 MHz, CDCl3) δ 0.60 (m, 1 H) 0.70 (m, 1H) 0.99 (m, 1H) 1.00 (d, 12 H, J=6.9 Hz) 1.25-1.40 (m, 2 H) 1.50 (m, 1 H) 1.70 (m, 1 H) 2.00 (m, 2 H) 2.25 (m, 2 H) 2.58 (m, 2 H) 2.90-3.10 (m, 4 H) 6.90 (m, 1 H) 7.00 (m, 1 H) 7.20-7.40 (m, 5 H) 10.80 (s, 1 H) LC/MS Tr 5.38 min. 495 (M+H).

The following compounds were prepared according to procedures similar to those described above.

| Example | Structure | Mass (M + H) | LC/MS (Tr min) |
|---|---|---|---|
| 357 | 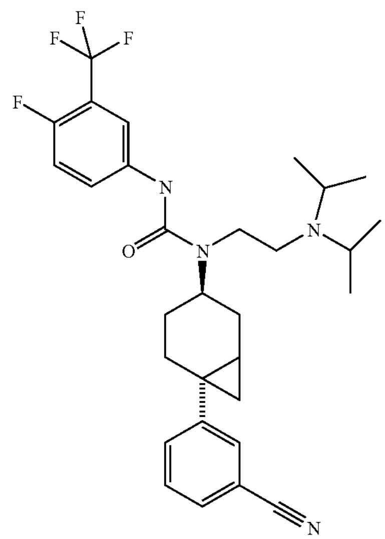 | 545 | 3.86 |
| 358 | 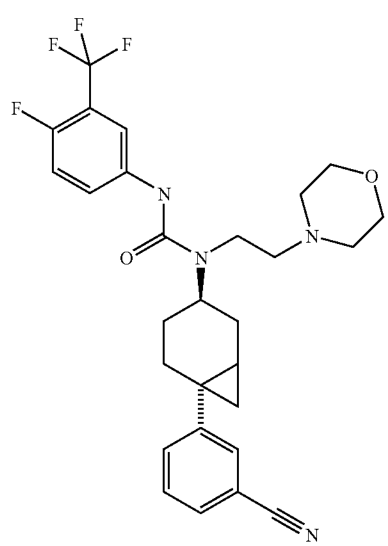 | 531 | 3.41 |

| Example | Structure | Mass (M + H) | LC/MS (Tr min) |
|---|---|---|---|
| 359 | 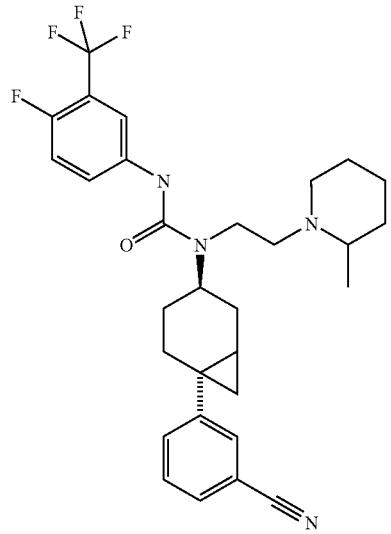 | 543 | 3.71 |
| 360 | 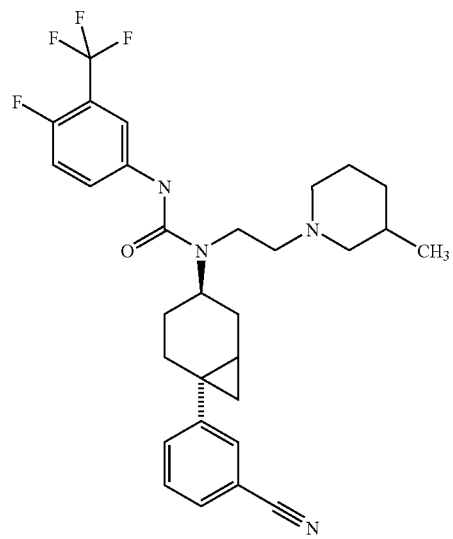 | 543 | 3.71 |
| 361 | 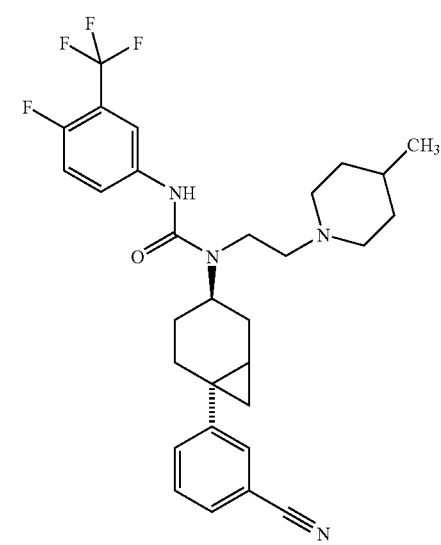 | 543 | 3.71 |

-continued
| Example | Structure | Mass (M + H) | LC/MS (Tr min) |
|---|---|---|---|
| 362 | 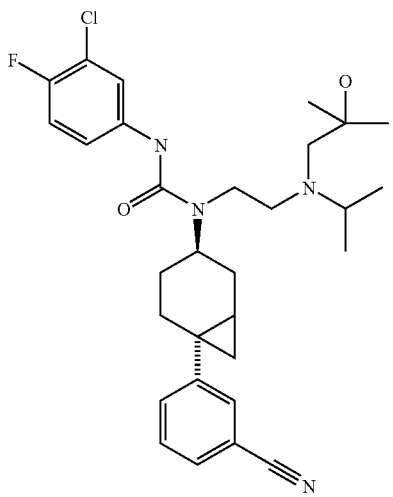 | 541 | 5.68 |
| 363 | 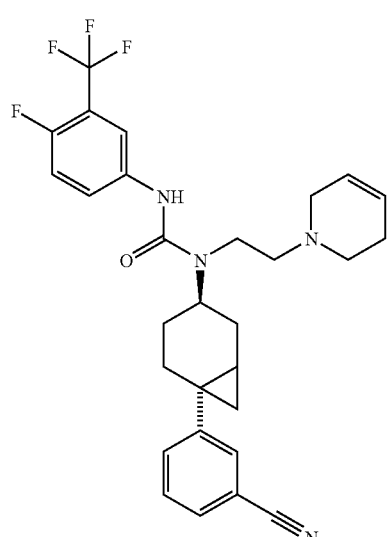 | 527 | 3.56 |
| 364 | 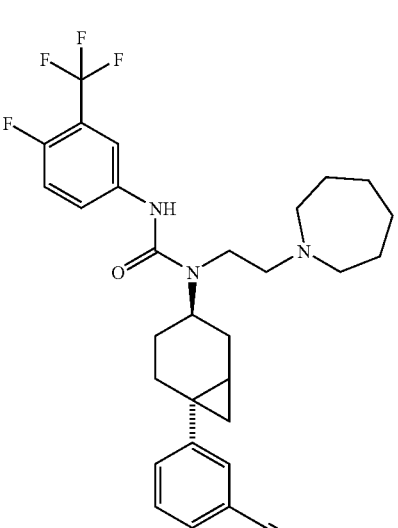 | 543 | 3.76 |

| Example | Structure | Mass (M + H) | LC/MS (Tr min) |
|---------|-----------|--------------|----------------|
| 365 | 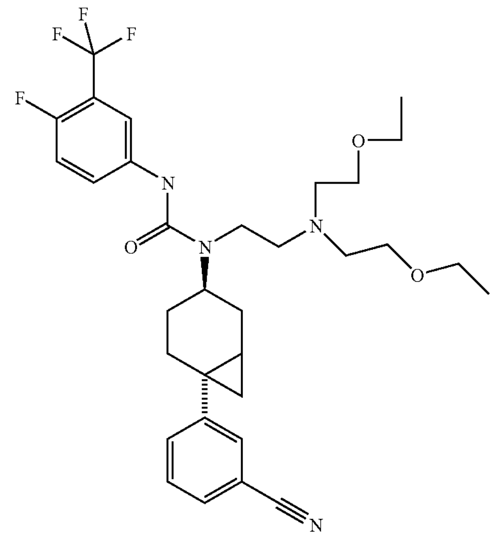 | 605 | 4.21 |
| 366 | 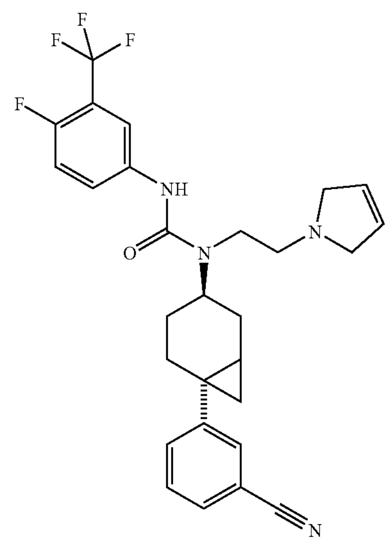 | 513 | 3.51 |
| 367 | 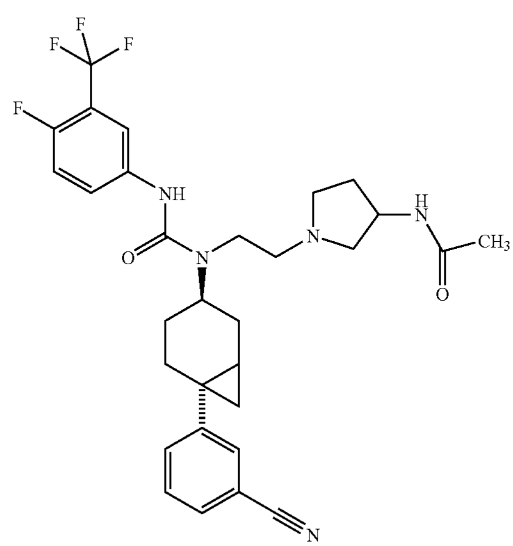 | 572 | 3.41 |

-continued
| Example | Structure | Mass (M + H) | LC/MS (Tr min) |
|---|---|---|---|
| 368 | 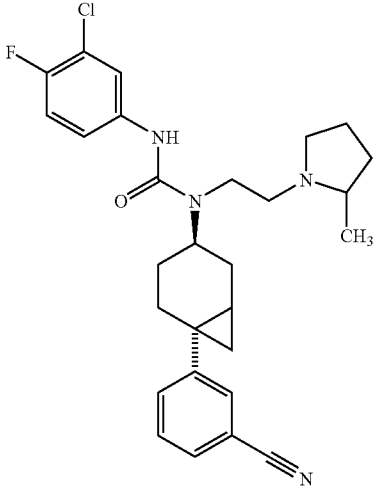 | 495 | 3.56 |
| 369 | 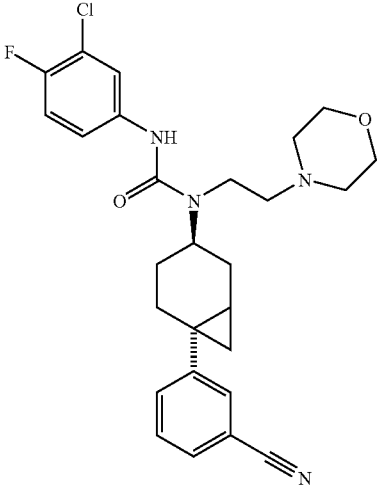 | 497 | 3.31 |
| 370 | 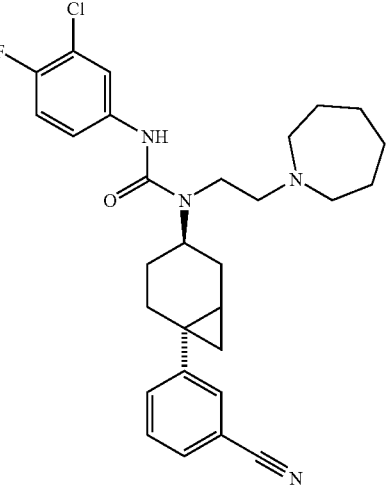 | 509 | 3.66 |

-continued
| Example | Structure | Mass (M + H) | LC/MS (Tr min) |
|---------|-----------|--------------|----------------|
| 371 | 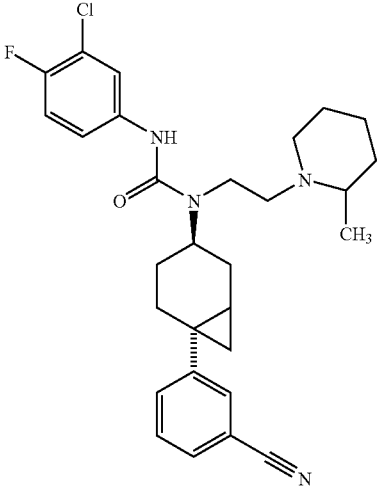 | 545 | 3.86 |
| 372 | 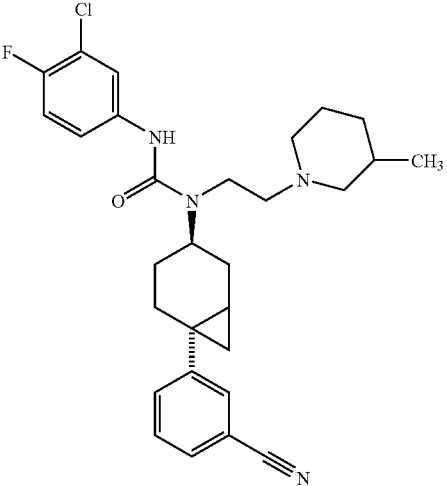 | 509 | 3.66 |
| 373 | 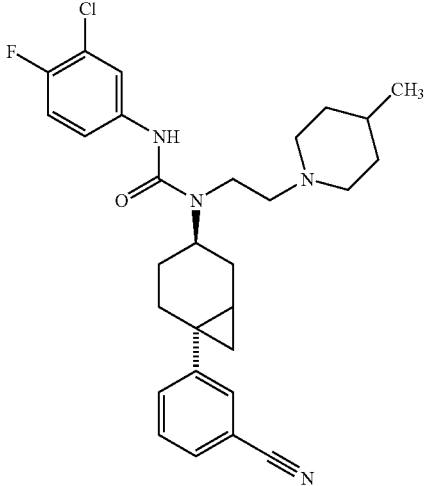 | 509 | 3.61 |

-continued
| Example | Structure | Mass (M + H) | LC/MS (Tr min) |
|---|---|---|---|
| 374 | 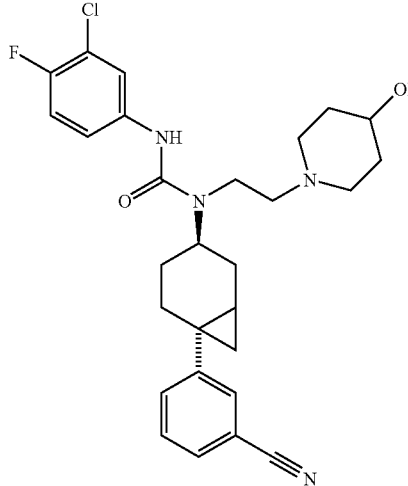 | 511 | 3.26 |
| 375 | 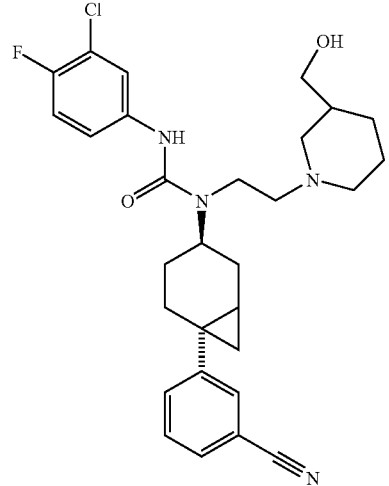 | 525 | 3.36 |
| 376 | 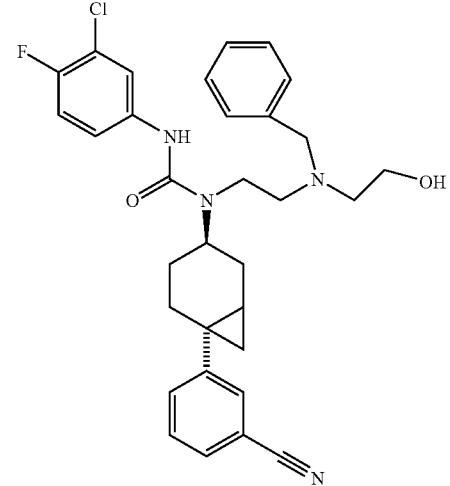 | 561 | 3.61 |

| Example | Structure | Mass (M + H) | LC/MS (Tr min) |
|---|---|---|---|
| 377 | 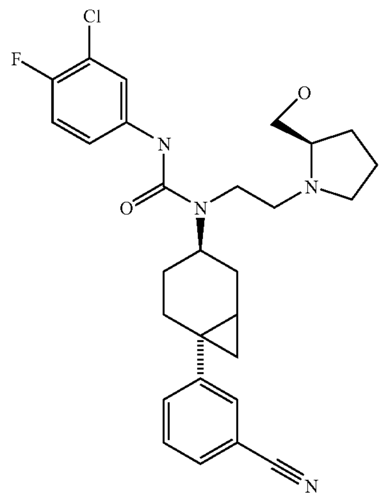 | 511 | 3.41 |
| 378 | 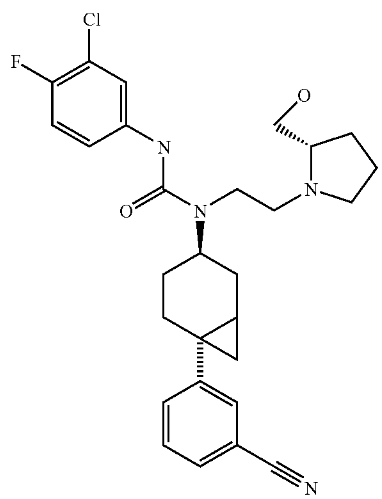 | 511 | 3.36 |
| 379 | 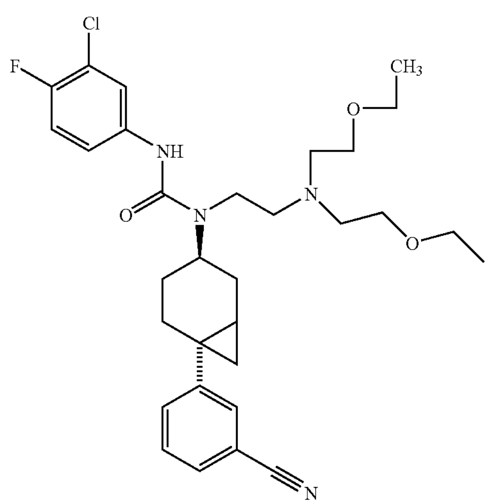 | 571 | 4.11 |

-continued

| Example | Structure | Mass (M + H) | LC/MS (Tr min) |
|---|---|---|---|
| 380 | 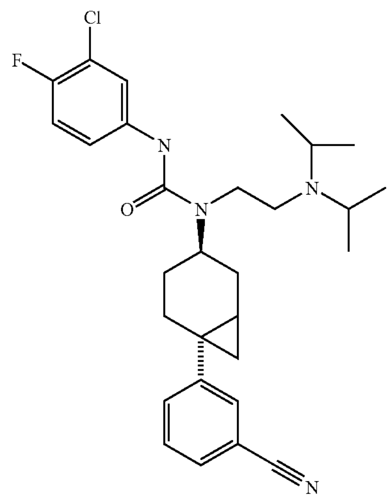 | 511 | 3.81 |
| 381 | 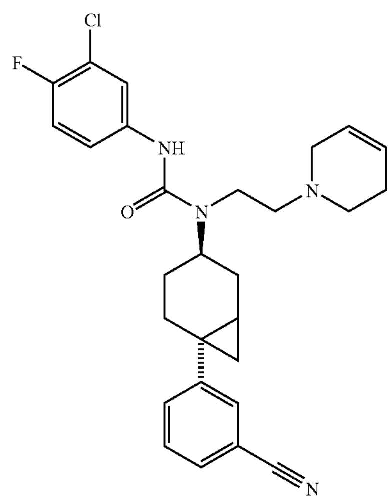 | 493 | 3.51 |
| 382 | 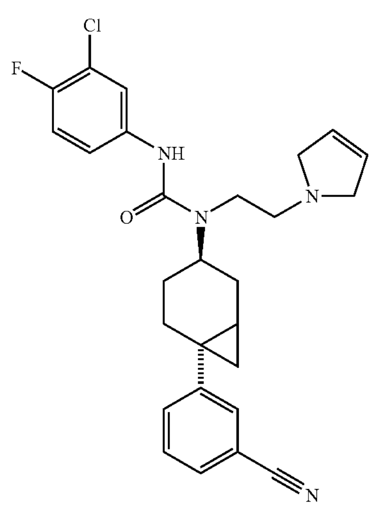 | 479 | 3.46 |

-continued

| Example | Structure | Mass (M + H) | LC/MS (Tr min) |
|---|---|---|---|
| 383 | 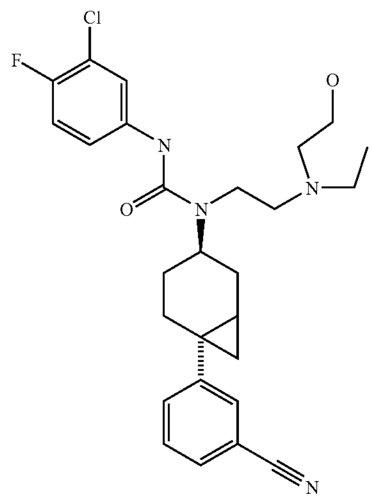 | 499 | 3.36 |
| 384 | 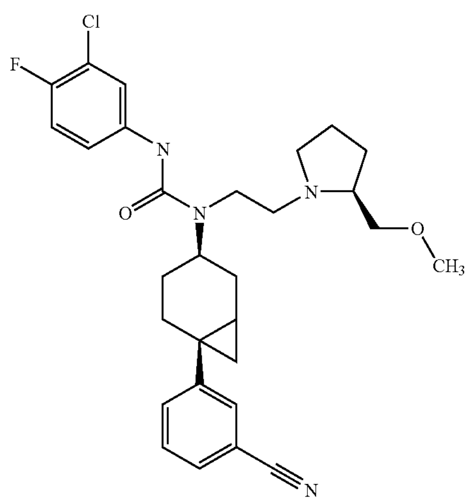 | 525 | 5.86 |
| 385 | 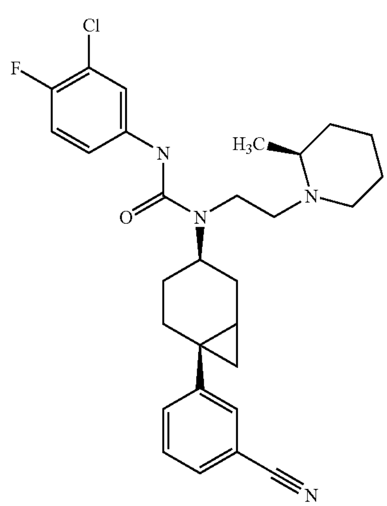 | 509 | 5.71 |

-continued

| Example | Structure | Mass (M + H) | LC/MS (Tr min) |
|---------|-----------|--------------|----------------|
| 386 | 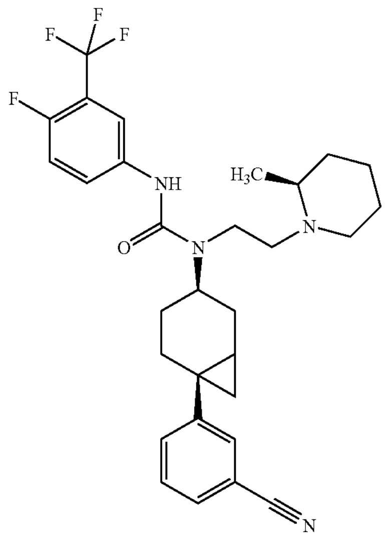 | 543 | 5.81 |
| 387 | 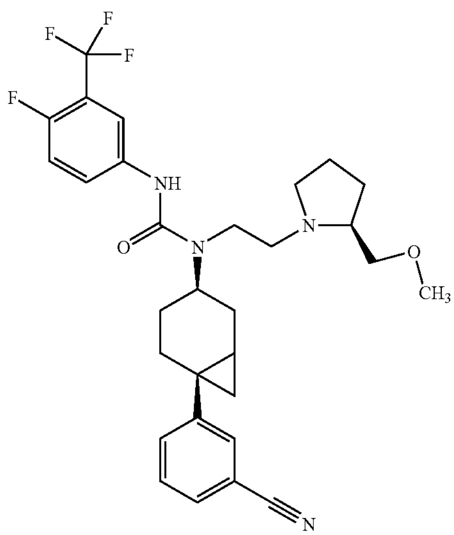 | 559 | 5.71 |
| 388 | 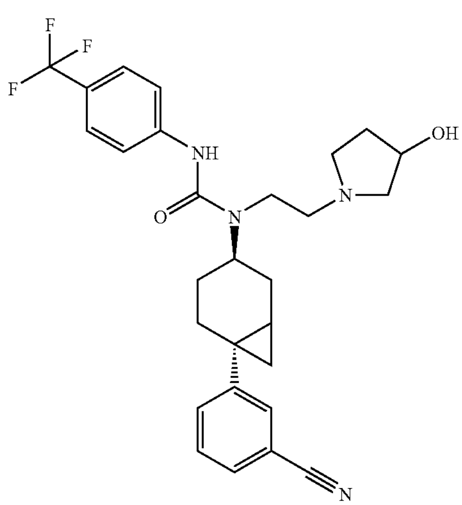 | 513 | 5.25 |

-continued

| Example | Structure | Mass (M + H) | LC/MS (Tr min) |
|---------|-----------|--------------|----------------|
| 389 | 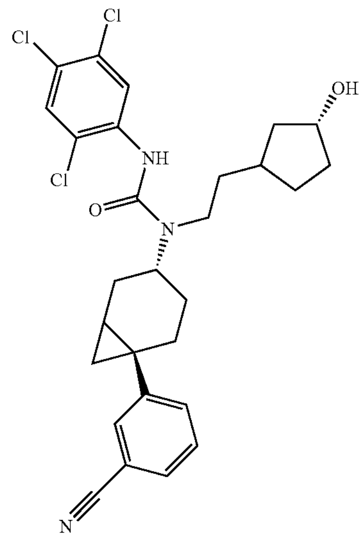 | 549 | 5.45 |
| 390 | 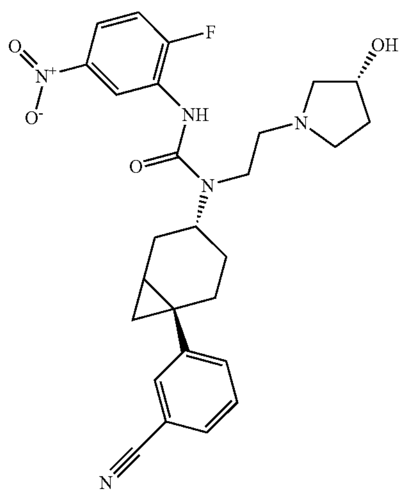 | 508 | 4.88 |
| 391 | 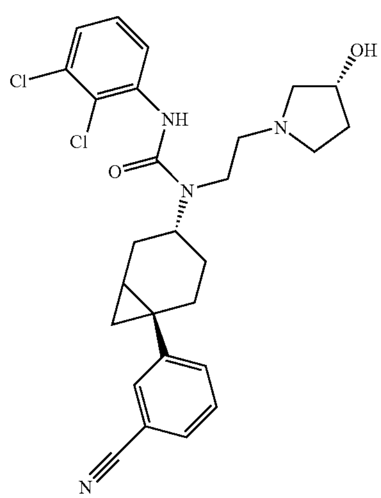 | 513 | 5.15 |

| Example | Structure | Mass (M + H) | LC/MS (Tr min) |
|---|---|---|---|
| 392 | 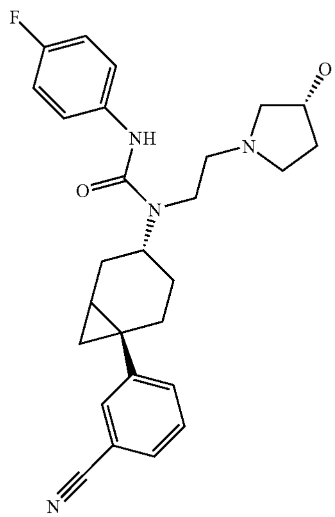 | 463 | 4.88 |
| 393 | 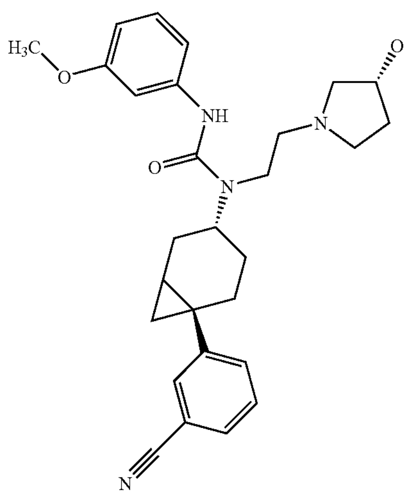 | 475 | 4.88 |
| 394 | 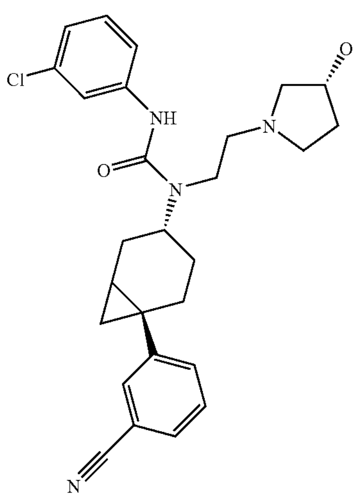 | 479 | 5.11 |

-continued

| Example | Structure | Mass (M + H) | LC/MS (Tr min) |
|---|---|---|---|
| 395 | 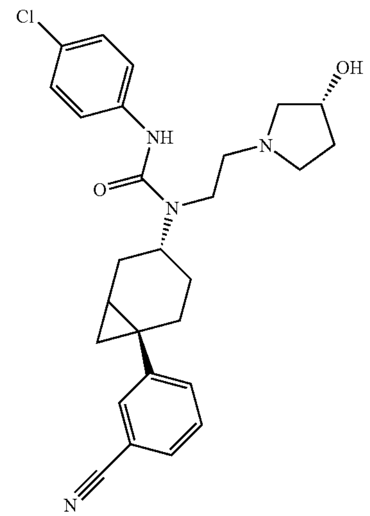 | 479 | 5.11 |
| 396 | 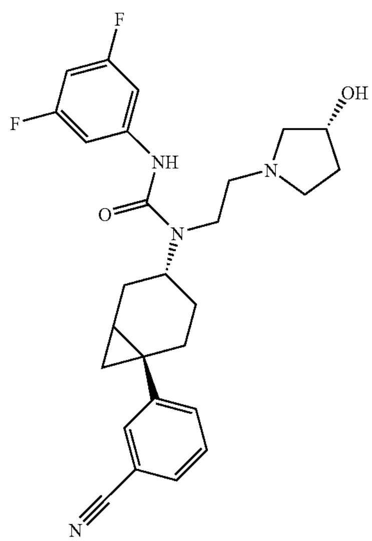 | 481 | 5.08 |
| 397 | 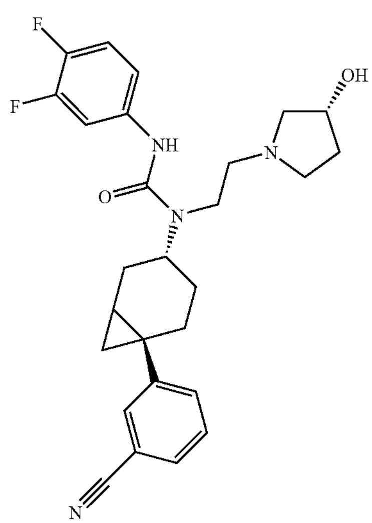 | 481 | 4.98 |

-continued
| Example | Structure | Mass (M + H) | LC/MS (Tr min) |
|---|---|---|---|
| 398 | 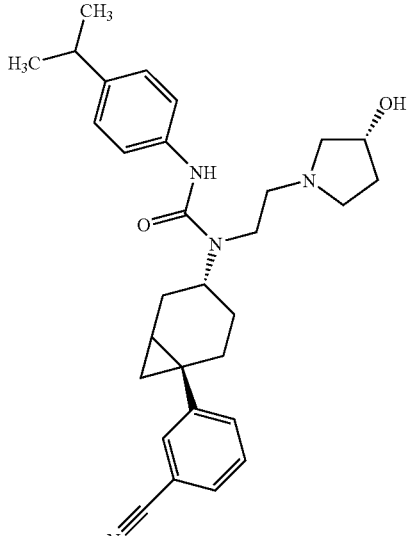 | 487 | 5.45 |
| 399 | 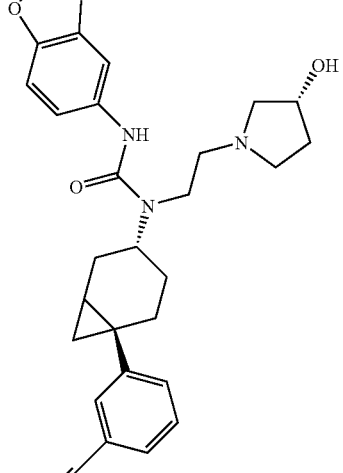 | 489 | 4.78 |
| 400 | 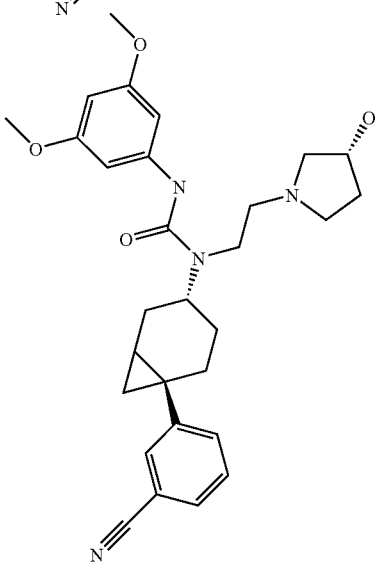 | 505 | 4.98 |

-continued

| Example | Structure | Mass (M + H) | LC/MS (Tr min) |
|---|---|---|---|
| 401 | 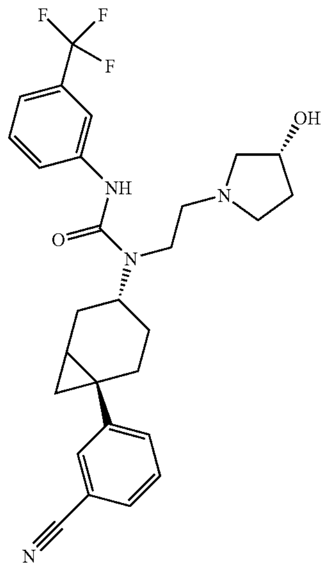 | 513 | 5.25 |
| 402 | 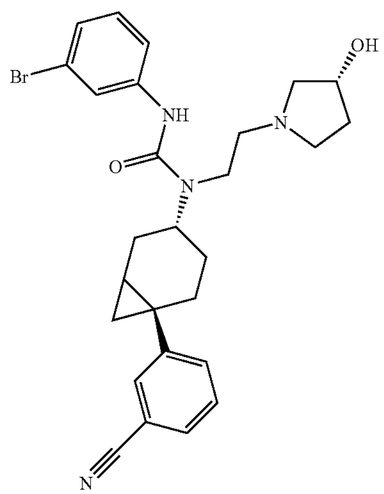 | 523 | 5.25 |
| 403 | 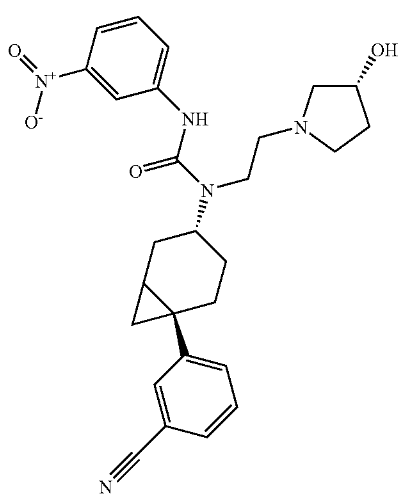 | 490 | 4.95 |

-continued
| Example | Structure | Mass (M + H) | LC/MS (Tr min) |
|---|---|---|---|
| 404 | 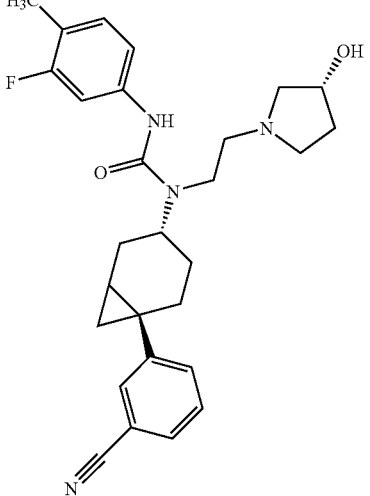 | 477 | 4.95 |
| 405 | 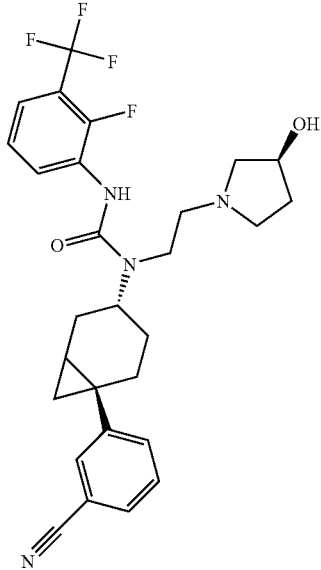 | 531 | 5.01 |
| 406 | 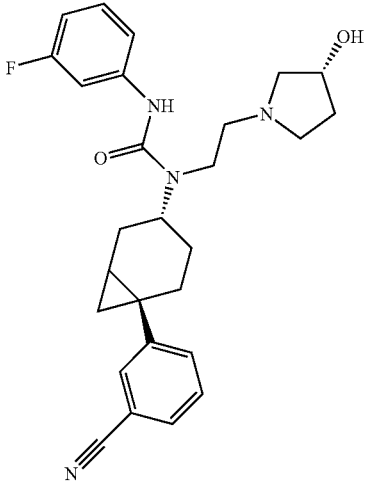 | 463 | 4.78 |

-continued
| Example | Structure | Mass (M + H) | LC/MS (Tr min) |
|---|---|---|---|
| 407 | 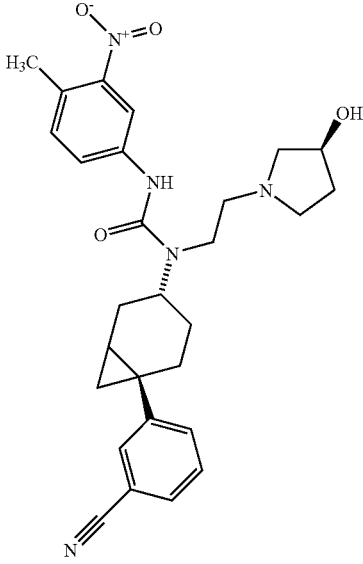 | 504 | 4.91 |
| 408 | 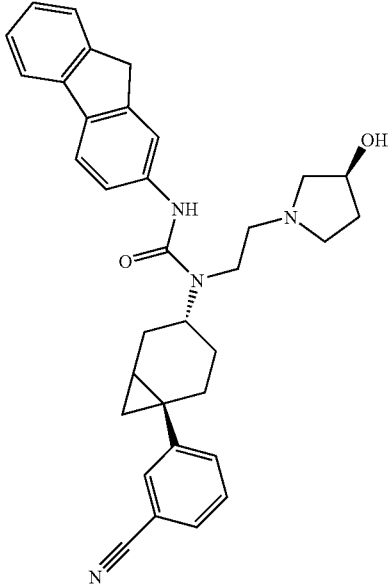 | 533 | 5.31 |

-continued
| Example | Structure | Mass (M + H) | LC/MS (Tr min) |
|---|---|---|---|
| 409 | 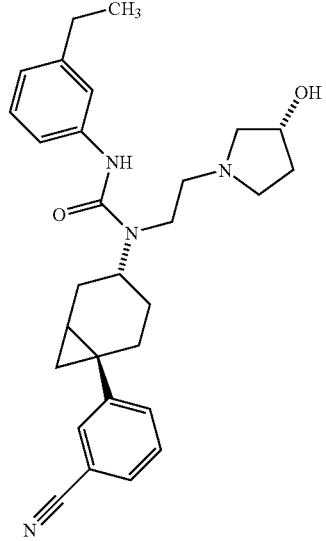 | 473 | 5.05 |
| 410 | 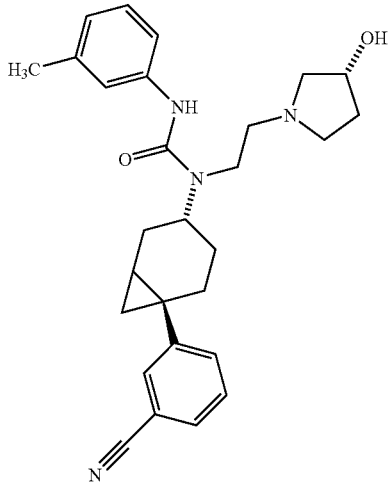 | 459 | 4.95 |
| 411 | 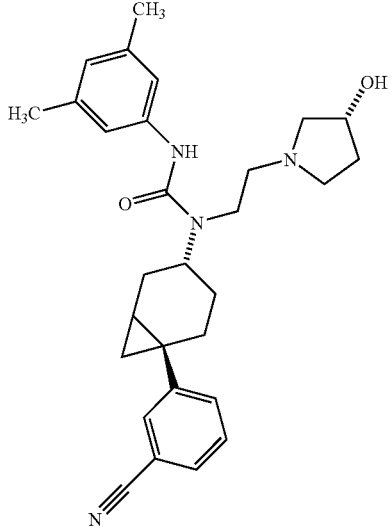 | 473 | 5.18 |

-continued

| Example | Structure | Mass (M + H) | LC/MS (Tr min) |
|---|---|---|---|
| 412 | 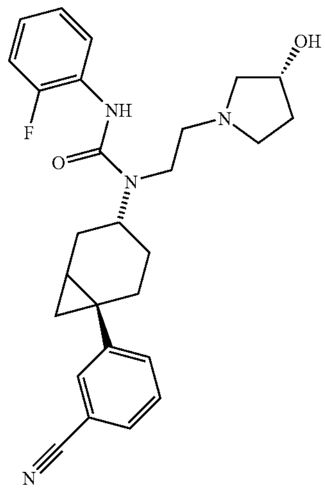 | 463 | 4.73 |
| 413 | 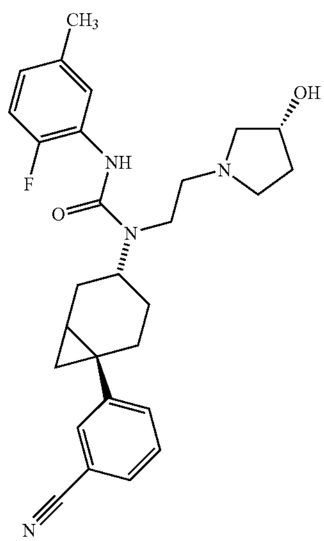 | 477 | 4.91 |
| 414 | 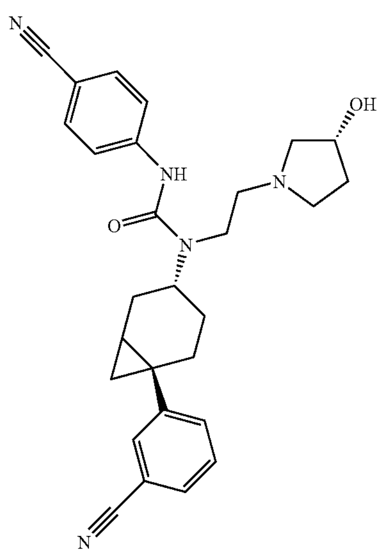 | 470 | 4.71 |

-continued

| Example | Structure | Mass (M + H) | LC/MS (Tr min) |
|---|---|---|---|
| 415 | 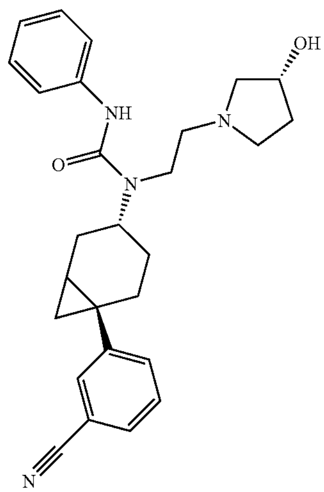 | 445 | 4.81 |
| 416 | 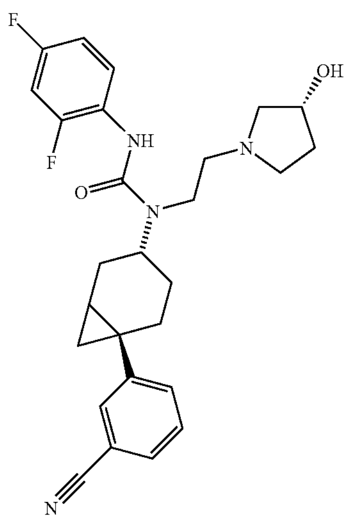 | 481 | 4.78 |
| 417 | 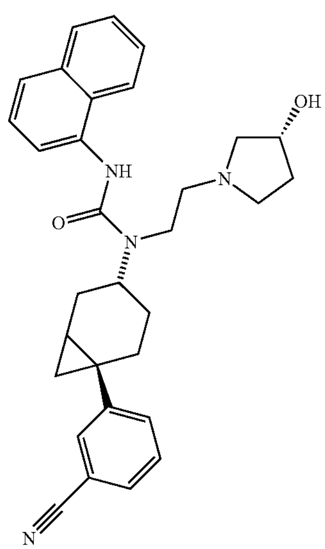 | 495 | 5.08 |

-continued

| Example | Structure | Mass (M + H) | LC/MS (Tr min) |
|---|---|---|---|
| 418 | 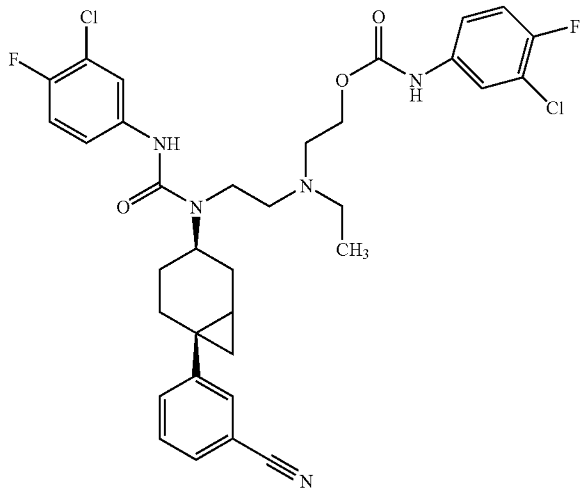 | 670 | 5.72 |
| 419 | 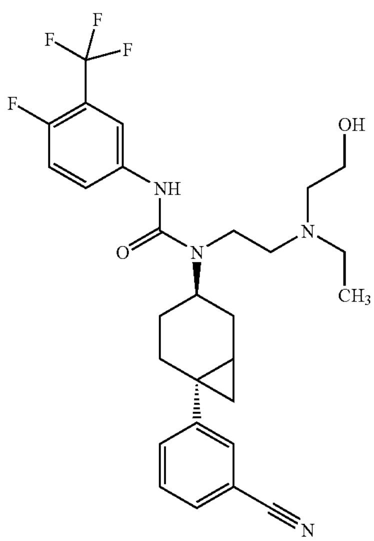 | 533 | 5.28 |
| 420 | 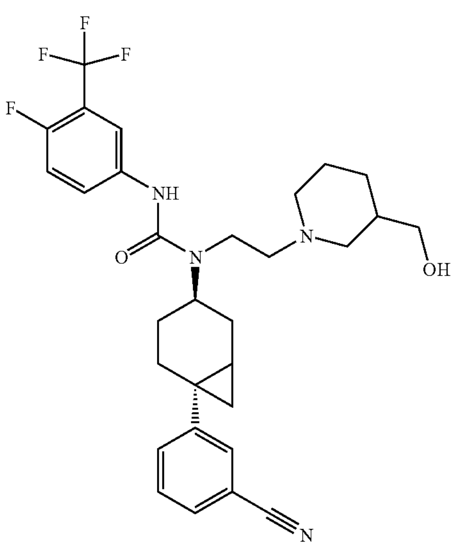 | 559 | 5.31 |

-continued

| Example | Structure | Mass (M + H) | LC/MS (Tr min) |
|---------|-----------|--------------|----------------|
| 421 | 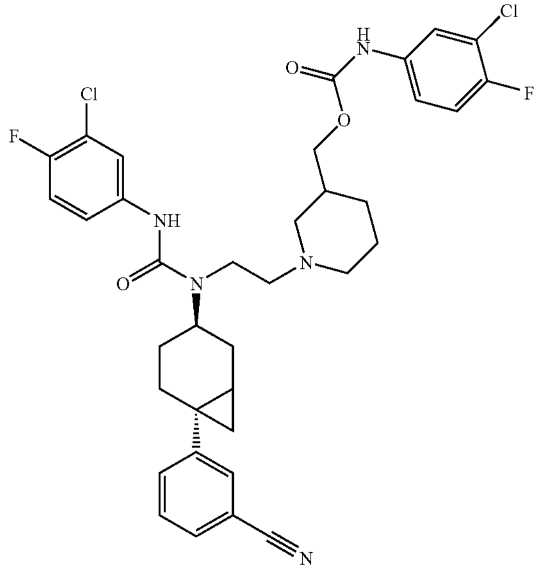 | 696 | 5.88 |
| 422 | 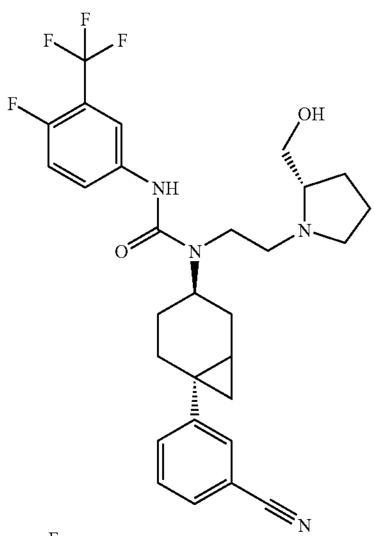 | 545 | 5.25 |
| 423 | 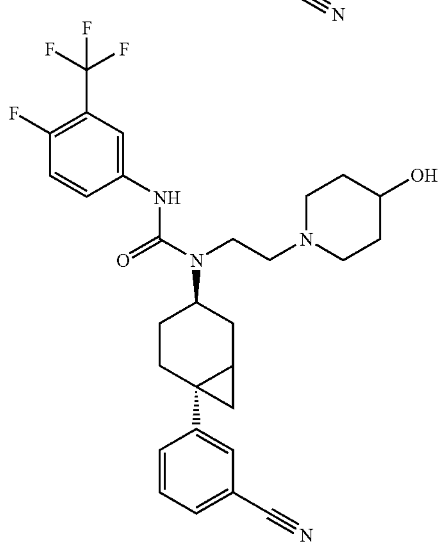 | 545 | 4.98 |

-continued
| Example | Structure | Mass (M + H) | LC/MS (Tr min) |
|---|---|---|---|
| 424 | 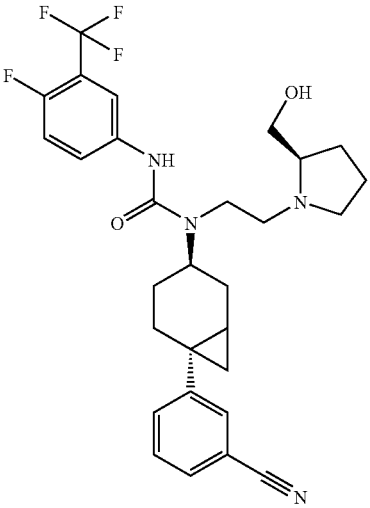 | 545 | 5.11 |
| 425 | 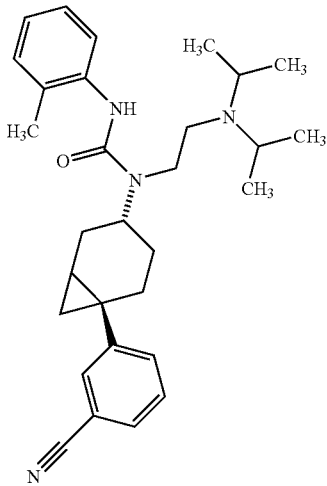 | 473 | 5.31 |
| 426 | 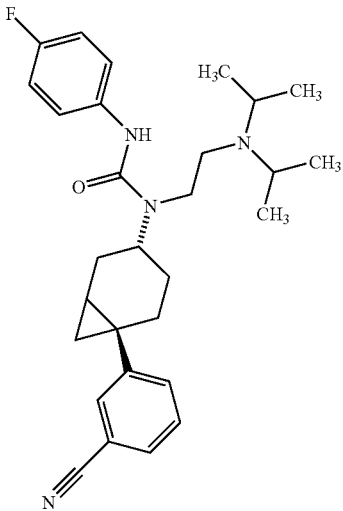 | 477 | 5.28 |

-continued

| Example | Structure | Mass (M + H) | LC/MS (Tr min) |
|---|---|---|---|
| 427 | 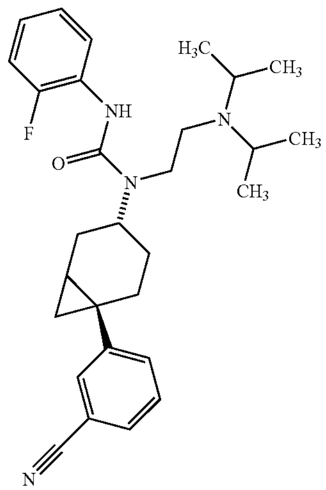 | 477 | 5.21 |
| 428 | 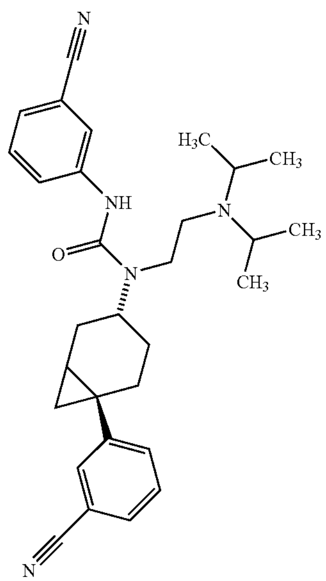 | 484 | 5.18 |
| 429 | 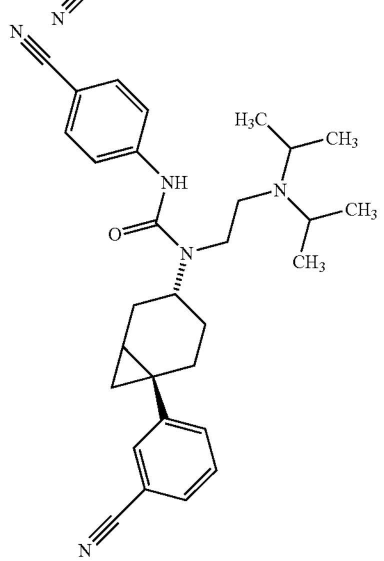 | 484 | 5.11 |

-continued

| Example | Structure | Mass (M + H) | LC/MS (Tr min) |
|---|---|---|---|
| 430 | 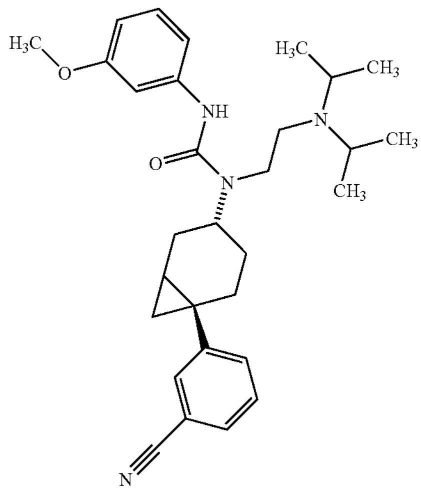 | 489 | 5.31 |
| 431 | 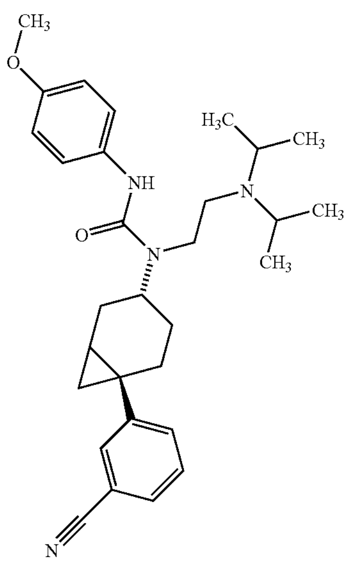 | 489 | 5.25 |
| 432 | 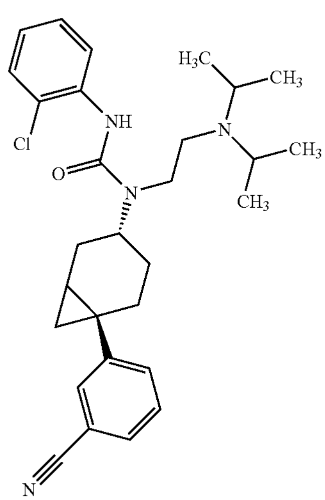 | 493 | 5.38 |

-continued

| Example | Structure | Mass (M + H) | LC/MS (Tr min) |
|---|---|---|---|
| 433 | 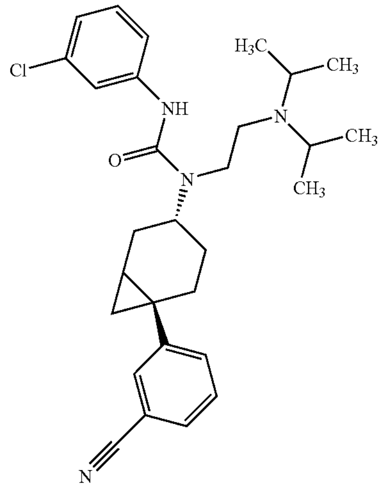 | 493 | 5.52 |
| 434 | 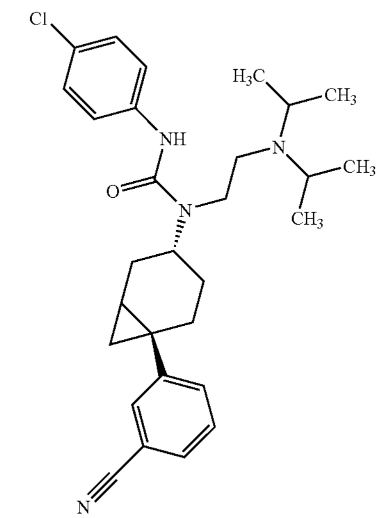 | 493 | 5.52 |
| 435 | 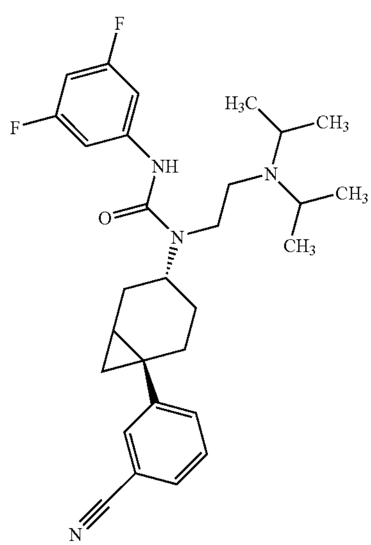 | 495 | 5.42 |

-continued

| Example | Structure | Mass (M + H) | LC/MS (Tr min) |
|---------|-----------|--------------|----------------|
| 436 | 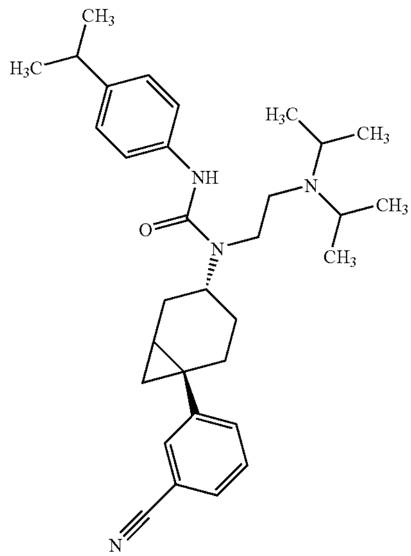 | 501 | 5.85 |
| 437 | 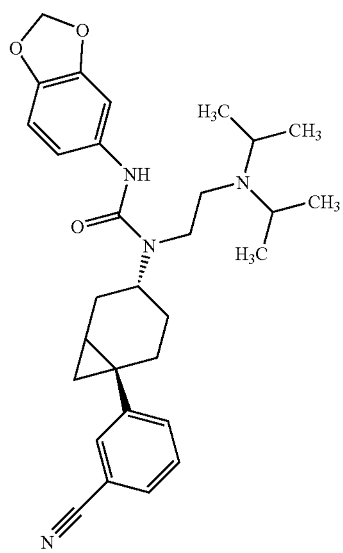 | 503 | 5.21 |
| 438 | 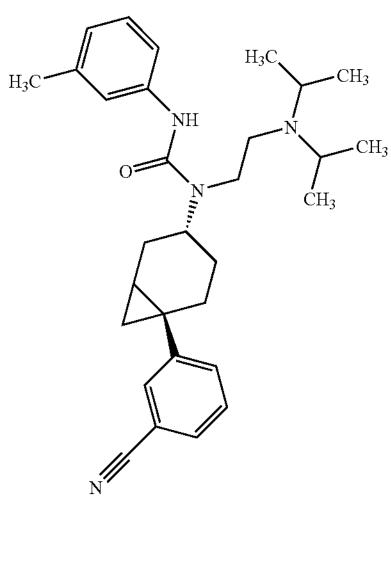 | 473 | 5.48 |

-continued
| Example | Structure | Mass (M + H) | LC/MS (Tr min) |
|---|---|---|---|
| 439 | 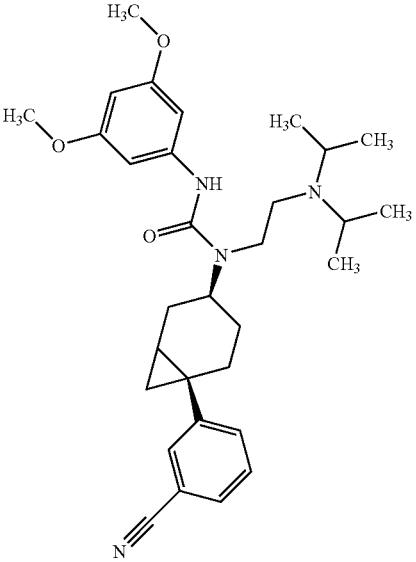 | 519 | 5.31 |
| 440 | 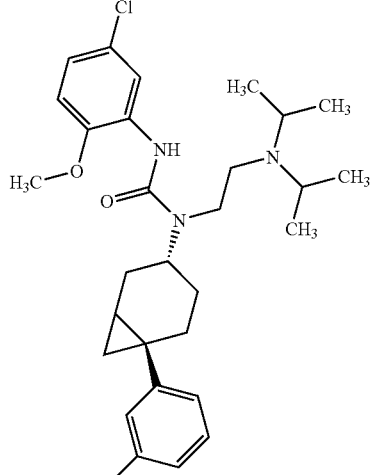 | 523 | 5.58 |
| 441 | 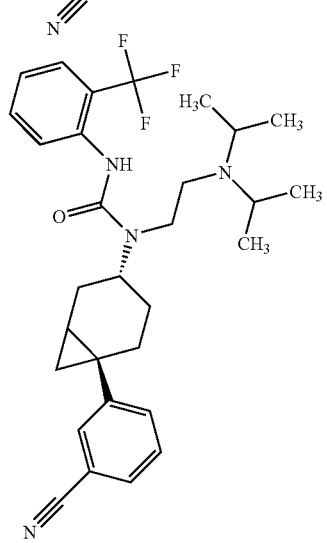 | 527 | 5.35 |

-continued

| Example | Structure | Mass (M + H) | LC/MS (Tr min) |
|---------|-----------|--------------|----------------|
| 442 | 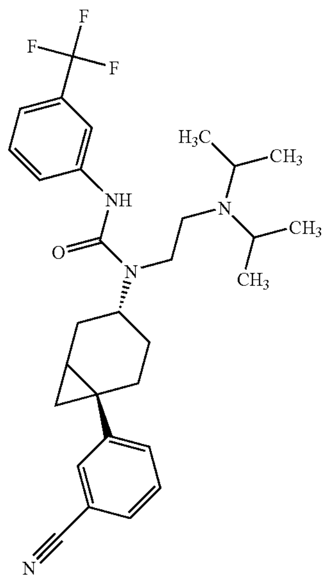 | 527 | 5.55 |
| 443 | 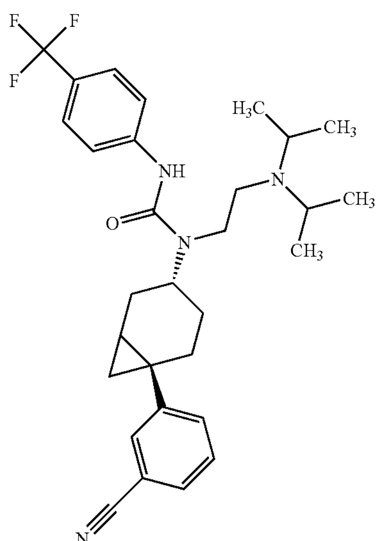 | 527 | 5.55 |
| 444 | 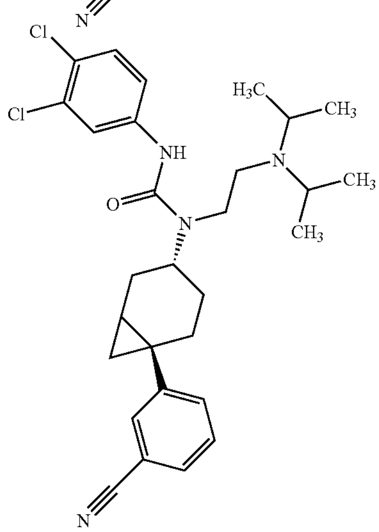 | 527 | 5.75 |

-continued
| Example | Structure | Mass (M + H) | LC/MS (Tr min) |
|---|---|---|---|
| 445 | 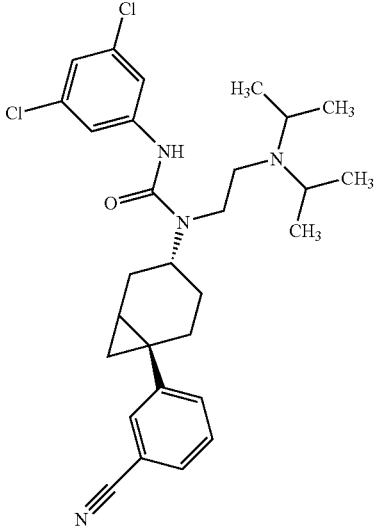 | 527 | 5.82 |
| 446 | 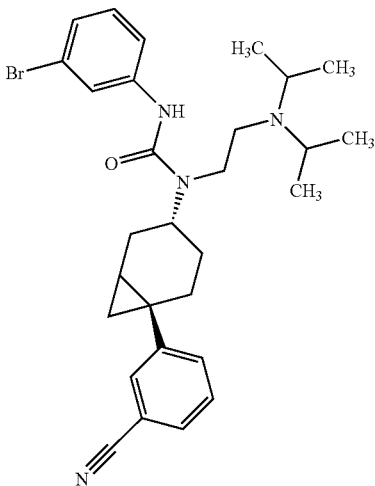 | 537 | 5.58 |
| 447 | 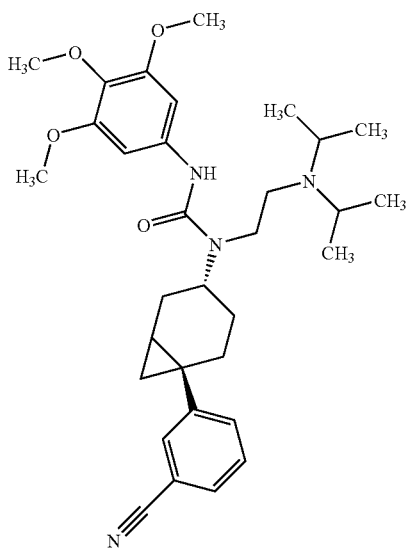 | 549 | 5.11 |

-continued
| Example | Structure | Mass (M + H) | LC/MS (Tr min) |
|---|---|---|---|
| 448 | 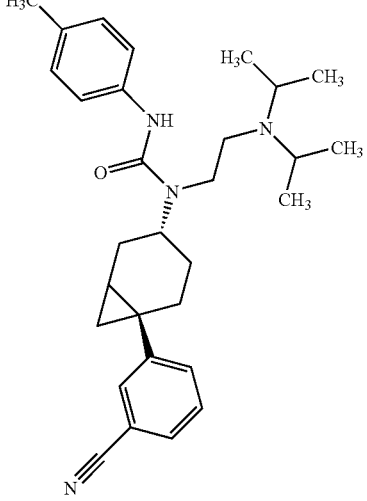 | 473 | 5.48 |
| 449 | 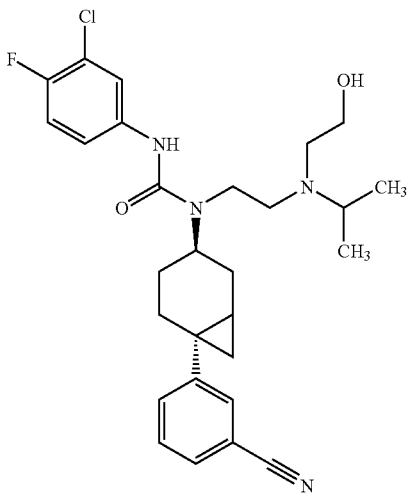 | 513 | 5.12 |
| 450 | 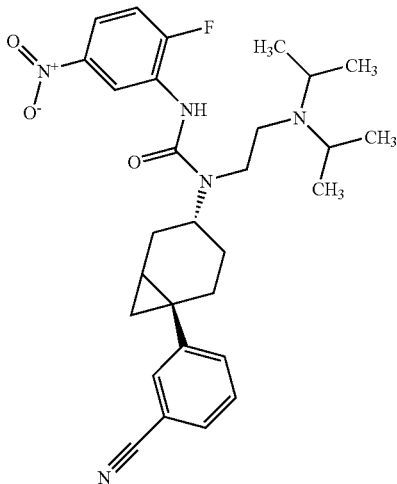 | 522 | 5.38 |

-continued
| Example | Structure | Mass (M + H) | LC/MS (Tr min) |
|---------|-----------|--------------|----------------|
| 451 | 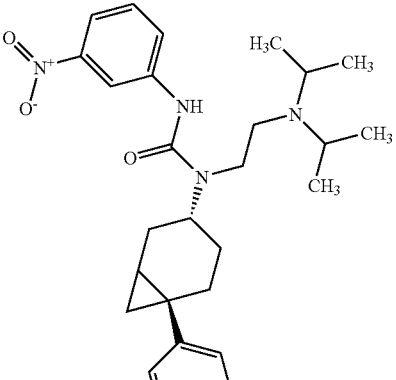 | 504 | 5.52 |
| 452 | 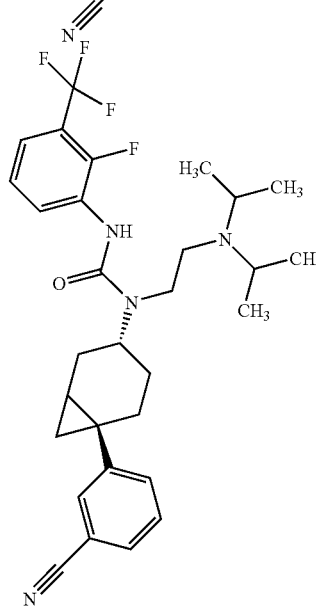 | 545 | 5.65 |
| 453 | 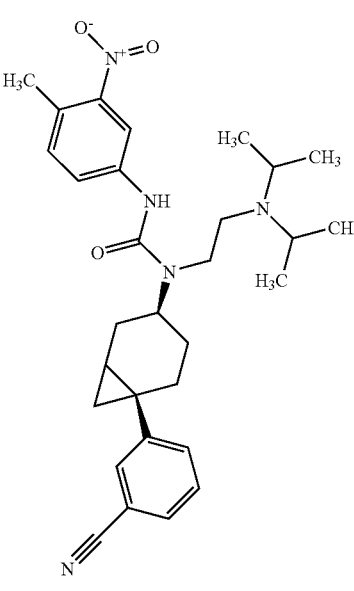 | 518 | 5.65 |

-continued

| Example | Structure | Mass (M + H) | LC/MS (Tr min) |
|---|---|---|---|
| 454 | 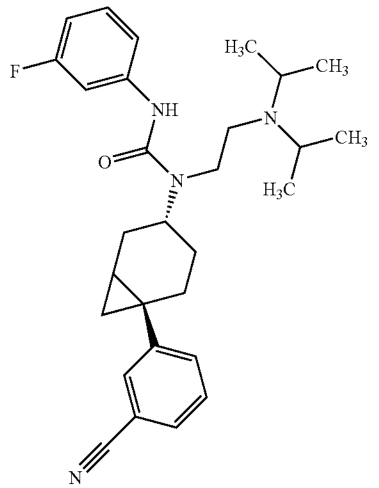 | 477 | 5.58 |
| 455 | 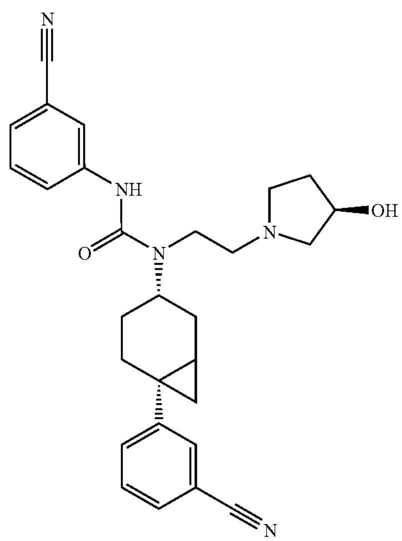 | 470 | 4.91 |
| 456 | 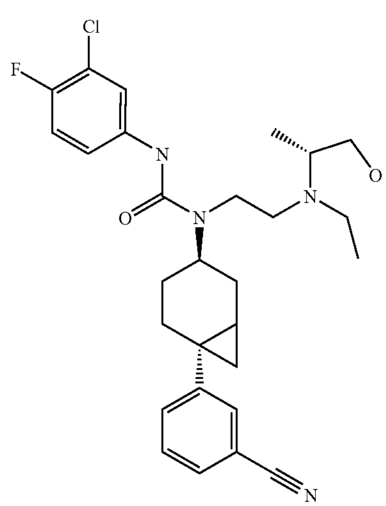 | 513 | 5.62 |

-continued

| Example | Structure | Mass (M + H) | LC/MS (Tr min) |
|---------|-----------|--------------|----------------|
| 457 | 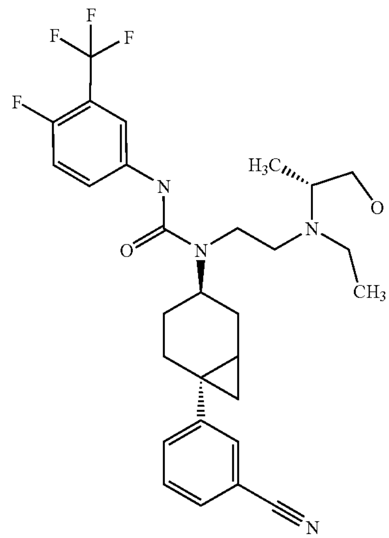 | 547 | 5.68 |
| 458 | 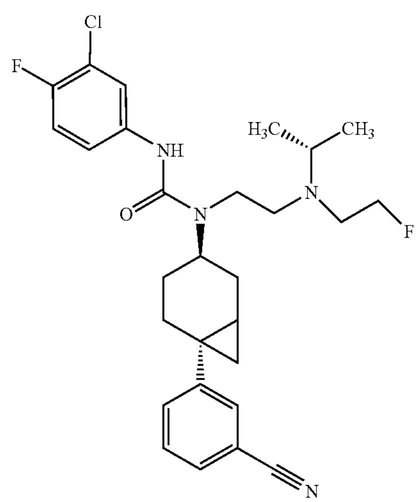 | 515 | 5.79 |
| 459 | 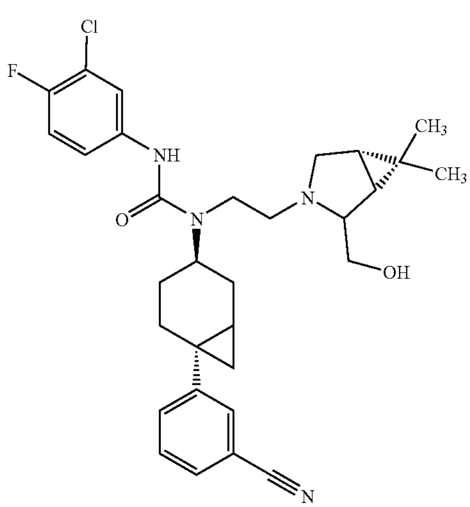 | 551 | 5.75 |

-continued

| Example | Structure | Mass (M + H) | LC/MS (Tr min) |
|---------|-----------|--------------|----------------|
| 460 | 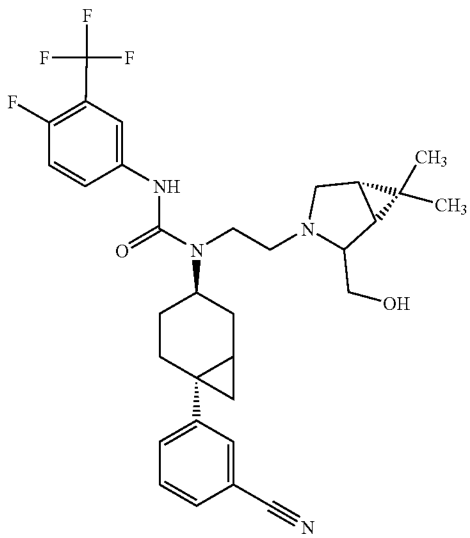 | 585 | 5.82 |
| 461 | 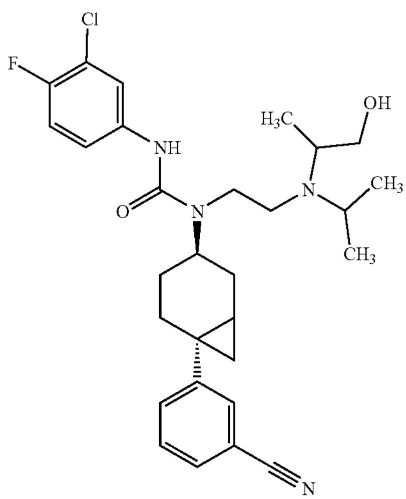 | 527 | 5.78 |
| 462 | 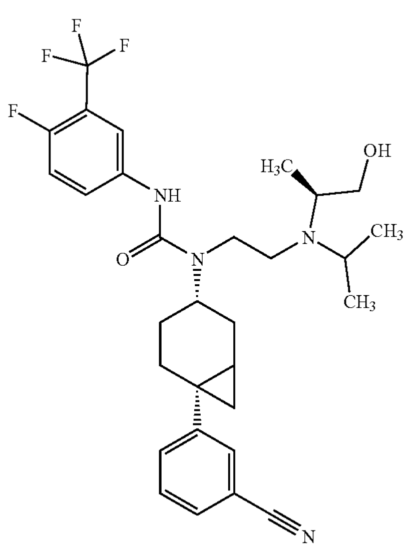 | 561 | 5.88 |

-continued

| Example | Structure | Mass (M + H) | LC/MS (Tr min) |
|---|---|---|---|
| 463 | 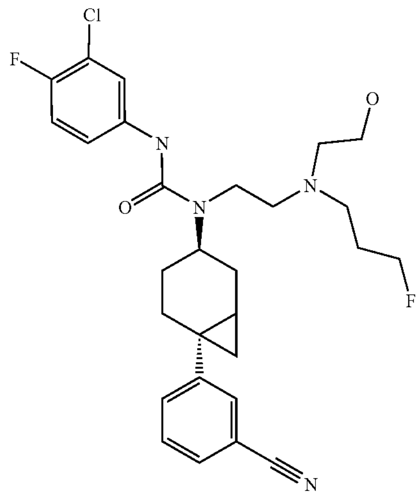 | 531 | 5.62 |
| 464 | 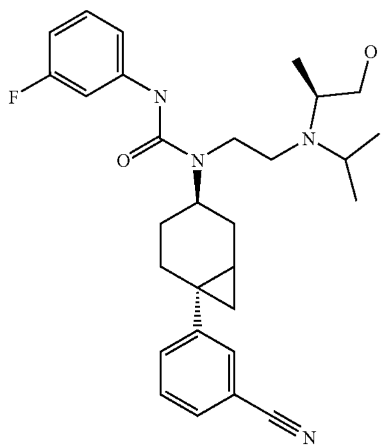 | 493 | 5.78 |
| 465 | 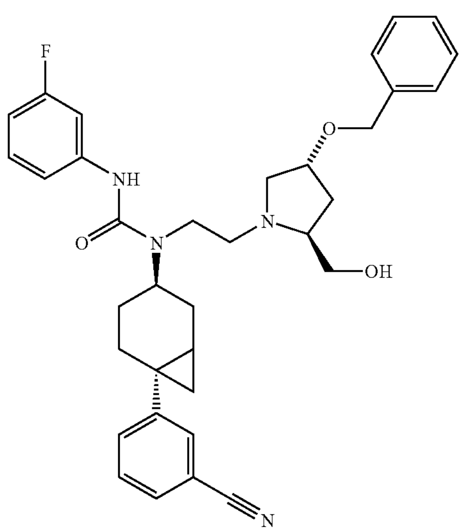 | 583 | 5.85 |

-continued

| Example | Structure | Mass (M + H) | LC/MS (Tr min) |
|---|---|---|---|
| 466 | 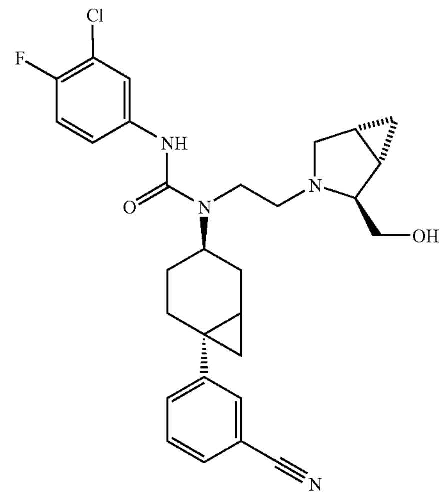 | 523 | 5.48 |
| 467 | 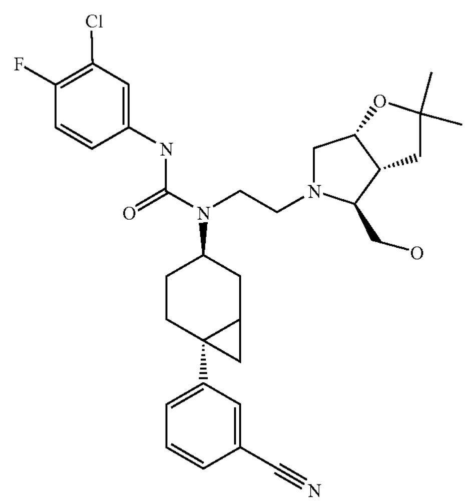 | 581 | 5.18 |
| 468 | 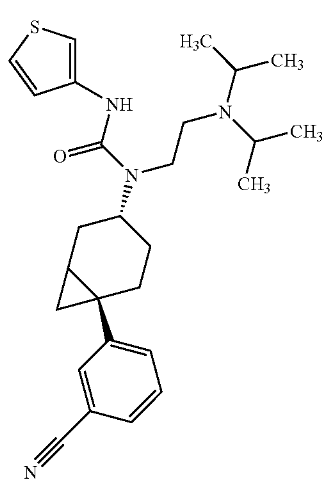 | 465 | 5.52 |

-continued

| Example | Structure | Mass (M + H) | LC/MS (Tr min) |
|---------|-----------|--------------|----------------|
| 469 | 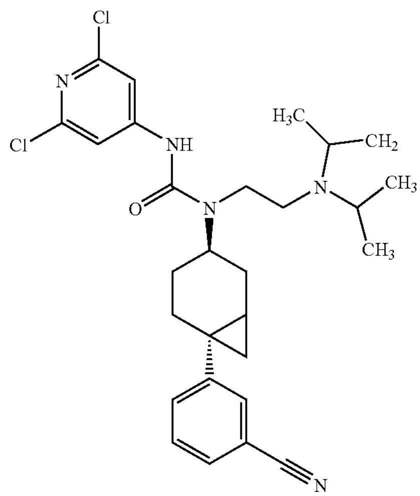 | 528 | 5.42 |
| 470 | 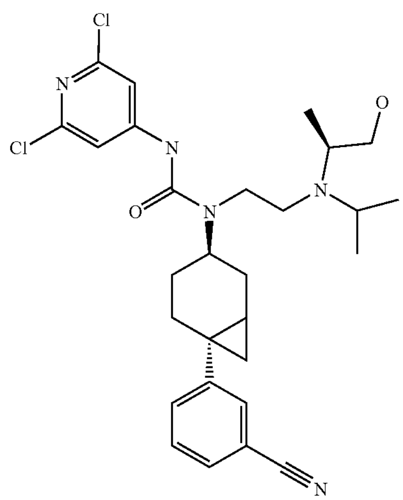 | 544 | 5.75 |
| 471 | 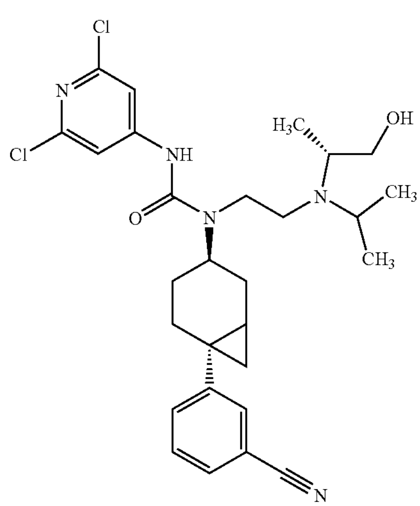 | 544 | 5.75 |

-continued

| Example | Structure | Mass (M + H) | LC/MS (Tr min) |
|---------|-----------|--------------|----------------|
| 472 | 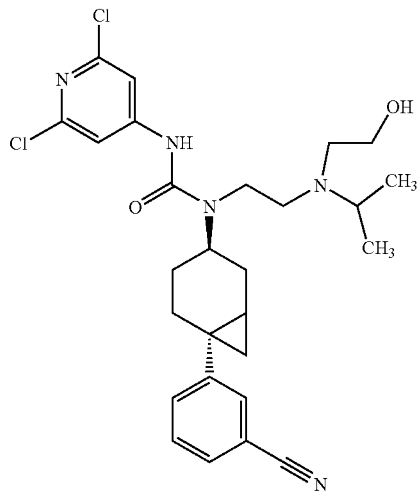 | 530 | 5.51 |
| 473 | 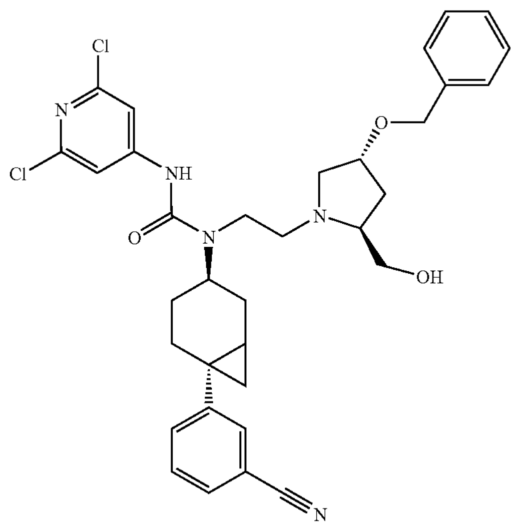 | 634 | 5.95 |
| 474 | 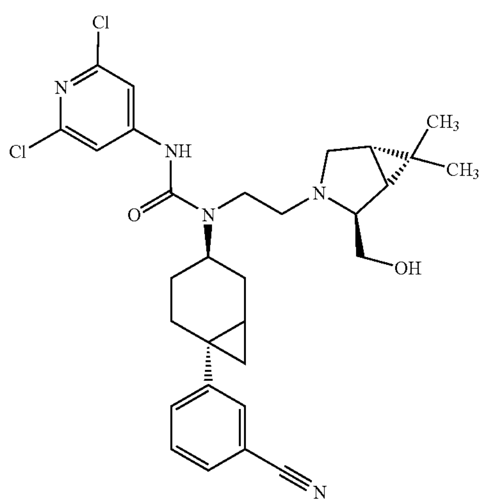 | 568 | 6.02 |

-continued

| Example | Structure | Mass (M + H) | LC/MS (Tr min) |
|---------|-----------|--------------|----------------|
| 475 | 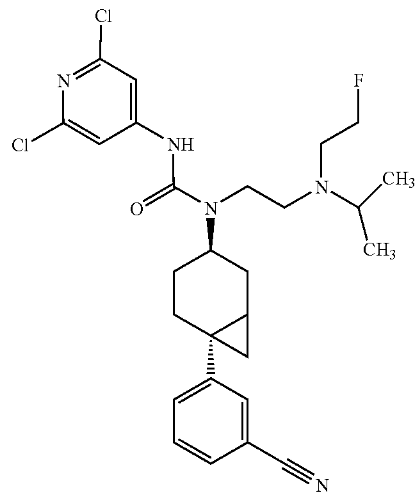 | 532 | 5.35 |
| 476 | 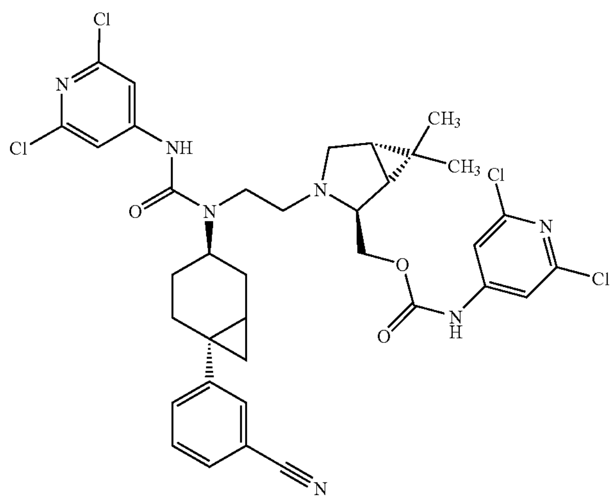 | 730 | 5.78 |
| 477 | 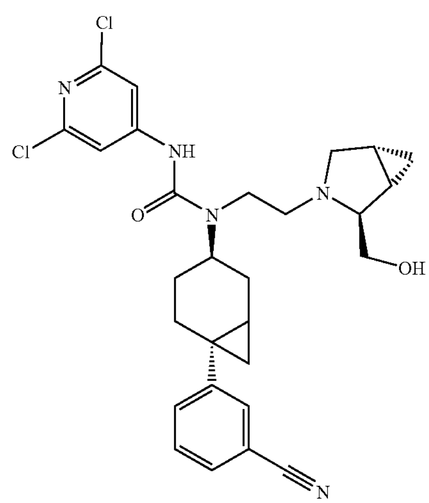 | 540 | 5.32 |

-continued

| Example | Structure | Mass (M + H) | LC/MS (Tr min) |
|---|---|---|---|
| 478 | 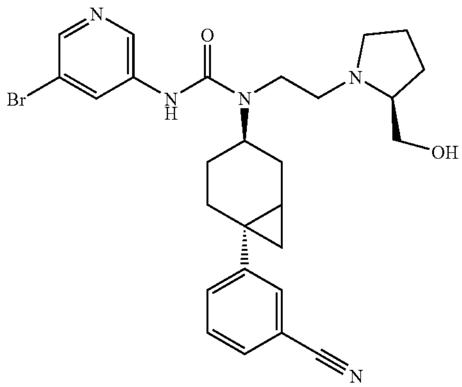 | 538 | 5.35 |
| 479 | 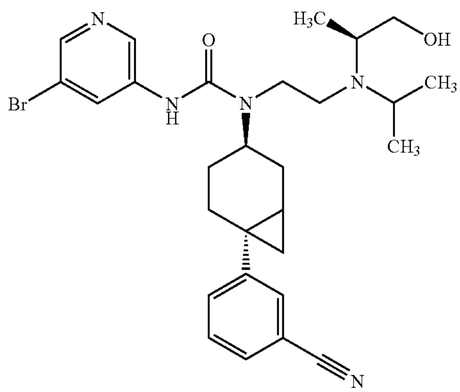 | 556 | 5.48 |
| 480 | 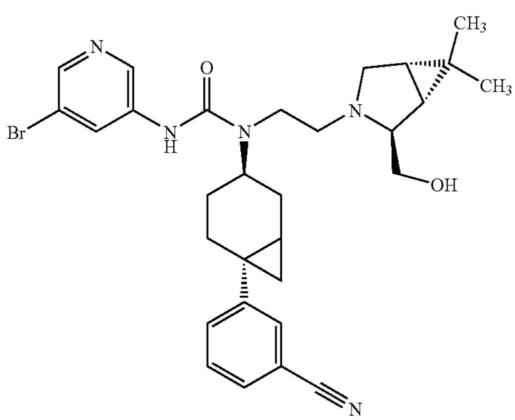 | 578 | 5.62 |
| 481 | 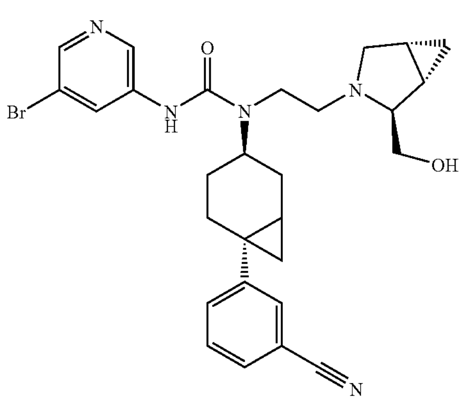 | 550 | 5.48 |

-continued
| Example | Structure | Mass (M + H) | LC/MS (Tr min) |
|---------|-----------|--------------|----------------|
| 482 | 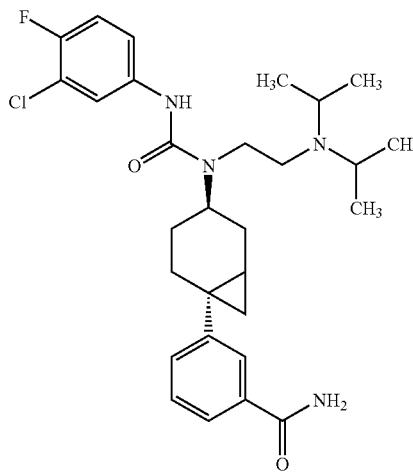 | 529 | 5.15 |
| 483 | 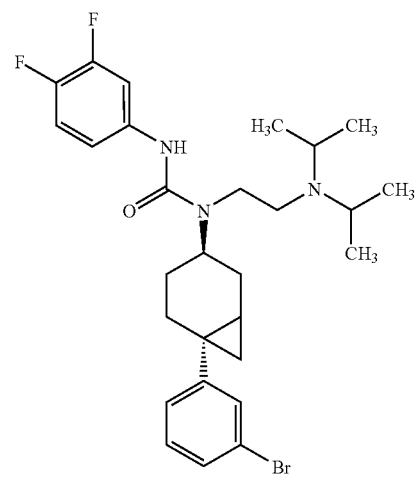 | 548 | 5.31 |
| 484 | 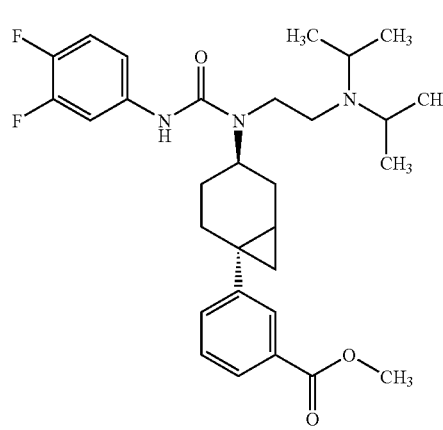 | 528 | 6.49 |

| Example | Structure | Mass (M + H) | LC/MS (Tr min) |
|---|---|---|---|
| 485 | 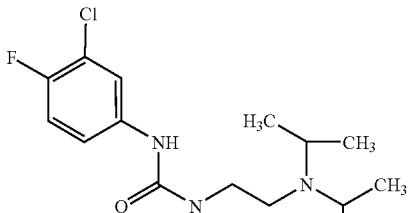 | 515 | 5.28 |

Example 486

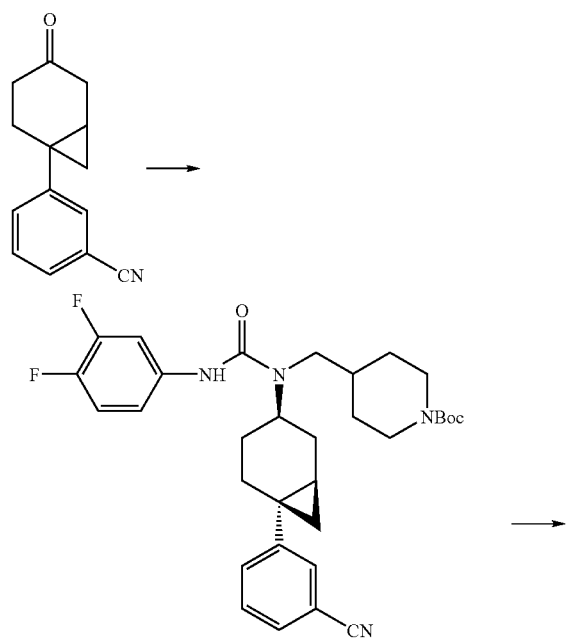

Synthesis of 1,1-DIMETHYLETHYL4-[[[TRANS-6-(3-CYANOPHENYL)BICYCLO[4.1.0]HEPT-3-YL][[(3,4-DIFLUOROPHENYL)AMINO]CARBONYL]AMINO]METHYL]-1-PIPERIDINECARBOXYLATE was accomplished according to Method 6. This compound (122 mg, 0.21 mmol) was treated with 50% TFA/DCM overnight. The solvent was removed and EtOAc, 1 N NaOH was added. After removal of the solvent, the crude was dissolved in 5 mL THF, Resin-Bound diisopropylethylamine (Argonaut, 0.22 g, 4 eq) and $MeSO_2Cl$ (49 mg, 2 eq) and stirred overnight. Resin-bound trisamine (0.19 g, 4 eq) was added and stirred for 6 h. Filtration afforded the filtrate which was treated with resin-bound P-TsOH (Argonaut, 0.65 g, 4 eq) for overnight and filtration provided the desired product 4-[[[TRANS-6-(3-CYANOPHENYL)BICYCLO[4.1.0]HEPT-3-YL][[(3,4-DIFLUOROPHENYL)AMINO]CARBONYL]AMINO]METHYL]-1-(METHYLSULFONYL)PIPERIDINE (65 mg).

$^1$H NMR (400 MHz, CDCl3) ☐ 0.80 (m, 1 H) 0.99 (m, 1 Hz) 1.30-1.42 (m, 3 H) 1.60-1.90 (m, 7 H) 2.10 (m, 1 H) 2.38 (m, 1 H) 2.60 (m, 2 H) 2.78 (s, 3 H) 3.10 (m, 2 H) 3.60-3.84 (m, 3 H) 6.60 (s, 1 H) 7.00 (m, 2 H) 7.40-7.60 (m, 4 H). LC/MS Tr 4.85 min. 543 (M+H).

The following compounds were prepared according to procedures similar to those described in the example

| Example | Structure | Mass (M + H) | LC/MS (Tr min) |
|---|---|---|---|
| 487 | 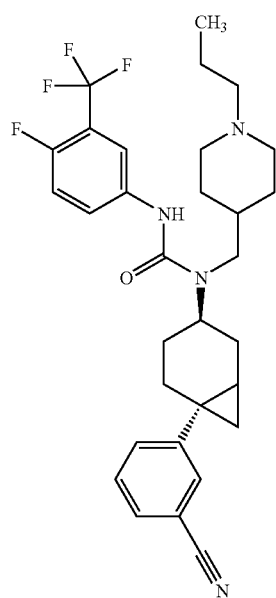 | 557 | 5.72 |
| 488 | 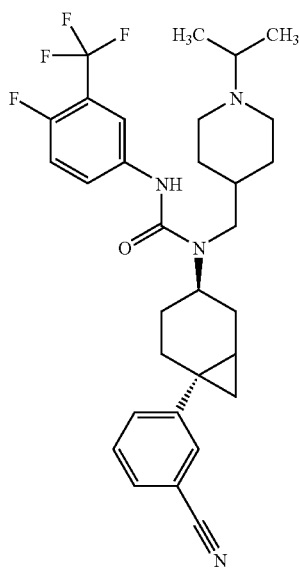 | 557 | 5.72 |

-continued
| Example | Structure | Mass (M + H) | LC/MS (Tr min) |
|---|---|---|---|
| 489 | 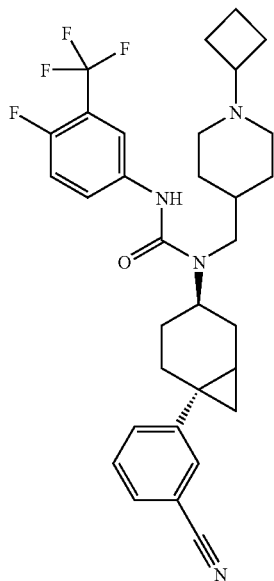 | 569 | 5.72 |
| 490 | 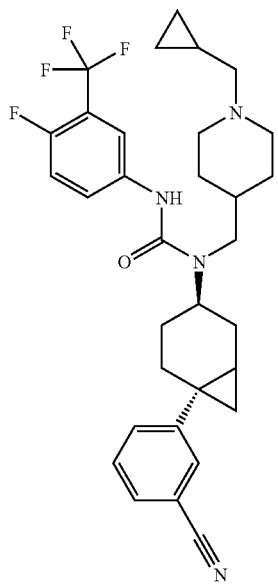 | 569 | 5.72 |

-continued
| Example | Structure | Mass (M + H) | LC/MS (Tr min) |
|---------|-----------|--------------|----------------|
| 491 | 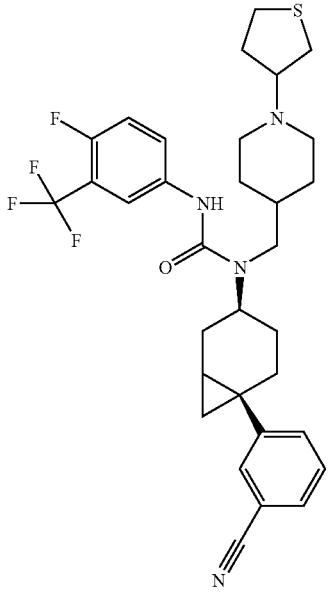 | 601 | 5.65 |
| 492 | 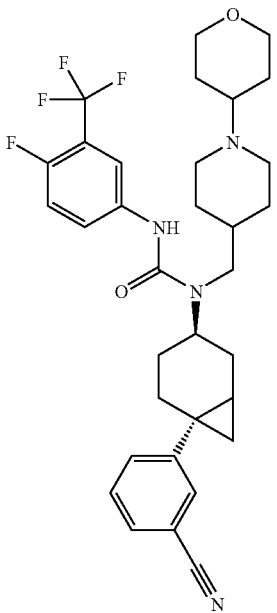 | 599 | 5.65 |

-continued
| Example | Structure | Mass (M + H) | LC/MS (Tr min) |
|---|---|---|---|
| 493 | 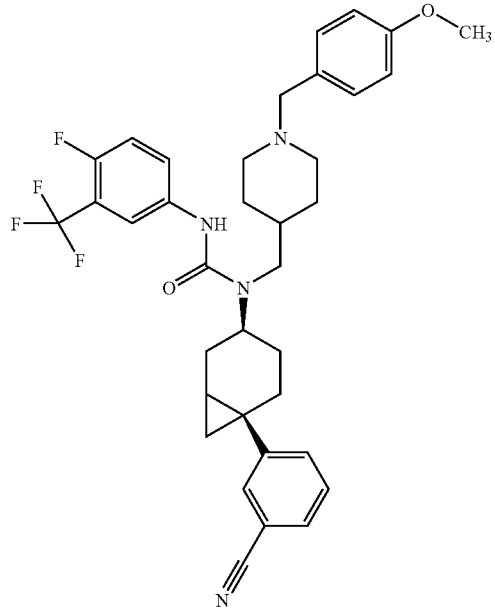 | 635 | 5.78 |
| 494 | 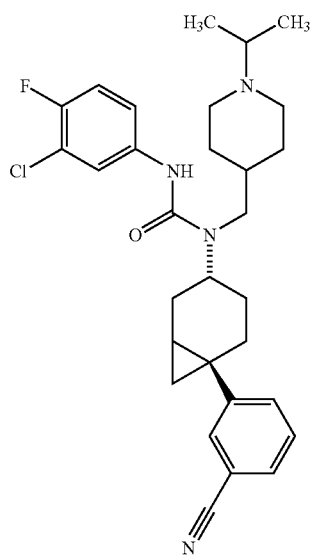 | 523 | 5.65 |

-continued

| Example | Structure | Mass (M + H) | LC/MS (Tr min) |
|---|---|---|---|
| 495 | 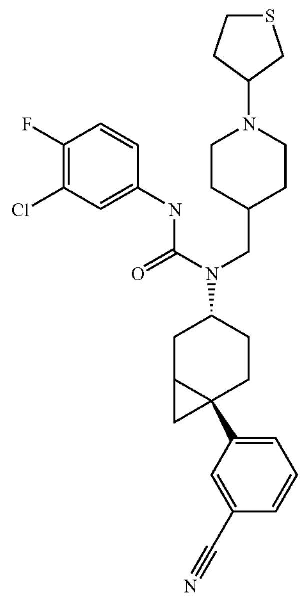 | 567 | 5.58 |
| 496 | 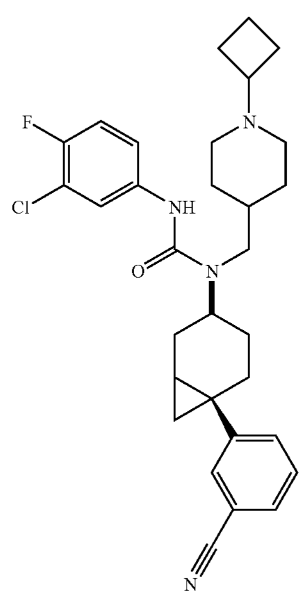 | 535 | 5.65 |

-continued
| Example | Structure | Mass (M + H) | LC/MS (Tr min) |
|---------|-----------|--------------|----------------|
| 497 | 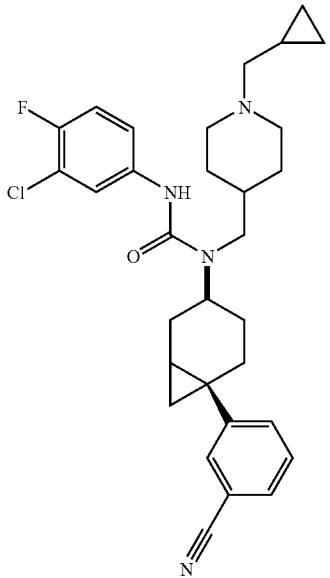 | 535 | 5.65 |
| 498 | 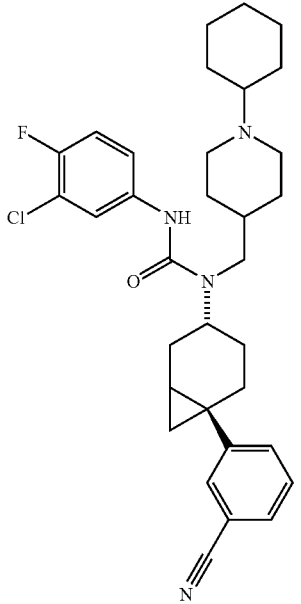 | 563 | 5.82 |

-continued
| Example | Structure | Mass (M + H) | LC/MS (Tr min) |
|---|---|---|---|
| 499 | 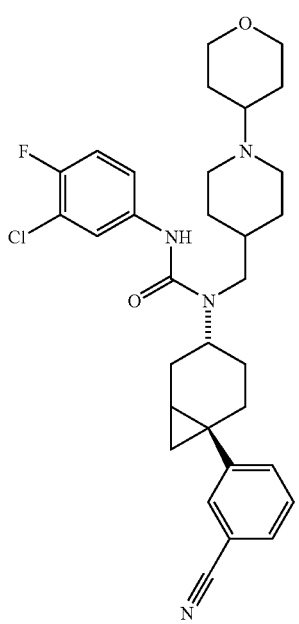 | 565 | 5.58 |
| 500 | 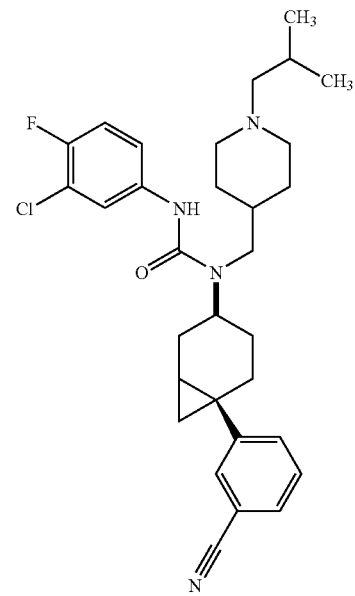 | 537 | 5.68 |

-continued

| Example | Structure | Mass (M + H) | LC/MS (Tr min) |
|---|---|---|---|
| 501 | 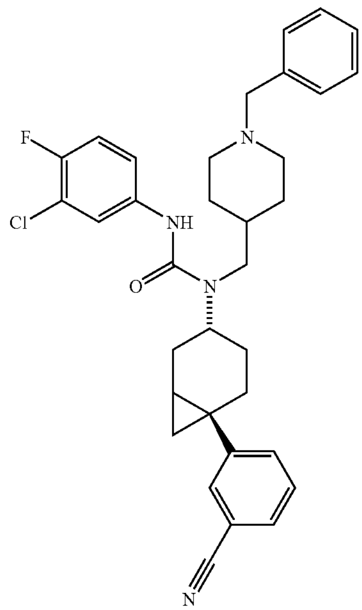 | 571 | 5.72 |
| 502 | 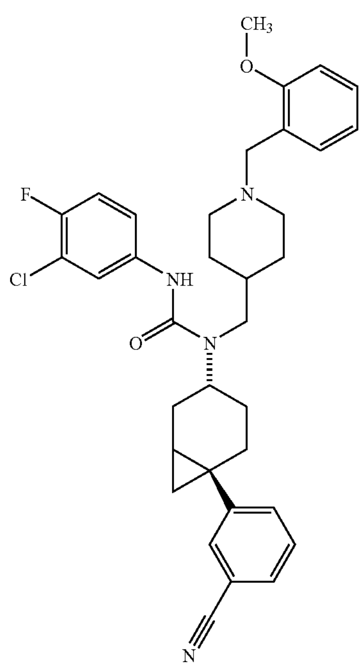 | 601 | 5.85 |

| Example | Structure | Mass (M + H) | LC/MS (Tr min) |
|---|---|---|---|
| 503 | 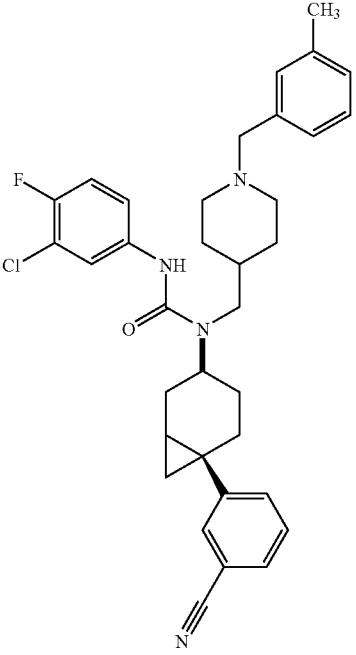 | 585 | 5.82 |
| 504 | 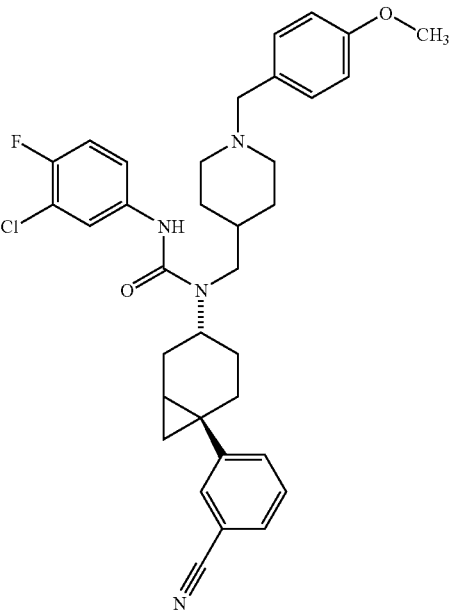 | 601 | 5.75 |

-continued
| Example | Structure | Mass (M + H) | LC/MS (Tr min) |
|---------|-----------|--------------|----------------|
| 505 | 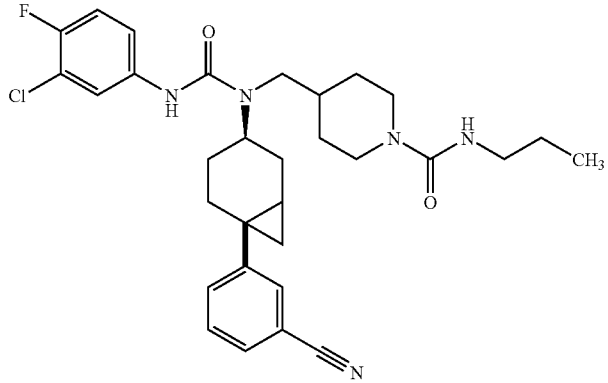 | 566 | 5.21 |
| 506 | 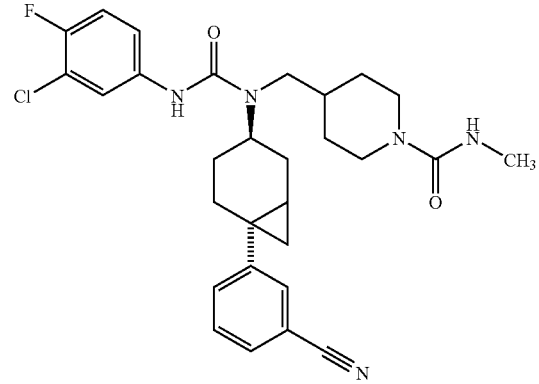 | 538 | 5.18 |
| 507 | 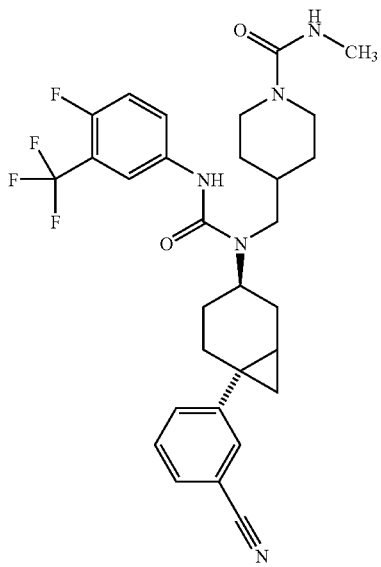 | 572 | 5.65 |

-continued
| Example | Structure | Mass (M + H) | LC/MS (Tr min) |
|---------|-----------|--------------|----------------|
| 508 | 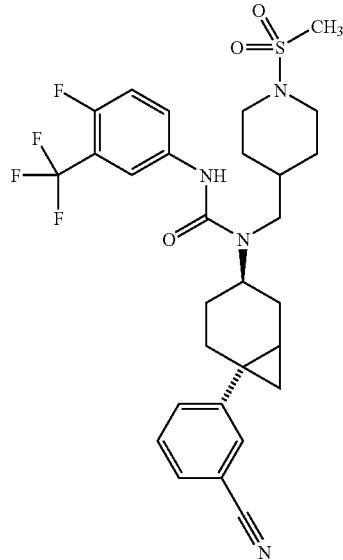 | 593 | 5.58 |
| 509 | 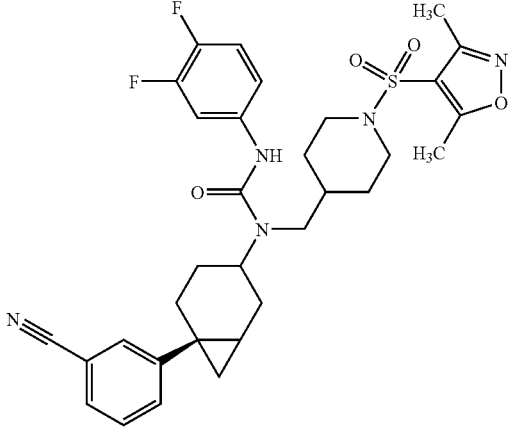 | 624 | 5.82 |
| 510 | 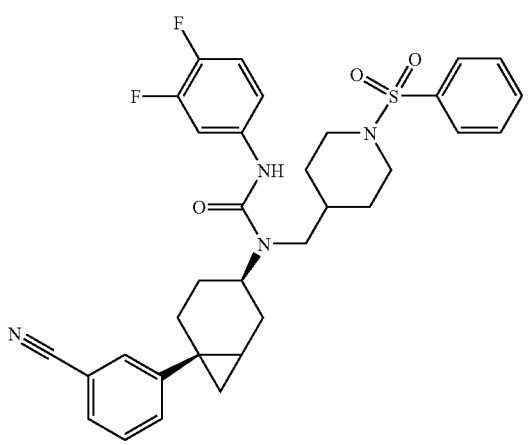 | 605 | 5.88 |

-continued

| Example | Structure | Mass (M + H) | LC/MS (Tr min) |
|---------|-----------|--------------|----------------|
| 511 | 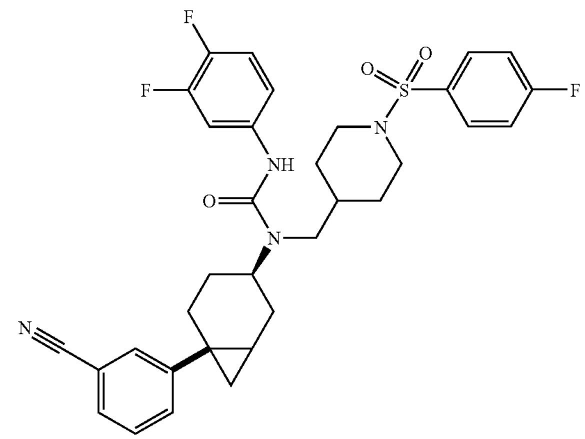 | 623 | 5.80 |
| 512 | 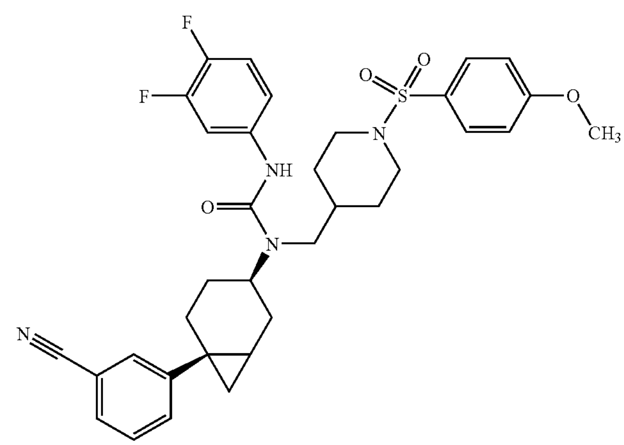 | 635 | 5.88 |
| 513 | 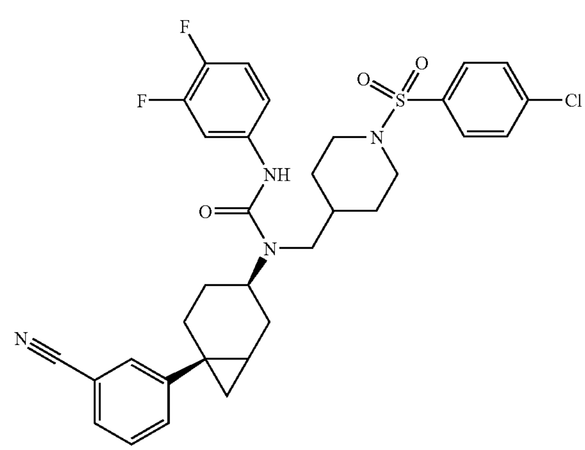 | 639 | 6.02 |

| Example | Structure | Mass (M + H) | LC/MS (Tr min) |
|---|---|---|---|
| 514 | 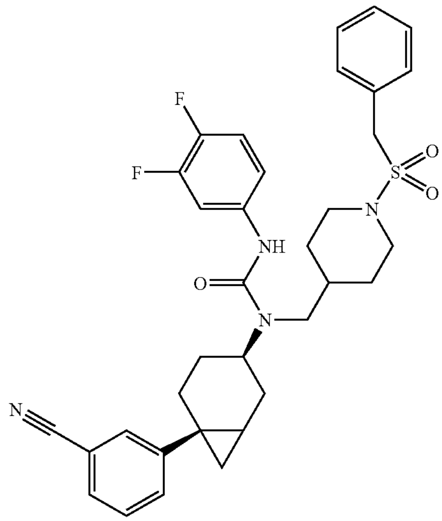 | 619 | 5.82 |
| 515 | 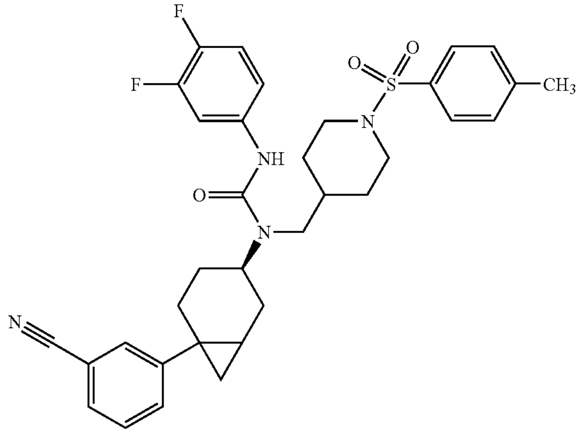 | 619 | 5.95 |
| 516 | 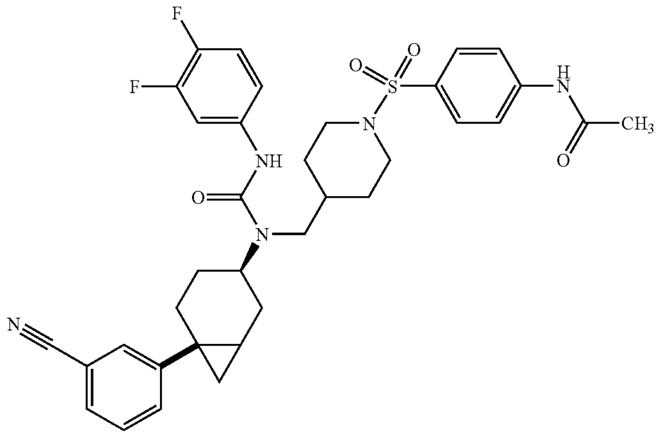 | 662 | 5.58 |

| Example | Structure | Mass (M + H) | LC/MS (Tr min) |
|---|---|---|---|
| 517 | 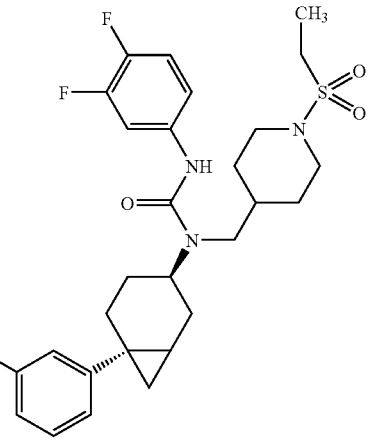 | 557 | 5.62 |
| 518 | 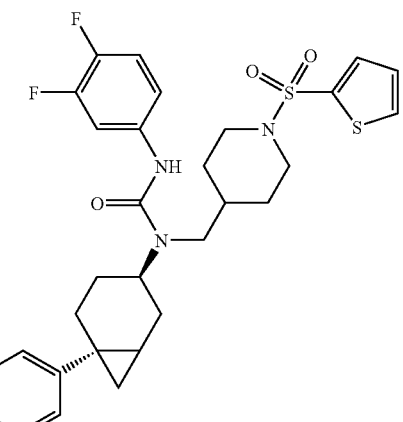 | 611 | 5.95 |
| 519 | 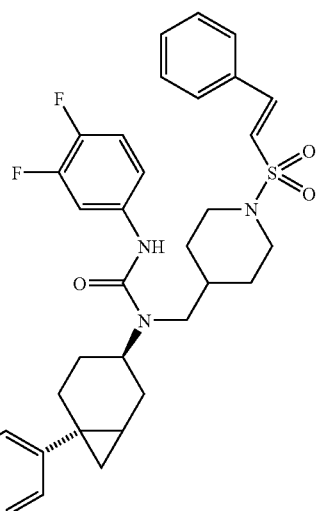 | 631 | 5.92 |

| Example | Structure | Mass (M + H) | LC/MS (Tr min) |
|---|---|---|---|
| 520 | 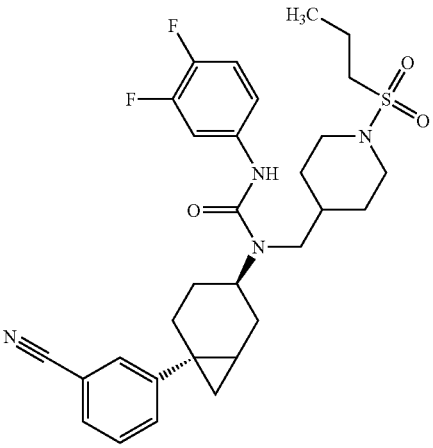 | 571 | 5.75 |
| 521 | 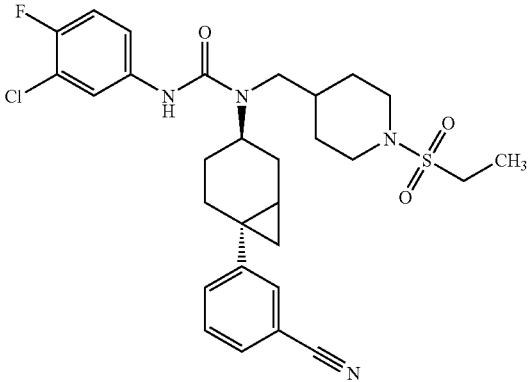 | 573 | 5.25 |
| 522 | 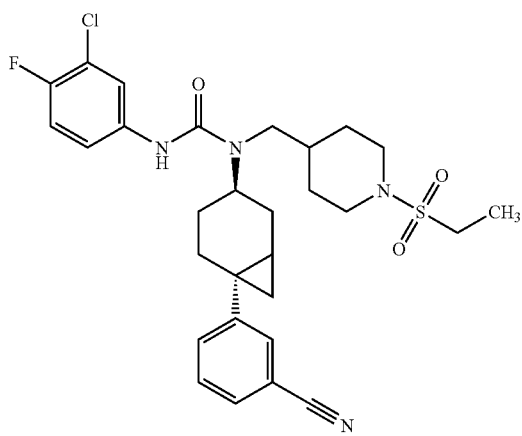 | 559 | 5.28 |

-continued
| Example | Structure | Mass (M + H) | LC/MS (Tr min) |
|---------|-----------|--------------|----------------|
| 523 | 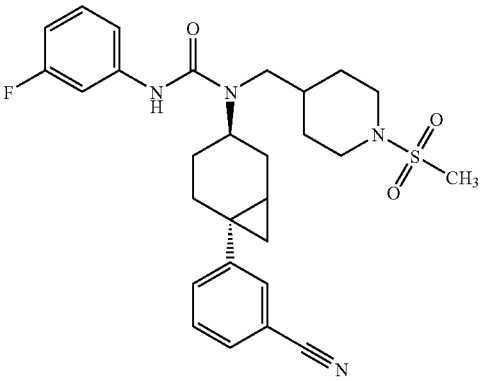 | 525 | 5.12 |
| 524 | 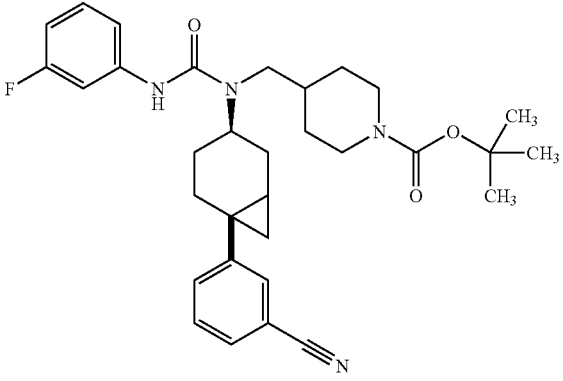 | 547 | 5.65 |
| 525 | 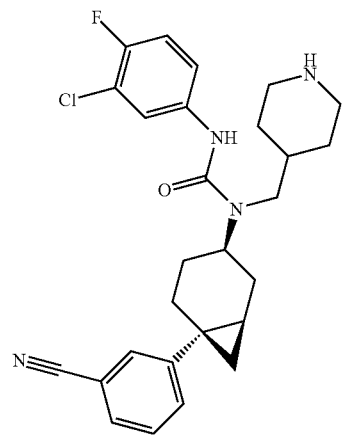 | 481 | 5.72 |

-continued
| Example | Structure | Mass (M + H) | LC/MS (Tr min) |
|---------|-----------|--------------|----------------|
| 526 | 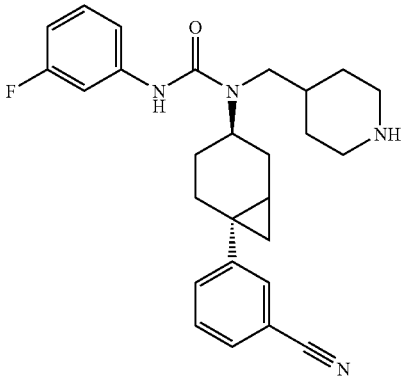 | 447 | 5.05 |
| 527 | 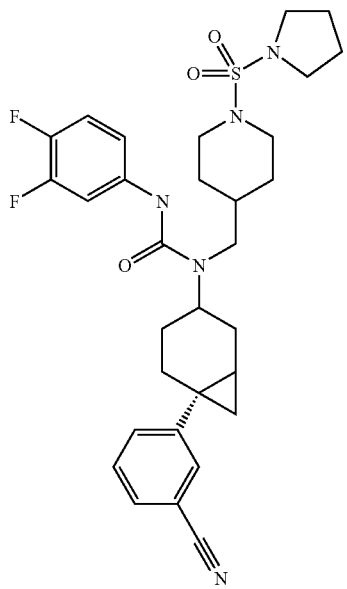 | 598 | 5.18 |
| 528 | 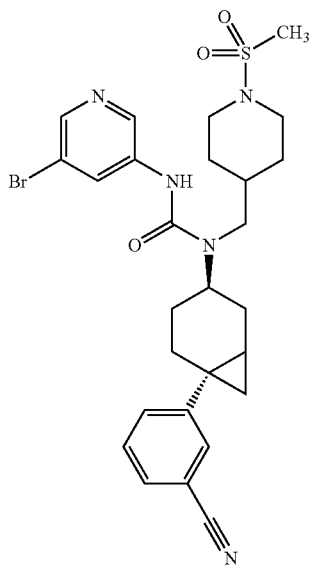 | 586 | 5.05 |

-continued

| Example | Structure | Mass (M + H) | LC/MS (Tr min) |
|---|---|---|---|
| 529 | 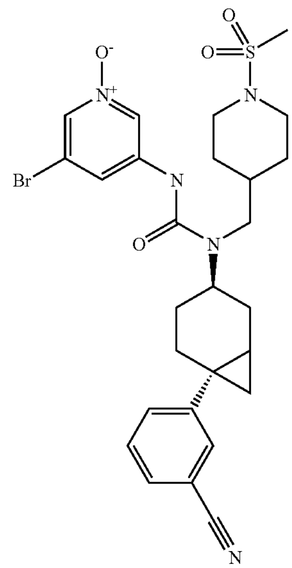 | 602 | 4.98 |
| 530 | 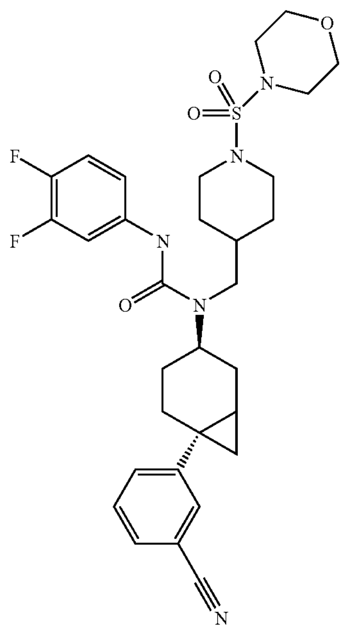 | 614 | 5.01 |
| 531 | 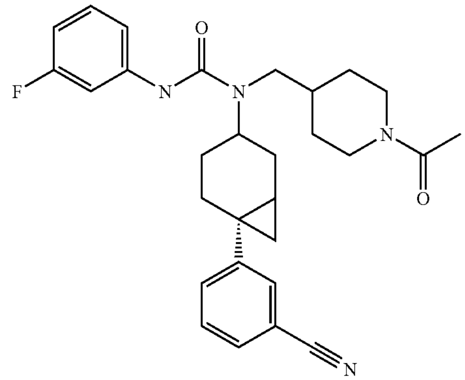 | 489 | 5.35 |

| Example | Structure | Mass (M + H) | LC/MS (Tr min) |
|---|---|---|---|
| 532 | 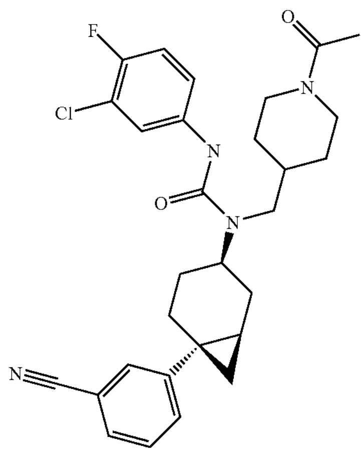 | 523 | 5.82 |
| 533 | 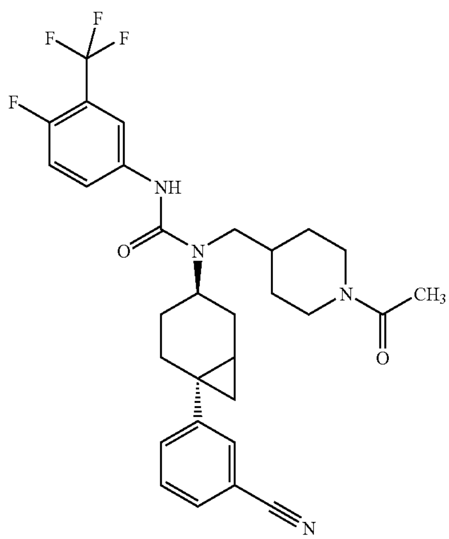 | 557 | 5.98 |
| 534 | 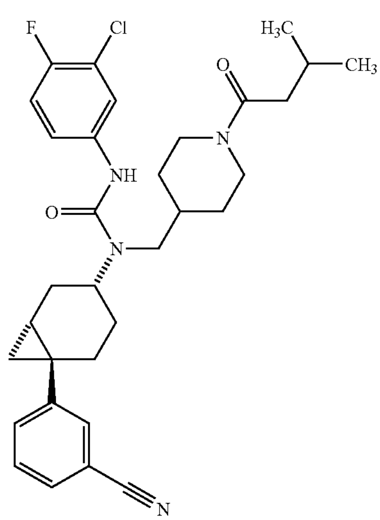 | 565 | 5.98 |

| Example | Structure | Mass (M + H) | LC/MS (Tr min) |
|---|---|---|---|
| 535 | 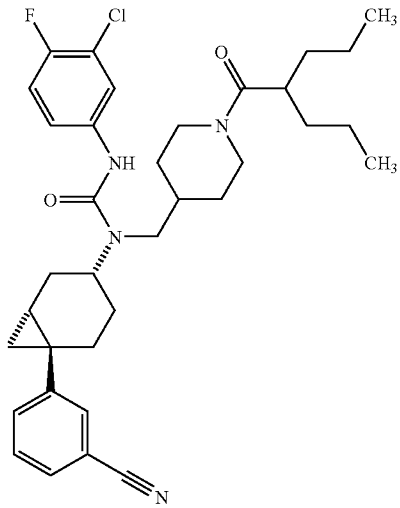 | 607 | 6.22 |
| 536 | 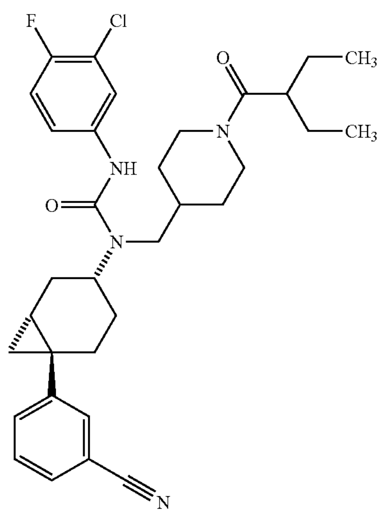 | 579 | 6.02 |
| 537 | 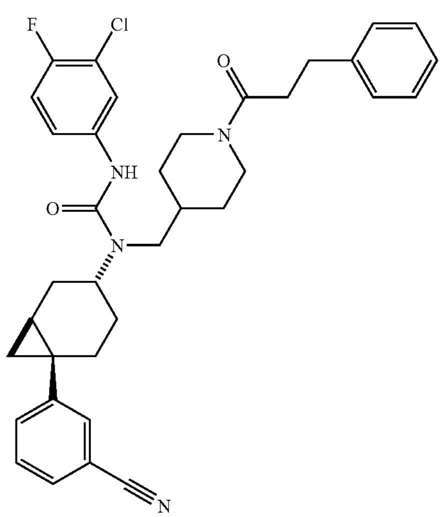 | 613 | 5.98 |

-continued
| Example | Structure | Mass (M + H) | LC/MS (Tr min) |
|---|---|---|---|
| 538 | 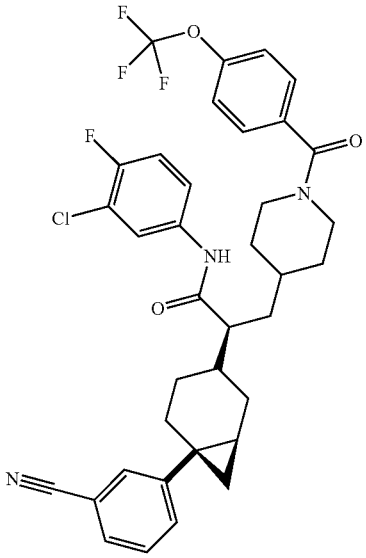 | 669 | 5.98 |
| 539 | 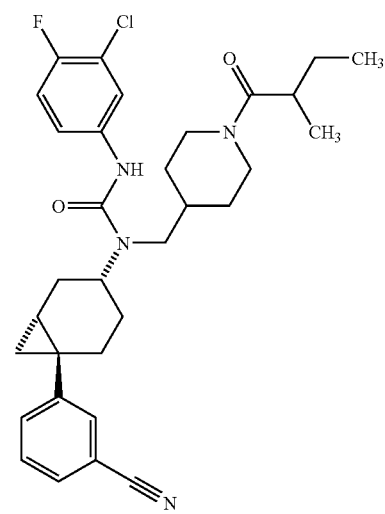 | 565 | 5.95 |
| 540 | 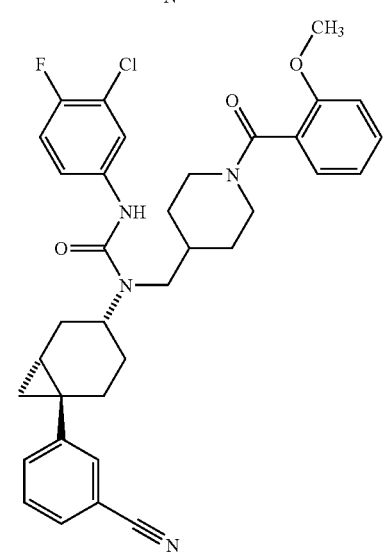 | 615 | 5.85 |

| Example | Structure | Mass (M + H) | LC/MS (Tr min) |
|---|---|---|---|
| 541 | 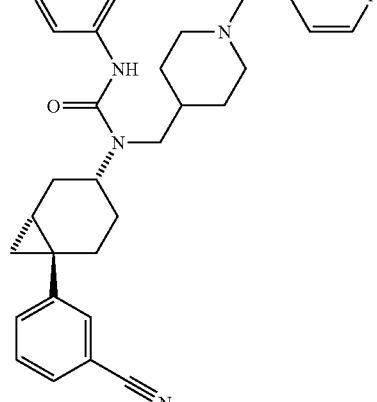 | 586 | 5.85 |
| 542 | 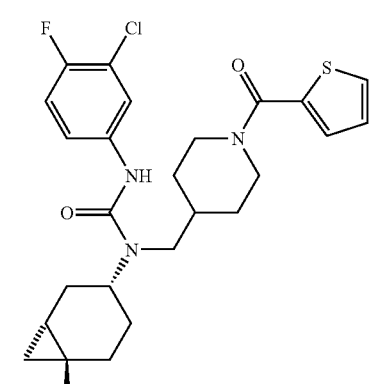 | 591 | 5.85 |
| 543 | 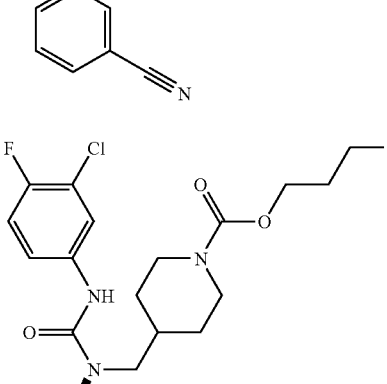 | 581 | 6.15 |

-continued

| Example | Structure | Mass (M + H) | LC/MS (Tr min) |
|---------|-----------|--------------|----------------|
| 544 | 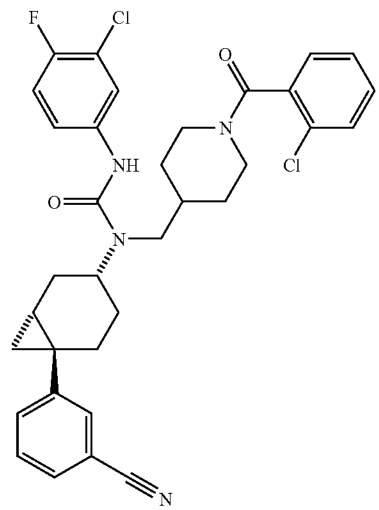 | 619 | 5.92 |
| 545 | 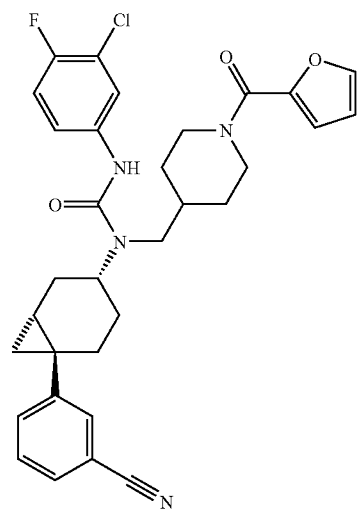 | 575 | 5.78 |
| 546 | 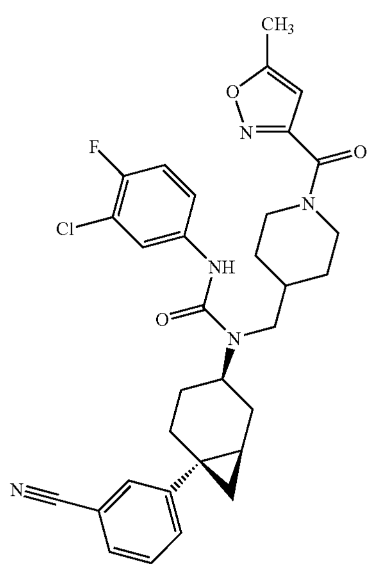 | 590 | 5.75 |

| Example | Structure | Mass (M + H) | LC/MS (Tr min) |
|---|---|---|---|
| 547 | 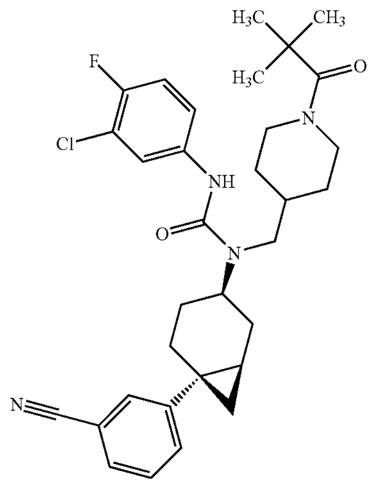 | 565 | 5.95 |

Example 548

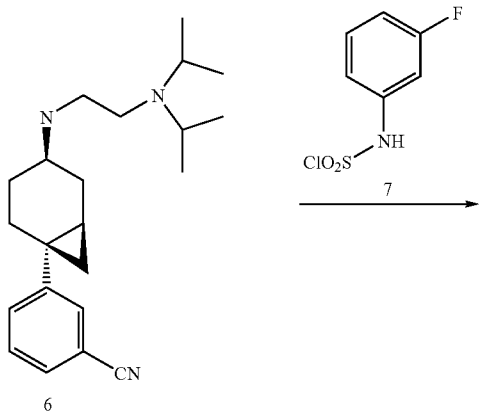

Synthesis of 6 was accomplished by the procedure described in method [[JS2]]. Synthesis of 7 was accomplished according to Chem. Ber. 1987, 1191. To 3-fluoroaniline (5 g, 45 mmol)/100 mL DCM at 0° C. was added dropwise chlorosulfonic acid (5.35 g, 1 eq). The mixture was stirred for 3 h. After removal of the solvent, 150 mL of toluene was added followed by $PCl_5$ (9.36 g, 1 eq). The solution was refluxed for 2 h. After cooling down, the solvent was removed and the crude was washed with pentane and dried under vacuum for 1 h. Then this intermediate (46.5 mg, 2 eq) was treated with 6 (38 mg, 0.111 mmol, 1 eq) and Hunig's base (29 mg, 2 eq) in 2 mL DCM for overnight. Prep TLC provided the final product 8 (42 mg).

$^1$H NMR (400 MHz, CDCl3) δ 0.70 (m, 1 H) 0.99 (m, 1 H) 1.00 (d, 12 H, J=6.5 Hz) 1.25 (m, 1 H) 1.38 (m, 1 H) 1.50 (m, 1 H) 1.65 (m, 1 H) 2.00 (m, 1 H) 2.25 (m, 2 H) 2.58 (m, 2 H) 3.00-3.20 (m, 4 H) 3.62 (m, 1 H) 6.80 (dt, 1 H, J=2.4, 8.3 Hz) 6.90 (d, 1 H, J=8.1 Hz) 6.95 (td, 1 H, J=2.4, 10.4 Hz) 7.30 (m, 1H) 7.40-7.60 (m, 3H). LC/MS Tr 4.85 min. 513 (M+H).

MCH Receptor Binding Assay:

Membranes from CHO cells expressing the MCH receptor were prepared by lysing cells with 5 mM HEPES for 15 min at 4C. Cell lysates were centrifuged (12.5000×g, 15 min) and the pellet was resuspended in 5 mM HEPES. For each 96-well plate (Microlite, Dynex Technologies), 1 mg of cell membranes were incubated with 10 mg of wheat germ agglutinin SPA beads (Amersham) for 5 min at 4 C. in a volume of 10 ml of binding buffer (25 mM HEPES, 10 mM $MGCl_2$, 10 mM NaCl, 5 mM $MnCl_2$, 0.1% BSA). The membrane/bead mixture was centrifuged (1500×g, 3.5 min), the supernatant was aspirated, and the pellet was resuspended in 10 ml binding buffer. The centrifugation, aspiration and resuspension were then repeated. The membrane/bead mixture (100 μl) was then added to 96-well plates containing 50 μl of 500 pM [$^{125}$I]-MCH (NEN) and 50 ml of the appropriate concentration of compound (4×the desired final concentration). Nonspecific binding was determined by including 1 μM MCH in the binding reaction. The binding reaction was incubated at room temperature for 2 h. Plates were then analyzed in a TOPCOUNT microplate scintillation counter (Packard). Data was analyzed and Ki values were determined using GraphPad Prim.

For the compounds of this invention, a range of MCH receptor binding activity (Ki values) of from about 1 nM to about 600 nM was observed. Compounds of this invention preferably have a binding activity in the range of from about 1 nM to about 250 nM, more preferably from about 1 to about 30 nM, and most preferably from about 1 to about 5 nM.

TABLE 2

Binding Activity of Examples 186-202

| Ex | MCH Ki (nM) |
|---|---|
| 186 | 605 |
| 187 | 14 |
| 188 | 15 |
| 189 | 18 |
| 190 | 13 |
| 191 | 22 |
| 192 | 18 |
| 193 | 7.1 |
| 194 | 4.1 |
| 195 | 10 |
| 196 | 3.9 |
| 197 | 79 |
| 198 | 11 |
| 199 | 23 |
| 206 | 30 |
| 207 | 22 |
| 208 | 9 |
| 209 | 10 |
| 210 | 20 |
| 225 | 2.6 |
| 226 | 2.2 |
| 227 | 1.6 |

From these test results and the background knowledge about the compounds described in the references in section "Background of the Invention", it would be apparent to the skilled artisan that the compounds of the invention have utility in treating metabolic and eating disorders and the like diseases stated earlier.

While the present invention has been described in conjunction with the specific embodiments set forth above, many alternatives, modifications and other variations thereof will be apparent to those of ordinary skill in the art. All such alternatives, modifications and variations are intended to fall with the spirit and scope of the present invention.

TABLE 1

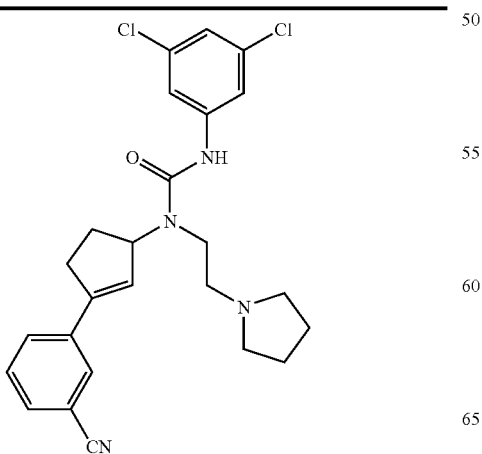

TABLE 1-continued

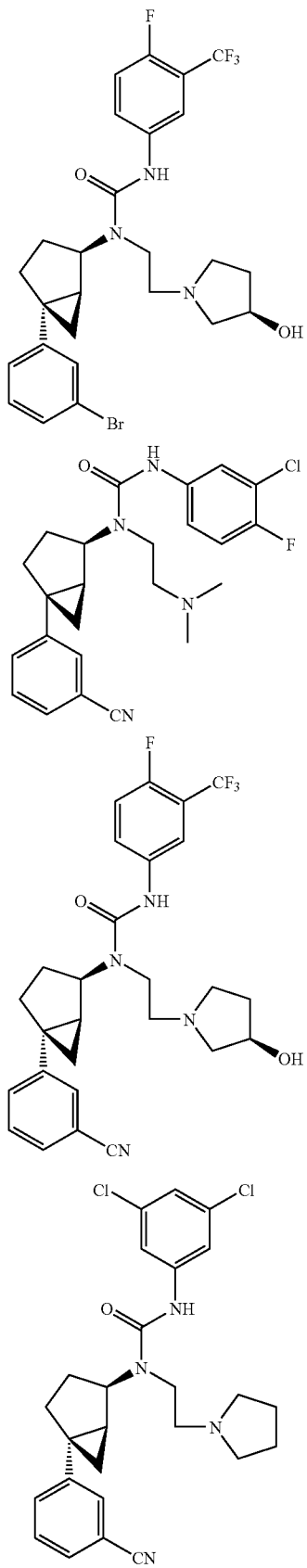

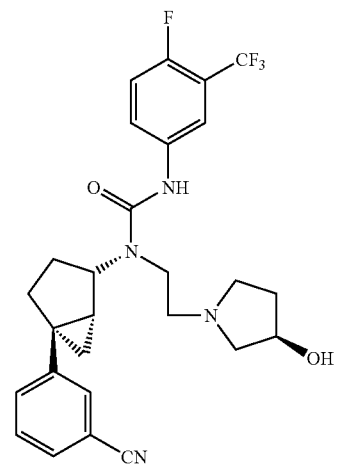
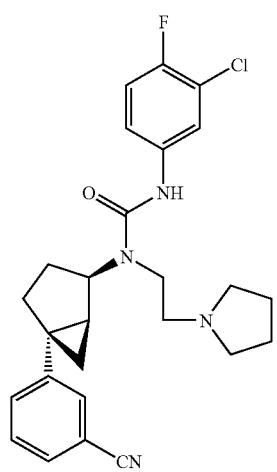
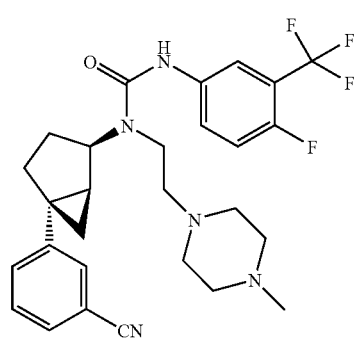
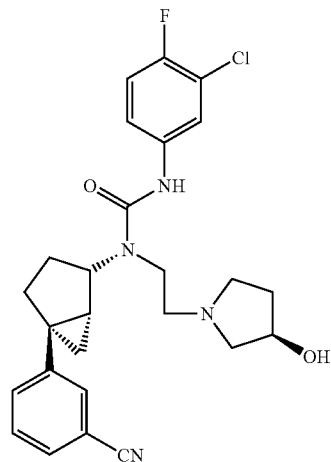
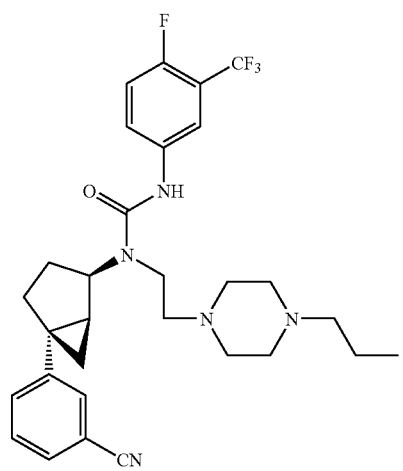
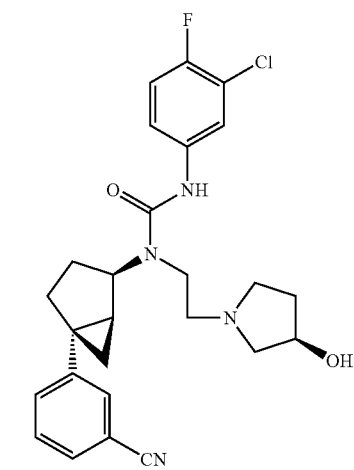

TABLE 1-continued
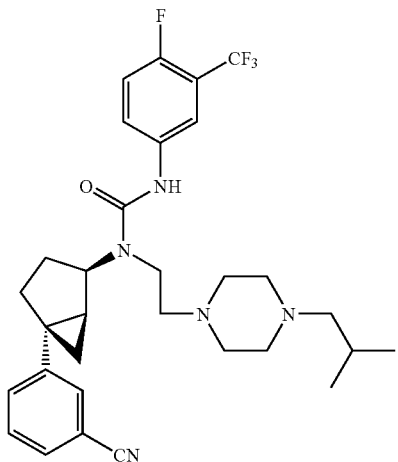
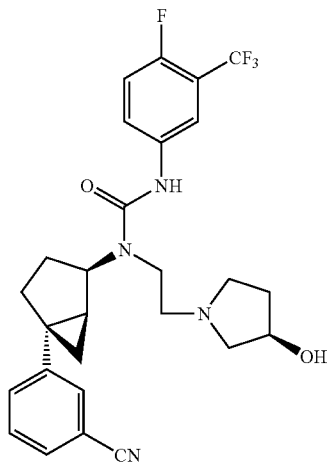
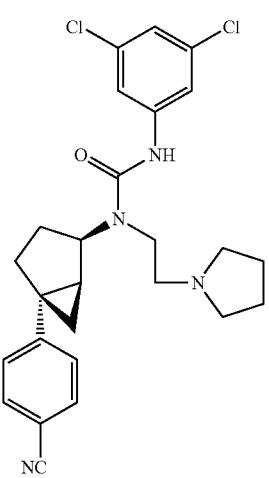
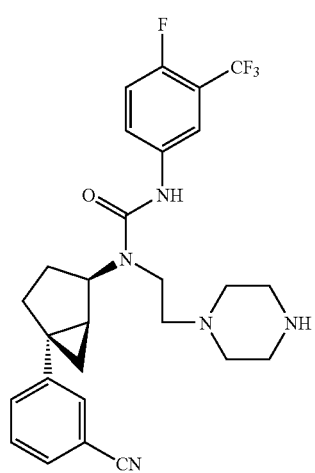
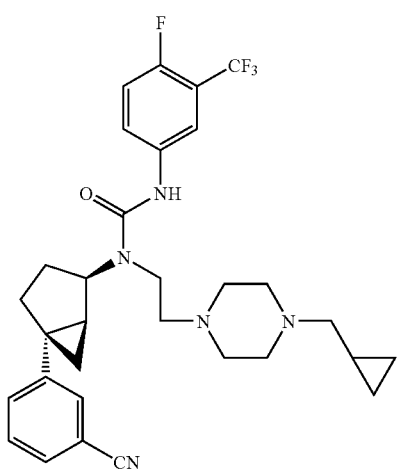
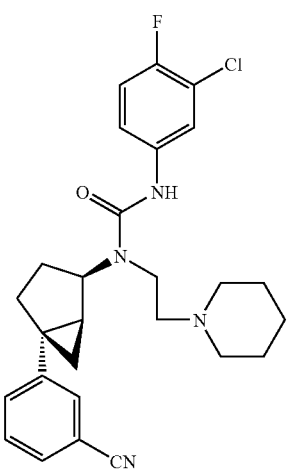

427
TABLE 1-continued
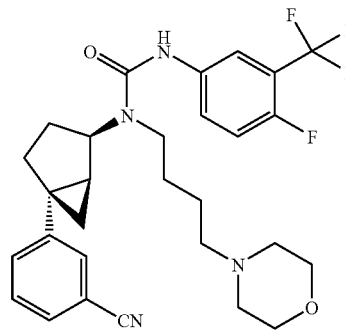
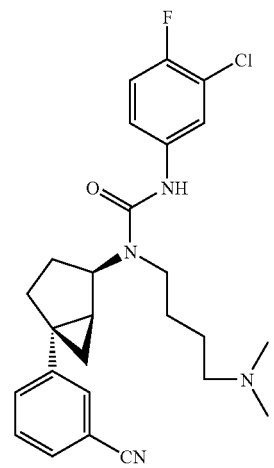
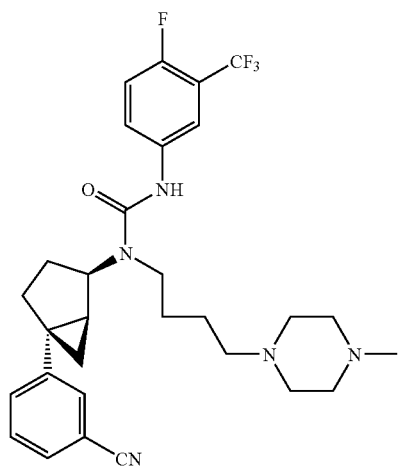
428
TABLE 1-continued
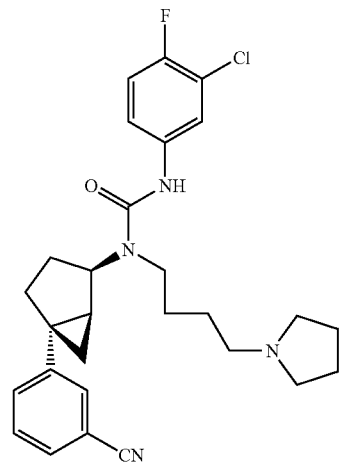
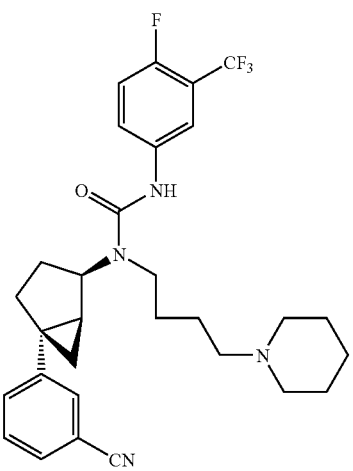
A further preferred group of compounds are those listed below in Table 1a.
TABLE 1a
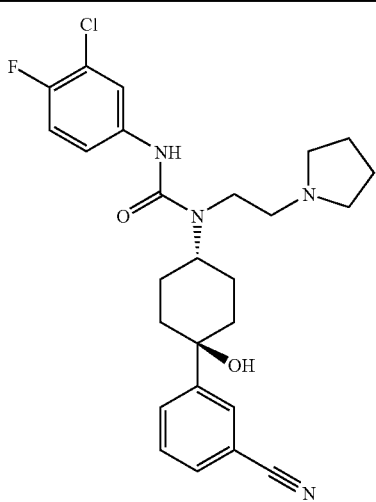

TABLE 1a-continued
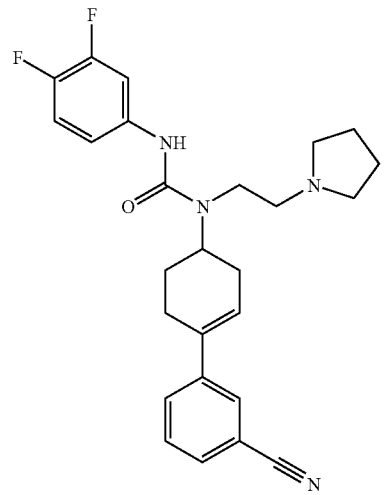
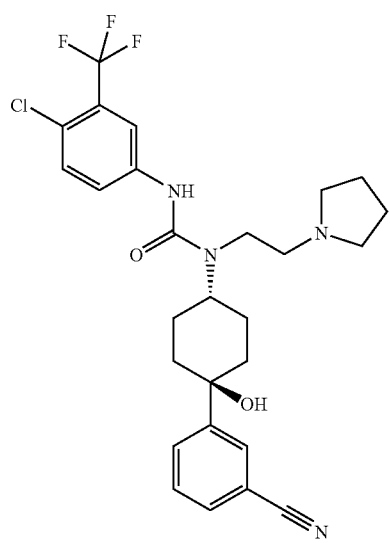
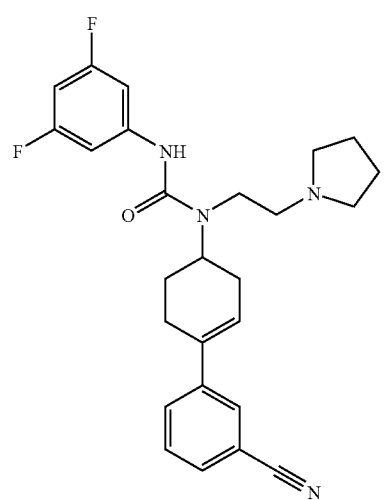
TABLE 1a-continued
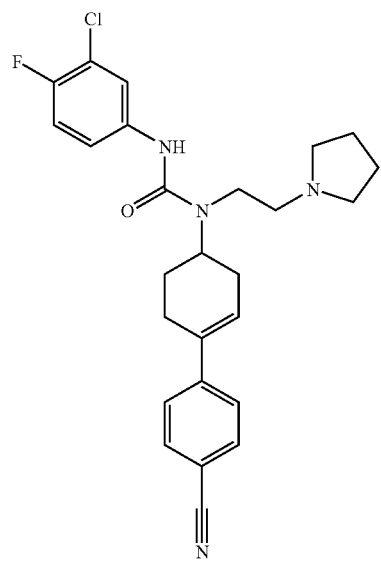
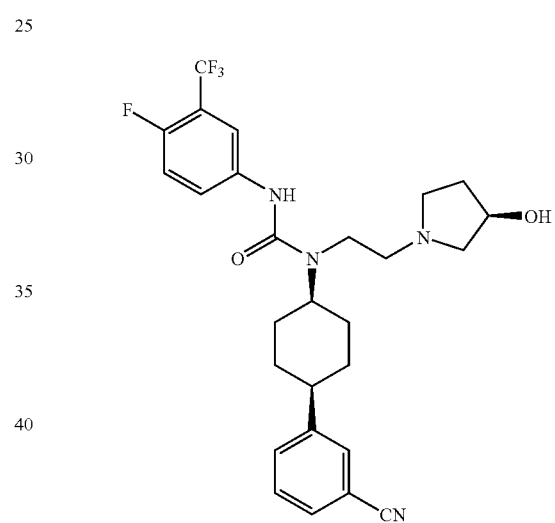
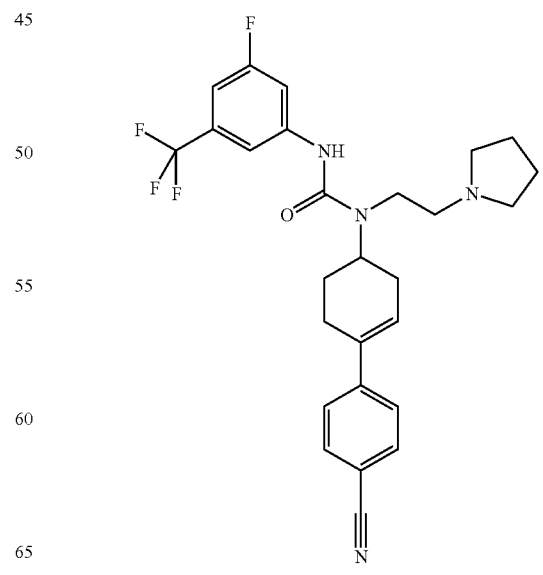

431
TABLE 1a-continued
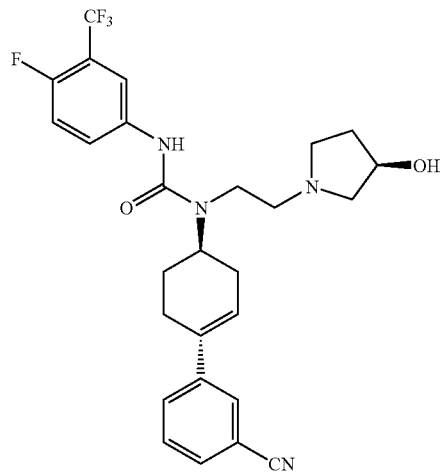
432
TABLE 1a-continued
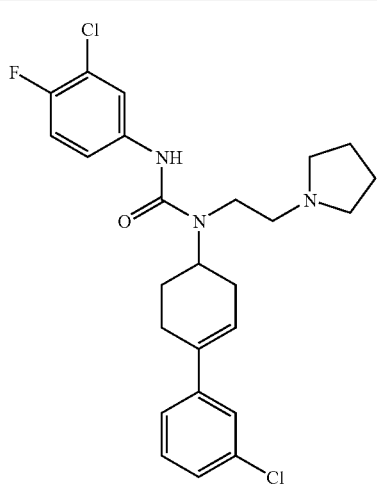
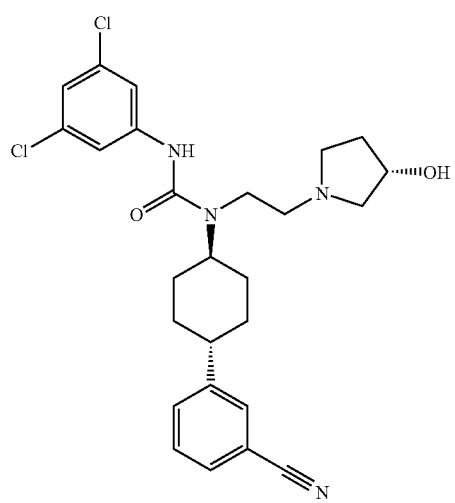

433
TABLE 1a-continued
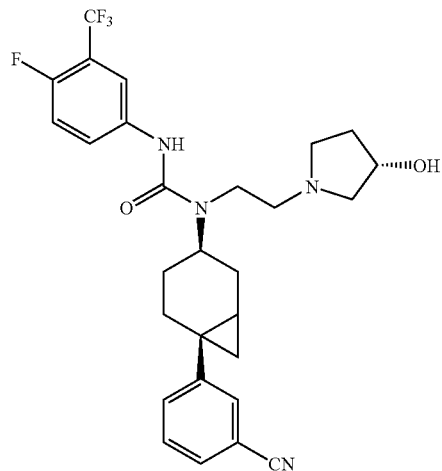
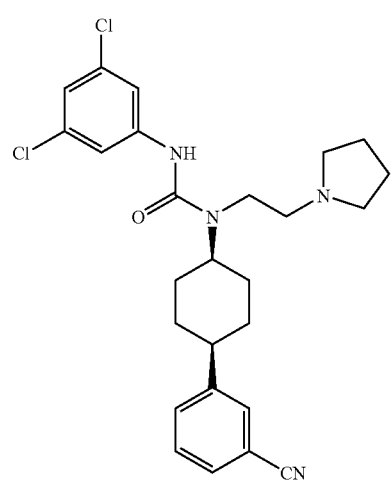
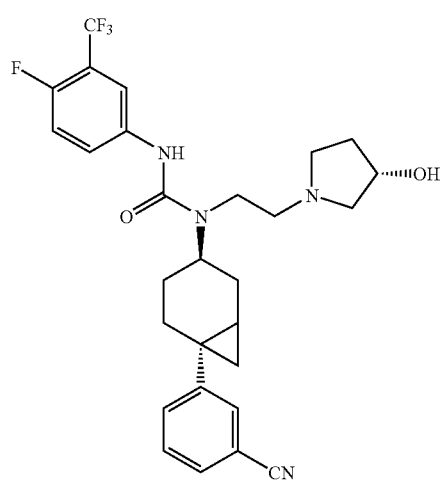
434
TABLE 1a-continued
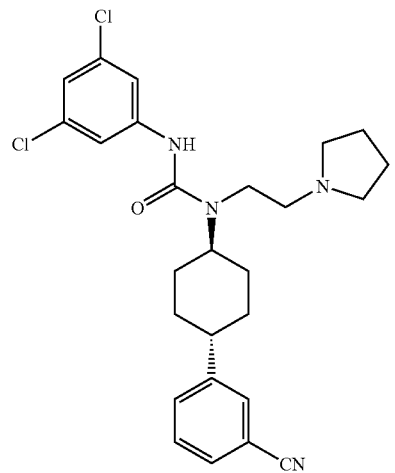
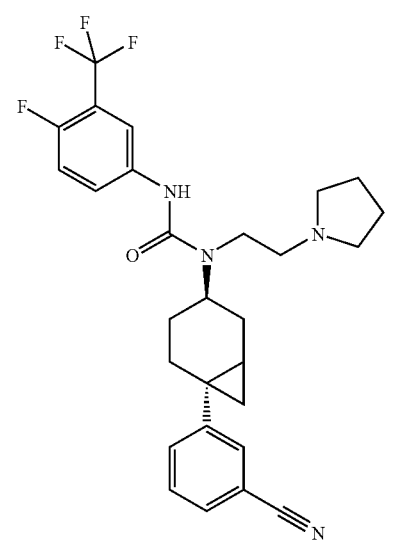
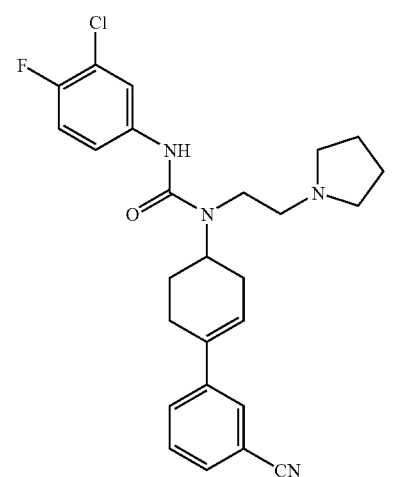

TABLE 1a-continued
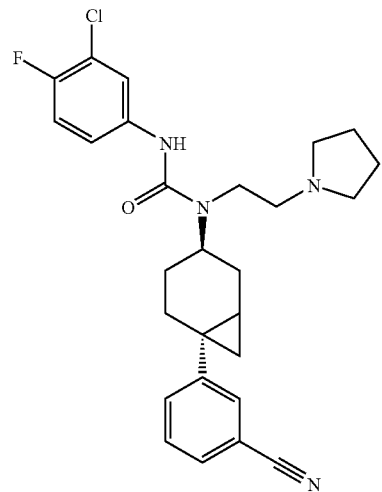
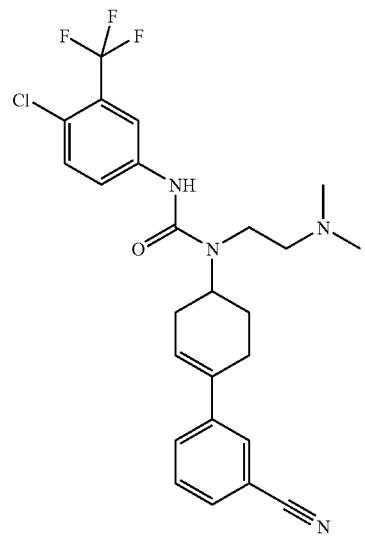
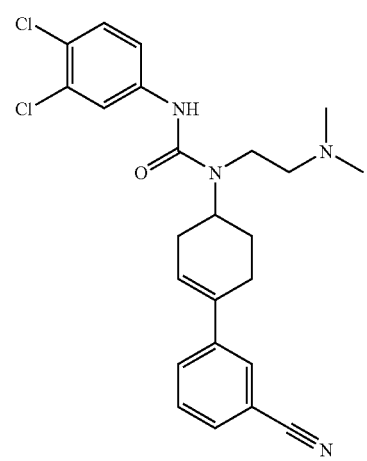
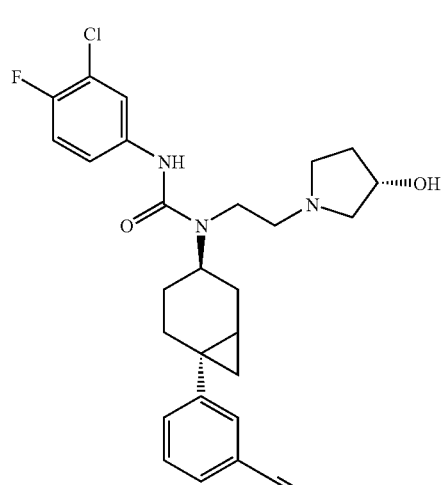
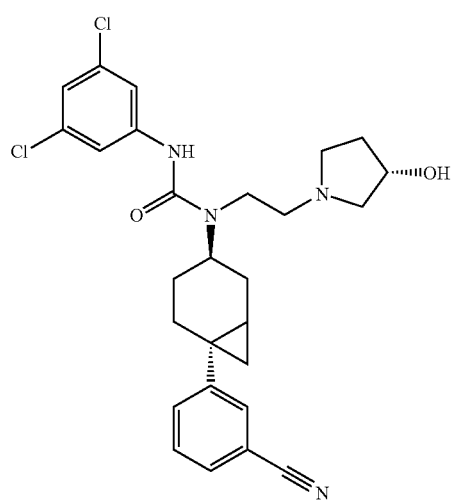
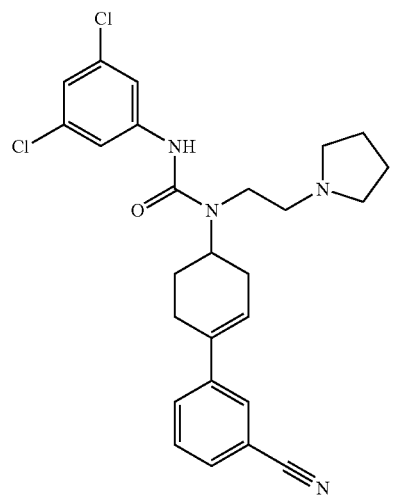

TABLE 1a-continued
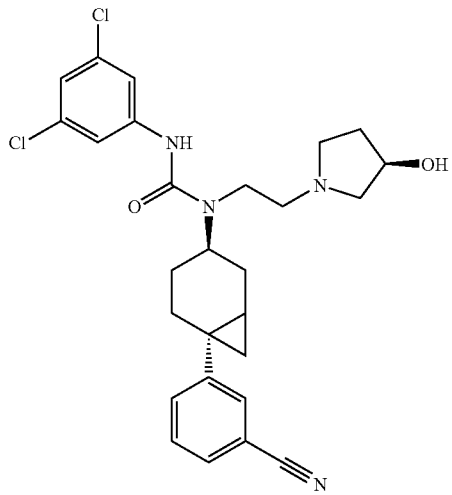
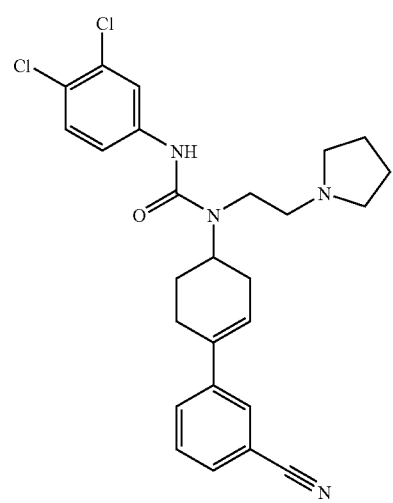
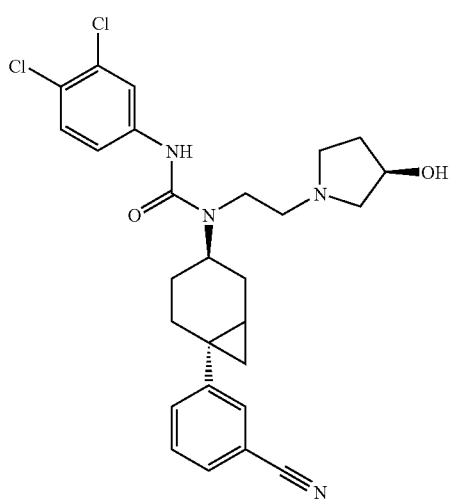
TABLE 1a-continued
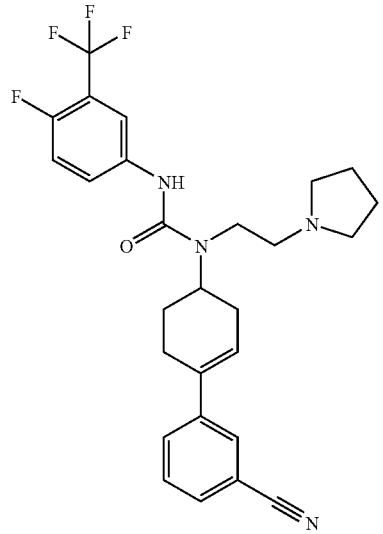
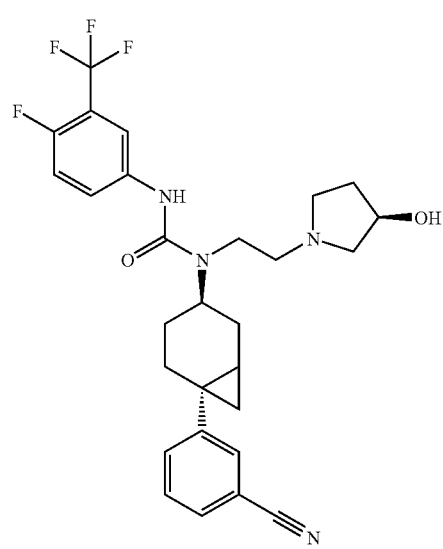
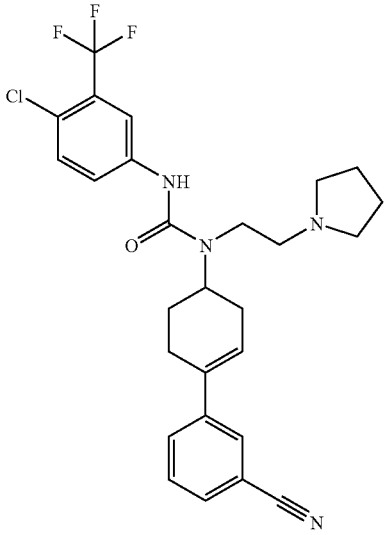

TABLE 1a-continued
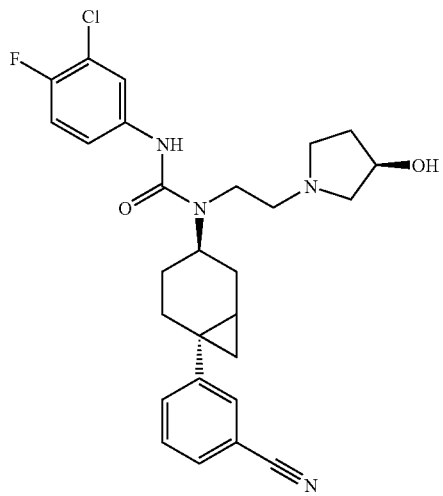
TABLE 1a-continued
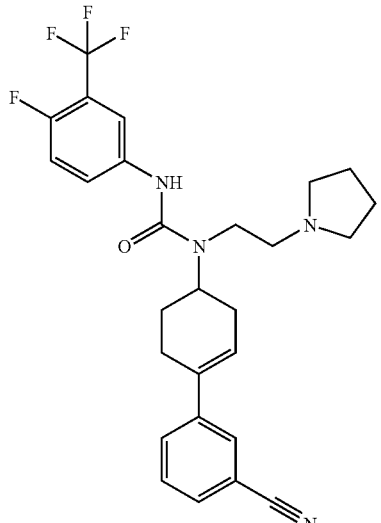
A further preferred group of compounds are those listed below in Table 1b.
TABLE 1b
| Structure | MCH R1 Ki (nM) |
|---|---|
| 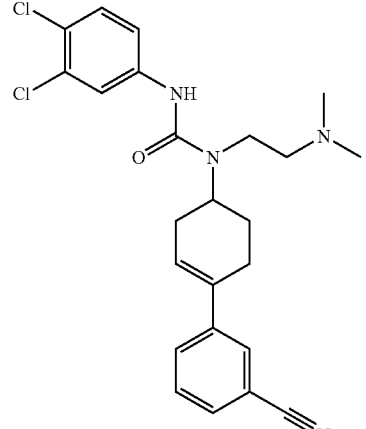 | 3.0 |
| 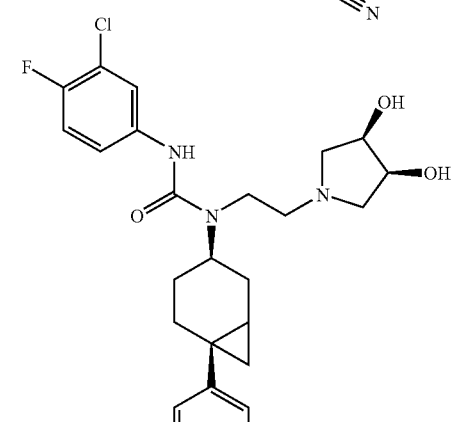 | 18.0 |

TABLE 1b-continued

| Structure | MCH R1 Ki (nM) |
|---|---|
| 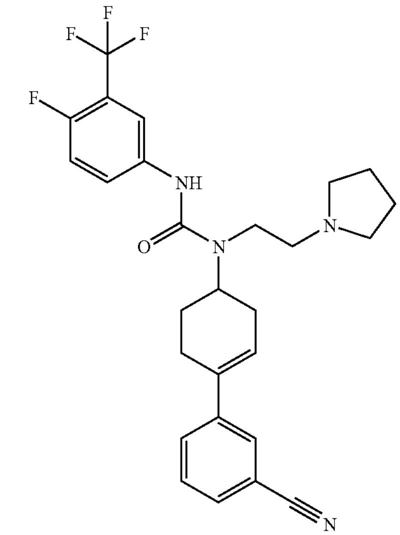 | 2.7 |
| 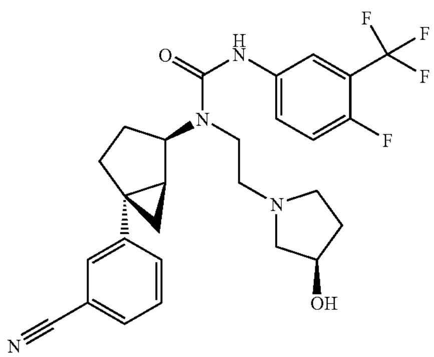 | 11.0 |
| 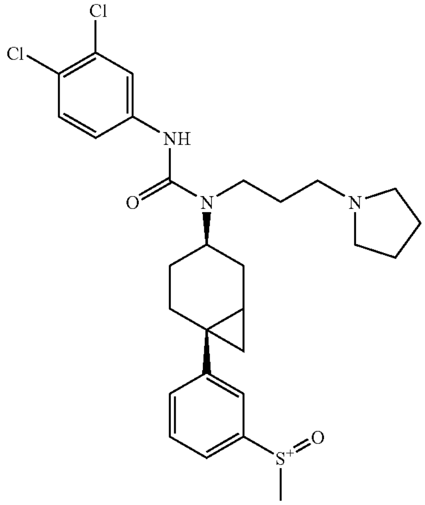 | 20.0 |

TABLE 1b-continued
| Structure | MCH R1 Ki (nM) |
|---|---|
| 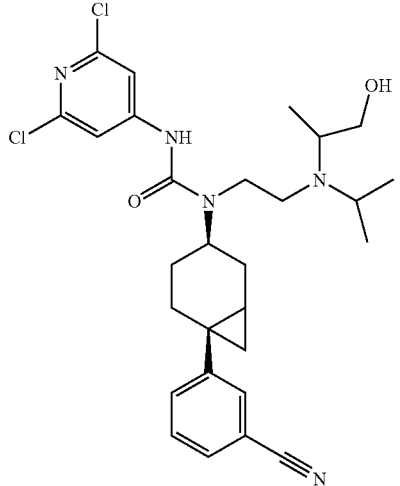 | 1.6 |
| 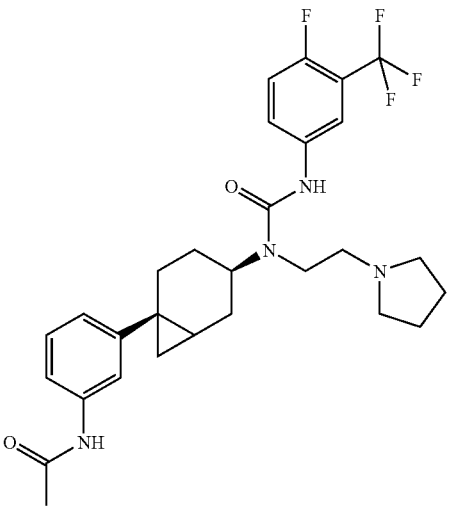 | 4.6 |
| 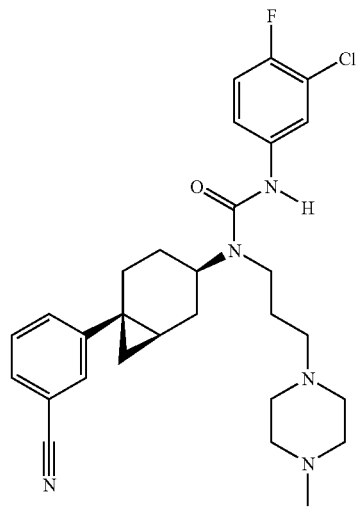 | 4.2 |

TABLE 1b-continued
| Structure | MCH R1 Ki (nM) |
|---|---|
| 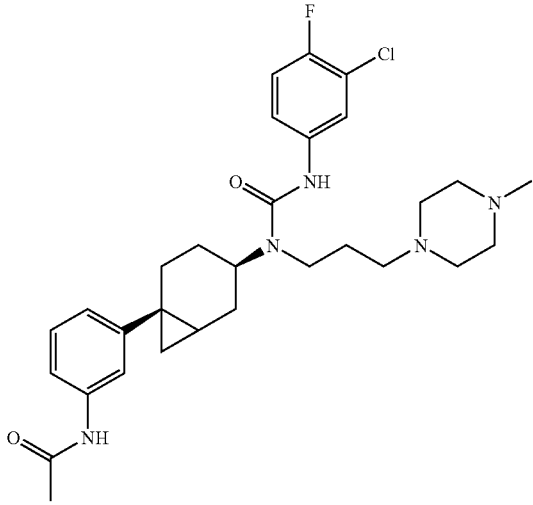 | 0.9 |
| 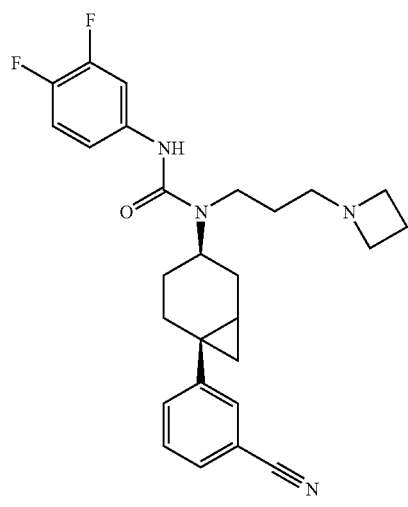 | 3.7 |
| 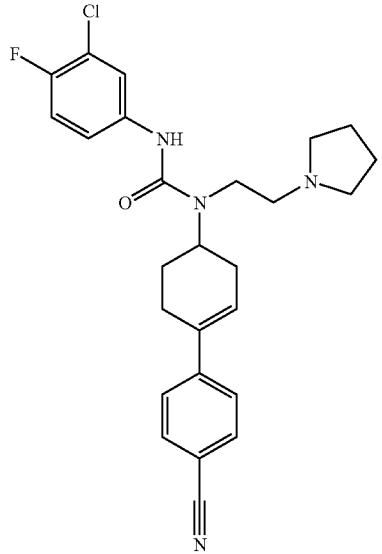 | 11.0 |

TABLE 1b-continued
| Structure | MCH R1 Ki (nM) |
|---|---|
| 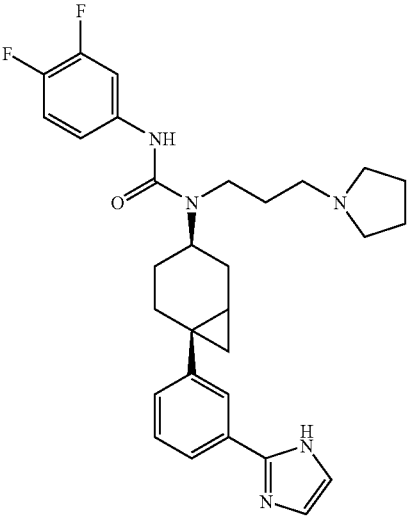 | 5.4 |
| 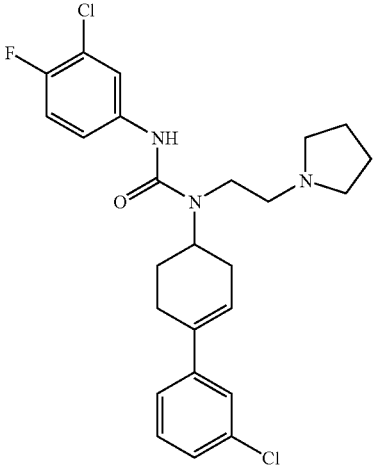 | 14.0 |
| 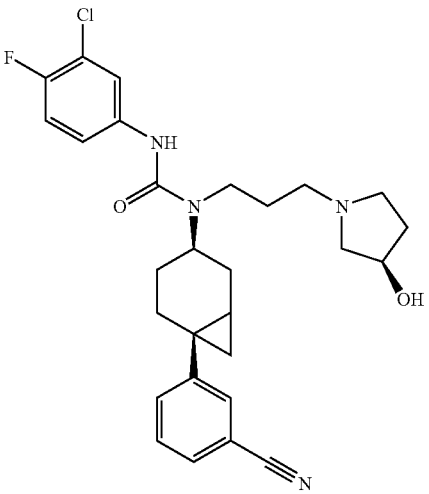 | 3.0 |

TABLE 1b-continued
| Structure | MCH R1 Ki (nM) |
|---|---|
| 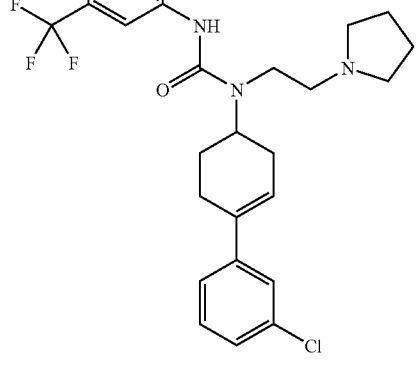 | 12.0 |
| 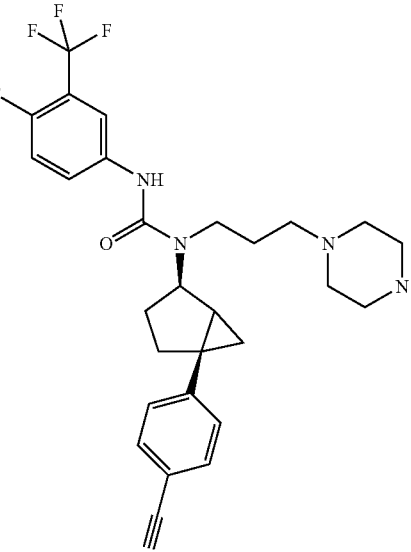 | 3.0 |
| 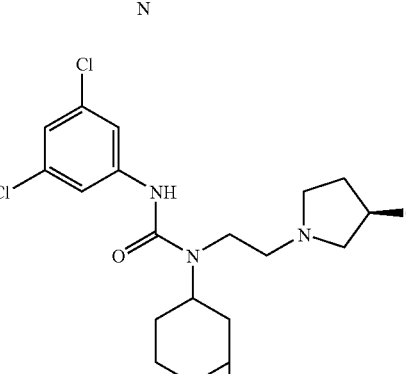 | 3.5 |

TABLE 1b-continued

| Structure | MCH R1 Ki (nM) |
|---|---|
| 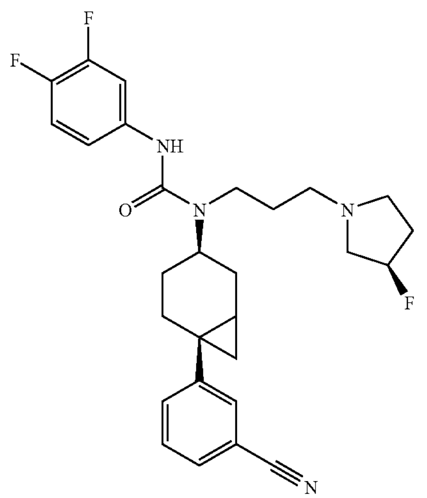 | 5.0 |
| 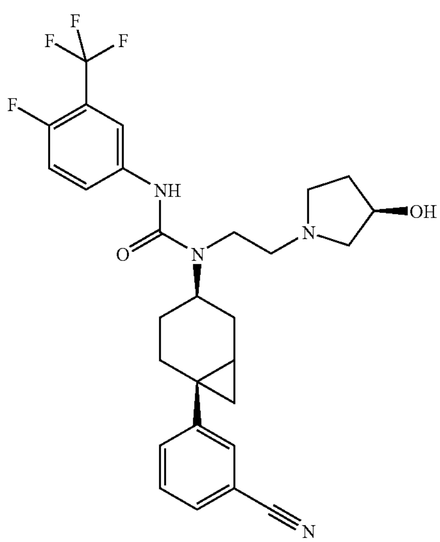 | 6.2 |
| 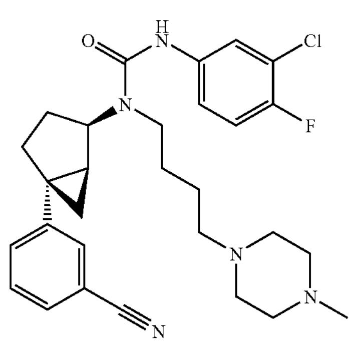 | 2.2 |

TABLE 1b-continued

| Structure | MCH R1 Ki (nM) |
|---|---|
| 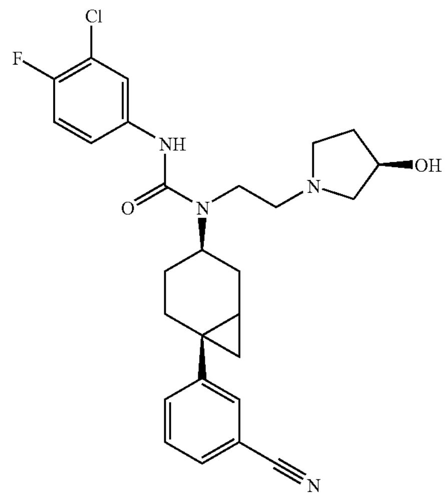 | 11.3 |
| 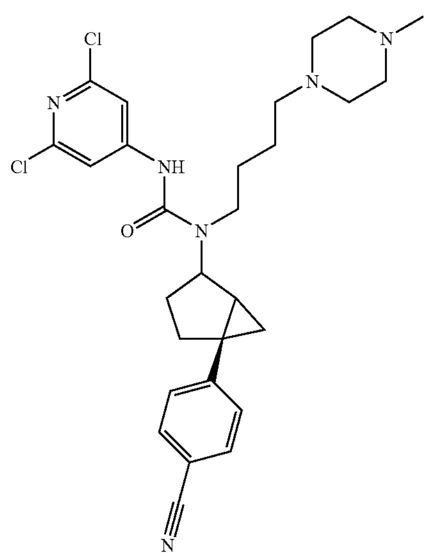 | 2.0 |
| 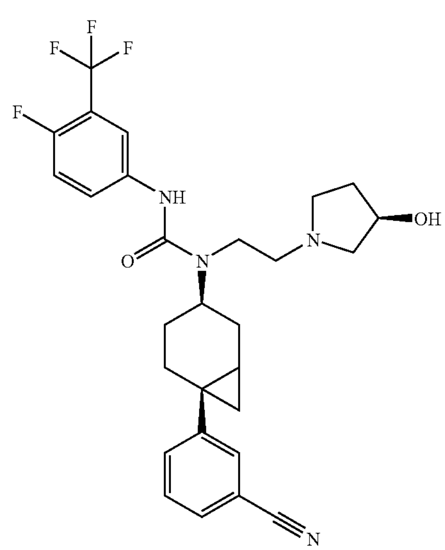 | 16.0 |

TABLE 1b-continued

| Structure | MCH R1 Ki (nM) |
|---|---|
| 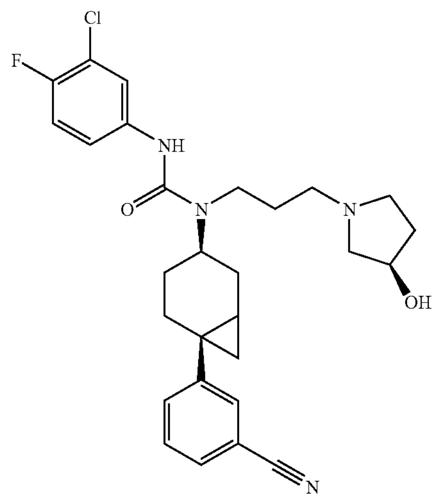 | 1.8 |
| 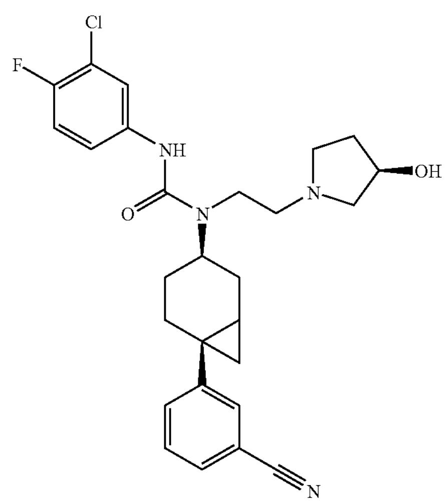 | 9.1 |
| 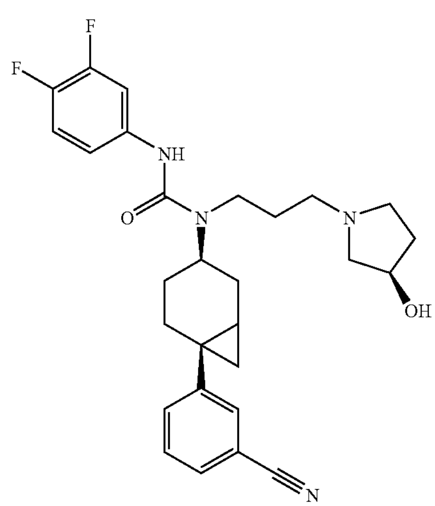 | 1.2 |

TABLE 1b-continued
| Structure | MCH R1 Ki (nM) |
|---|---|
| 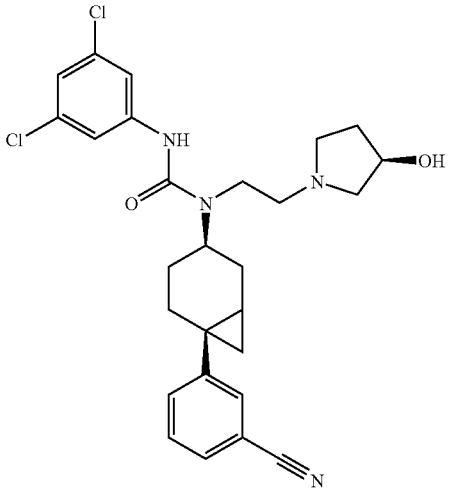 | 13.0 |
| 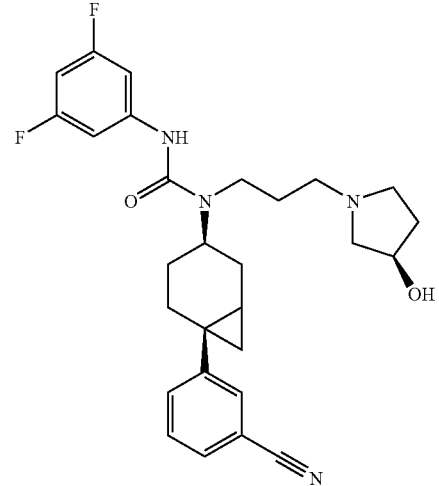 | 1.8 |
| 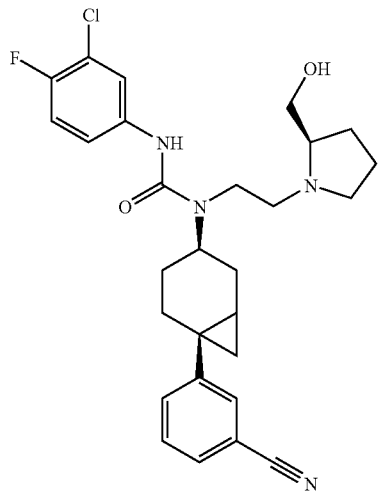 | 7.0 |

TABLE 1b-continued
| Structure | MCH R1 Ki (nM) |
|---|---|
| 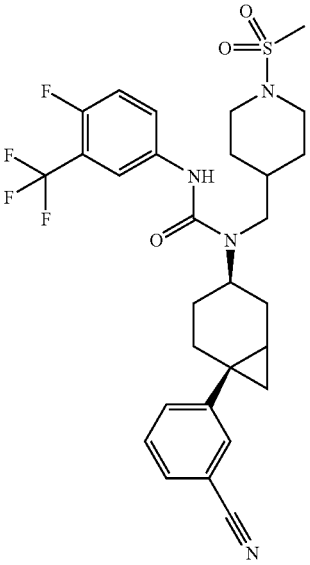 | 26.0 |
| 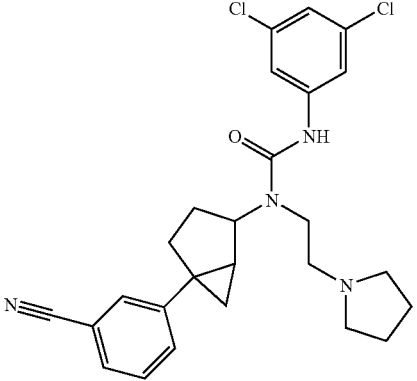 | 15.0 |
| 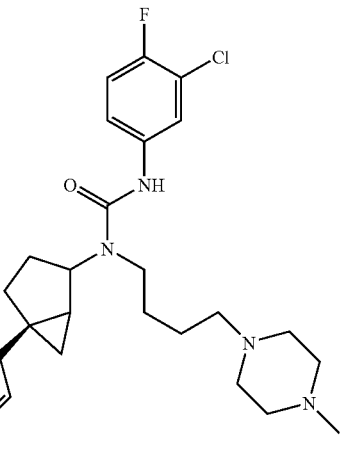 | 2.9 |

TABLE 1b-continued
| Structure | MCH R1 Ki (nM) |
|---|---|
| 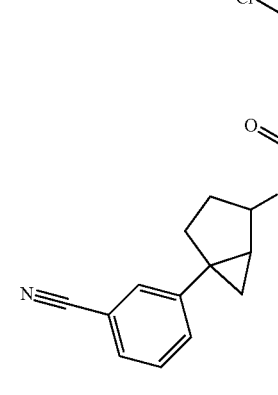 | 18.0 |
| 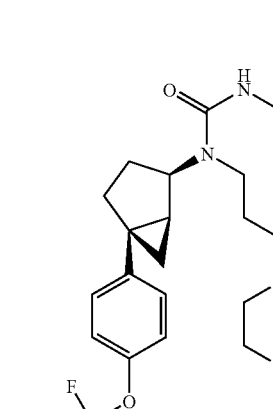 | 13.0 |
| 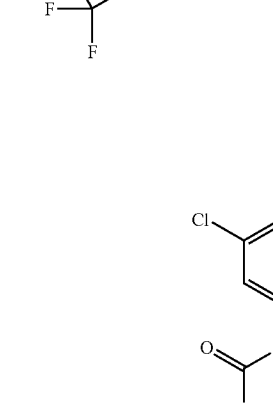 | 13.0 |

TABLE 1b-continued

| Structure | MCH R1 Ki (nM) |
| --- | --- |
| 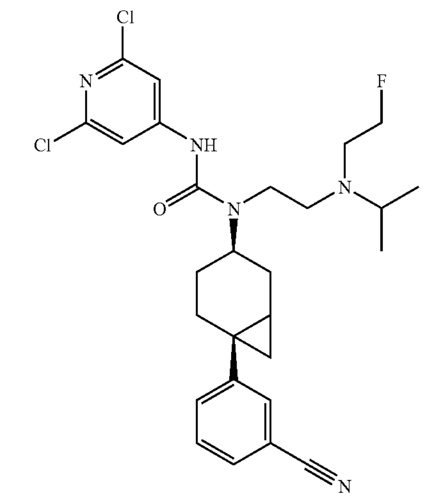 | 10.2 |
| 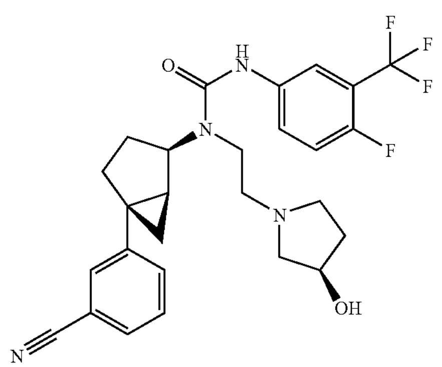 | 7.1 |
| 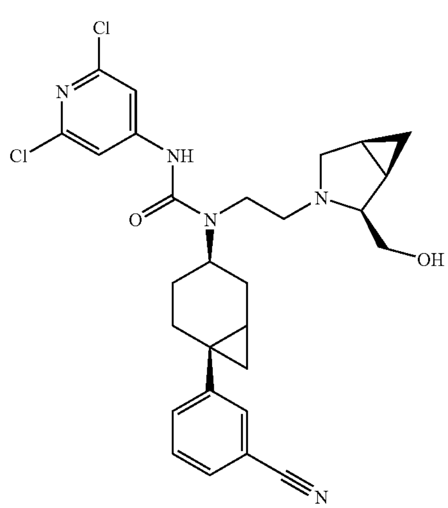 | 3.0 |

TABLE 1b-continued

| Structure | MCH R1 Ki (nM) |
|---|---|
| 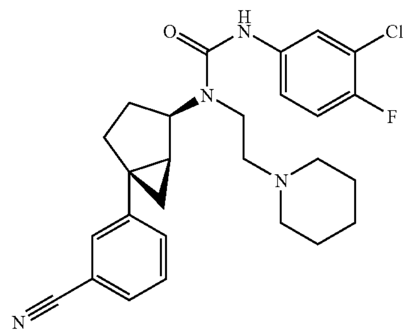 | 4.1 |
| 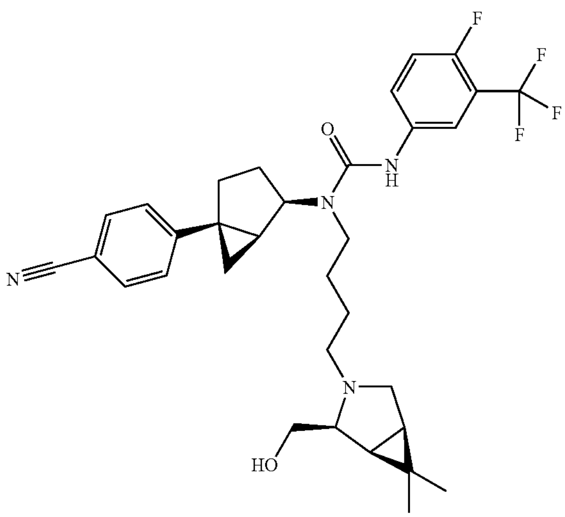 | 8.0 |
| 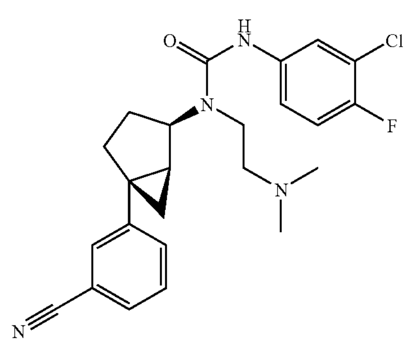 | 14.0 |

TABLE 1b-continued

| Structure | MCH R1 Ki (nM) |
|---|---|
| 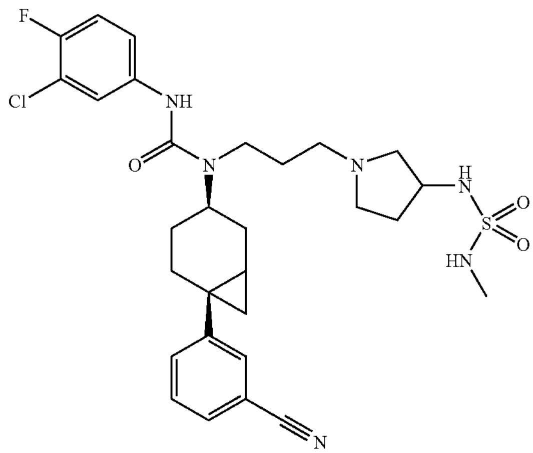 | 4.9 |
| 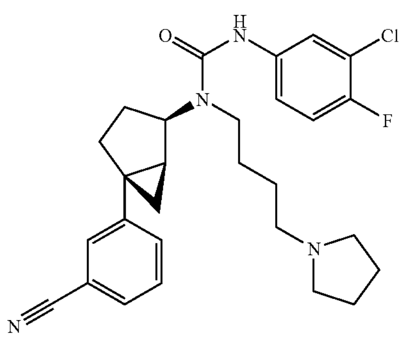 | 3.9 |
| 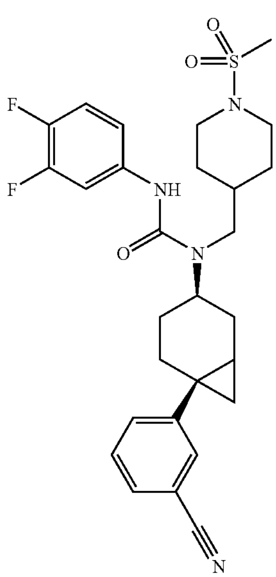 | 5.4 |

TABLE 1b-continued

| Structure | MCH R1 Ki (nM) |
|---|---|
| 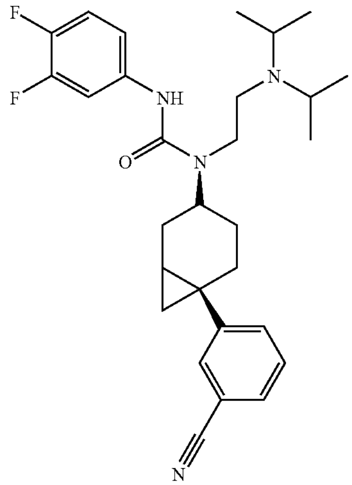 | 2.8 |
| 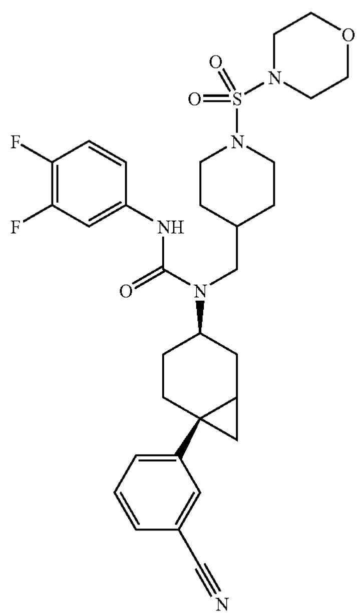 | 45.0 |
| 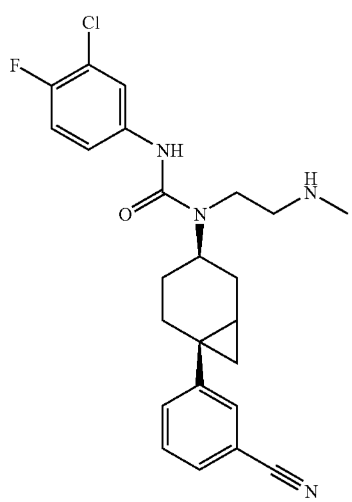 | 9.1 |

TABLE 1b-continued
| Structure | MCH R1 Ki (nM) |
|---|---|
| 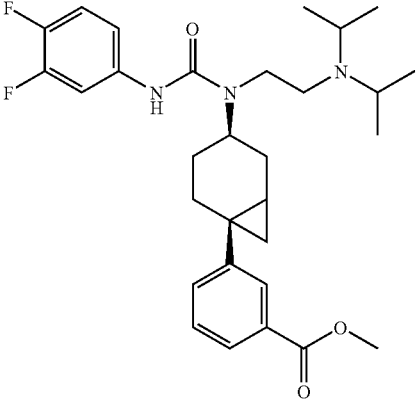 | 34.0 |
| 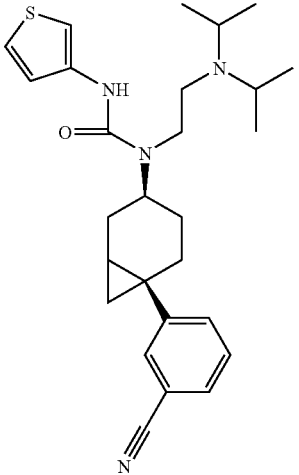 | 11.2 |
| 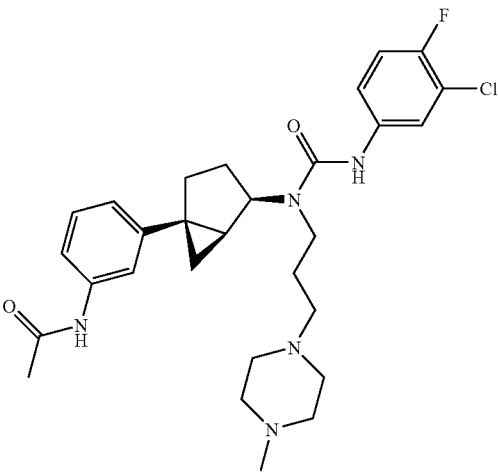 | 1.9 |

TABLE 1b-continued
| Structure | MCH R1 Ki (nM) |
|---|---|
| 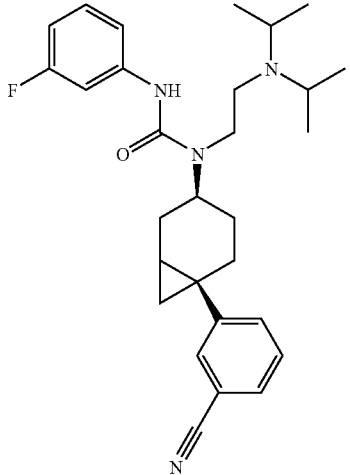 | 2.1 |
| 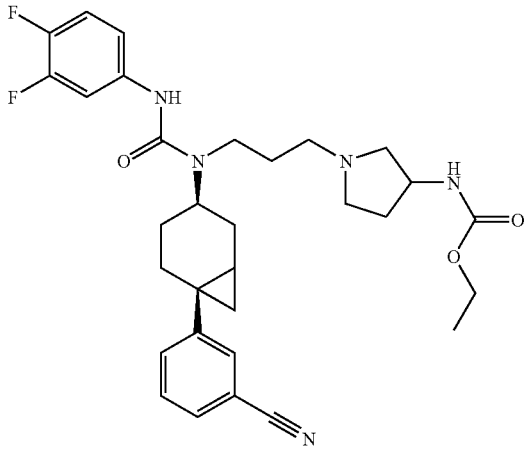 | 5.9 |
| 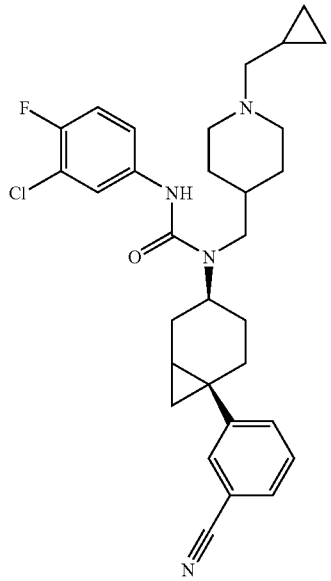 | 10.0 |

TABLE 1b-continued

| Structure | MCH R1 Ki (nM) |
|---|---|
| 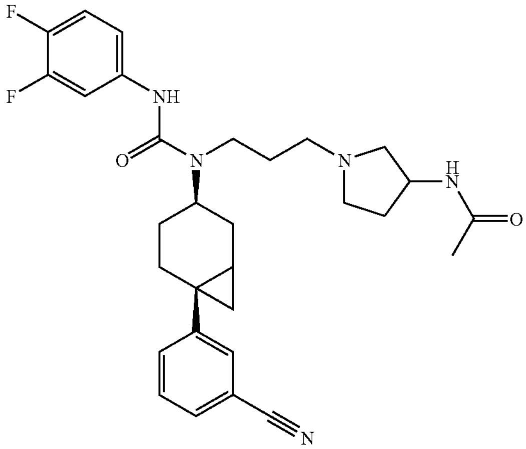 | 5.8 |
| 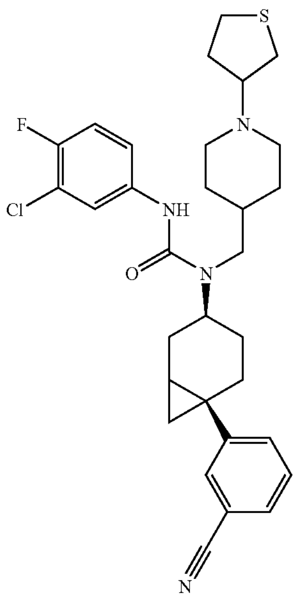 | 7.5 |
| 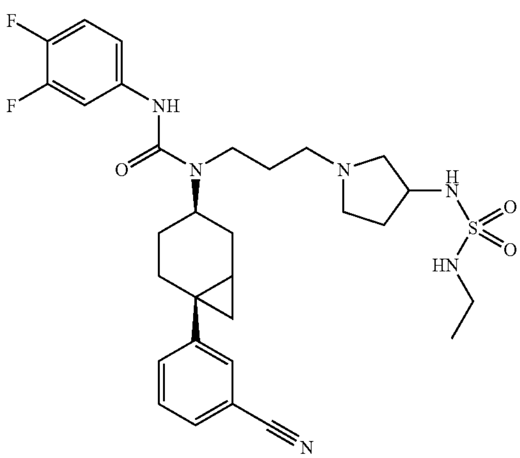 | 7.1 |

TABLE 1b-continued
| Structure | MCH R1 Ki (nM) |
|---|---|
| 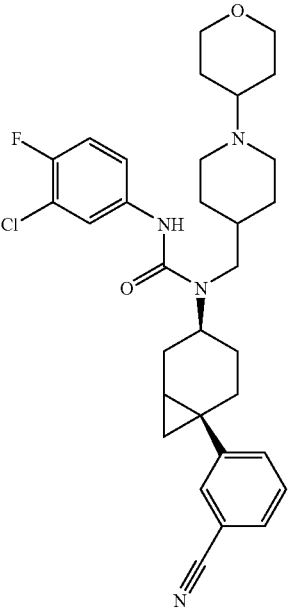 | 8.7 |
| 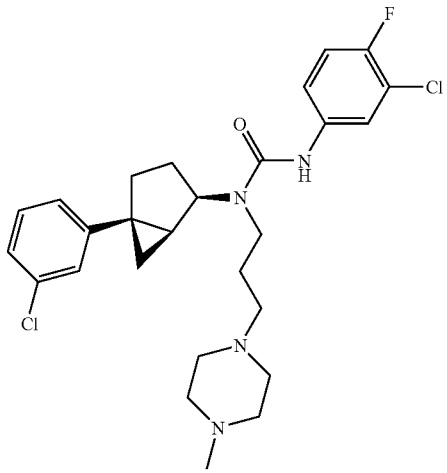 | 15.0 |
| 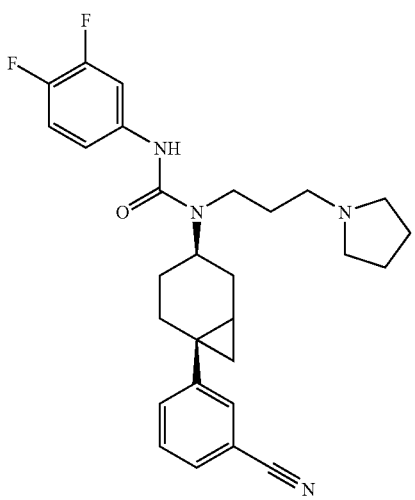 | 1.1 |

TABLE 1b-continued
| Structure | MCH R1 Ki (nM) |
|---|---|
| 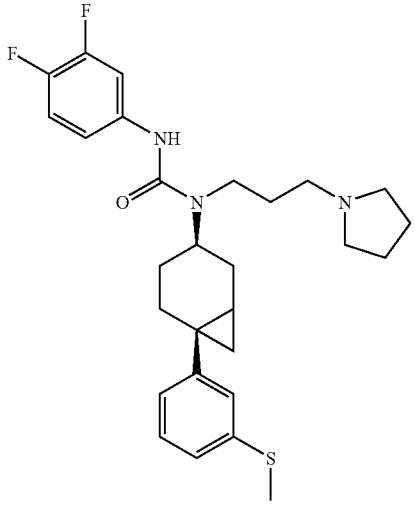 | 22.0 |
| 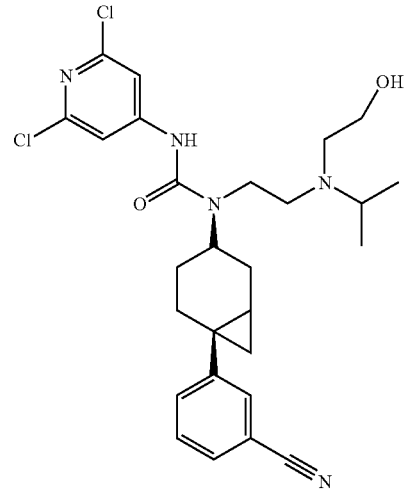 | 1.6 |
| 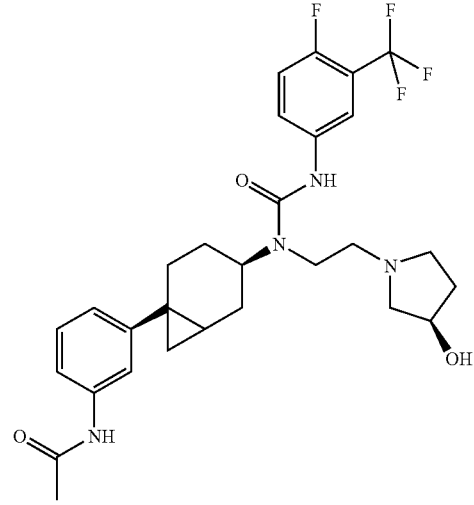 | 4.8 |

TABLE 1b-continued

| Structure | MCH R1 Ki (nM) |
|---|---|
| 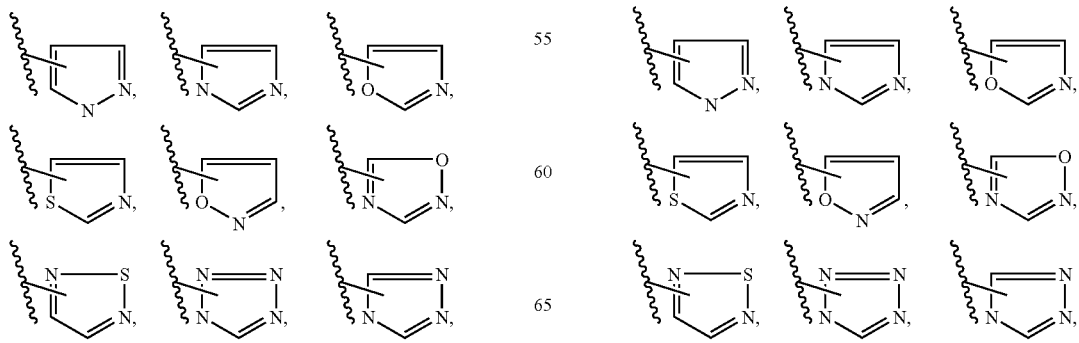 | 7.2 |

What is claimed is:

1. A compound represented by the structural formula

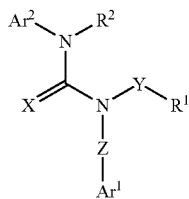
formula I or a pharmaceutically acceptable salt of said compound, isomer or racemic mixture wherein Ar$^1$ is aryl, heteroaryl, (R$^7$)$_p$-substituted aryl or (R$^7$)$_p$-substituted heteroaryl, wherein p is a number from 1 to 3 and when p is more than 1, each R$^7$ can be the same or different and is independently selected from the group consisting of alkyl, cycloalkyl, halo, —CN, alkoxy, —CF$_3$, —OCF$_3$, —C(O)N(R$^8$)$_2$, —N(R$^9$)$_2$, (C$_1$-C$_6$)alkylene-N(R$^9$)$_2$—S-alkyl, —S(O)-alkyl, —S(O$_2$)-alkyl, —S(O$_2$)N(R$^8$)$_2$, —N(R$^8$)C(O)R$^5$, (C$_1$-C$_6$)N(R$^8$)C(O)R$^5$, NO$_2$, —C(O)alkyl, C(O$_2$)R$^8$, C(R$^8$)$_2$OR$^8$, C=NOR$^8$ and a cyclic moiety selected from the group consisting of

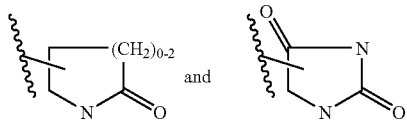 and wherein said cyclic moiety, together with Ar$^1$, can optionally form a fused aromatic moiety such as indole, indolone, benzimidazole, benzoxazole, benzthiazole, benzisoxazole, or benztriazole; and further wherein if two R$^7$ groups are adjacent, said adjacent R$^7$ moieties can optionally be joined together to form a methylenedioxy or ethylenedioxy moiety, Ar$^1$ is aryl, heteroaryl, (R$^7$)$_p$-substituted aryl or (R$^7$)$_p$-substituted heteroaryl, wherein p is a number from 1 to 3 and when p is more than 1, each R$^7$ can be the same or different and is independently selected from the group consisting of alkyl, cycloalkyl, halo, —CN, alkoxy, —CF$_3$, —OCF$_3$, —C(O)N(R$^8$)$_2$, —N(R$^9$)$_2$, (C$_1$-C$_6$)alkylene-N(R$^9$)$_2$—S-alkyl, —S(O)-alkyl, —S(O$_2$)-alkyl, —S(O$_2$)N(R$^8$)$_2$, —N(R$^8$)C(O)R$^5$, (C$_1$-C$_6$)N(R$^8$)C(O)R$^5$, NO$_2$, —C(O)alkyl, C(O$_2$)R$^8$, C(R$^8$)$_2$OR$^8$, C=NOR$^8$ and a cyclic moiety selected from the group consisting of -continued

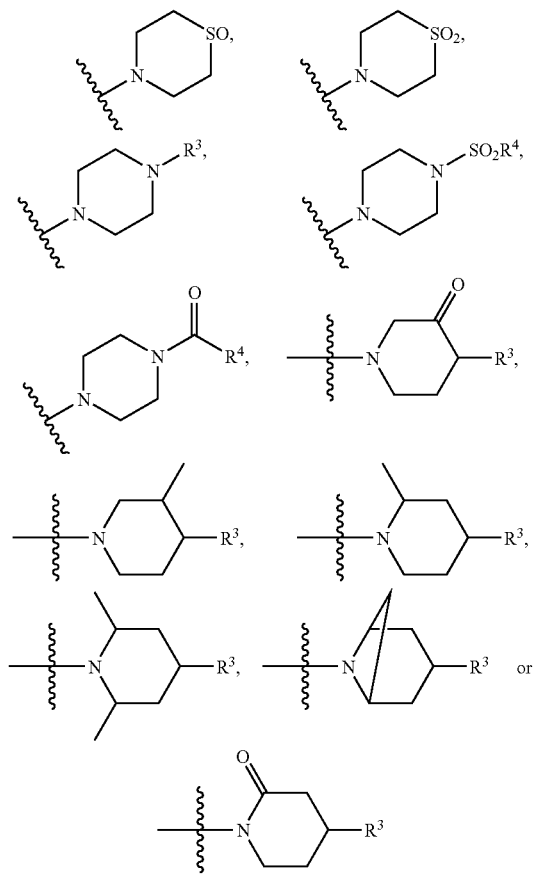

wherein said cyclic moiety, together with Ar¹, can optionally form a fused aromatic moiety such as indole, indolone, benzimidazole, benzoxazole, benzthiazole, benzisoxazole, or benztriazole; and further wherein if two $R^7$ groups are adjacent, said adjacent $R^7$ moieties can optionally be joined together to form a methylenedioxy or ethylenedioxy moiety;

X is O, S or N—(CN);

Y is a single bond or alkylene group;

Z is a $C_4$-$C_8$ cycloalkylene or $C_4$-$C_8$ heterocycloalkylene wherein each of said $C_4$-$C_8$ cycloalkylene or $C_4$-$C_8$ heterocycloalkylene group optionally containing one or two double bonds inside the cyclic ring and optionally substituted with 1 to 4 $R^6$ groups on the ring wherein each $R^6$ is independently selected from the group consisting of alkyl, cycloalkyl, —OH, —N($R^9$)$_2$, —NR$^9$COalkyl, alkoxy and —OC(O)-alkyl, with the proviso that when $R^6$ is —OH or —N($R^9$)$_2$, $R^6$ is not attached to a carbon adjacent to a nitrogen and when two $R^6$ groups are —OH, neither $R^6$ is on the same carbon on Z and further that two $R^6$ groups can be optionally joined together so that Z and said two $R^6$ groups together form a bicycloalkylene or bicycloheteroalkylene group containing from 5 to 12 atoms;

R¹ is $R^2$ is hydrogen or alkyl;

each $R^3$ is independently hydrogen, alkyl, cycloalkyl, cycloalkylalkyl, alkoxyalkylene-, aryl, aralkyl, heteroaryl, heterocyclyl, heteroaralkyl, —S(O$_2$)alkyl, —S(O$_2$)aryl, —S(O$_2$)N(H)alkyl, —S(O$_2$)N(alkyl)$_2$, —S(O$_2$)alkyl, —S(O$_2$)heterocycloalkyl, —C(O)alkyl, —C(O)aryl, —C(O)heteroaryl, —C(O)heterocycloalkyl, —C(O)N(H)alkyl, —C(O)N(alkyl)$_2$, —C(O)N(H)aryl, —C(O)Oalkyl, —C(O)Oaryl or alkylene-C(O)Oalkyl, wherein each of said alkyl, alkylene, alkoxy, aralkyl, aryl, heteroaryl, heteroaralkyl or cycloalkyl group can independently be nonsubstituted, halosubstituted or hydroxysubstituted;

$R^4$ is $R^3$, alkoxy or —N($R^3$)$_2$, with the proviso that when $R^4$ is attached to a sulfur atom then $R^4$ is not hydrogen;

$R^5$ is hydrogen, —N($R^3$)$_2$, alkyl, cycloalkyl, cycloalkylalkyl, aryl, aralkyl, heteroaralkyl, alkoxy or alkoxyalkylene-, wherein each of said alkyl, alkylene, alkoxy, aralkyl, aryl, heteroaralkyl or cycloalkyl group can independently be nonsubstituted, halosubstituted or hydroxysubstituted;

$R^8$ is hydrogen, alkyl or cycloalkyl;

$R^9$ is hydrogen, —C(O)alkyl or —S(O$_2$)alkyl, $R^{10}$ is $R^5$ or halogen;

with the following provisos:

that each $R^3$ of —N($R^3$)$_2$ can be same or different and is independently selected;

that each $R^8$ and $R^9$ of —C(O)N($R^8$)$_2$, —N($R^9$)$_2$ and —S(O$_2$)N($R^8$)$_2$ can be the same or different and is independently selected; and that in the above chemical formulas, each $R^3$ and $R^4$ can be the same or different and is independently selected.

2. The compound of claim 1 wherein

Ar¹ and A² are independently phenyl, pyridyl, $R^7$-substituted phenyl or $R^7$-substituted pyridyl, wherein said Ar¹ and Ar² are the same or different and is independently selected, and $R^7$ numbers 1 to 3 which can be the same or different, each being independently selected from the group consisting of alkyl, cycloalkyl, halo, —CN, alkoxy, —CF$_3$, —OCF$_3$, —C(O)N($R^8$)$_2$, —N($R^9$)$_2$, —S-alkyl, —S(O)-alkyl, —S(O$_2$)-alkyl, —S(O$_2$)N($R^8$)$_2$, —N($R^8$)C(O)$R^5$, —NO$_2$,

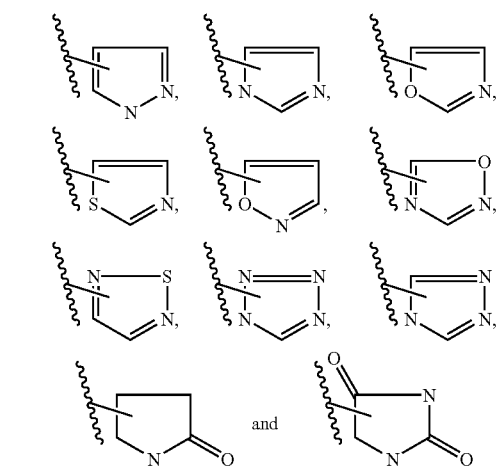

wherein each $R^8$ and $R^9$ can be the same or different and is independently selected, or two adjacent $R^7$ groups can be joined together to form a methylenedioxy or ethylenedioxy group;

X is O;

Y is —CH₂CH₂—, —CH₂CH₂CH₂— or —CH₂CH₂CH₂CH₂—;

R¹ is

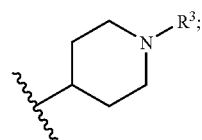

R³ is hydrogen, —(C₁-C₆)alkyl, —(C₃-C₇)cycloalkyl, —(C₃-C₇)cycloalkyl(C₁-C₆)alkyl, (C₁-C₆)alkoxy(C₁-C₆)alkylene-, aryl, aralkyl, heterocyclyl, heteroaryl or heteroaralkyl, wherein each of said alkyl, alkylene, alkoxy, aralkyl, aryl, heteroaryl, heteroaralkyl or cycloalkyl group can independently be nonsubstituted, halosubstituted or hydroxysubstituted;

R⁴ is R³, (C₁-C₆)alkoxy or —N(R³)₂ wherein each R³ can be same or different and is independently selected, with the proviso that when R⁴ is attached to a sulfur atom then R⁴ is not hydrogen;

R⁵ is hydrogen, —(C₁-C₆)alkyl, —(C₃-C₇)cycloalkyl, —(C₃-C₇)cycloalkyl(C₁-C₆)alkyl, aryl, aralkyl, heteroaralkyl, (C₁-C₆)alkoxy or (C₁-C₆)alkoxy(C₁-C₆)alkylene-, wherein each of said alkyl, alkylene, alkoxy, aralkyl, aryl, heteroaralkyl or cycloalkyl group can independently be nonsubstituted, halosubstituted or hydroxysubstituted; and R⁸ is hydrogen, —(C₁-C₆)alkyl or —(C₃-C₇)cycloalkyl.

3. The compound of claim 2 wherein Ar¹ is R⁷-substituted phenyl and said R⁷ is one group positioned at the 3-position of said substituted phenyl with respect to the linking point to Z.

4. The compound of claim 3 wherein R⁷ is —CN, —OCF₃, chloro, —C(O)N(R⁸)₂, —N(R⁹)₂, or —N(R⁸)C(O)R⁵.

5. The compound of claim 2 wherein Ar¹ is pyridyl and Ar² is halo-substituted phenyl or (CF₃)-substituted phenyl.

6. The compound of claim 2 wherein Ar¹ is pyridyl and A² is halo-substituted pyridyl or (CF₃)-substituted pyridyl.

7. A compound selected from the group consisting of

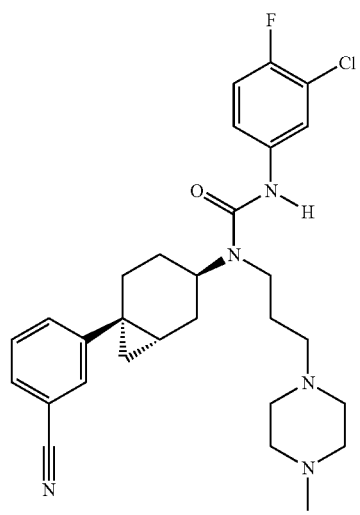

-continued

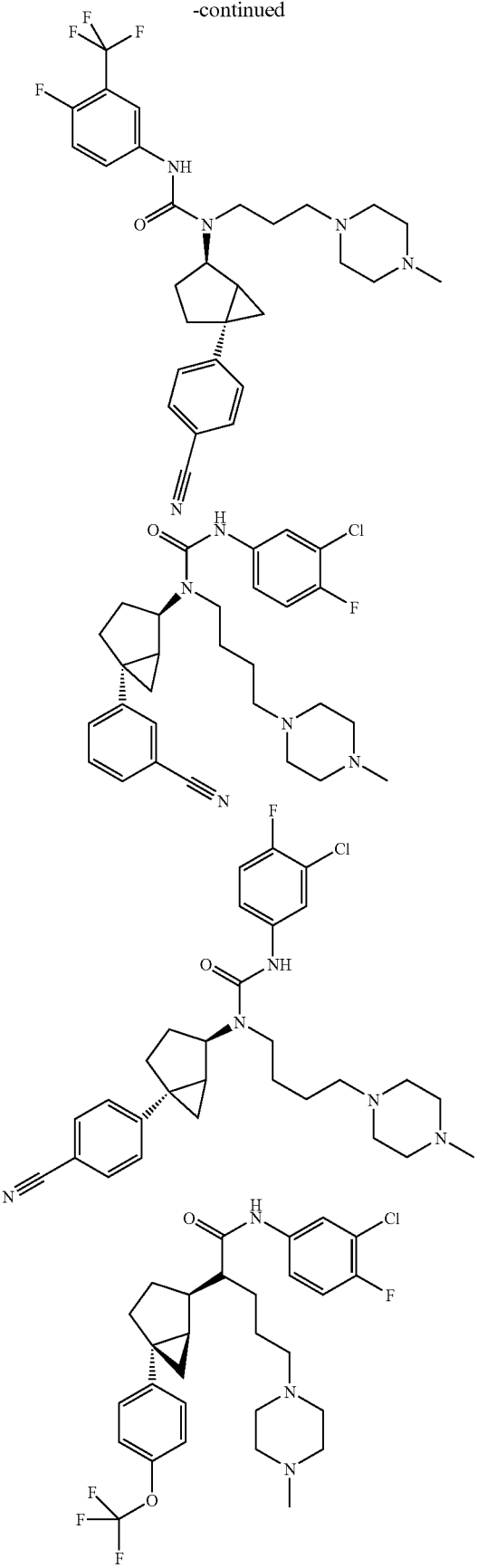

487
-continued
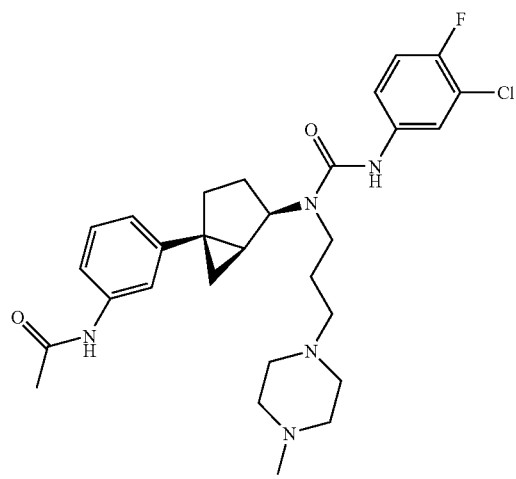
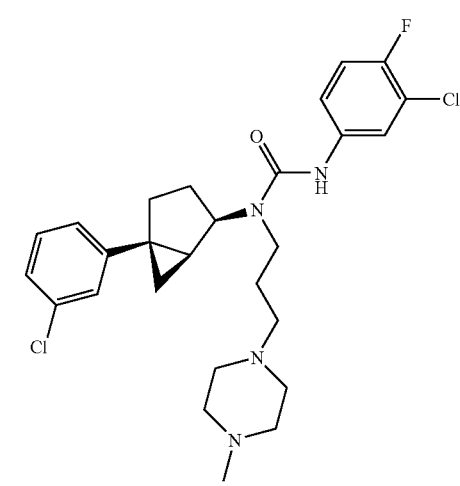
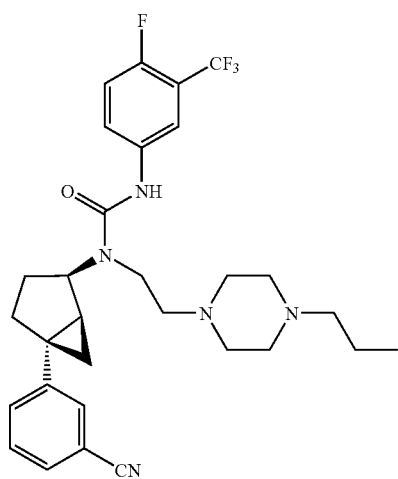
488
-continued
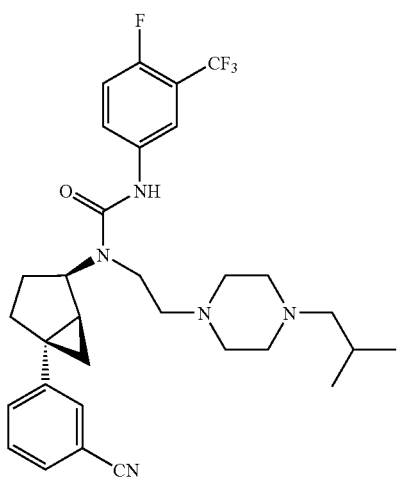
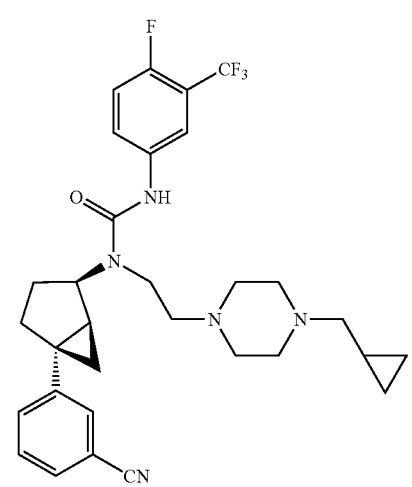
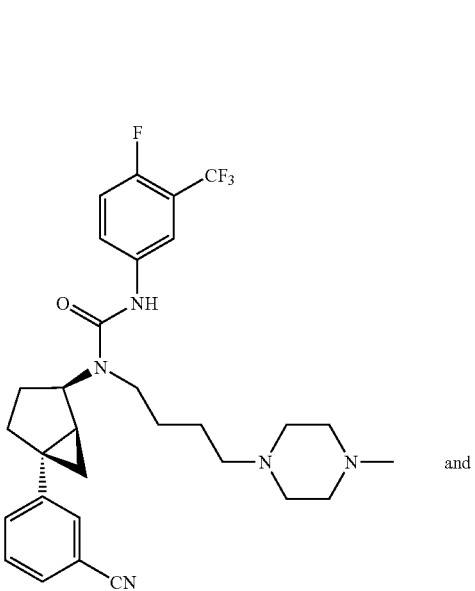
and -continued

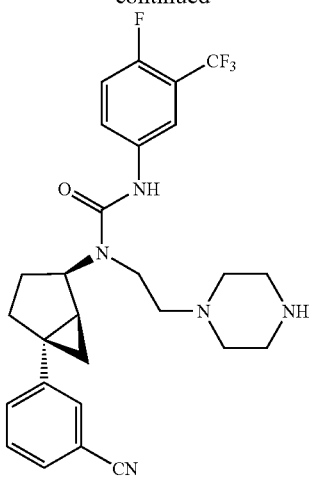

or a pharmaceutically acceptable salt thereof.

8. A pharmaceutical composition comprising a therapeutically effective amount of at least one compound of claim 1 in combination with at least one pharmaceutically acceptable carrier.

9. A pharmaceutical composition comprising a therapeutically effective amount of at least one compound of claim 7 in combination with at least one pharmaceutically acceptable carrier.

10. A compound of the formula

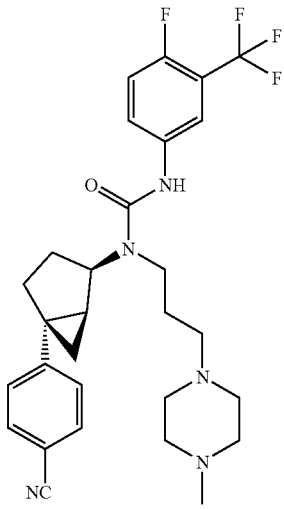

or a pharmaceutically acceptable salt thereof.

* * * * *